(12) United States Patent
Muller et al.

(10) Patent No.: US 7,470,723 B2
(45) Date of Patent: Dec. 30, 2008

(54) DIPHENYLETHYLENE COMPOUNDS AND USES THEREOF

(75) Inventors: George W. Muller, Bridgewater, NJ (US); Faribourz Payvandi, Belle Mead, NJ (US); Ling H. Zhang, Parsippany, NJ (US); Michael J. Robarge, North Plainfield, NJ (US); Roger Chen, Edison, NJ (US); Hon-Wah Man, Princeton, NJ (US); Alexander L. Ruchelman, Robbinsville, NJ (US)

(73) Assignee: Celgene Corporation, Summit, NJ (US)

( * ) Notice: Subject to any disclaimer, the term of this patent is extended or adjusted under 35 U.S.C. 154(b) by 305 days.

(21) Appl. No.: 10/934,974

(22) Filed: Sep. 3, 2004

(65) Prior Publication Data

US 2005/0107339 A1    May 19, 2005

Related U.S. Application Data

(63) Continuation-in-part of application No. 10/794,931, filed on Mar. 5, 2004, now Pat. No. 7,312,241.

(60) Provisional application No. 60/452,460, filed on Mar. 5, 2003.

(51) Int. Cl.
*A61K 31/36* (2006.01)
*A61K 31/277* (2006.01)
*C07D 317/60* (2006.01)
*C07C 255/08* (2006.01)

(52) U.S. Cl. .................. 514/466; 514/520; 549/442; 558/410

(58) Field of Classification Search ............... 549/442; 514/466, 520; 558/410
See application file for complete search history.

(56) References Cited

U.S. PATENT DOCUMENTS

| 4,118,742 | A | 10/1978 | Paget et al. |
|---|---|---|---|
| 4,492,708 | A | 1/1985 | Spitzer |
| 5,414,008 | A | 5/1995 | Muller et al. |
| 5,466,861 | A | 11/1995 | Dawson et al. |
| 5,929,117 | A | 7/1999 | Muller et al. |
| 6,130,226 | A | 10/2000 | Muller et al. |
| 6,262,101 | B1 | 7/2001 | Muller et al. |
| 2001/0056107 | A1 | 12/2001 | Muller et al. |
| 2005/0107339 | A1 | 5/2005 | Muller et al. |

FOREIGN PATENT DOCUMENTS

| EP | 0091795 | 10/1983 |
|---|---|---|
| EP | 0316594 | 5/1989 |
| JP | 58188868 | 11/1983 |
| JP | 05066591 | 3/1993 |
| WO | WO 96/21435 | 7/1996 |
| WO | WO 98/06692 | 2/1998 |
| WO | WO 00/01387 | 1/2000 |
| WO | WO 2004/078144 | 9/2004 |

OTHER PUBLICATIONS

Bedford et al. 1996, Synthesis of water-soluble prodrugs of the cytotoxic agent combretastatin A4. Bioorganic & Medicinal Chemistry Lett. 6(2):157-160.
Chen et al., 2000, Preparation of New Anti-Tubulin Ligands through a Dual-Mode, Addition-Elimination Reaction to a Bromo-Substituted $\alpha$, $\beta$-Unsaturated Sulfoxide. J. Org. Chem. 65:8811-8815.
Cummins et al., 1971, Aust. J. Chem., v. 24(11), pp. 2257-2266.
Cushman et al., 1993, Synthesis and evaluation of analogues of (Z)-1-(4-methoxyphenyl)-2-(3,4,5-trimethoxyphenyl)ethene as potential cytotoxic and antimitotic agents. J Med Chem. 35(12):2293-2306.
Danion et al., 1972, Tetrahedron, v. 28(15), pp. 4223-4229 (including English language abstract).
Fischer et al., 1993, J. Organomet. Chem., v. 454(1-2), pp. 133-149 (including English language abstract).
Groundwater et al., 1992, Electrocyclic Aromatic Substitution by Nitrile Ylides to Give 3H-2-Benzazepines: Substituent Effects and Mechanism. Tetrahedron, 48(37):7951-7964.
Gwaltney et al., 2001, Novel sulfonate analogues of combretastatin A-4: potent antimitotic agents. Bioorg Med Chem Lett. 11(7):871-874.
Hamel E. 1996, Antimitotic natural products and their interactions with tubulin. Med Res Rev. 16(2):207-231.
Hastie SB. 1991, Interactions of colchicine with tubulin. Pharmacol Ther. 51(3):377-401.
Ilg et al., 2001, Organometallics, v. 20(17), pp. 3782-3794.
Laubender et al., 1998, Angewandte Chemie, Int. Ed., v. 37(1/2), pp. 150-152.
Laubender et al., 1999, Chemistry-A European Journal, v. 5(10), pp. 2937-2946.
Li et al., 2002, Synthesis and biological evaluation of 2-indolyloxazolines as a new class of tubulin polymerization inhibitors. Discovery of A-289099 as an orally active antitumor agent. Bioorg Med Chem Lett. 12(3):465-469.
Liou et al., 2002, Synthesis and structure-activity relationship of 2-aminobenzophenone derivatives as antimitotic agents. J Med Chem. 45(12):2556-2562.
Luduena et al., 1991, Tubulin sulfhydryl groups as probes and targets for antimitotic and antimicrotubule agents. Pharmacol Ther. 49(1-2):133-152.

(Continued)

*Primary Examiner*—Rei-tsang Shiao
*Assistant Examiner*—Joseph R Kosack
(74) *Attorney, Agent, or Firm*—Jones Day

(57) ABSTRACT

The present invention relates to Diphenylethylene Compounds and compositions comprising a Diphenylethylene Compound. The present invention also relates to methods for preventing or treating various diseases and disorders by administering to a subject in need thereof one or more Diphenylethylene Compounds. In particular, the invention relates to methods for preventing or treating cancer or an inflammatory disorder by administering to a subject in need thereof one or more Diphenylethylene Compounds. The present invention further relates to articles of manufacture and kits comprising one or more Diphenylethylene Compounds.

3 Claims, No Drawings

OTHER PUBLICATIONS

McGown and Fox, 1990, Differential cytotoxicity of combretastatins A1 and A4 in two daunorubicin-resistant P388 cell lines. Cancer Chemother Pharmacol. 26(1):79-81.

Medarde et al., 1999, Synthesis and pharmacological activity of diarylindole derivatives. Cytotoxic agents based on combretastatins. Bioorg Med Chem Lett. 9(16):2303-2308.

Mu et al., 2001, Design, synthesis, and biological evaluation of a series of lavendustin A analogues that inhibit EGFR and Syk tyrosine kinases, as well as tubulin polymerization. J Med Chem. 44(3):441-452.

Nam et al., 2002, Synthesis and anti-tumor activity of novel combretastatins: combretocyclopentenones and related analogues. Bioorg Med Chem Lett. 12(15):1955-1958.

Ohsumi et al., 1998, Novel combretastatin analogues effective against murine solid tumors: design and structure-activity relationships. J Med Chem. 41(16):3022-3032.

Ohsumi et al., 1998, Syntheses and antitumor activity of cis-restricted combretastatins: 5-membered heterocyclic analogues. Bioorg Med Chem Lett. 8(22):3153-3158.

Pac et al., 1984, J. Org. Chem., v. 49(1), pp. 26-34 (1984).

Pettit et al., 1989, Isolation and structure of the strong cell growth and tubulin inhibitor combretastatin A-4. Experientia. 45(2):209-211.

Pettit et al., 1998, Antineoplastic agents. 379. Synthesis of phenstatin phosphate. J Med Chem. 41(10):1688-1695.

Pettit et al., 1999, Antineoplastic agents. 410. Asymmetric hydroxylation of trans-combretastatin A-4. J Med Chem. 42(8):1459-1465.

Pettit et al., 2000, Antineoplastic agents. 443. Synthesis of the cancer cell growth inhibitor hydroxyphenstatin and its sodium diphosphate prodrug. J Med Chem. 43(14):2731-2737.

Pettit et al., 2002, Antineoplastic agents. 465. Structural modification of resveratrol: sodium resverastatin phosphate. J Med Chem. 45(12):2534-2542.

Profitt et al., 1975, A Reagent for the $\alpha$, $\beta$ Reduction of Conjugated Nitriles. J. Org. Chem., 40(1), pp. 127-128.

Shirai et al., 1998, Asymmetric synthesis of antimitotic combretadioxolane with potent antitumor activity against multi-drug resistant cells. Bioorg Med Chem Lett. 8(15):1997-2000.

Thorpe PE, 2004, Vascular targeting agents as cancer therapeutics. Clin Cancer Res. 10(2):415-427.

Update on Spindle Poisons—Part II: Vinca Alkaloids and Analogs/Formulations. Future Oncology, vol. 6 (12):1457-1484 (2002).

Update on Spindle Poisons—Part III: Novel Agents in Development. Future Oncology, 7 (1/2):1485-1528 (2002).

Verdier-Pinard et al., 1998, Structure-activity analysis of the interaction of curacin A, the potent colchicine site antimitotic agent, with tubulin and effects of analogs on the growth of MCF-7 breast cancer cells. Mol Pharmacol. 53(1):62-76.

Wang et al., 2002, Potent, orally active heterocycle-based combretastatin A-4 analogues: synthesis, structure-activity relationship, pharmacokinetics, and in vivo antitumor activity evaluation. J Med Chem. 45(8):1697-1711.

Yoon et al., 2002, CP248, a derivative of exisulind, causes growth inhibition, mitotic arrest, and abnormalities in microtubule polymerization in glioma cells. Mol Cancer Ther. 1(6):393-404.

DIPHENYLETHYLENE COMPOUNDS AND USES THEREOF

This application is a continuation-in-part of U.S. non-provisional application Ser. No. 10/794,931, filed Mar. 5, 2004 now U.S. Pat. No. 7,312,241, which claims the benefit of U.S. provisional application No. 60/452,460, filed Mar. 5, 2003, the contents of each are incorporated by reference herein in their entirety.

1 FIELD OF THE INVENTION

The present invention relates to Diphenylethylene Compounds and compositions comprising a Diphenylethylene Compound. The present invention also relates to methods for preventing or treating various diseases and disorders by administering to a subject in need thereof one or more Diphenylethylene Compounds. In particular, the invention relates to methods for preventing or treating cancer or an inflammatory disorder by administering to a subject in need thereof one or more Diphenylethylene Compounds. The present invention further relates to certain compounds wherein one of the phenyl groups is replaced with a heterocycle.

2 BACKGROUND OF THE INVENTION

2.1 Microtubules

The cytoskeleton of eukaryotic cells consists of an extensive network of microfilaments, microtubules and intermediate filaments. Microtubules play an important role in mitosis. α-, β-, and γ-tubulin subunits are eukaryotic cytoskeleton proteins that are responsible for the formation of microtubules. Microtubules are hollow cylinders which are comprised of α,β-tubulin heterodimers, joined end-to-end along the microtubule axis. γ-tubulin is involved in microtubule organization. Once formed, the microtubules exist in an equilibrium, with tubulin dimers constantly being added to one end of the microtubule and removed from the opposite end. This equilibrium allows for control of the length of the microtubule and such control is essential for the microtubules to carry out their numerous functions in cells.

During cell division microtubules are responsible for transporting the set of daughter chromosomes to each individual daughter cell. In particular, during prophase, the DNA in the nucleus is replicated and the two sets of genetic material are organized into the individual sets of daughter chromosomes. Toward the end of prophase, microtubules grow from the centrosomes at either end of the dividing parent cell and toward the two identical sets of chromosomes. This growing bundle of microtubules forms a structure known as the mitotic spindle. During prometaphase, the microtubules attach themselves to the chromosomes, and upon entry into anaphase, the microtubules destabilize and shorten, drawing the daughter chromosomes apart to their respective daughter cells at opposite ends of the dividing cell. Thus, microtubules are intimately involved with the cell division process.

2.2 Cancer and Neoplastic Disease

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, can be contraindicated due to the health of the patient or can be unacceptable to the patient. Additionally, surgery might not completely remove the neoplastic tissue. Radiation therapy is effective only when the irradiated neoplastic tissue exhibits a higher sensitivity to radiation than normal tissue, and radiation therapy often elicits serious side effects. (Id.)

With respect to chemotherapy, there are a variety of chemotherapeutic agents available for treatment of neoplastic disease. Specific examples of chemotherapeutic agents include drugs that target tubulin (e.g., inhibit tubulin polymerization or stability or tubulin stability) or microtubules such as colchicine (an alkaloid extracted from the meadow suffron), the vinca alkaloids (e.g., vincristine, vinblastine and vinorlbine) and the taxanes (e.g., paclitaxel (Taxol®) and docetaxel (Taxotere®)). Colchicine exerts its cytotoxic effect by binding to the tubulin heterodimer at a single high-affinity binding site known as the colchicine site. This binding induces an alteration in the structure of the dimer and hinders the assembly of the dimers into microtubules. The colchicine binding site displays affinity for a diverse group of molecular structures, including, but not limited to, the podophyllotoxins, steganacin, the chalcones, nocodazole and TN-16. Exposure of rapidly dividing cells such as cancer cells to Colchicine causes the disappearance of the mitotic spindle and blocks the cells in M phase of the cell cyle and eventually kills the cells. The vinca alkaloids bind to a site on β-tubulin known as the vinca alkaloid binding site, resulting in a destabilization of the tubulin dimers. The poisoned dimers can then be incorporated into the microtubule polymer and prevent further growth of the microtubule. The taxanes bind directly to tubulin subunits of intact microtubules, stabilize the microtubules, and inhibit depolymerization or stability. When the dividing cell enters anaphase, the stabilized microtubules are prevented from contracting and are not able to draw each set of daughter chromosomes to their respective daughter cells. Thus, cell division cannot take place and the cells are blocked in M phase of the cell cycle and eventually apoptosis results.

Despite the availability of a variety of chemotherapeutic agents, traditional chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy can cause significant, and often dangerous, side effects, including severe nausea, bone marrow depression, immunosuppression, etc. Additionally, many tumor cells are resistant or develop resistance to chemotherapeutic agents through multidrug resistance. Therefore, there is a significant need in the art for novel compounds, compositions, and methods that are useful for treating cancer or neoplastic disease with minimal or no side effects. Further, there is a need for cancer treatments that provide cancer-cell-specific therapies with increased specificity and decreased toxicity.

2.3 Inflammatory Disorders

Inflammation plays a fundamental role in host defenses and the progression of immune-mediated diseases. The inflammatory response is initiated in response to injury (e.g., trauma, ischemia, and foreign particles) and infection (e.g., bacterial or viral infection) by a complex cascade of events, including chemical mediators (e.g., cytokines and prostaglandins) and inflammatory cells (e.g., leukocytes). The inflammatory response is characterized by increased blood flow, increased capillary permeability, and the influx of phagocytic cells. These events result in swelling, redness, warmth (altered heat patterns), and pus formation at the site of injury or infection.

Cytokines and prostaglandins control the inflammatory response, and are released in an ordered and self-limiting cascade into the blood or affected tissues. This release of cytokines and prostaglandins increases the blood flow to the area of injury or infection, and may result in redness and warmth. Some of these chemicals cause a leak of fluid into the tissues, resulting in swelling. This protective process may stimulate nerves and cause pain. These changes, when occurring for a limited period in the relevant area, work to the benefit of the body.

A delicate well-balanced interplay between the humoral and cellular immune elements in the inflammatory response enables the elimination of harmful agents and the initiation of the repair of damaged tissue. When this delicately balanced interplay is disrupted, the inflammatory response may result in considerable damage to normal tissue and may be more harmful than the original insult that initiated the reaction. In these cases of uncontrolled inflammatory responses, clinical intervention is needed to prevent tissue damage and organ dysfunction. Diseases such as rheumatoid arthritis, osteoarthritis, Crohn's disease, asthma, allergies or inflammatory bowel disease, are characterized by chronic inflammation.

Current treatments for inflammatory disorders involve symptomatic medications and immunosuppressive agents to control symptoms. For example, nonsteroidal anti-inflammatory drugs (NSAIDs) such as aspirin, ibuprofen, fenoprofen, naproxen, tolmetin, sulindac, meclofenamate sodium, piroxicam, flurbiprofen, diclofenac; oxaprozin, nabumetone, etodolac, and ketoprofen have analgesic and anti-inflammatory effects. However, NSAIDs are believed not to be capable of altering progression of the disease. (Tierney et al. (eds), Current Medical Diagnosis & Treatment, 37 ed., Appleton & Lange (1998), p793). Moreover, NSAIDs frequently cause gastrointestinal side effects, affect the lower intestinal tract causing perforation or aggravating inflammatory bowel disease, produce renal toxicity and prolong bleeding time. Corticosteroids are another class of drugs that are commonly used to control inflammatory symptoms. Corticosteroids, like NSAIDs, do not alter the natural progression of the disease, and thus, clinical manifestations of active disease commonly reappear when the drug is discontinued. The serious problem of untoward reactions resulting from prolonged corticosteroid therapy (e.g., osteoporosis, increased risk of infection, increased appetite, hypertension, edema, peptic ulcers, psychoses) greatly limits its long-term use.

Low doses of immunosuppressive agents such as cytotoxic agents are also commonly used to in treatment of inflammatory disorders. For example, methotrexate, an antagonist of folic acid, is often used in treatment of psoriasis, rheumatoid arthritis and other inflammatory diseases. Methotrexate, like other cytotoxic agents, frequently causes stomatitis, erythema, slopecia, nausea, vomiting, diarrhea, and damage to major organs such kidney and liver. The long-term usage of immunosuppressive agents usually leaves the patient defenseless to infections.

New treatments for inflammatory disorders are constantly being sought. In particular, any new treatment that reduces the dosage and/or frequency of administration of agents currently being used, or is capable of making a currently used treatment more effective is constantly being sought.

2.4 Central Nervous System Disorders

Central nervous system disorders affect a wide range of the population with differing severity. Generally, one major feature of this class of disorders includes the significant impairment of cognition or memory that represents a marked deterioration from a previous level of functioning. Dementia, for example, is characterized by several cognitive impairments including significant memory deficit and can stand alone or be an underlying characteristic feature of a variety of diseases, including Alzheimer disease, Parkinson disease, Huntington disease, and Multiple Sclerosis to name but a few. Other central nervous system disorders include delerium, or disturbances in consciousness that occur over a short period of time, and amnestic disorder, or discreet memory impairments that occur in the absence of other central nervous system impairments.

3 SUMMARY OF THE INVENTION

The present invention provides novel compounds, novel pharmaceutical compositions and uses of those compounds or pharmaceutical compositions in the prevention, treatment or management of various disorders. The present invention also provides new uses for previously disclosed compounds including those disclosed in PCT International Publication No. WO 98/06692, published Feb. 19, 1998 (see, e.g., page 6, line 4 to page 7, line 29) and U.S. Pat. No. 5,929,117, issued Jul. 22, 1999 (see, e.g., column 4, line 45 to column 5, line 38), each of which is incorporated by reference herein in its entirety. In particular, the invention provides methods for preventing, managing or treating cancer including cancer refractory or non-responsive to conventional or currently available cancer therapy utilizing certain immunotherapeutic compounds disclosed in PCT International Publication No. WO 98/06692 and U.S. Pat. No. 5,929,117.

The present invention provides compounds having formulas I-XI and those of Table 1 forth below.

In one embodiment, the invention provides compounds having the formula:

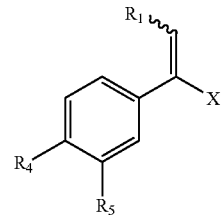

and pharmaceutically acceptable salts, solvates or hydrates thereof, wherein $R_1$, $R_4$, $R_5$ and X are as described herein.

In one embodiment, the invention provides compounds having the formula:

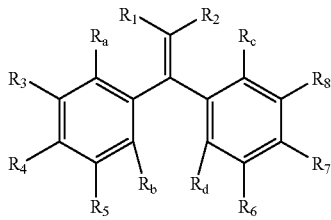

II and pharmaceutically acceptable salts, solvates or hydrates thereof, wherein $R_1$, $R_2$, $R_3$, $R_4$, $R_5$, $R_6$, $R_7$, $R_8$, $R_a$, $R_b$, $R_c$ and $R_d$ are as described herein.

In one embodiment, the invention provides compounds having the formula:

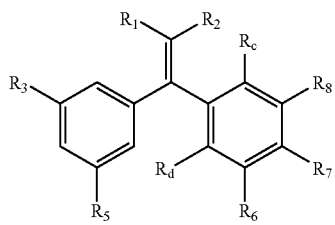

III and pharmaceutically acceptable salts, solvates or hydrates thereof, wherein $R_1$, $R_2$, $R_3$, $R_5$, $R_6$, $R_7$, $R_8$, $R_c$ and $R_d$ are as described herein.

In one embodiment, the invention provides compounds having the formula:

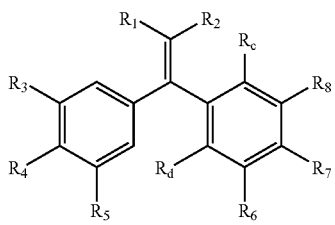

IV and pharmaceutically acceptable salts, solvates or hydrates thereof, wherein $R_1$, $R_2$, $R_3$, $R_4$, $R_5$, $R_6$, $R_7$, $R_8$, $R_c$ and $R_d$ are as described herein, In one embodiment, the invention provides compounds having the formula:

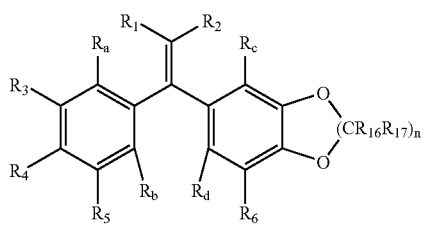

V and pharmaceutically acceptable salts, solvates or hydrates thereof, wherein $R_1$, $R_2$, $R_3$, $R_4$, $R_5$, $R_6$, $R_{16}$, $R_{17}$, $R_a$, $R_b$, $R_c$, $R_d$ and n are as described herein.

In one embodiment, the invention provides compounds having the formula:

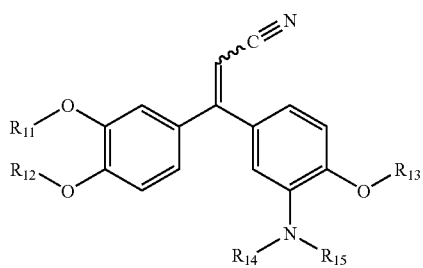

VI and pharmaceutically acceptable salts, solvates or hydrates thereof, wherein $R_{11}$, $R_{12}$, $R_{13}$, $R_{14}$ and $R_{15}$ are as described herein.

In one embodiment, the invention provides compounds having the formula:

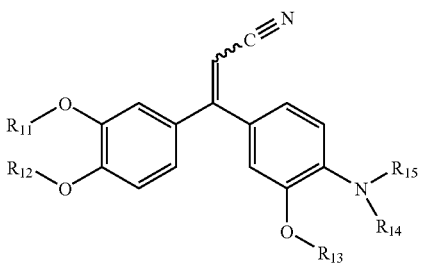

VII and pharmaceutically acceptable salts, solvates or hydrates thereof, wherein $R_{11}$, $R_{12}$, $R_{13}$, $R_{14}$ and $R_{15}$ are as described herein.

In one embodiment, the invention provides compounds having the formula:

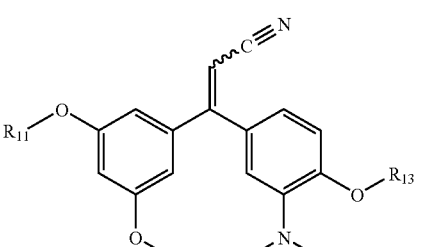

VIII and pharmaceutically acceptable salts, solvates or hydrates thereof, wherein $R_{11}$, $R_{12}$, $R_{13}$, $R_{14}$ and $R_{15}$ are as described herein.

In one embodiment, the invention provides compounds having the formula:

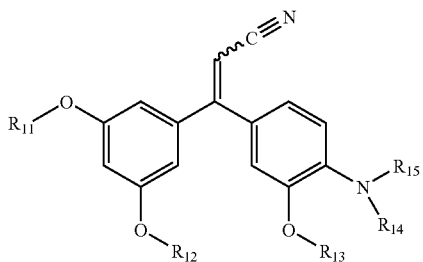

IX and pharmaceutically acceptable salts, solvates or hydrates thereof, wherein $R_{11}$, $R_{12}$, $R_{13}$, $R_{14}$ and $R_{15}$ are as described herein.

In one embodiment, the invention provides compounds having the formula:

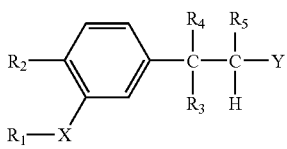

X and pharmaceutically acceptable salts, solvates or hydrates thereof, wherein Y, X, $R_1$, $R_2$, $R_4$ and $R_5$ are as described herein.

In one embodiment, the invention provides compounds having the formula:

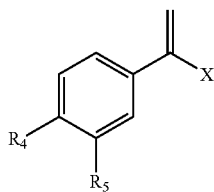

XI and pharmaceutically acceptable salts, solvates or hydrates thereof, wherein X, $R_4$ and $R_5$ are as described herein.

The present invention also provides pharmaceutical compositions comprising one or more compounds of the invention, or a pharmaceutically acceptable salt, solvate, or hydrate thereof; in particular the invention encompasses pharmaceutical compositions of one or more of the compounds of the invention.

The present invention provides pharmaceutical compositions comprising one or more compounds of the invention, or a pharmaceutically acceptable salt, solvate, or hydrate thereof, and one or more prophylactic or therapeutic agents, said prophylactic or therapeutic agents known to be useful, or having been or currently being used in the prevention, treatment or amelioration of a disease or disorder associated with or characterized by aberrant angiogenesis, a central nervous system disorder, a proliferative disorder, an inflammatory disorder, a disease or disorder prevented, managed, treated or ameliorated by the inhibition of phosphodiesterase IV ("PDE4") activity and/or the inhibition of tubulin polymerization or stability, or one or more symptoms thereof. In another embodiment, the pharmaceutical compositions of the invention can comprise one or more compounds of the invention, or a pharmaceutically acceptable salt, solvate, or hydrate thereof, and one or more vascular targeting agents.

The present invention also provides a method for inhibiting or reducing tubulin polymerization or stability, said method comprising contacting a cell with an effective amount of a compound of the invention.

The present invention also provides a method for inhibiting or reducing tubulin polymerization or stability and PDE4 activity, said method comprising contacting a cell with an effective amount of a compound of the invention.

The present invention further provides a method for inhibiting PDE4 activity, said method comprising contacting a cell with an effective amount of a compound of the invention.

The present invention further provides a method for targeting, blocking or destroying the function of tumor vasculature, said method comprising contacting a tumor with an effective amount of a compound of the invention.

The present invention further provides a method for targeting, blocking or destroying the endothelium of tumor vessels, said method comprising contacting a tumor with an effective amount of a compound of the invention.

The present invention further provides a method for occluding pre-existing blood vessels of a tumor, said method comprising contacting a tumor with an effective amount of a compound of the invention.

The present invention further provides a method for killing a tumor cell, said method comprising contacting a tumor cell with an effective amount of a compound of the invention.

The present invention further provides a method for causing acute vascular collapse in a tumor cell, said method comprising contacting a tumor cell with an effective amount of a compound of the invention.

The present invention further provides a method for blocking angiogenesis through vascular inhibition, said method comprising contacting a cell with an effective amount of a compound of the invention.

The present invention provides a method for inhibiting angiogenesis, said method comprising administering to a subject in need thereof an effective amount of a compound of the invention.

In another embodiment, the present invention provides a method of preventing, treating, managing, or ameliorating a proliferative disorder or an inflammatory disorder or one or more symptoms thereof, said method comprising administering a prophylactically or therapeutically effective amount of a compound of the invention, alone or in combination with a prophylactically or therapeutically effective amount of one or more therapies, other than a compound the invention, used or known to be effective in preventing, treating, managing or ameliorating a proliferative disorder or an inflammatory disorder or one or more symptoms thereof.

In another embodiment, the present invention provides a method of preventing, treating, managing, or ameliorating a central nervous system disorder or one or more symptoms thereof, said method comprising administering a prophylactically or therapeutically effective amount of a compound of the invention, alone or in combination with a prophylactically or therapeutically effective amount of one or more therapies, other than a compound the invention, used or known to be effective in preventing, treating, managing or ameliorating a central nervous system disorder or one or more symptoms thereof.

In a specific embodiment, the present invention provides a method of preventing, treating, managing, or ameliorating cancer resistant to a tubulin binding agent (e.g., Colchicine, Taxol or Vinca Alkaloids) or one or more symptoms thereof, said method comprising administering a prophylactically or therapeutically effective amount of compound of the invention, alone or in combination with a prophylactically or therapeutically effective amount of one or more therapies (e.g., Colchicine, Taxol or Vinca Alkaloids), other than a compound the invention, used or known to be effective in preventing, treating, managing or ameliorating a proliferative disorder or an inflammatory disorder or one or more symptoms thereof.

3.1 Terminology and Abbreviations

As used herein, the term "alkoxy" refers to a compound having the formula —O-alkyl, —O-lower alkyl, —O-cycloalkyl, —O-lower alkyl-cycloalkyl, —O-benzyl, —O-lower alkyl-benzyl, wherein alkyl, lower alkyl and cycloalkyl are as defined below. Representative —O-lower alkyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4-dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl. Representative —O-cycloalkyl groups include, but are not limited to, —O-cyclopropyl, —O-cyclobutyl, —O-cyclopentyl, —O-cyclohexyl, —O-cycloheptyl, —O-cyclooctyl, —O-cyclononyl and —O-cyclodecyl. Representative —O-lower alkyl-cycloalkyl groups include, but are not limited to, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl and —O—$(CH_2)_2$-cyclodecyl.

As used herein, the term "alkyl" refers to a straight chain or branched, saturated or unsaturated hydrocarbon having from 1 to 20 carbon atoms. Representative straight-chain alkyl groups include, but are not limited to, -methyl, -ethyl, -n-propyl, -n-butyl, -n-pentyl, -n-hexyl, -n-heptyl, -n-octyl, -n-nonyl, -n-decyl, -n-undecyl, -n-dodecyl, -n-tridecyl, -n-tetradecyl, -n-pentadecyl and the like; while branched alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl; unsaturated alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1-butynyl, -1-hexynyl, -2-hexynyl, -1-heptynyl, -2-heptynyl, -1-octynyl, -2-octynyl, -1-nonynyl, -2-nonynyl, -1-decynyl, -2-decynyl.

As used herein, the term "alkenyl" means a straight chain or branched non-cyclic hydrocarbon having from 2 to 10 carbon atoms and including at least one carbon-carbon double bond. Representative straight chain and branched alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

As used herein, the term "alkynyl" means a straight chain or branched non-cyclic hydrocarbon having from 2 to 10 carbon atoms and including at lease one carbon-carbon triple bond. Representative straight chain and branched —($C_2$-$C_{10}$) alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. An alkynyl group can be unsubstituted or substituted.

As used herein, the terms "antibody" and "antibodies" refer to monoclonal antibodies, multispecific antibodies, human antibodies, humanized antibodies, camelised antibodies, chimeric antibodies, single domain antibodies, single chain Fvs (scFv), single chain antibodies, Fab fragments, F(ab') fragments, disulfide-linked Fvs (sdFv), and anti-idiotopic (anti-Id) antibodies (including, e.g., anti-Id antibodies to antibodies of the invention), and epitope-binding fragments of any of the above. In particular, antibodies include immunoglobulin molecules, e.g., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "aryl" refers to a carbocyclic aromatic group. Examples of aryl groups include, but are not limited to, phenyl, benzyl, naphthyl and anthracenyl.

As used herein, the term "cycloalkyl" refers to a 3-, 4-, 5-, 6-, 7- or 8-membered saturated or unsaturated non-aromatic carbocyclic ring. Representative $C_3$-$C_8$ cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. The term "cycloalkyl" also includes -lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl and —$CH_2$-cyclooctyl.

As used herein, the terms "compound" and "compound of the invention," are used interchangeably to refer to any compound, including pharmaceutically acceptable salts, hydrates or solvates thereof, disclosed herein specifically or generically. In one embodiment, the compounds of the invention are compounds of formulas I-IX and those of Table 1, and pharmaceutically acceptable salts, hydrates or solvates thereof. In another embodiment, the compounds of the invention also include those set forth in PCT International Publication No. WO 98/06692, published Feb. 19, 1998 (see, e.g., formula I at page 6, line 6 to page 7, line 11 and Examples 1-30) and U.S. Pat. No. 5,929,117, issued Jul. 22, 1999 (see, e.g., formula I at column 4, line 45 to column 5, line 37 and Examples 1-34), each of which is incorporated by reference herein in its entirety. In another embodiment, the compounds of the invention also include componds of formula X, and pharmaceutically acceptable salts, solvates and hydrates thereof.

As used herein, the terms "disorder" and "disease" are used interchangeably to refer to a condition in a subject. Certain conditions may be characterized as more than one disorder. For example, certain conditions may be characterized as both non-cancerous proliferative disorders and inflammatory disorders. In one embodiment, a proliferative disorder is cancer.

As used herein, the term "effective amount" refers to the amount of a compound of the invention which is sufficient to reduce or ameliorate the severity or duration of a disorder (e.g., a disorder characterized by aberrant angiogenesis, a central nervous system disorder, a proliferative disorder or a disorder characterized by inflammation (i.e., an inflammatory disorder)) or one or more symptoms thereof, prevent the advancement of a disorder (e.g., a disorder characterized by aberrant angiogenesis, a proliferative disorder or an inflammatory disorder), cause regression of a disorder (e.g., a proliferative disorder or an inflammatory disorder), prevent the recurrence, development, or onset of one or more symptoms associated with a disorder (e.g., a disorder characterized by aberrant angiogenesis, a proliferative disorder or an inflammatory disorder), or enhance or improve the prophylactic or therapeutic effect(s) of another therapy. In a specific embodiment, with respect to the treatment of cancer, an effective amount refers to the amount of a compound of the invention that inhibits or reduces the proliferation of cancerous cells, inhibits or reduces the spread of tumor cells (metastasis), inhibits or reduces the onset, development or progression of one or more symptoms associated with cancer, reduces the size of a tumor or kills a tumor cell. In one embodiment, a therapeutically effective amount of a compound of the invention is that amount which attacks the tumor vascular system and shuts off the supply of blood and/or oxygen to the tumor. Preferably, a therapeutically effective of a compound of the invention inhibits or reduces the proliferation of cancerous cells or the size of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline ("PBS"). In another embodiment, with respect to inflammation, an effective amount refers to the amount of a compound of the invention that reduces the inflammation of a joint, organ or tissue. Preferably, an effective of a compound of the invention reduces the inflammation of a joint, organ or tissue by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline. In another embodiment, with respect to the treatment of psoriasis, an effective amount preferably refers to the amount of a compound of the invention that reduces a human's Psoriasis Area and Severity Index (PASI) score by at least 20%, at least 35%, at least 30%, at least 40%, at least 45%, at least 50%, at least 55%, at least 60%, at least 65%, at least 70%, at least 75%, at least 80%, or at least 85%. In an alternative embodiment, with respect to the treatment of psoriasis, an effective amount preferably refers to the amount of a compound of the invention that improves a human's global assessment score by at least 25%, at least 35%, at least 30%, at least 40%, at least 45%, at least 50%, at least 55%, at least 60%, at least 65%, at least 70%, at least 75%, at least 80%, at least 85%, at least 90%, or at least 95%. Examples of therapeutically effective amounts of compounds of the invention are provided in Section 4.4.5 infra.

As used herein, the term "halogen" means —F, —Cl, —Br or —I.

As used herein, the term "heterocycle" refers to an aromatic or non-aromatic cycloalkyl in which one to four of the ring carbon atoms are independently replaced with a heteroatom from the group consisting of O, S and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl and tetrazolyl. Heterocycles can be substituted or unsubstituted. Heterocycles can also be bonded at any ring atom (i.e., at any carbon atom or heteroatom of the heterocyclic ring).

As used herein, the term "in combination" refers to the use of more than one therapies (e.g., one or more prophylactic and/or therapeutic agents). The use of the term "in combination" does not restrict the order in which therapies (e.g., prophylactic and/or therapeutic agents) are administered to a subject with a disorder (e.g., a disorder characterized by aberrant angiogenesis, a proliferative disorder or an inflammatory disorder). A first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-inflammatory agent or anti-angiogenic agent) to a subject with a disorder (e.g., a disorder characterized by aberrant angiogenesis, a proliferative disorder or an inflammatory disorder).

As used herein, the term "isolated" in the context of a compound such as, e.g., a compound of the invention, refers to a compound that is substantially free of chemical precursors, other chemicals when chemically synthesized or other isomers. In a specific embodiment, the compound is 60%, 65%, 75%, 80%, 85%, 90%, 95%, or 99% free of other, different compounds (e.g., other isomers). Preferably, compounds of the invention are isolated.

As used herein, the term "lower alkyl" refers to a straight chain or branched, saturated or unsaturated hydrocarbon having from 1 to 8 carbon atoms. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl.

As used herein, the term "lower hydroxyalkyl" refers to a lower alkyl group as described herein substituted with one or more hydroxy groups. Representative lower hydroxyalkyl groups include, but are not limited to, —CH$_2$OH, —(CH$_2$)$_2$OH, —(CH$_2$)$_3$OH, —(CH$_2$)$_4$OH, —(CH$_2$)$_5$OH, —CH(OH)CH$_3$, —CH(OH)CH$_2$CH$_3$, —CH(OH)(CH$_2$)$_2$CH$_3$, —CH$_2$CH(OH)CH$_3$, —CH$_2$CH(OH)CH$_2$CH$_3$, and the like.

When the groups described herein are said to be "substituted or unsubstituted," when substituted, they may be substituted with any desired substituent or substituents that do not adversely affect the desired activity of the compound. Examples of preferred substituents are those found in the exemplary compounds and embodiments disclosed herein, as well as halogen (e.g., chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; acetyl; acetoxy; carbamoyl; oxygen (=O); haloalkyl (e.g., trifluoromethyl); susbtituted aminoacyl and aminoalkyl; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl; aryl; aryl-lower alkyl; CO$_2$CH$_3$; CONH$_2$; OCH$_2$CONH$_2$; NH$_2$; SO$_2$NH$_2$; OCHF$_2$; CF$_3$; OCF$_3$; and such moieties may also be optionally substituted by a fused-ring structure or bridge, for example —OCH$_2$O— or —O-lower alkyl-O—. These substituents may optionally be further substituted with a substituent selected from such groups. In one embodiment, when a lower alkyl group (e.g., methylene) is substituted, it is substituted with the side chain of a naturally occurring amino acid.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the compounds of the invention include E and Z isomers, or a mixture thereof, and cis and trans isomers or a mixture thereof. In certain embodiments, the compounds of the invention are isolated as either the E or Z isomer. In other embodiments, the compounds of the invention are a mixture of the E and Z isomers.

As used herein and unless otherwise indicated, the term "stereomerically pure" means a composition that comprises one stereoisomer of a compound and is substantially free of other stereoisomers of that compound or one geometric isomer (e.g., about a double bond) that is substantially free of the other geometric isomer. For example, a stereomerically pure compound of the invention having one chiral center, or a composition thereof, will be substantially free of the opposite enantiomer of the compound. A stereomerically pure compound of the invention having two chiral centers, or a composition thereof, will be substantially free of other diastereomers of the compound. A stereomerically pure compound of the invention having a double bond capable of E/Z isomerism, or a composition thereof, will be substantially free of one of the E/Z isomers. A typical stereomerically pure compound comprises greater than about 80% by weight of one stereoisomer or E/Z isomer of the compound and less than about 20% by weight of other stereoisomers or E/Z isomer of the compound, more preferably greater than about 90% by weight of one stereoisomer or E/Z isomer of the compound and less than about 10% by weight of the other stereoisomers or E/Z isomer of the compound, even more preferably greater than about 95% by weight of one stereoisomer or E/Z isomer of the compound and less than about 5% by weight of the other stereoisomers or E/Z isomer of the compound, and most preferably greater than about 97% by weight of one stereoisomer or E/Z isomer of the compound and less than about 3% by weight of the other stereoisomers or E/Z isomer of the compound. As used herein and unless otherwise indicated, the term "stereomerically enriched" means a compound of the invention, or a composition thereof, that comprises greater than about 60% by weight of one stereoisomer or E/Z isomer of a compound of the invention, preferably greater than about 70% by weight, more preferably greater than about 80% by weight of one stereoisomer or E/Z isomer of a compound of the invention. As used herein and unless otherwise indicated, the term "enantiomerically pure" means a stereomerically pure compound of the invention having one chiral center, or a composition thereof. Similarly, the term "stereomerically enriched" means a stereomerically enriched compound of the invention having one chiral center, or a composition thereof.

It should be noted that if the stereochemistry of a structure or a portion of a structure is not indicated with, for example, bold or dashed lines, the structure or portion of the structure is to be interpreted as encompassing all stereoisomers of it.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease or a symptom thereof so as to prevent the progression or worsening of the disease or symptom thereof.

As used herein, the terms "non-responsive" and "refractory" describe patients treated with a currently available therapy (e.g., a prophylactic or therapeutic agent) for a disorder (e.g., a disorder characterized by aberrant angiogenesis, a proliferative disorder or an inflammatory disorder), which is not clinically adequate to relieve one or more symptoms associated with such disorder. Typically, such patients suffer from severe, persistently active disease and require additional therapy to ameliorate the symptoms associated with their disorder (e.g., a disorder characterized by aberrant angiogenesis, a proliferative disorder or an inflammatory disorder).

As used herein, the phrase "pharmaceutically acceptable salt" refers to pharmaceutically acceptable organic or inorganic salts of a compound of the invention. Preferred salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate))salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion.

As used herein, the term "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine.

As used herein, the term "pharmaceutically acceptable hydrate" refers to a compound of the invention, or a salt thereof, that further includes a stoichiometric or non-stoichiometric amount of water bound by non-covalent intermolecular forces.

As used herein, the terms "prevent," "preventing" and "prevention" refer to the prevention of the recurrence, onset, or development of a disorder or one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the phrase "prophylactically effective amount" refers to the amount of a therapy (e.g., prophylactic agent) which is sufficient to result in the prevention of the development, recurrence or onset of a disorder or one or more symptoms associated with a disorder (e.g., a disorder characterized by aberrant angiogenesis, a proliferative disorder or an inflammatory disorder), or to enhance or improve the prophylactic effect(s) of another therapy (e.g., another prophylactic agent). Examples of prophylactically effective amounts of compounds are provided in Section 4.4.5 infra.

As used herein, the phrase "side effects" encompasses unwanted and adverse effects of a therapy (e.g., a prophylactic or therapeutic agent). Side effects are always unwanted, but unwanted side effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a monkey such as a cynomolgous monkey, a chimpanzee and a human), and more preferably a human. In one embodiment, the subject is refractory or non-responsive to current treatments for a disorder (e.g., a disorder characterized by aberrant angiogenesis, a proliferative disorder or an inflammatory disorder). In another embodiment, the subject is a farm animal (e.g., a horse, a cow, or a pig) or a pet (e.g., a dog or a cat). In another embodiment, the subject is not an immunocompromised or immunosuppressed mammal, preferably a human (e.g., an HIV patient). In another embodiment, the subject is not a mammal, preferably a human, with a lymphocyte count under approximately 500 cells/mm$^3$. In a preferred embodiment, the subject is a human.

As used herein, the term "synergistic" refers to a combination of a compound of the invention and another therapy (e.g., a prophylactic or therapeutic agent) which has been or is currently being used to prevent, manage or treat a disorder (e.g., a disorder characterized by aberrant angiogenesis, a proliferative disorder, an inflammatory disorder or an autoimmune disorder), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder (e.g., a disorder characterized by aberrant angiogenesis, a proliferative disorder or an inflammatory disorder). The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder (e.g., a disorder characterized by aberrant angiogenesis, a proliferative disorder or an inflammatory disorder). In addition, a synergistic effect can result in improved efficacy of agents in the prevention, management or treatment of a disorder (e.g., a disorder characterized by aberrant angiogenesis, a proliferative disorder or an inflammatory disorder). A synergistic effect of a combination of therapies (e.g., a combination of prophylactic or therapeutic agents) may avoid or reduce adverse or unwanted side effects associated with the use of either therapy alone. In one embodiment, the term synergistic refers to the biological effect of a single compound of the invention on a tumor or tumor cell. Without being limited by theory, it is thought that because the compounds of the invention have both vascular targeting activity, which is particularly effective against central tumor cells, and anti-angioenic activity, which is particularly effective against peripheral tumor cells, the compounds of the invention are particularly useful in eradicating the majority of a tumor and, in one embodiment, completely eradicating a tumor. Accordingly, the compounds of the invention are particularly active against tumors due to the synergistic effects of their dual activity as both vascular targeting agents and anti-angiogenic agents.

As used herein, the terms "treat", "treatment" and "treating" refer to the reduction or amelioration of the progression, severity and/or duration of a disorder (e.g., a disorder characterized by aberrant angiogenesis, a proliferative disorder or an inflammatory disorder), or the amelioration of one or more symptoms thereof resulting from the administration of one or more therapies (e.g., one or more therapeutic agents such as a compound of the invention). In specific embodiments, such terms refer to the inhibition or reduction in the proliferation of cancerous cells, the inhibition or reduction in the spread of tumor cells (metastasis), the inhibition or reduction in the onset, development or progression of one or more symptoms associated with cancer, the reduction in the size of a tumor, or the improvement in a patient's ECOG or Karnofsky score. In other embodiments, such terms refer to a reduction in the swelling of one or more joints, organs or tissues, or a reduction in the pain associated with an inflammatory disorder. In yet other embodiments, such terms refer to a reduction a human's PASI score or an improvement in a human's global assessment score.

As used herein, the terms "tubulin binder," "tubulin binding agent" or variants thereof refer to any cytostatic or cytotoxic agent that can bind to tubulin, an α,β-tubulin dimer or to an intact microtubule in a cell. In one embodiment, the tubulin binder or tubulin binding agent inhibits tubulin polymerization or stability. In another embodiment, the tubulin binder or tubulin binding agent is a tubulin destabilizer.

As used herein, the terms "inhibit tubulin polymerization or stability" or "inhibition of tubulin polymerization or stability" refer to any alteration in the structure of tubulin dimers, any hinderance of the assembly of tubulin dimers into microtubules or any destabilization of tubulin dimers.

The following abbreviations are used herein and have the indicated definitions: Dess-Martin Periodinane is 1,1,1-triacetoxy-1,1-dihydro-1,2-benziodoxol-3-(1H)-one, DMF is N,N-dimethylformamide, DMSO is dimethylsulfoxide, EtOAc is ethyl acetate, HPLC is high performance liquid chromatography, HUVEC is human umbilical vein endothelial cell, KHMDS is potassium hexamethyldisilazide, LHMDS is lithium hexamethyldisilazide, PBMC is peripheral blood mononuclear cells, PCC is pyridinium chlorochromate, PDC is pyridinium dichromate, Ph is phenyl, THF is tetrahydrofuran, TLC is thin-layer chromatography and TPAP is tetra-n-propylammonium perruthenate.

4 DETAILED DESCRIPTION OF THE INVENTION

The present invention provides compounds and uses of said compounds. The present invention encompasses the use of compounds of the invention to inhibit tubulin polymerization and/or tubulin stability and/or inhibit mitosis. The present invention also encompasses the use of the compounds of the invention to inhibit angiogenesis. The present invention also encompasses the use of the compounds of the invention to inhibit the activity of PDE4. The present invention also encompasses the use of the compounds of the invention as vascular targeting agents.

The present invention encompasses treatment protocols that provide better prophylactic or therapeutic profiles than current single agent therapies or combination therapies for various disorders (e.g., disorders characterized by aberrant angiogenesis, proliferative disorders and inflammatory disorders), or one or more symptoms thereof. In particular, the invention provides prophylactic and therapeutic protocols for the prevention, treatment, management, or amelioration of proliferative disorders (e.g., cancer), macular degeneration or inflammatory diseases, or one or more symptoms thereof, comprising administering to a subject a prophylactically or therapeutically effective amount of one or more of the compounds of the invention alone or in combination with a prophylactically or therapeutically effective amount of at least one other prophylactic or therapeutic agent other than a compound of the invention.

4.1 The Compounds of the Invention

The present invention encompasses compounds having formulas I-XI and those set forth in Table 1, below.

In one embodiment, the invention provides methods for treating, preventing or managing a disease or disorder described herein comprising administering to a patient in need thereof a compound having the formula:

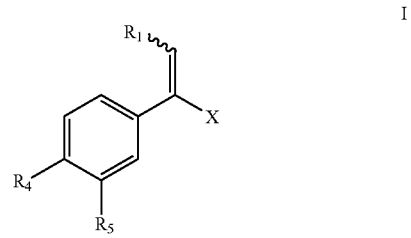

and pharmaceutically acceptable salts, solvates or hydrates thereof, wherein:

$R_1$ is halogen, —CN, lower alkyl, —COOH, —C(O)—N$(R_9)_2$, —C(O)-lower alkyl, —C(O)-benzyl, —C(O)O-lower alkyl, —C(O)O-benzyl;

$R_4$ is —H, —NO$_2$, cyano, substituted or unsubstituted lower alkyl, substituted or unsubstituted alkoxy, halogen, —OH, —C(O)($R_{10})_2$, —COOH, —NH$_2$, —OC(O) —N($R_{10})_2$;

$R_5$ is substituted or unsubstituted lower alkyl, substituted or unsubstituted alkoxy, or substituted or unsubstituted alkenyl;

X is substituted or unsubstituted phenyl, substituted or unsubstituted pyridine, substituted or unsubstituted pyrrolidine, substituted or unsubstituted imidizole, substituted or unsubstituted naphthalene, substituted or unsubstituted thiophene, or substituted or unsubstituted cycloalkyl;

each occurrence of $R_9$ is independently —H or substituted or unsubstituted lower alkyl; and each occurrence of $R_{10}$ is independently —H or substituted or unsubstituted lower alkyl.

In one embodiment, compounds of formula I are those wherein $R_4$ and $R_5$ are alkoxy (e.g., methoxy).

In another embodiment, compounds of formula I are those wherein X is substituted or unsubstituted phenyl.

In another embodiment, the compound of formula I is the E isomer.

In another embodiment, the compound of formula I is the Z isomer.

In one embodiment, the invention provides compounds having the formula:

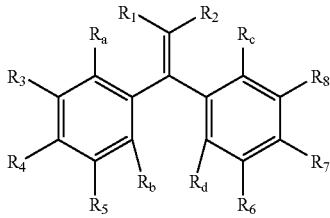

and pharmaceutically acceptable salts, solvates or hydrates thereof, wherein:

$R_1$ and $R_2$ are independently —H, —CN, halogen, substituted or unsubstituted lower alkyl, substituted or unsubstituted alkenyl, substituted or unsubstituted alkynyl, —NHC(O)O$R_9$, —COOH, —C(O)-lower alkyl, —C(O)O-lower alkyl, —C(O)—N($R_9$)$_2$, substituted or unsubstituted aryl, or substituted or unsubstituted heterocycle;

each occurrence of $R_a$, $R_b$, $R_c$ and $R_d$ is independently —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —C(O)N($R_{10}$)$_2$, —NHC(O)—$R_{10}$, —NHS(O)$_2$—$R_{10}$, —S(O)$_2$—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$;

$R_3$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$, or $R_3$ with either $R_a$ or with $R_4$, together form —O—C($R_{16}R_{17}$)—O— or —O—(C($R_{16}R_{17}$))$_2$—O—;

$R_4$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$;

$R_5$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$;

$R_6$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$;

$R_7$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$;

$R_8$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$, or $R_8$ with either $R_c$ or with $R_7$, together form —O—C($R_{16}R_{17}$)—O— or —O—(C($R_{16}R_{17}$))$_2$—O—;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate; and each occurrence of $R_{16}$ and $R_{17}$ is independently —H or halogen.

In a further embodiment, the invention provides compounds of formula II wherein: (1) at least one of $R_1$ and $R_2$ is halogen or —NHC(O)O$R_9$; (2) at least one of $R_3$, $R_4$, $R_5$, $R_6$, $R_7$ and $R_8$ is —OS(O)$_2$—N($R_{10}$)$_2$, —NHC(O)O—$R_{10}$ or substituted or unsubstituted heterocycle; or (3) $R_3$ with either $R_a$ or with $R_4$, together form —O—(C($R_{16}R_{17}$))$_3$—O— or $R_8$ with either $R_c$ or with $R_7$, together form —O—(C($R_{16}R_{17}$))$_3$—O—.

In a further embodiment, the invention provides compounds of formula II wherein $R_3$, $R_5$, $R_6$ and $R_8$ are other than —H. In particular, this embodiment encompasses 3,3'-bis-3,5-disubstituted phenyl compounds of formula II. This embodiment further encompasses compounds of formula II wherein:

$R_1$, $R_2$, $R_4$, $R_7$, $R_9$, $R_{10}$, $R_{16}$, $R_{17}$, $R_a$, $R_b$, $R_c$, and $R_d$ are as defined above for formula II;

$R_3$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$, or R$_3$ with R$_a$, together form —O—C(R$_{16}$R$_{17}$)—O— or —O—(C(R$_{16}$R$_{17}$))$_2$—O—;

$R_5$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_6$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$; and $R_8$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$, or R$_8$ with R$_c$, together form —O—C(R$_{16}$R$_{17}$)—O— or —O—(C(R$_{16}$R$_{17}$))$_2$—O—.

In a further embodiment, the invention provides compounds of formula II wherein if one of R$_3$ or R$_5$ is H, then the other is not lower alkyl or alkoxy and if one of R$_6$ or R$_8$ is H, then the other is not lower alkyl or alkoxy. In particular, this embodiment encompasses compounds of formula II wherein:

$R_1$, $R_2$, $R_3$, $R_4$, $R_5$, $R_6$, $R_7$, $R_8$, $R_9$, $R_{10}$, $R_{16}$, $R_{17}$, $R_a$, $R_b$, $R_c$ and $R_d$ are as described above for formula II, with the proviso that if one of R$_3$ or R$_5$ is H, then the other is not substituted or unsubstituted lower alkyl or substituted or unsubstituted alkoxy and if one of R$_6$ or R$_8$ is H, then the other is not substituted or unsubstituted lower alkyl or substituted or unsubstituted alkoxy.

In a further embodiment, the invention provides compounds of formula II wherein one of R$_4$ and R$_7$ are other than —H, substituted or unsubstituted lower alkyl, substituted or unsubstituted alkoxy, halogen, cyano, —$NO_2$ or —OH. In particular, this embodiment encompasses 3,3-bis-4-substituted phenyl compounds of formula II. This embodiment further encompasses compounds of formula II wherein:

$R_1$, $R_2$, $R_3$, $R_4$, $R_5$, $R_6$, $R_7$, $R_8$, $R_{10}$, $R_{16}$, $R_{17}$, $R_a$, $R_b$, $R_c$, and $R_d$ are as defined above for formula II;

wherein one of R$_4$ and R$_7$ is —OPO(OH)$_2$, —N(R$_9$)$_2$, —OC(O)—R$_{10}$—N(R$_{10}$)$_2$, —OC(O)—R$_{10}$—NH$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$), —NHC(O)—R$_{10}$—NH$_2$ or substituted or unsubstituted heterocycle; and $R_9$ is substituted or unsubstituted lower alkyl, or substituted or unsubstituted cycloalkyl.

In a further embodiment, the invention provides compounds of formula II wherein at least one of R$_3$, R$_4$, R$_5$, R$_6$, R$_7$ or R$_8$ is other than —H, substituted or unsubstituted lower alkyl, substituted or unsubstituted alkoxy, halogen, cyano, —$NO_2$, —OH, amino. In particular, this embodiment encompasses 3-(3-, 4- or 5-)-substituted phenyl compounds of formula II. This embodiment further encompasses compounds of formula II wherein:

$R_1$, $R_2$, $R_3$, $R_4$, $R_5$, $R_6$, $R_7$, $R_8$, $R_{10}$, $R_{16}$, $R_{17}$, $R_a$, $R_b$, $R_c$, and $R_d$ are as defined above for formula II;

$R_9$ is substituted or unsubstituted lower alkyl, or substituted or unsubstituted cycloalkyl;

wherein at least one of R$_3$, R$_4$, R$_5$, R$_6$, R$_7$, R$_8$, R$_a$, R$_b$, R$_c$ or R$_d$ is —O—(C$_4$-C$_{10}$ alkyl)-cycloalkyl, —OPO(OH)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —N(R$_9$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$), —NHC(O)—R$_{10}$—NH$_2$ or substituted or unsubstituted heterocycle. This embodiment also encompasses compounds of formula II wherein at least one of R$_3$, R$_4$, R$_5$, R$_6$, R$_7$, R$_8$, R$_a$, R$_b$, R$_c$ or R$_d$ is —OPO(OH)$_2$, —OC(O)—R$_{10}$—N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$), —NHC(O)—R$_{10}$—NH$_2$ or substituted or unsubstituted heterocycle.

In a further embodiment, the invention provides compounds of formula II wherein at least one of R$_a$ and R$_b$ and at least one of R$_c$ and R$_d$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$. In particular, this embodiment encompasses 3-(2- or 6-)-substituted-3'-(2- or 6-)-substituted phenyl compounds of formula II. This embodiment further encompasses compounds of formula II wherein:

$R_1$, $R_2$, $R_3$, $R_4$, $R_5$, $R_6$, $R_7$, $R_8$, $R_9$, $R_{10}$, $R_{16}$, $R_{17}$, $R_a$, $R_b$, $R_c$, and $R_d$ are as defined above for formula II; and wherein at least one R$_a$ and R$_b$ and at least one of R$_c$ and R$_d$ is other than —H.

In a further embodiment, the invention provides compounds of formula II wherein either R$_3$ and one of R$_a$ and R$_4$, together form —O—(C(R$_{16}$R$_{17}$))$_2$—O— or —O—(C(R$_{16}$R$_{17}$))$_3$—O— or R$_8$ and one of R$_c$ and R$_7$, together form —O—(C(R$_{16}$R$_{17}$))$_2$—O— or —O—(C(R$_{16}$R$_{17}$))$_3$—O—.

In a further embodiment, the invention provides compounds of formula II wherein R$_1$ and R$_2$ are both other than —H. In particular, this embodiment encompasses compounds of formula II wherein:

R$_1$ and R$_2$ are independently —CN, halogen, substituted or unsubstituted lower alkyl, substituted or unsubstituted alkynyl, —NHC(O)OR$_9$, —COOH, —C(O)-lower alkyl, —C(O)O-lower alkyl, —C(O)—N(R$_9$)$_2$, substituted or unsubstituted aryl, or substituted or unsubstituted heterocycle; and R$_3$, R$_4$, R$_5$, R$_6$, R$_7$, R$_8$, R$_9$, R$_{10}$, R$_{16}$, R$_{17}$, R$_a$, R$_b$, R$_c$, and R$_d$ are as defined above for formula II.

In a further embodiment, the invention provides compounds of formula II wherein if wherein if either R$_1$ or R$_2$ is H, the other is not —CN, substituted or unsubstituted lower alkyl, —COOH, —C(O)-lower alkyl, —C(O)O-lower alkyl or —C(O)—N(R$_9$)$_2$.

In a further embodiment, the invention provides compounds of formula II wherein R$_1$ and R$_2$ are both —H.

The following embodiments relate to the compounds of formula II and, where applicable, to the further embodiments of the compounds of formula II described above.

In one embodiment, the compounds of formula II are those wherein all occurrences of R$_a$, R$_b$, R$_c$ and R$_d$ are —H.

In another embodiment, the compounds of formula II are those wherein at least one occurrence of R$_a$, R$_b$, R$_c$ or R$_d$ is other than —H.

In another embodiment, the compounds of formula II are those wherein at least one occurrence of R$_a$ and R$_b$ and at least one occurrence of R$_c$ and R$_d$ is other than —H.

In another embodiment, the compounds of formula II are those wherein at least one occurrence of R$_a$, R$_b$, R$_c$ or R$_d$ is alkoxy.

In another embodiment, the compounds of formula II are those wherein at least one occurrence of R$_a$, R$_b$, R$_c$ or R$_d$ is methoxy.

In another embodiment, the compounds of formula II are those wherein R$_1$ is —H and R$_2$ is —CN.

In another embodiment, the compounds of formula II are those wherein R$_1$ is —CN and R$_2$ is —H.

In another embodiment, the compounds of formula II are those wherein the compound is the E isomer.

In another embodiment, the compounds of formula II are those wherein the compound is the Z isomer.

In another embodiment, the compounds of formula II are those wherein at least one of R$_3$, R$_4$ and R$_5$ and at least one of R$_6$, R$_7$ and R$_8$ is other than —H.

In another embodiment, the compounds of formula II are those wherein R$_3$ is alkoxy and R$_4$ is alkoxy.

In another embodiment, the compounds of formula II are those wherein R$_3$ is methoxy and R$_4$ is methoxy.

In another embodiment, the compounds of formula II are those wherein at least one of R$_3$, R$_4$ and R$_5$ and at least one of R$_6$, R$_7$ and R$_8$ is alkoxy.

In another embodiment, the compounds of formula II are those wherein at least one of R$_3$, R$_4$ and R$_5$ and at least one of R$_6$, R$_7$ and R$_8$ is methoxy.

In another embodiment, the compounds of formula II are those wherein at least one of R$_3$, R$_4$ and R$_5$ and at least one of R$_6$, R$_7$ and R$_8$ is ethoxy.

In another embodiment, the compounds of formula II are those wherein at least one of R$_3$, R$_4$, R$_5$, R$_6$, R$_7$ and R$_8$ is alkoxy.

In another embodiment, the compounds of formula II are those wherein at least one of R$_3$, R$_4$, R$_5$, R$_6$, R$_7$ and R$_8$ is methoxy.

In another embodiment, the compounds of formula II are those wherein at least one of R$_3$, R$_4$, R$_5$, R$_6$, R$_7$ and R$_8$ is ethoxy.

In another embodiment, the compounds of formula II are those wherein either R$_3$ and R$_5$ or R$_6$ and R$_8$ are both alkoxy.

In another embodiment, the compounds of formula II are those wherein either R$_3$ and R$_5$ or R$_6$ and R$_8$ are both methoxy.

In another embodiment, the compounds of formula II are those wherein one of R$_3$ and R$_5$ is methoxy and the other is ethoxy or one of R$_6$ and R$_8$ is methoxy and the other is ethoxy.

In another embodiment, the compounds of formula II are those wherein either R$_3$, R$_4$ and R$_5$ or R$_6$, R$_7$ and R$_8$ are all alkoxy.

In another embodiment, the compounds of formula II are those wherein either R$_3$, R$_4$ and R$_5$ or R$_6$, R$_7$ and R$_8$ are all methoxy.

In another embodiment, the compounds of formula II are those wherein R$_3$ and R$_5$ are methoxy and one of R$_6$ and R$_8$ is methoxy.

In another embodiment, the compounds of formula II are those wherein when R$_{10}$ is substituted lower alkyl (e.g., methylene), R$_{10}$ is substituted with the side chain of a natural amino acid. In particular, R$_{10}$ may be substituted with: —H, —CH$_3$, —(CH$_2$)$_3$NHC(=NH)NH$_2$, —CH$_2$C(=O)NH$_2$, —CH$_2$C(=O)OH, —CH$_2$SH, —(CH$_2$)$_2$C(=O)NH$_2$, —(CH$_2$)$_2$C(=O)OH, —CH$_2$-imidazole, —CH(CH$_3$)(CH$_2$CH$_3$), —CH$_2$CH(CH$_3$)$_2$, —(CH$_2$)$_3$NH$_2$, —(CH$_2$)$_2$SCH$_3$, —CH$_2$-phenyl, —CH$_2$OH, =CH(OH)(CH$_3$), —CH$_2$-indole, —CH$_2$-phenol or —CH(CH$_3$)$_2$.

In another embodiment, the compounds of formula II are those wherein R$_3$ and R$_5$ are methoxy, R$_7$ is methoxy and one of R$_6$ and R$_8$ is —NHC(O)—R$_{10}$—NH$_2$.

In one embodiment, the invention provides compounds having the formula:

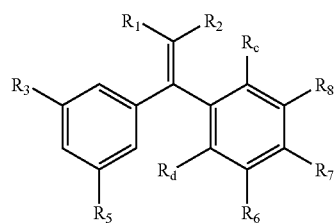

III and pharmaceutically acceptable salts, solvates or hydrates thereof, wherein:

R$_1$ and R$_2$ are independently —H, —CN, halogen, substituted or unsubstituted lower alkyl, substituted or unsubstituted alkenyl, substituted or unsubstituted alkynyl, —NHC(O)OR$_9$, —COOH, —C(O)-lower alkyl, —C(O)O-lower alkyl, —C(O)—N(R$_9$)$_2$, substituted or unsubstituted aryl, or substituted or unsubstituted heterocycle;

each occurrence of R$_c$ and R$_d$ is independently —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_3$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_5$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_6$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_7$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

R$_8$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$, or R$_8$ with either R$_c$ or with R$_7$, together form —O—C(R$_{16}$R$_{17}$)—O— or —O—(C(R$_{16}$R$_{17}$))$_2$—O—;

each occurrence of R$_9$ is independently —H, substituted or unsubstituted lower alkyl, or substituted or unsubstituted cycloalkyl;

each occurrence of R$_{10}$ is independently substituted or unsubstituted lower alkyl, substituted or unsubstituted cycloalkyl, substituted or unsubstituted aryl, substituted or unsubstituted lower hydroxyalkyl, or R$_{10}$ and a nitrogen to which it is attached form a substituted or unsubstituted heterocycle, or R$_{10}$ is —H where appropriate; and each occurrence of R$_{16}$ and R$_{17}$ is independently —H or halogen.

In one embodiment, the compounds of formula III are those wherein R$_c$ and R$_d$ are —H.

In another embodiment, the compounds of formula III are those wherein at least one of R$_c$ or R$_d$ is other than —H.

In another embodiment, the compounds of formula III are those wherein at least one of R$_c$ or R$_d$ is -alkoxy.

In another embodiment, the compounds of formula III are those wherein at least one of R$_c$ or R$_d$ is methoxy.

In another embodiment, the compounds of formula III are those wherein R$_1$ is —H and R$_2$ is —CN.

In another embodiment, the compounds of formula III are those wherein R$_1$ is —CN and R$_2$ is —H.

In another embodiment, the compounds of formula III are those wherein the compound is the E isomer.

In another embodiment, the compounds of formula III are those wherein the compound is the Z isomer.

In another embodiment, the compounds of formula III are those wherein at least one of R$_6$, R$_7$ and R$_8$ is other than —H.

In another embodiment, the compounds of formula III are those wherein at least one of R$_3$ and R$_5$ and at least one of R$_6$, R$_7$ and R$_8$ is alkoxy.

In another embodiment, the compounds of formula III are those wherein at least one of R$_3$ and R$_5$ and at least one of R$_6$, R$_7$ and R$_8$ is methoxy.

In another embodiment, the compounds of formula III are those wherein at least one of R$_3$ and R$_5$ and at least one of R$_6$, R$_7$ and R$_8$ is ethoxy.

In another embodiment, the compounds of formula III are those wherein at least one of R$_3$, R$_5$, R$_6$, R$_7$ and R$_8$ is -alkoxy.

In another embodiment, the compounds of formula III are those wherein at least one of R$_3$, R$_5$, R$_6$, R$_7$ and R$_8$ is methoxy.

In another embodiment, the compounds of formula III are those wherein at least one of R$_3$R$_5$, R$_6$, R$_7$ and R$_8$ is ethoxy.

In another embodiment, the compounds of formula III are those wherein R$_3$ and R$_5$ are both alkoxy.

In another embodiment, the compounds of formula III are those wherein R$_3$ and R$_5$ are both methoxy.

In another embodiment, the compounds of formula III are those wherein one of R$_3$ and R$_5$ is methoxy and the other is alkoxy.

In another embodiment, the compounds of formula III are those wherein R$_3$ and R$_5$ are methoxy and one of R$_6$ and R$_8$ is methoxy.

In another embodiment, the compounds of formula III are those wherein one of R$_6$ and R$_8$ is heterocycle or —NHC(O)R$_{10}$—N(R$_9$)$_2$.

In another embodiment, the compounds of formula III are those wherein R$_3$ and R$_5$ are methoxy, R$_7$ is methoxy and one of R$_6$ and R$_8$ is —NHC(O)—R$_{10}$—NH$_2$.

In another embodiment, the compounds of formula III do not include 3-(3,4-dimethoxyphenyl)-3-(3',5'-dimethoxyphenyl)-acrylonitrile.

In one embodiment, the invention provides compounds having the formula:

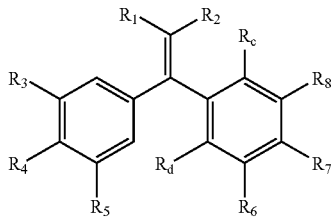

IV and pharmaceutically acceptable salts, solvates or hydrates thereof, wherein:

$R_1$ and $R_2$ are independently —H, —CN, halogen, substituted or unsubstituted lower alkyl, substituted or unsubstituted alkenyl, substituted or unsubstituted alkynyl, —NHC(O)OR$_9$, —COOH, —C(O)-lower alkyl, —C(O)O-lower alkyl, —C(O)—N(R$_9$)$_2$, substituted or unsubstituted aryl, or substituted or unsubstituted heterocycle;

each occurrence of $R_c$ and $R_d$ is independently —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$; —NHC(O)CH(R$_{10}$)(N(R$_9$)$_2$) or —NHC(O)—R$_{10}$—NH$_2$;

$R_3$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_4$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_{29}$—C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_5$ is substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_6$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_7$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_8$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$, or $R_8$ with either $R_c$ or with $R_7$, together form —O—C(R$_{16}$R$_{17}$)—O— or —O—(C(R$_{16}$R$_{17}$))$_2$—O—;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate; and each occurrence of $R_{16}$ and $R_{17}$ is independently —H or halogen.

In one embodiment, the compounds of formula IV are those $R_c$ and $R_d$ are —H.

In another embodiment, the compounds of formula IV are those wherein at least one of $R_c$ or $R_d$ is other than —H.

In another embodiment, the compounds of formula IV are those wherein at least one of $R_c$ or $R_d$ is -alkoxy.

In another embodiment, the compounds of formula IV are those wherein at least one of $R_c$ or $R_d$ is methoxy.

In another embodiment, the compounds of formula IV are those wherein $R_1$ is —H and $R_2$ is —CN.

In another embodiment, the compounds of formula IV are those wherein $R_1$ is —CN and $R_2$ is —H.

In another embodiment, the compounds of formula IV are those wherein the compound is the E isomer.

In another embodiment, the compounds of formula IV are those wherein the compound is the Z isomer.

In another embodiment, the compounds of formula IV are those wherein at least one of $R_6$, $R_7$ and $R_8$ is other than —H.

In another embodiment, the compounds of formula IV are those wherein at least one of $R_3$, $R_4$ and $R_5$ is alkoxy.

In another embodiment, the compounds of formula IV are those wherein at least one of $R_3$, $R_4$ and $R_5$ is methoxy.

In another embodiment, the compounds of formula IV are those wherein at least one of $R_3$, $R_4$ and $R_5$ is ethoxy.

In another embodiment, the compounds of formula IV are those wherein $R_3$, $R_5$, $R_6$ and $R_8$ are alkoxy.

In another embodiment, the compounds of formula IV are those wherein either $R_3$, $R_5$, $R_6$ and $R_8$ are methoxy.

In another embodiment, the compounds of formula IV are those wherein one of $R_3$ and $R_5$ is methoxy and the other is ethoxy.

In another embodiment, the compounds of formula IV are those wherein $R_3$ and $R_5$ are methoxy and one of $R_6$ and $R_8$ is methoxy.

In another embodiment, the compounds of formula IV are those wherein $R_3$ and $R_5$ are methoxy, $R_7$ is methoxy and one of $R_6$ and $R_8$ is —NHC(O)—$R_{10}$—NH$_2$.

In one embodiment, the invention provides compounds having the formula:

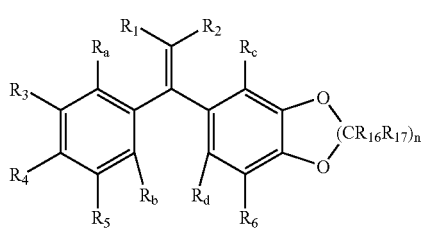

V and pharmaceutically acceptable salts, solvates or hydrates thereof, wherein:

$R_1$ and $R_2$ are independently —H, —CN, halogen, substituted or unsubstituted lower alkyl, substituted or unsubstituted alkenyl, substituted or unsubstituted alkynyl, —NHC(O)OR$_9$, —COOH, —C(O)-lower alkyl, —C(O)O-lower alkyl, —C(O)—N(R$_9$)$_2$, substituted or unsubstituted aryl, or substituted or unsubstituted heterocycle;

each occurrence of $R_a$, $R_b$, $R_c$ and $R_d$ is independently —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —C(O)N(R$_{10}$)$_2$, —NHC(O)—R$_{10}$, —NHS(O)$_2$—R$_{10}$, —S(O)$_2$—R$_{10}$, —NHC(O)NH—R$_{10}$, —NHC(O)N(R$_{10}$)$_2$, —NHC(O)NHSO$_2$R$_{10}$—NHC(O)—R$_{10}$—N(R$_{10}$)$_2$; —NHC(O)CH(R$_{10}$)(N(R$_9$)$_2$) or —NHC(O)—R$_{10}$—NH$_2$;

$R_3$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$, or $R_3$ with either $R_a$ or with $R_4$, together form —O—C(R$_{16}$R$_{17}$)—O— or —O—(C(R$_{16}$R$_{17}$))$_2$—O—;

$R_4$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_5$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

$R_6$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$_9$)$_2$, —OC(O)—R$_{10}$, —OC(O)—R$_{10}$—N(R$_{10}$)$_2$, —OC(O)—R$_{10}$—NH$_2$, —C(O)N(R$_{10}$)$_2$, —NHC(O)—R$_{10}$, —NHS(O)$_2$—R$_{10}$, —S(O)$_2$—R$_{10}$, —OS(O)$_2$—R$_{10}$, —OS(O)$_2$—NH$_2$, —OS(O)$_2$—N(R$_{10}$)$_2$, —SO$_2$NH$_2$, —SO$_2$—N(R$_{10}$)$_2$, —NHC(O)O—R$_{10}$, —NHC(O)NH—R$_{10}$, —NHC(O)N(R$_{10}$)$_2$, —NHC(O)NHSO$_2$—R$_{10}$, —NHC(O)—R$_{10}$—N(R$_{10}$)$_2$, —NHC(O)CH(R$_{10}$)(N(R$_9$)$_2$) or —NHC(O)—R$_{10}$—NH$_2$;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate;

each occurrence of $R_{16}$ and $R_{17}$ is independently —H or halogen; and n is 1, 2 or 3.

In one embodiment, the compounds of formula V are those wherein all occurrences of $R_a$, $R_b$, $R_c$ and $R_d$ are —H.

In another embodiment, the compounds of formula V are those wherein at least one occurrence of $R_a$, $R_b$, $R_c$ or $R_d$ is other than —H.

In another embodiment, the compounds of formula V are those wherein at least one occurrence of $R_a$ and $R_b$ and at least one occurrence of $R_c$ and $R_d$ is other than —H.

In another embodiment, the compounds of formula V are those wherein at least one occurrence of $R_a$, $R_b$, $R_c$ or $R_d$ is -alkoxy.

In another embodiment, the compounds of formula V are those wherein at least one occurrence of $R_a$, $R_b$, $R_c$ or $R_d$ is methoxy.

In another embodiment, the compounds of formula V are those wherein $R_1$ is —H and $R_2$ is —CN.

In another embodiment, the compounds of formula V are those wherein $R_1$ is —CN and $R_2$ is —H.

In another embodiment, the compounds of formula V are those wherein the compound is the E isomer.

In another embodiment, the compounds of formula V are those wherein the compound is the Z isomer.

In another embodiment, the compounds of formula V are those wherein at least one of $R_3$, $R_4$ and $R_5$ is other than —H and $R_6$ is other than —H.

In another embodiment, the compounds of formula V are those wherein at least one of $R_3$, $R_4$ and $R_5$ is alkoxy and $R_6$ is alkoxy.

In another embodiment, the compounds of formula V are those wherein at least one of $R_3$, $R_4$ and $R_5$ is methoxy and $R_6$ is methoxy.

In another embodiment, the compounds of formula V are those wherein at least one of $R_3$, $R_4$ and $R_5$ is ethoxy and $R_6$ is ethoxy.

In another embodiment, the compounds of formula V are those wherein $R_3$, $R_5$ and $R_6$ are alkoxy.

In another embodiment, the compounds of formula V are those wherein $R_3$, $R_5$ and $R_6$ are methoxy.

In another embodiment, the compounds of formula V are those wherein one of $R_3$ and $R_5$ is methoxy and the other is ethoxy.

In another embodiment, the compounds of formula V are those wherein $R_3$, $R_4$ and $R_5$ are all alkoxy.

In another embodiment, the compounds of formula V are those wherein $R_3$, $R_4$ and $R_5$ are all methoxy.

In another embodiment, the compounds of formula V are those wherein $R_3$ and $R_5$ are methoxy and $R_6$ is methoxy.

In another embodiment, the compounds of formula V are those wherein n is 2 or 3.

In one embodiment, the invention provides compounds having the formula:

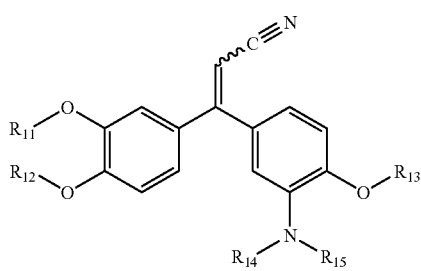

VI and pharmaceutically acceptable salts, solvates or hydrates thereof, wherein:

$R_{11}$, $R_{12}$ and $R_{13}$ are independently substituted or unsubstituted lower alkyl, substituted or unsubstituted alkyl, substituted or unsubstituted cycloalkyl;

$R_{14}$ and $R_{15}$ are independently —H, O, substituted or unsubstituted lower alkyl, substituted or unsubstituted aryl, substituted or unsubstituted heterocycle, substituted or unsubstituted cycloalkyl, —C(O)—$R_{10}$, —C(O)—$R_{10}$—N($R_{10}$)$_2$, —C(O)N($R_{10}$)$_2$, —C(O)—$R_{10}$, —S(O)$_2$—$R_{10}$, —C(O)NH—$R_{10}$, —C(O)N($R_{10}$)$_2$, —C(O)—$R_{10}$—NH$_2$, —C(O)NHSO$_2$—$R_{10}$, —C(O)—$R_{10}$—N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or $R_{14}$ and $R_{15}$ and the nitrogen to which they are attached form a heterocycle;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate;

with the proviso that $R_{14}$ and $R_{15}$ cannot both be —H.

In one embodiment, the compounds of formula VI are those wherein $R_{11}$ is methyl, ethyl, propyl or —CH$_2$-cyclopropyl.

In another embodiment, the compounds of formula VI are those wherein $R_{12}$ is methyl, difluoromethyl or trifluoromethyl.

In another embodiment, the compounds of formula VI are those wherein $R_{13}$ is methyl.

In another embodiment, the compounds of formula VI are those wherein $R_{14}$ is —H and $R_{15}$ is —C(O)NH—$R_{10}$, —C(O)N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or —C(O)N($R_{10}$)$_2$.

In another embodiment, the compounds of formula VI are those wherein $R_{14}$ and $R_{15}$ and the nitrogen to which they are attached form a heterocycle.

In another embodiment, the compounds of formula VI are those wherein $R_{11}$, $R_{12}$ and/or $R_{13}$ are lower alkyl substituted with cycloalkyl and/or halogen.

In one embodiment, the invention provides compounds having the formula:

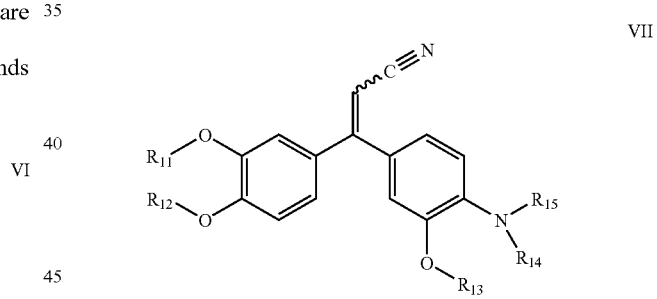

VII and pharmaceutically acceptable salts, solvates or hydrates thereof, wherein:

$R_{11}$, $R_{12}$ and $R_{13}$ are independently substituted or unsubstituted lower alkyl, substituted or unsubstituted alkyl, substituted or unsubstituted cycloalkyl;

$R_{14}$ and $R_{15}$ are independently —H, O, substituted or unsubstituted lower alkyl, substituted or unsubstituted aryl, substituted or unsubstituted heterocycle, substituted or unsubstituted cycloalkyl, —C(O)—$R_{10}$, —C(O)—$R_{10}$—N($R_{10}$)$_2$, —C(O)N($R_{10}$)$_2$, —C(O)—$R_{10}$, —S(O)$_2$—$R_{10}$, —C(O)NH—$R_{10}$, —C(O)N($R_{10}$)$_2$, —C(O)—$R_{10}$—NH$_2$, —C(O)NHSO$_2$—$R_{10}$, —C(O)—$R_{10}$—N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or $R_{14}$ and $R_{15}$ and the nitrogen to which they are attached form a heterocycle;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate;

with the proviso that $R_{14}$ and $R_{15}$ cannot both be —H.

In one embodiment, the compounds of formula VII are those wherein $R_{11}$ is methyl, ethyl, propyl or —CH$_2$-cyclopropyl.

In another embodiment, the compounds of formula VII are those wherein $R_{12}$ is methyl, difluoromethyl or trifluoromethyl.

In another embodiment, the compounds of formula VII are those wherein $R_{13}$ is methyl.

In another embodiment, the compounds of formula VII are those wherein $R_{14}$ is —H and $R_{15}$ is —C(O)NH—$R_{10}$, —C(O)N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or —C(O)N($R_{10}$)$_2$.

In another embodiment, the compounds of formula VII are those wherein $R_{14}$ and $R_{15}$ and the nitrogen to which they are attached form a heterocycle.

In another embodiment, the compounds of formula VII are those wherein $R_{11}$, $R_{12}$ and/or $R_{13}$ are lower alkyl substituted with cycloalkyl and/or halogen.

In one embodiment, the invention provides compounds having the formula:

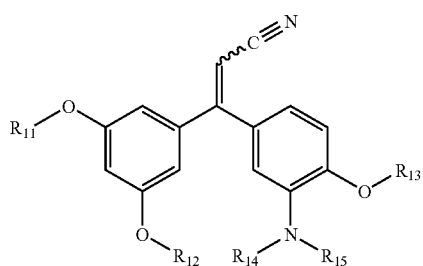

VIII and pharmaceutically acceptable salts, solvates or hydrates thereof, wherein:

$R_{11}$, $R_{12}$ and $R_{13}$ are independently substituted or unsubstituted lower alkyl, substituted or unsubstituted alkyl, substituted or unsubstituted cycloalkyl;

$R_{14}$ and $R_{15}$ are independently —H, O, substituted or unsubstituted lower alkyl, substituted or unsubstituted aryl, substituted or unsubstituted heterocycle, substituted or unsubstituted cycloalkyl, —C(O)—$R_{10}$, —C(O)—$R_{10}$—N($R_{10}$)$_2$, —C(O)—$R_{10}$—NH$_2$, —C(O)N($R_{10}$)$_2$, —C(O)—$R_{10}$, —S(O)$_2$—$R_{10}$, —C(O)NH—$R_{10}$, —C(O)N($R_{10}$)$_2$, —C(O)NHSO$_2$—$R_{10}$, —C(O)—$R_{10}$—N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or $R_{14}$ and $R_{15}$ and the nitrogen to which they are attached form a heterocycle;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate;

with the proviso that $R_{14}$ and $R_{15}$ cannot both be —H.

In one embodiment, the compounds of formula VIII are those wherein $R_{11}$ is methyl, ethyl, propyl or —CH$_2$-cyclopropyl.

In another embodiment, the compounds of formula VIII are those wherein $R_{12}$ is methyl, difluoromethyl or trifluoromethyl.

In another embodiment, the compounds of formula VIII are those wherein $R_{13}$ is methyl.

In another embodiment, the compounds of formula VIII are those wherein $R_{14}$ is —H and $R_{15}$ is —C(O)NH—$R_{10}$, —C(O)N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or —C(O)N($R_{10}$)$_2$.

In another embodiment, the compounds of formula VIII are those wherein $R_{14}$ and $R_{15}$ and the nitrogen to which they are attached form a heterocycle.

In another embodiment, the compounds of formula VIII are those wherein $R_{11}$, $R_{12}$ and/or $R_{13}$ are lower alkyl substituted with cycloalkyl and/or halogen.

In one embodiment, the invention provides compounds having the formula:

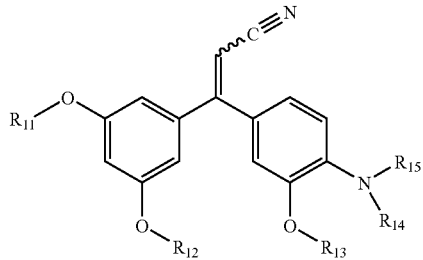

IX and pharmaceutically acceptable salts, solvates or hydrates thereof, wherein:

$R_{11}$, $R_{12}$ and $R_{13}$ are independently substituted or unsubstituted lower alkyl, substituted or unsubstituted alkyl, substituted or unsubstituted cycloalkyl;

$R_{14}$ and $R_{15}$ are independently —H, O, substituted or unsubstituted lower alkyl, substituted or unsubstituted aryl, substituted or unsubstituted heterocycle, substituted or unsubstituted cycloalkyl, —C(O)—$R_{10}$, —C(O)—$R_{10}$—N($R_{10}$)$_2$, —C(O)—$R_{10}$—NH$_2$, —C(O)N($R_{10}$)$_2$, —C(O)—$R_{10}$, —S(O)$_2$—$R_{10}$, —C(O)NH—$R_{10}$, —C(O)N($R_{10}$)$_2$, —C(O)NHSO$_2$—$R_{10}$, —C(O)—$R_{10}$—N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or $R_{14}$ and $R_{15}$ and the nitrogen to which they are attached form a heterocycle;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate;

with the proviso the $R_{14}$ and $R_{15}$ cannot both be —H.

In one embodiment, the compounds of formula IX are those wherein $R_{11}$ is methyl, ethyl, propyl or —CH$_2$-cyclopropyl.

In another embodiment, the compounds of formula IX are those wherein $R_{12}$ is methyl, difluoromethyl or trifluoromethyl.

In another embodiment, the compounds of formula IX are those wherein $R_{13}$ is methyl.

In another embodiment, the compounds of formula IX are those wherein $R_{14}$ is —H and $R_{15}$ is —C(O)NH—$R_{10}$, —C(O)N($R_{10}$)$_2$, —C(O)—$R_{10}$—NH$_2$, —C(O)—CH($R_{10}$)(N($R_9$)$_2$), —C(O)-lower alkyl-N($R_9$)$_2$ or —C(O)N($R_{10}$)$_2$.

In another embodiment, the compounds of formula IX are those wherein $R_{14}$ and $R_{15}$ and the nitrogen to which they are attached form a heterocycle.

In another embodiment, the compounds of formula IX are those wherein $R_{11}$, $R_{12}$ and/or $R_{13}$ are lower alkyl substituted with cycloalkyl and/or halogen.

In one embodiment, the invention provides compounds having the formula:

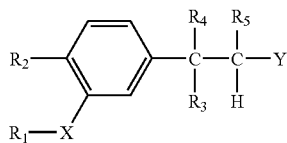

X and pharmaceutically acceptable salts, solvates or hydrates thereof,
wherein:
(a) X is —O— or —($C_nH_{2n}$)— in which n has a value of 0, 1, 2, or 3, and $R_1$ is alkyl of one to 10 carbon atoms, monocycloalkyl of up to 10 carbon atoms, polycycloalkyl of up to 10 carbon atoms, or benzocyclic alkyl of up to 10 carbon atoms, or (b) X is —CH= and $R_1$ is alkylidene of up to 10 carbon atoms, monocycloalkylidene of up to 10 carbon atoms, or bicycloalkylidene of up to 10 carbon atoms;

$R_2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

$R_3$ is (i) phenyl, unsubstituted or substituted with 1 or more substituents each selected independently from nitro, cyano, halo, trifluoromethyl, carbethoxy, carbomethoxy, carbopropoxy, acetyl, carbamoyl, carbamoyl substituted with alkyl of 1 to 3 carbon atoms, acetoxy, carboxy, hydroxy, amino, amino substituted with an alkyl of 1 to 5 carbon atoms, alkyl of up to 10 carbon atoms, cycloalkyl of up to 10 carbon atoms, alkoxy of up to 10 carbon atoms, cycloalkoxy of up to 10 carbon atoms, alkylidenemethyl of up to 10 carbon atoms, cycloalkylidenemethyl of up to 10 carbon atoms, phenyl, or methylenedioxy; (ii) pyridine, substituted pyridine, pyrrolidine, imidizole, naphthalene, or thiophene; (iii) cycloalkyl of 4-10 carbon atoms, unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl;

each of $R_4$ and $R_5$ taken individually is hydrogen or $R_4$ and $R_5$ taken together are a carbon-carbon bond;

Y is —COZ, —C≡N, or lower alkyl of 1 to 5 carbon atoms;
Z is —OH, —NR$_6$R$_6$, —R$_7$, or —OR$_7$;
$R_6$ is hydrogen or lower alkyl; and
$R_7$ is alkyl or benzyl.

In one embodiment, the invention provides compounds having the formula:

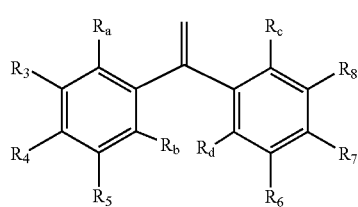

XI and pharmaceutically acceptable salts, solvates or hydrates thereof,
wherein:
each occurrence of $R_a$, $R_b$, $R_c$ and $R_d$ is independently —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$, —OC(O)—$R_{10}$—N($R_{10}$)$_2$, —C(O)N($R_{10}$)$_2$, —NHC(O)—$R_{10}$, —NHS(O)$_2$—$R_{10}$, —S(O)$_2$—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$;

$R_3$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$,—OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$, or $R_3$ with either $R_a$ or with $R_4$, together form —O—C($R_{16}R_{17}$)—O— or —O—(C($R_{16}R_{17}$))$_2$—O—;

$R_4$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$,—OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_{29}$—NHC(O)CH($R_{10}$)(N($R_9$)$_2$) or —NHC(O)—$R_{10}$—NH$_2$;

$R_5$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N($R_9$)$_2$, —OC(O)—$R_{10}$,—OC(O)—$R_{10}$—N($R_{10}$)$_2$, —OC(O)—$R_{10}$—NH$_2$, —C(O)N($R_{10}$)$_2$, —NHC(O)—$R_{10}$, —NHS(O)$_2$—$R_{10}$, —S(O)$_2$—$R_{10}$, —OS(O)$_2$—$R_{10}$, —OS(O)$_2$—NH$_2$, —OS(O)$_2$—N($R_{10}$)$_2$, —SO$_2$NH$_2$, —SO$_2$—N($R_{10}$)$_2$, —NHC(O)O—$R_{10}$, —NHC(O)NH—$R_{10}$, —NHC(O)N($R_{10}$)$_2$, —NHC(O)NHSO$_2$—$R_{10}$, —NHC(O)—$R_{10}$—N($R_{10}$)$_2$, —NHC(O)CH($R_{10}$)(N($R_9$)$_2$) or —NHC(O)—$R_{10}$—NH$_2$;

$R_6$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —$OPO(OH)_2$, —$N(R_9)_2$, —OC(O)—$R_{10}$, —OC(O)—$R_{10}$—$N(R_{10})_2$, —OC(O)—$R_{10}$—$NH_2$, —C(O)$N(R_{10})_2$, —NHC(O)—$R_{10}$, —$NHS(O)_2$—$R_{10}$, —$S(O)_2$—$R_{10}$, —$OS(O)_2$—$R_{10}$, —$OS(O)_2$—$NH_2$, —$OS(O)_2$—$N(R_{10})_2$, —$SO_2NH_2$, —$SO_2$—$N(R_{10})_2$, —NHC(O)O—$R_{10}$, —NHC(O)NH—$R_{10}$, —NHC(O)$N(R_{10})_2$, —NHC(O)$NHSO_2$—$R_{10}$, —NHC(O)—$R_{10}$—$N(R_{10})_2$, —NHC(O)CH($R_{10}$)($N(R_9)_2$) or —NHC(O)—$R_{10}$—$NH_2$;

$R_7$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —$OPO(OH)_2$, —$N(R_9)_2$, —OC(O)—$R_{10}$, —OC(O)—$R_{10}$—$N(R_{10})_2$, —OC(O)—$R_{10}$—$NH_2$; —C(O)$N(R_{10})_2$, —NHC(O)—$R_{10}$, —$NHS(O)_2$—$R_{10}$, —$S(O)_2$—$R_{10}$, —$OS(O)_2$—$R_{10}$, —$OS(O)_2$—$NH_2$, —$OS(O)_2$—$N(R_{10})_2$, —$SO_2NH_2$, —$SO_2$—$N(R_{10})_2$, —NHC(O)O—$R_{10}$, —NHC(O)NH—$R_{10}$, —NHC(O)$N(R_{10})_2$, —NHC(O)$NHSO_2$—$R_{10}$, —NHC(O)—$R_{10}$—$N(R_{10})_2$, —NHC(O)CH($R_{10}$)($N(R_9)_2$) or —NHC(O)—$R_{10}$—$NH_2$;

$R_8$ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —$NO_2$, —OH, —$OPO(OH)_2$, —$N(R_9)_2$, —OC(O)—$R_{10}$, —OC(O)—$R_{10}$—$N(R_{10})_2$, —OC(O)—$R_{10}$—$NH_2$, —C(O)$N(R_{10})_2$, —NHC(O)—$R_{10}$, —$NHS(O)_2$—$R_{10}$, —$S(O)_2$—$R_{10}$, —$OS(O)_2$—$R_{10}$, —$OS(O)_2$—$NH_2$, —$OS(O)_2$—$N(R_{10})_2$, —$SO_2NH_2$, —$SO_2$—$N(R_{10})_2$, —NHC(O)O—$R_{10}$, —NHC(O)NH—$R_{10}$, —NHC(O)$N(R_{10})_2$, —NHC(O)$NHSO_2$—$R_{10}$, —NHC(O)—$R_{10}$—$N(R_{10})_2$, —NHC(O)CH($R_{10}$)($N(R_9)_2$) or —NHC(O)—$R_{10}$—$NH_2$, or $R_8$ with either $R_c$ or with $R_7$, together form —O—C($R_{16}R_{17}$)—O— or —O—(C($R_{16}R_{17}$))$_2$—O—;

each occurrence of $R_9$ is independently —H, substituted or unsubstituted lower alkyl, or substituted or unsubstituted cycloalkyl;

each occurrence of $R_{10}$ is independently substituted or unsubstituted lower alkyl, substituted or unsubstituted cycloalkyl, substituted or unsubstituted aryl, substituted or unsubstituted lower hydroxyalkyl, or $R_{10}$ and a nitrogen to which it is attached form a substituted or unsubstituted heterocycle, or $R_{10}$ is —H where appropriate; and each occurrence of $R_{16}$ and $R_{17}$ is independently —H or halogen.

Illustrative examples of the compounds of the invention include those set forth in Table 1, below, and pharmaceutically acceptable salts, solvates or hydrates thereof. It should be noted that the E/Z and cis/trans isomers of these compounds are specifically contemplated.

TABLE 1

| Comp. | Structure |
|---|---|
| 1 | 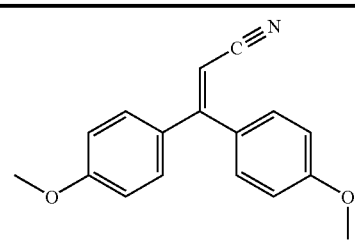 |
| 2 | 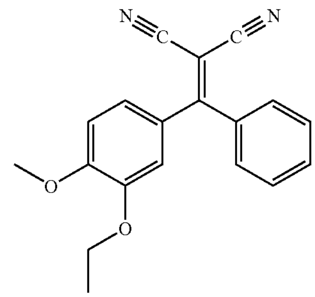 |
| 3 | 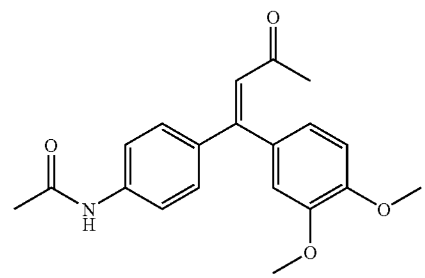 |
| 4 | 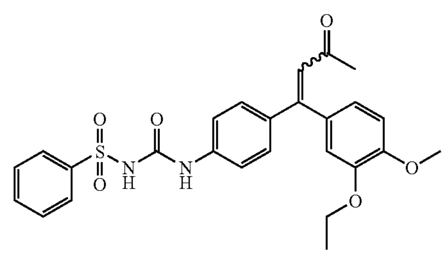 |
| 5 | 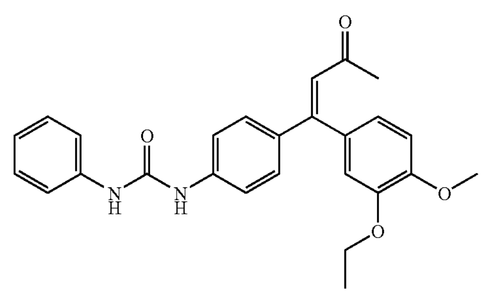 |
| 6 | 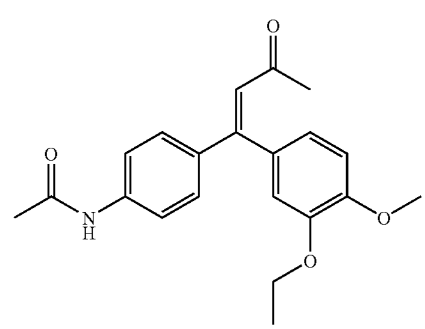 |

TABLE 1-continued
| Comp. | Structure |
|---|---|
| 7 | 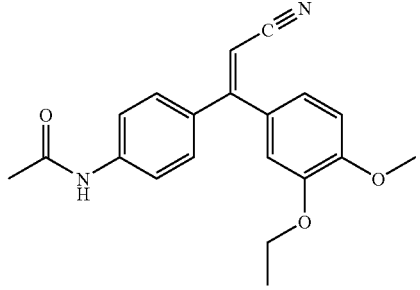 |
| 8 | 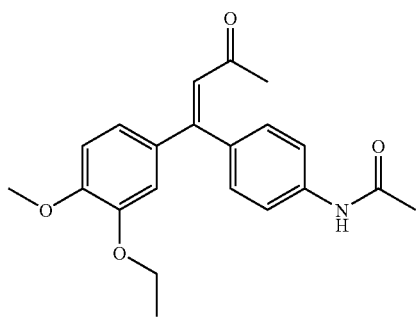 |
| 9 | 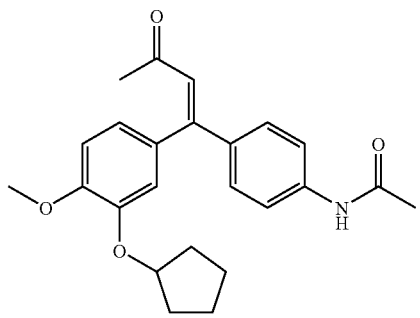 |
| 10 | 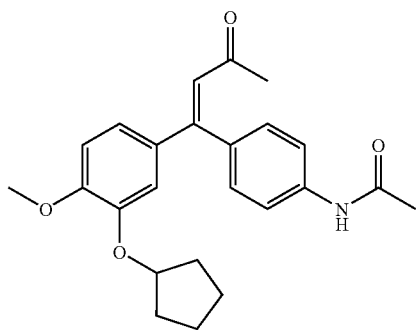 |
| 11 | 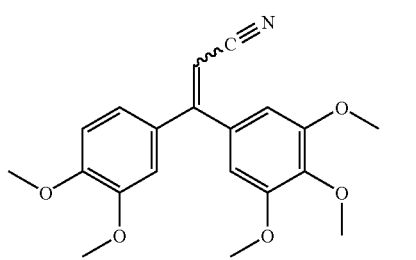 |
| 12 | 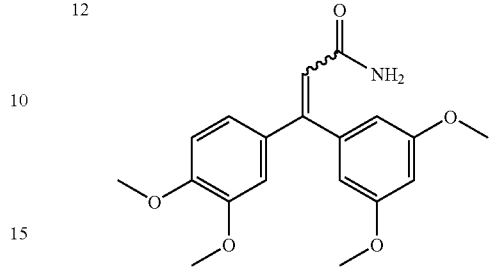 |
| 13 | 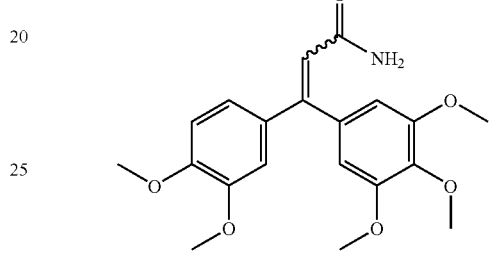 |
| 14 | 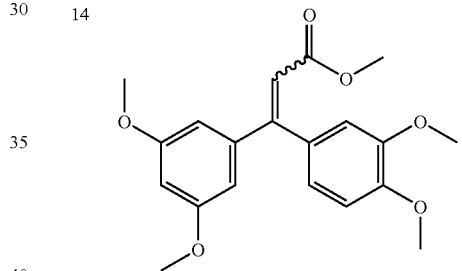 |
| 15 | 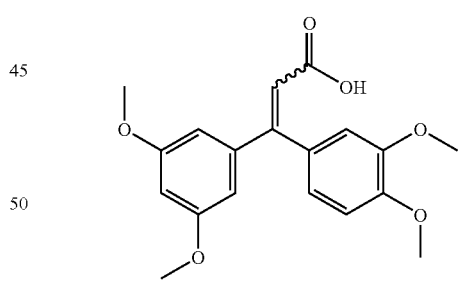 |
| 16 | 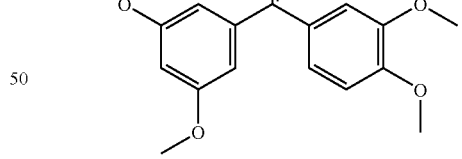 |

TABLE 1-continued
| Comp. | Structure |
|---|---|
| 17 | 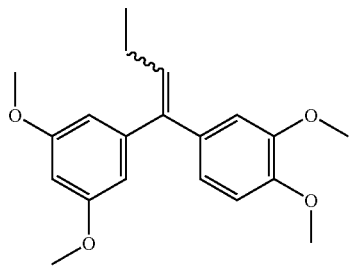 |
| 18 | 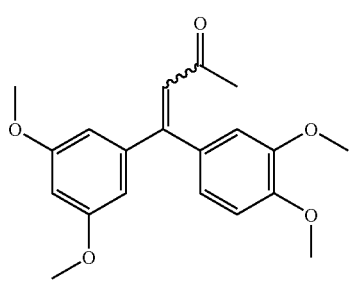 |
| 19 | 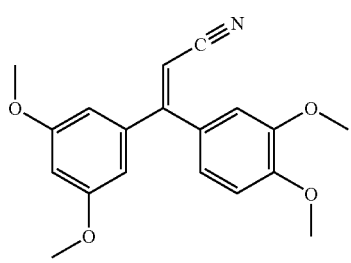 |
| 20 | 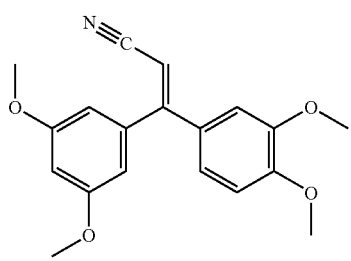 |
| 21 | 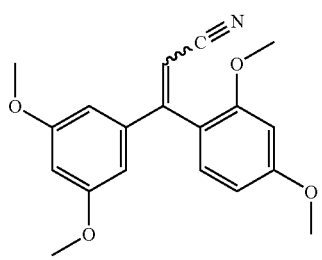 |
TABLE 1-continued
| Comp. | Structure |
|---|---|
| 22 | 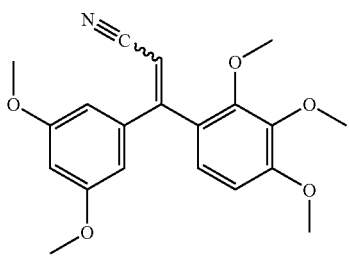 |
| 23 | 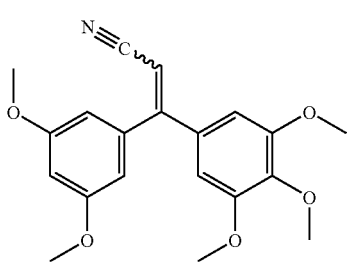 |
| 24 | 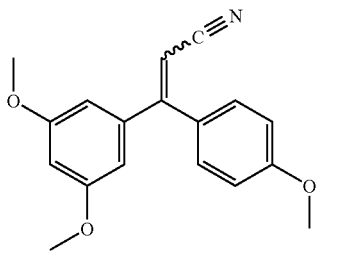 |
| 25 | 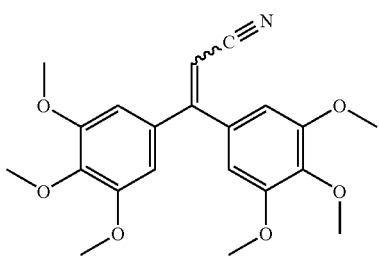 |
| 26 | 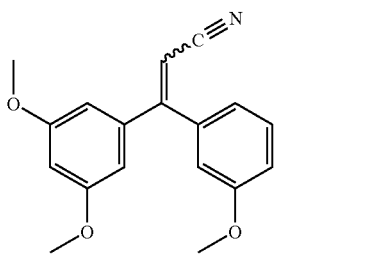 |

TABLE 1-continued
| Comp. | Structure |
|---|---|
| 27 | 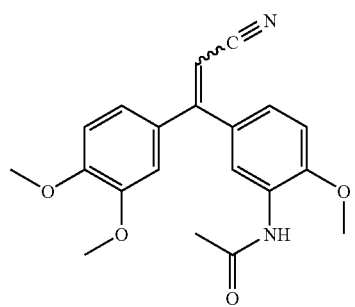 |
| 28 | 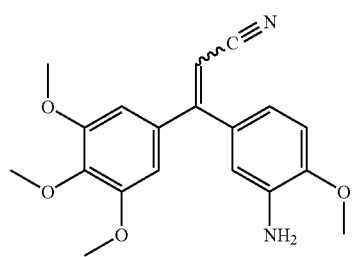 |
| 29 | 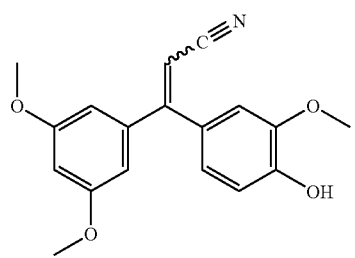 |
| 30 | 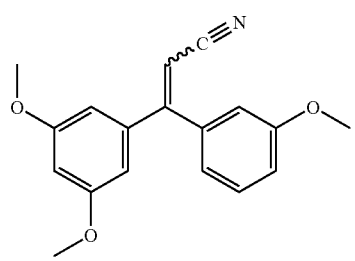 |
| 31 | 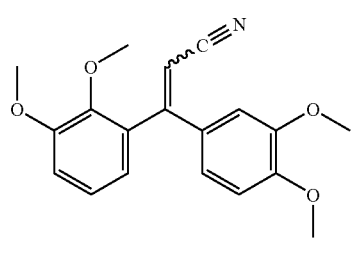 |
| 32 | 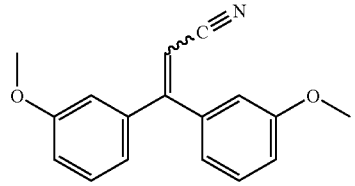 |
TABLE 1-continued
| Comp. | Structure |
|---|---|
| 33 | 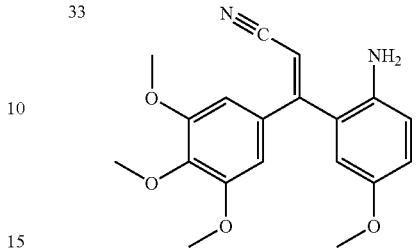 |
| 34 | 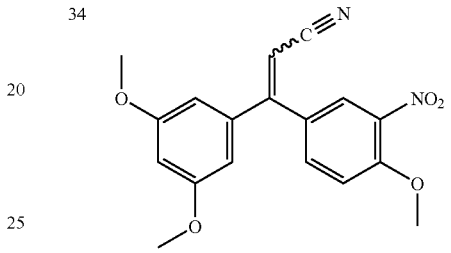 |
| 35 | 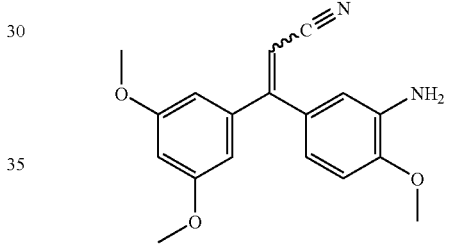 |
| 36 | 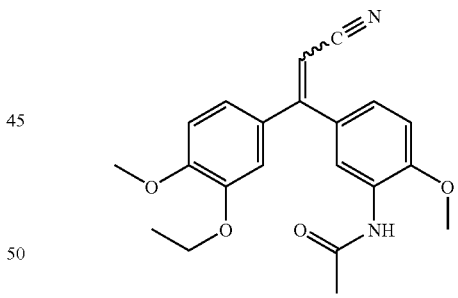 |
| 37 | 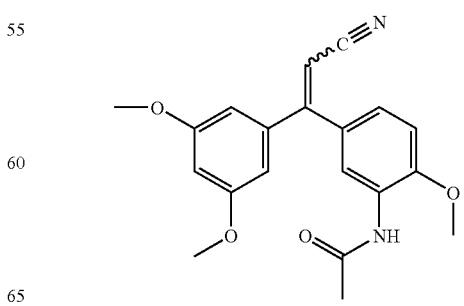 |

TABLE 1-continued
| Comp. | Structure |
|---|---|
| 38 | 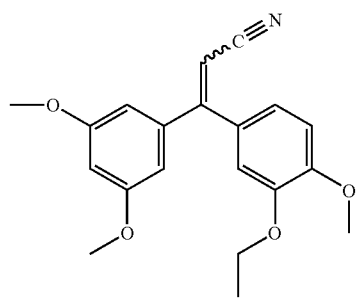 |
| 39 | 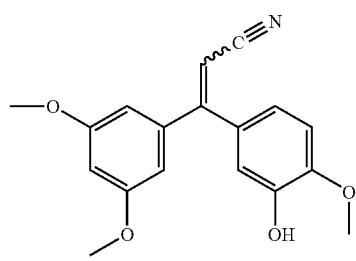 |
| 40 | 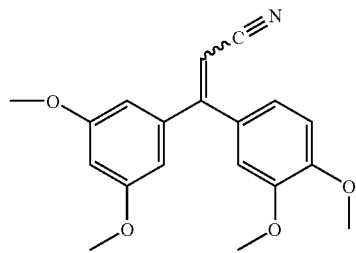 |
| 41 | 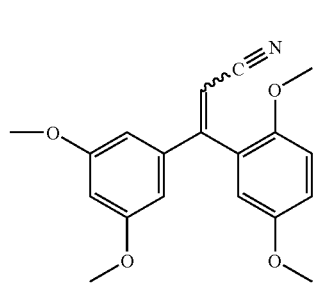 |
| 42 | 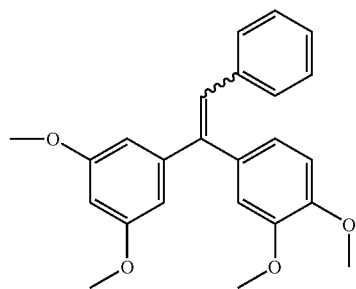 |
| 43 | 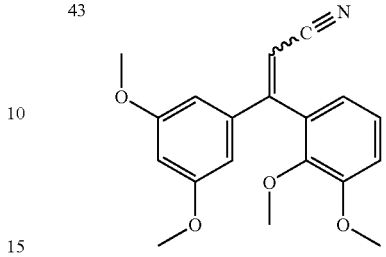 |
| 44 | 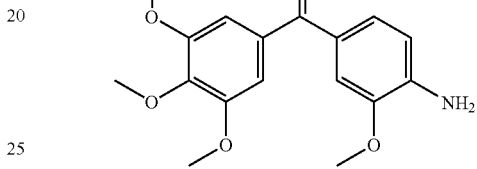 |
| 45 | 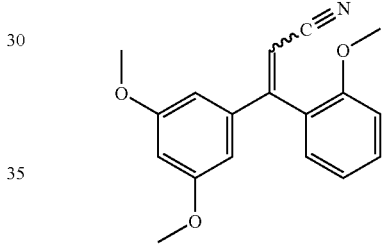 |
| 46 | 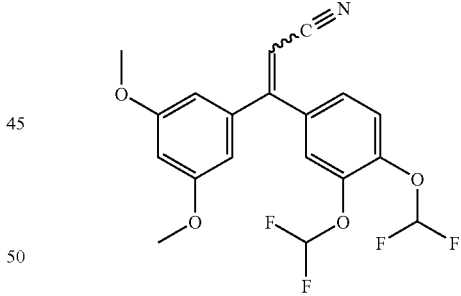 |
| 47 | 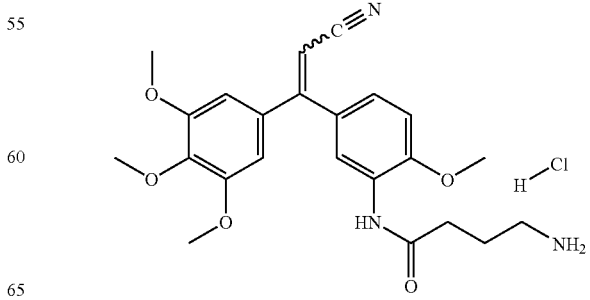 |

TABLE 1-continued

| Comp. | Structure |
|---|---|
| 48 | 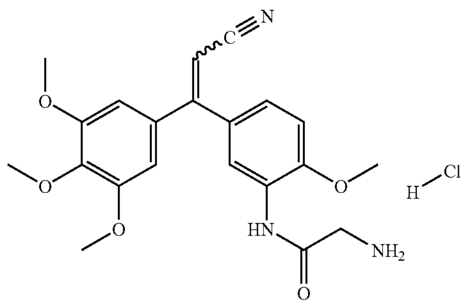 |
| 49 | 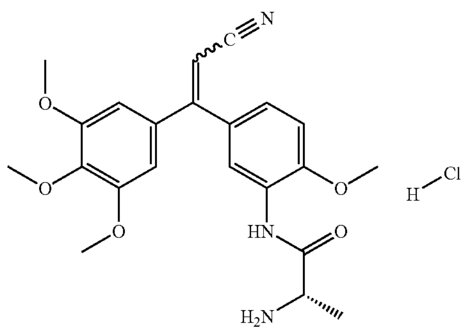 |
| 50 | 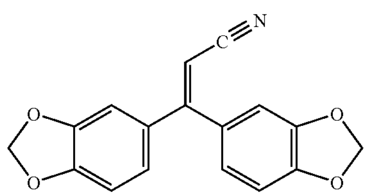 |
| 51 | 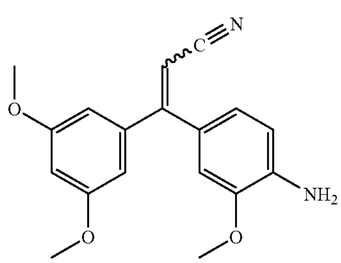 |
| 52 | 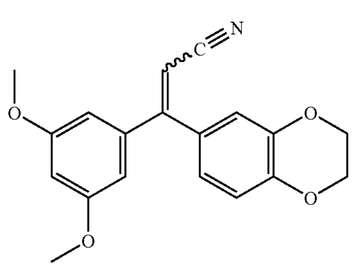 |
| 53 | |
| 54 | |
| 55 | |
| 56 | |
| 57 | |

TABLE 1-continued
| Comp. | Structure |
|---|---|
| 58 | 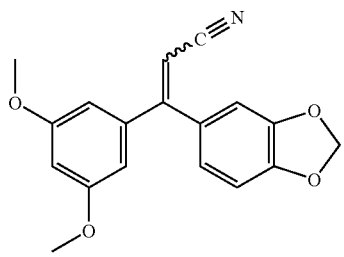 |
| 59 | 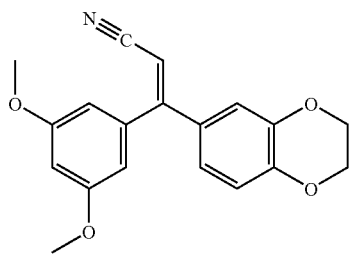 |
| 60 | 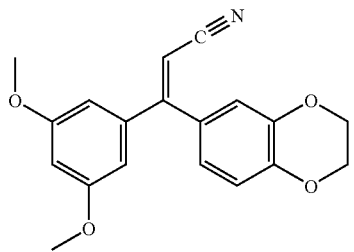 |
| 61 | 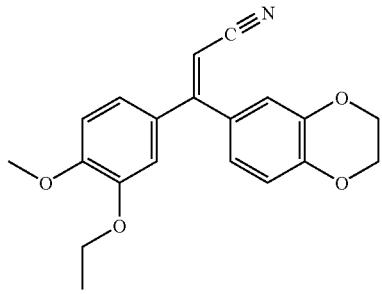 |
| 62 | 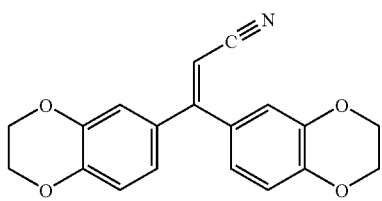 |
| 63 | 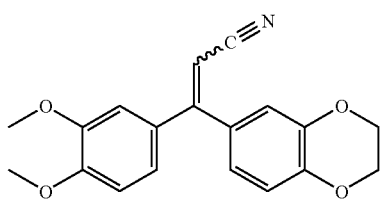 |
TABLE 1-continued
| Comp. | Structure |
|---|---|
| 64 | 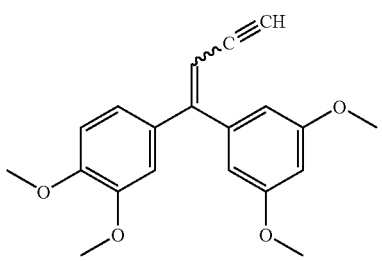 |
| 65 | 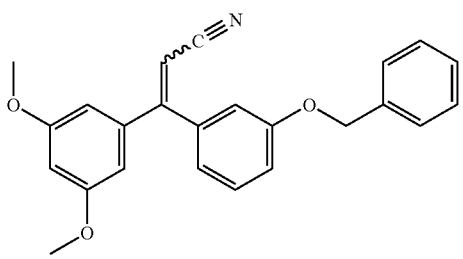 |
| 66 | 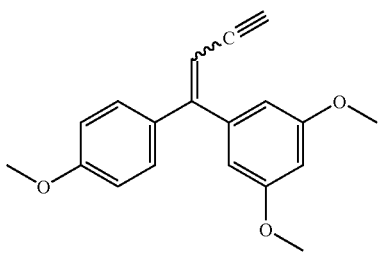 |
| 67 | 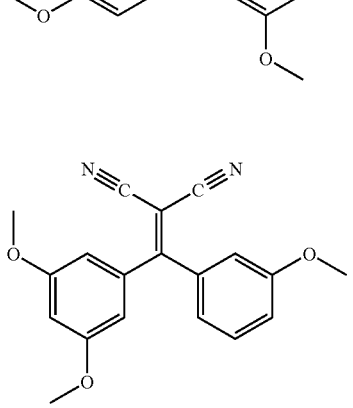 |
| 68 | 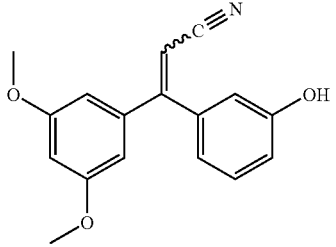 |

TABLE 1-continued

| Comp. | Structure |
|---|---|
| 69 | (structure) |
| 70 | (structure) |
| 71 | (structure) |
| 72 | (structure) |
| 73 | (structure) |
| 74 | (structure) |
| 75 | (structure) |
| 76 | (structure) |
| 77 | (structure) |
| 78 | (structure) |

TABLE 1-continued
| Comp. | Structure |
|---|---|
| 79 | 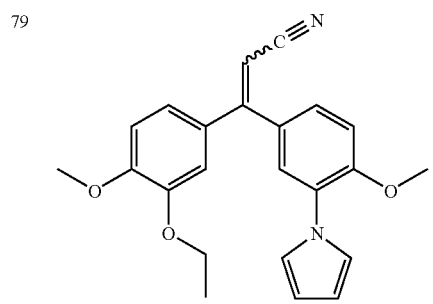 |
| 80 | 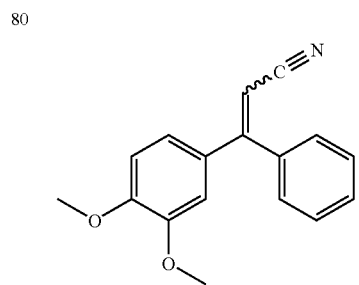 |
| 81 | 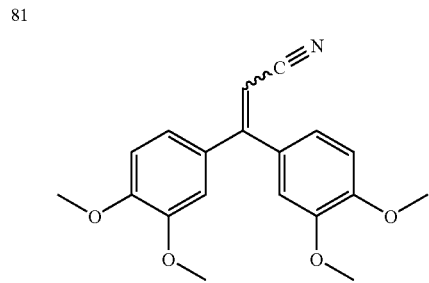 |
| 82 | 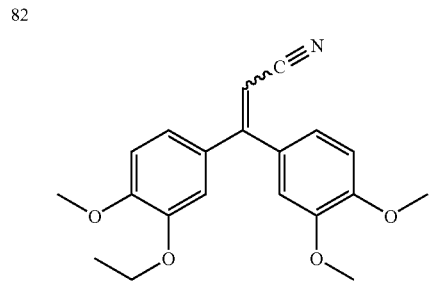 |
| 83 | 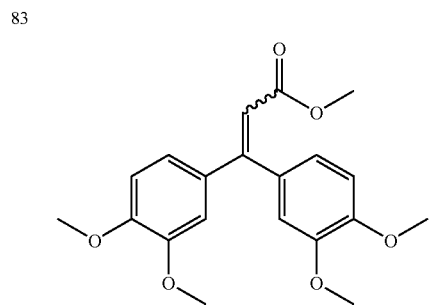 |
| 84 | 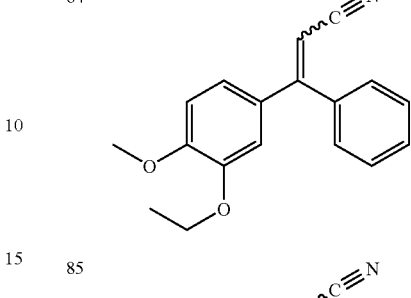 |
| 85 | 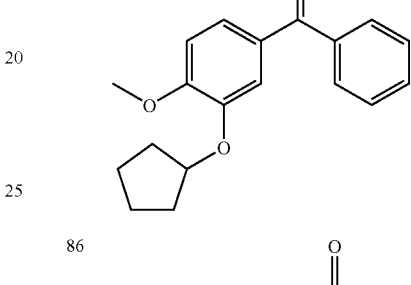 |
| 86 | 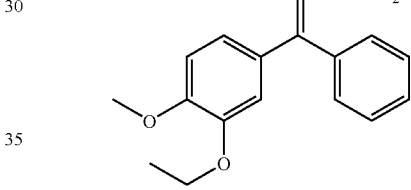 |
| 87 | 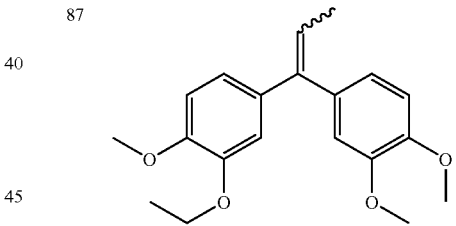 |
| 88 | 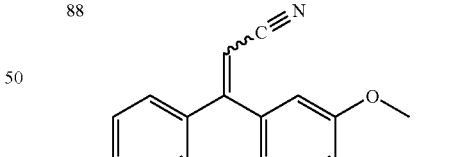 |
| 89 | 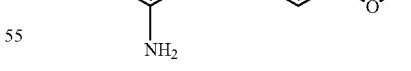 |

TABLE 1-continued
| Comp. | Structure |
|---|---|
| 90 | 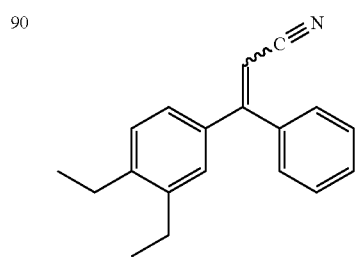 |
| 91 | 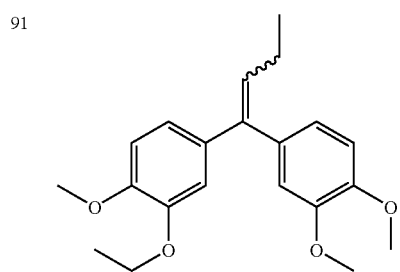 |
| 92 | 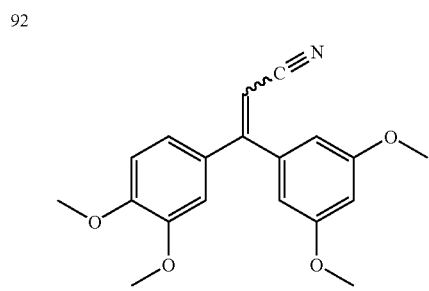 |
| 93 | 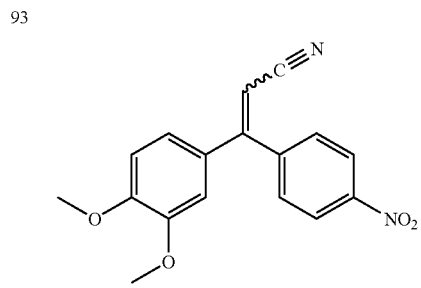 |
| 94 | 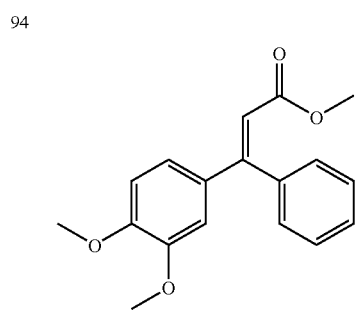 |
| 95 | 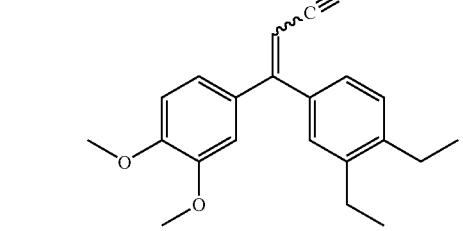 |
| 96 | 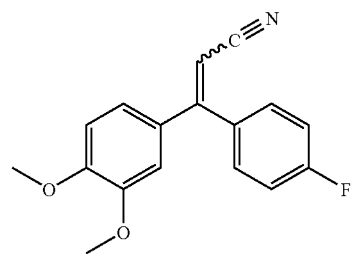 |
| 97 | 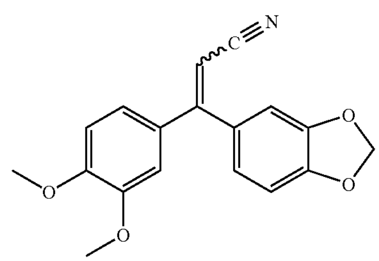 |
| 98 | 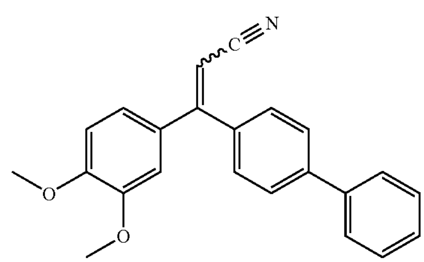 |
| 99 | 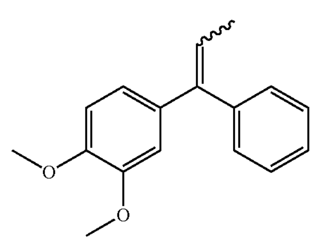 |
| 100 | 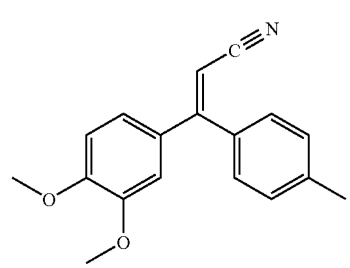 |

TABLE 1-continued
| Comp. | Structure |
|---|---|
| 101 | 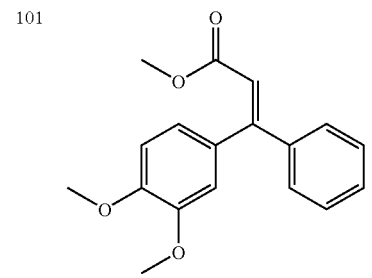 |
| 102 | 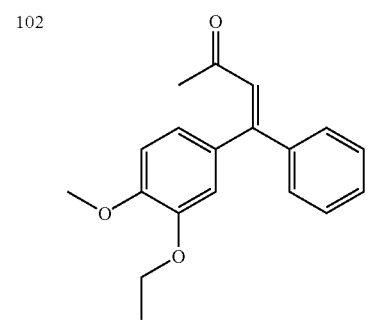 |
| 103 | 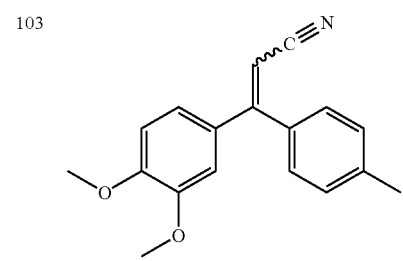 |
| 104 | 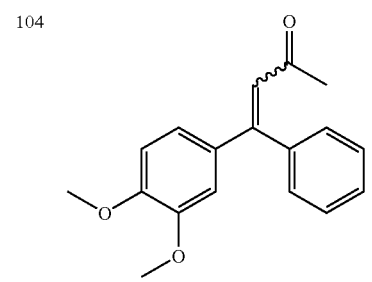 |
| 105 | 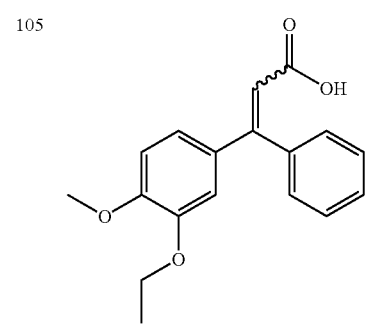 |
| 106 | 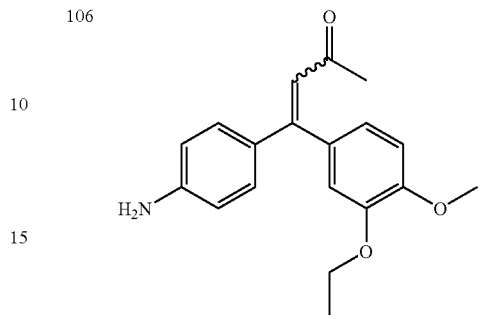 |
| 107 | 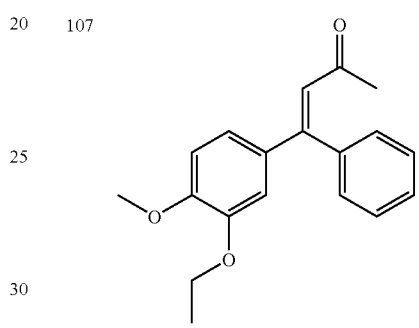 |
| 108 | 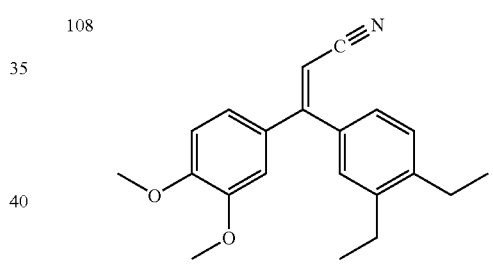 |
| 109 | 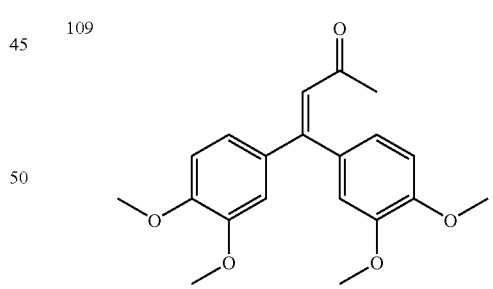 |
| 110 | 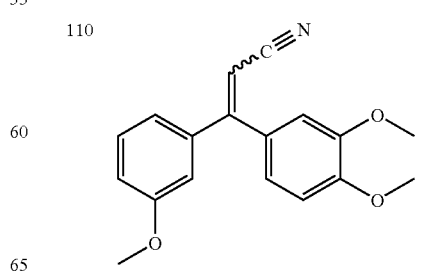 |

TABLE 1-continued
| Comp. | Structure |
|---|---|
| 111 | 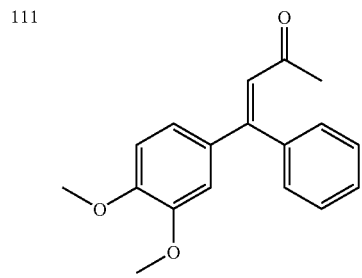 |
| 112 | 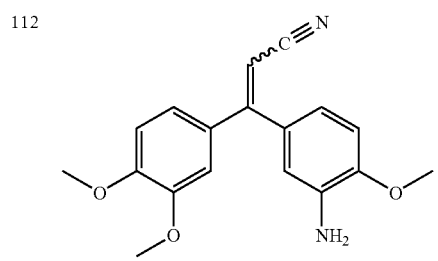 |
| 113 | 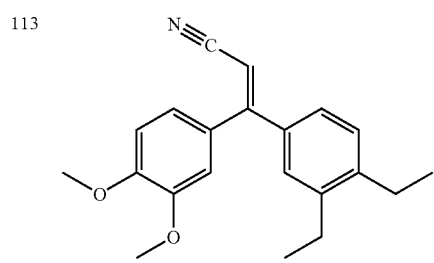 |
| 114 | 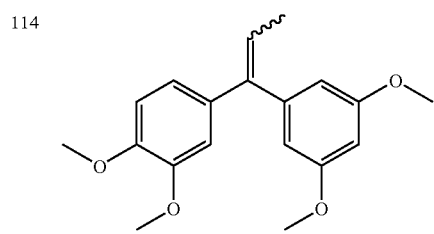 |
| 115 | 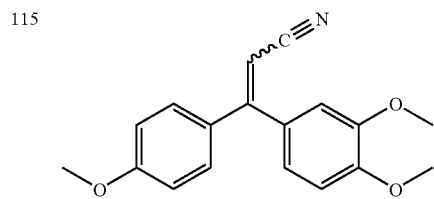 |
| 116 | 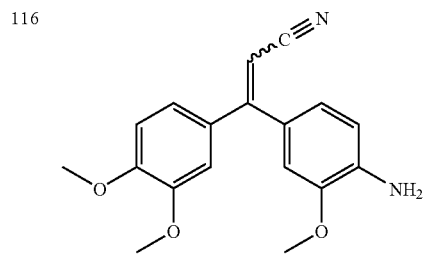 |
| 117 | 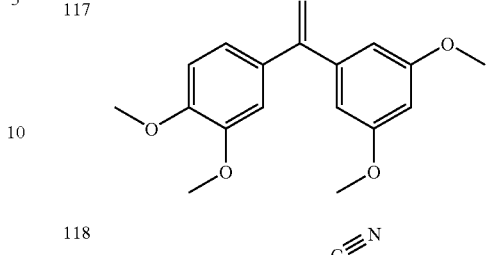 |
| 118 | 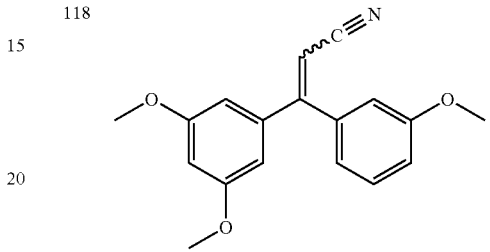 |
| 119 | 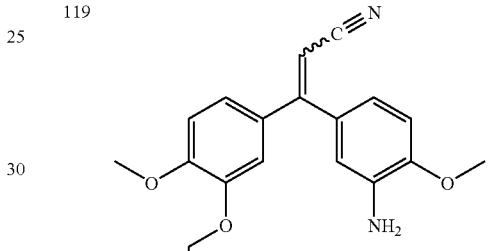 |
| 120 | 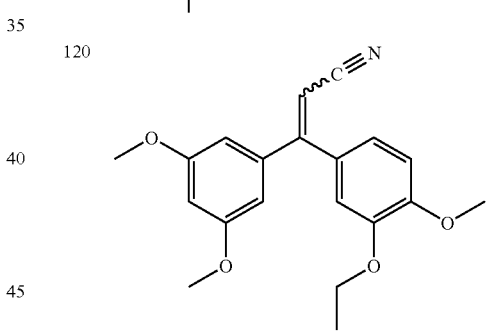 |
| 121 | 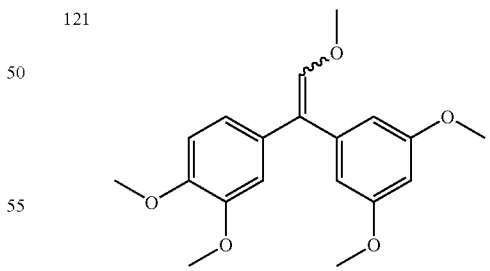 |
| 122 | 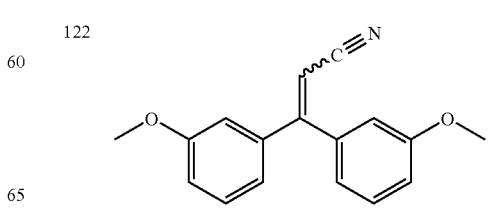 |

TABLE 1-continued
| Comp. | Structure |
|---|---|
| 123 | 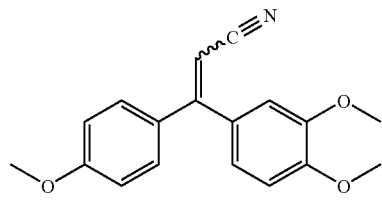 |
| 124 | 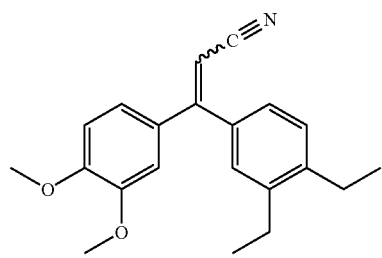 |
| 125 | 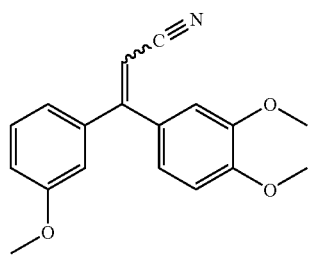 |
| 126 | 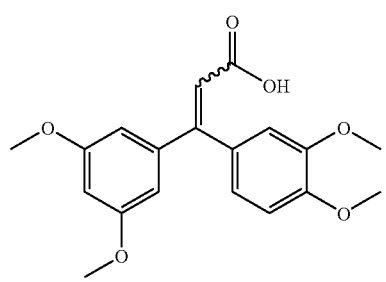 |
| 127 | 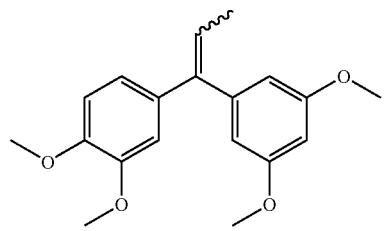 |
| 128 | 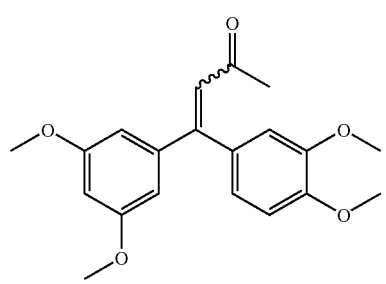 |
| 129 | 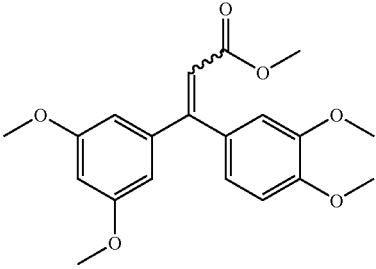 |
| 130 | 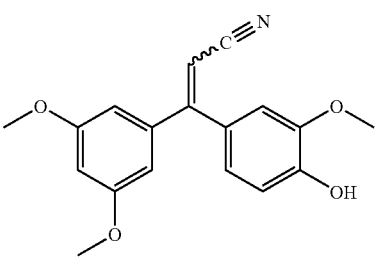 |
| 131 |  |
| 132 |  |
| 133 |  |

TABLE 1-continued
| Comp. | Structure |
|---|---|
| 134 | 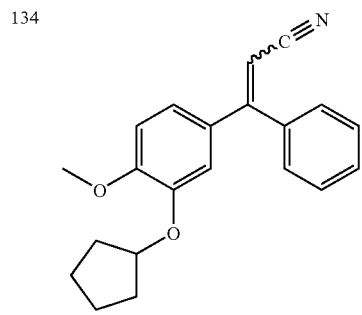 |
| 135 | 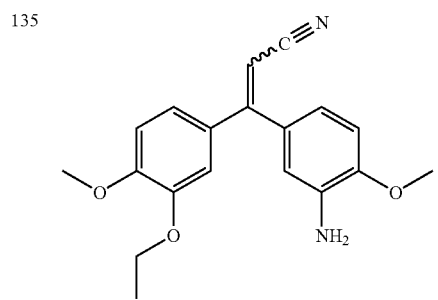 |
| 136 | 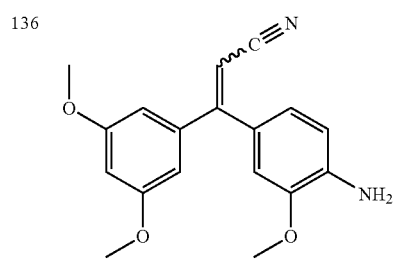 |
| 137 | 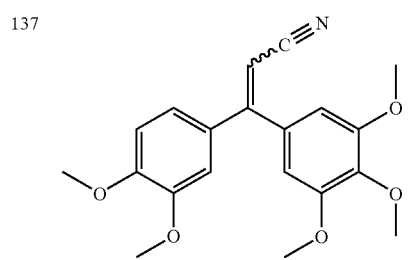 |
| 138 | 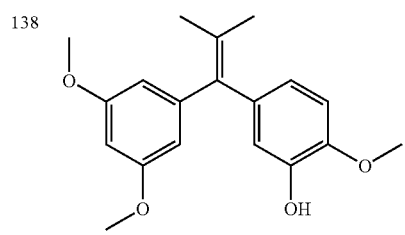 |
| 139 | 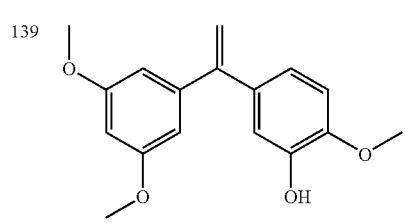 |
| 140 | 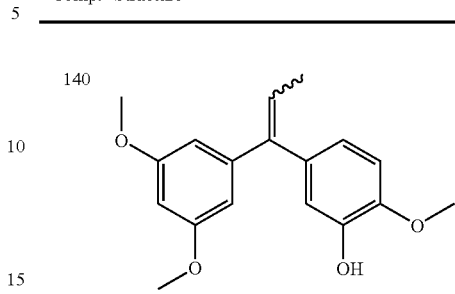 |
| 141 | 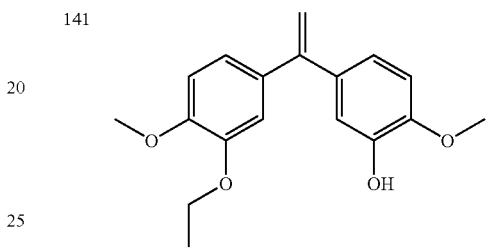 |
| 142 | 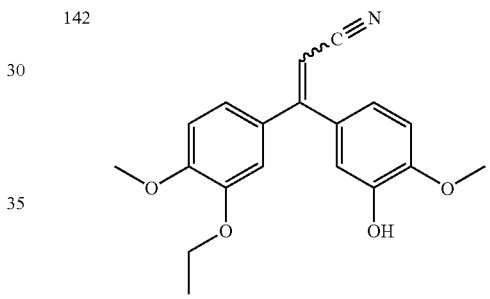 |
| 143 | 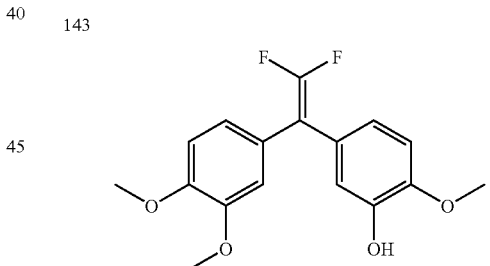 |
| 144 | 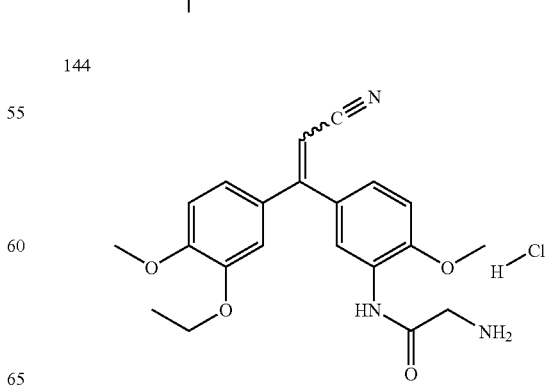 |

TABLE 1-continued
| Comp. | Structure |
|---|---|
| 145 | 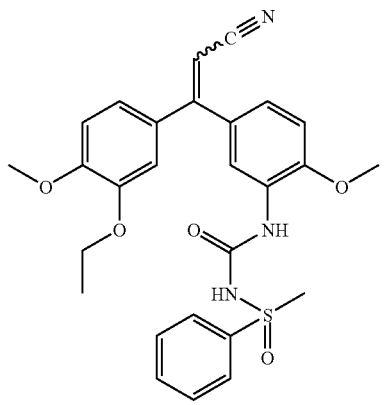 |
| 146 | 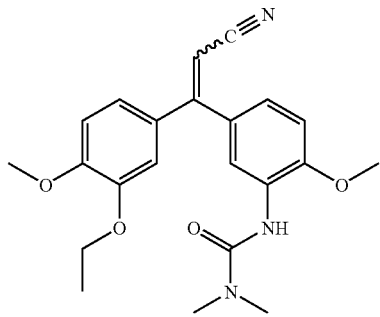 |
| 147 | 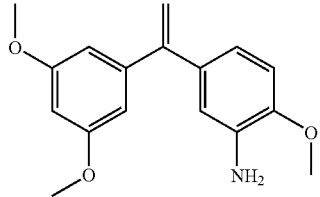 |
| 148 | 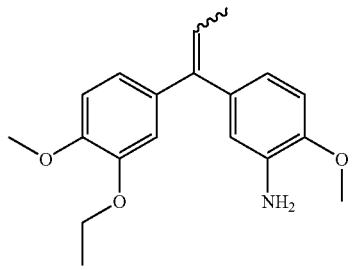 |
| 149 | 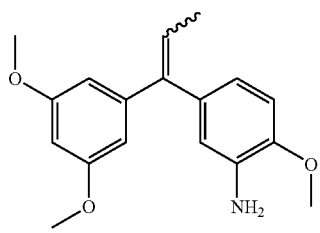 |
| 150 | 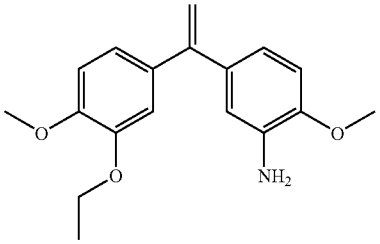 |
| 151 | 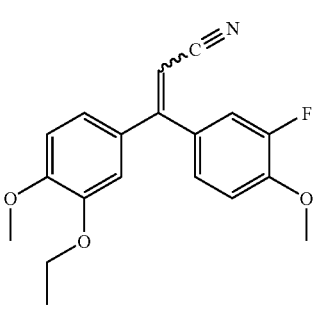 |
| 152 | 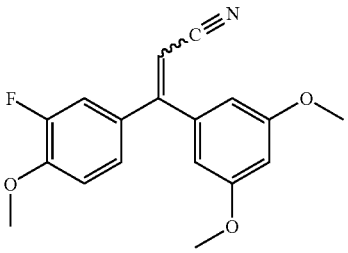 |
| 153 | 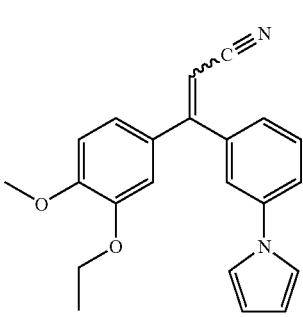 |
| 154 | 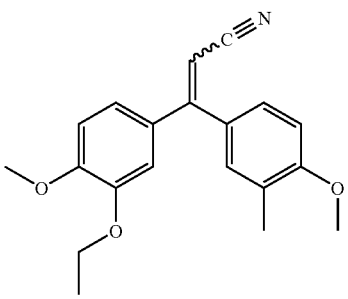 |

TABLE 1-continued
| Comp. | Structure |
|---|---|
| 155 | 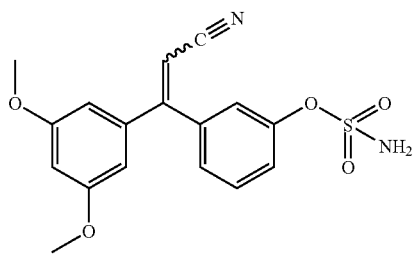 |
| 156 | 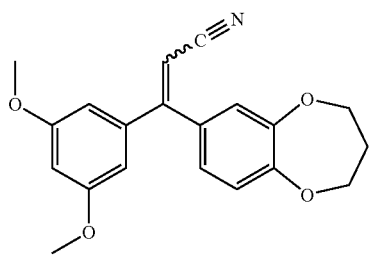 |
| 157 | 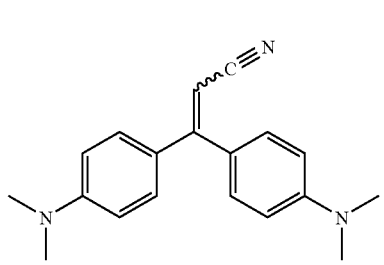 |
| 158 | 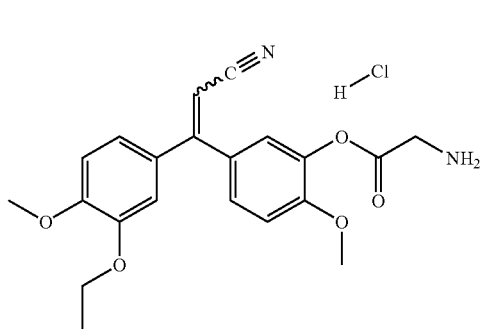 |
| 159 | 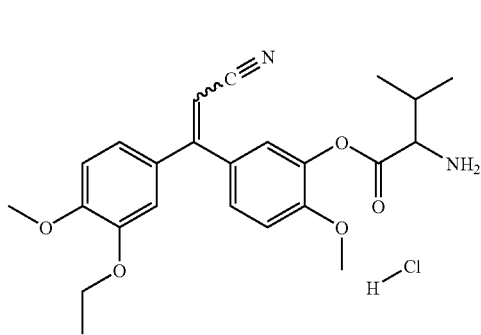 |
| 160 | 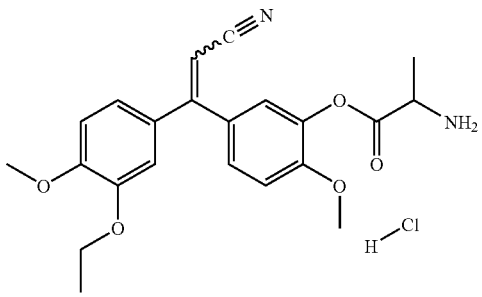 |
| 161 | 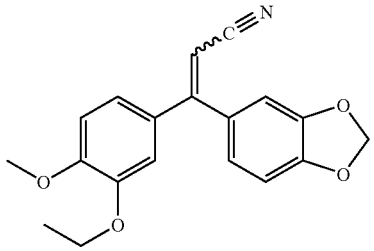 |
| 162 | 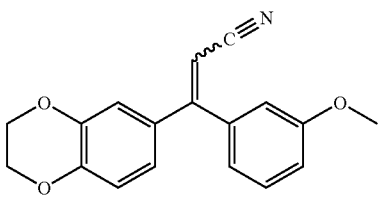 |
| 163 | 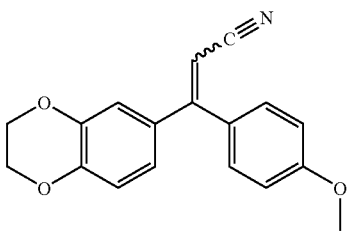 |
| 164 | 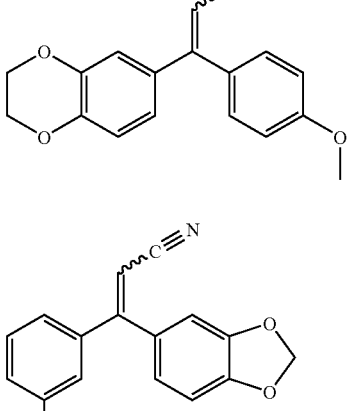 |
| 165 | 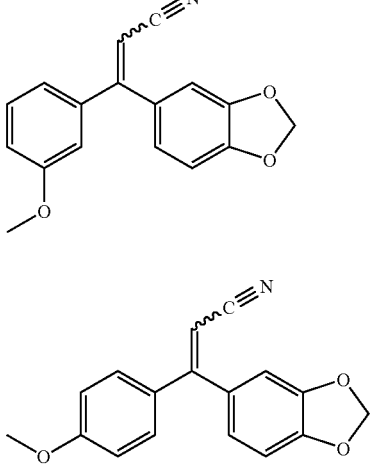 |

TABLE 1-continued

| Comp. | Structure |
|---|---|
| 166 | 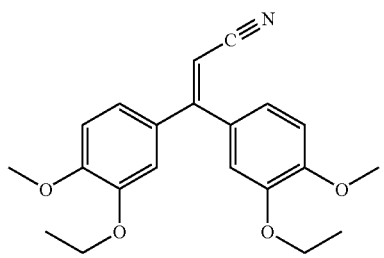 |
| 167 | 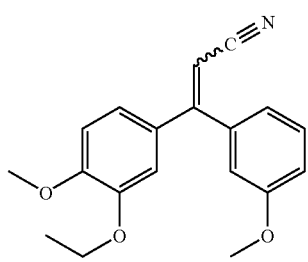 |
| 168 | 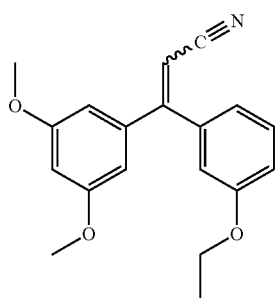 |
| 169 | 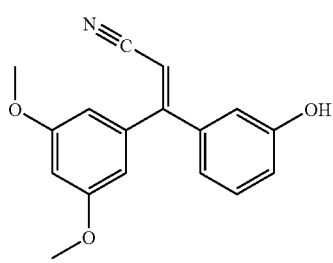 |
| 170 | 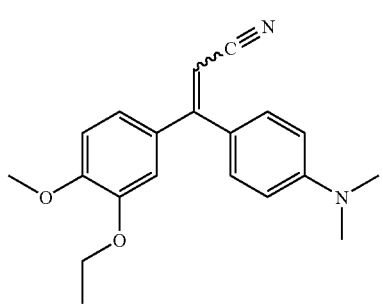 |
| 171 | 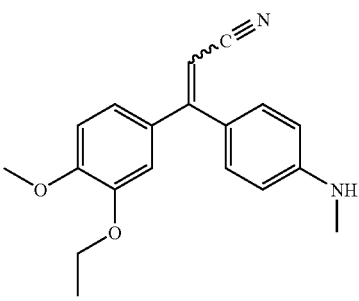 |
| 172 | 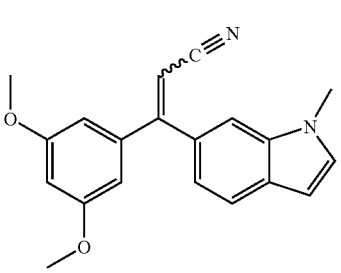 |
| 173 | 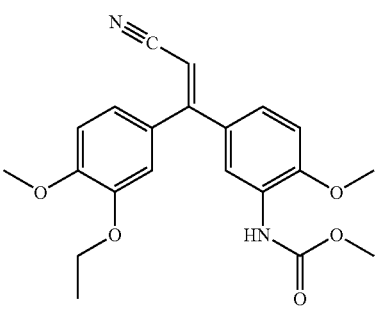 |
| 174 | 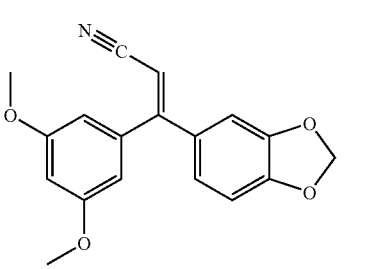 |
| 175 | 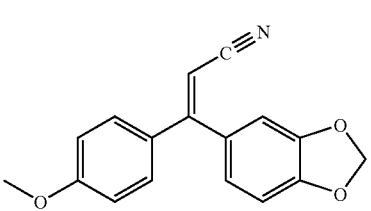 |

Compounds of the invention also include those set forth in PCT International Publication No. WO 98/06692, published Feb. 19, 1998 (see, e.g., formula I at page 6, line 6 to page 7, line 11 and Examples 1-30) and U.S. Pat. No. 5,929,117, issued Jul. 22, 1999 (see, e.g., formula I at column 4, line 45 to column 5, line 37 and Examples 1-34), each of which is incorporated by reference herein in its entirety.

In a particular embodiment, the compounds of the invention include: 3,3-bis-(3,4-dimethoxyphenyl)acrylonitrile, 3,3-bis-(3-ethoxy-4-methoxyphenyl)acrylonitrile, methyl 3,3-bis-(3-ethoxy-4-methoxyphenyl)-propenoate, methyl 3-(3-ethoxy-4-methoxyphenyl)-3-phenylpropenoate, 3-(3-propoxy-4-methoxyphenyl)-3-phenylacrylonitrile, 3-(3-ethoxy-4-methoxyphenyl)-3-phenylacrylonitrile, 3,3-bis-(3-cyclopentoxy-4-methoxyphenyl)-acrylonitrile, methyl 3-(3-cyclopentoxy-4-methoxyphenyl)-3-phenylpropenoate, 3-(3-cyclopentoxy-4-methoxyphenyl)-3-phenylacrylonitrile, 3-(3-cyclopentoxy-4-methoxyphenyl)-3-phenylpropene, 1-(3-cyclopentoxy-4-methoxyphenyl)-1-phenylpropane, 3-(3-cyclopentoxy-4-methoxyphenyl)-3-phenylpropanenitrile, methyl 3-(3-cyclopentoxy-4-methoxyphenyl)-3-phenylpropanoate, 3-(3-ethoxy-4-methoxyphenyl)-3-phenylpropanenitrile, methyl 3-(3-ethoxy-4-methoxyphenyl)-3-phenylpropanoate, 3,3-bis-(3,4-dimethoxyphenyl)-propanenitrile, 3,3-bis-(3-ethoxy-4-methoxyphenyl)propanenitrile, 3-(3,4-dimethoxyphenyl)-3-phenylacrylonitrile, 3-(3-ethoxy-4-methoxyphenyl)-3-naphthylpropanenitrile, 3-(3,4-dimethoxyphenyl)-3-phenylpropanenitrile; 3-(3,4-dimethoxyphenyl)-3-(3-ethoxy-4-methoxyphenyl)propanenitrile, 4,4-bis-(3,4-dimethoxyphenyl)but-3-en-2-one; 4-(3,4-dimethoxyphenyl)-4-(3-ethoxy-4-methoxyphenyl)but-3-en-2one; 4-(3,4-dimethoxyphenyl)-4-phenylbut-3-en-2-one; 4-(3,4-dimethoxyphenyl)-4-(3-cyclopentoxy-4-methoxyphenyl)but-3-en-2-one; 4-(3,4-dimethoxyphenyl)-4-(3-indan2-yloxy-4-methoxyphenyl)but-3-en-2-one; 4-(3-ethoxy-4-methoxyphenyl)-4-(4-pyridyl)but-3-en-2-one; 4-(3-ethoxy-4-methoxyphenyl)-4-(4-pyridyl)butan-2-one; 4-(3-cyclopentoxy-4-methoxyphenyl)-4-(4-pyridyl)but-3-en-2-one; 4-(3-cyclopentoxy-4-methoxyphenyl)-4-(4-pyridyl)butan-2-one; methyl 3-(3-cyclopentoxy-4-methoxyphenyl)-3-(4-pyridyl)prop-2-enoate; methyl 3-(3-ethoxy-4-methoxyphenyl)-3-(4-pyridyl)prop-2-enoate; methyl 3-(3-ethoxy-4-methoxyphenyl)-3-(4-pyridyl)propanoate; 4-(3-ethoxy-4-methoxyphenyl)-4-(2-furyl)but-3-en-2-one; 3-(3-ethoxy-4-methoxyphenyl)-3-(2-furyl)prop-2-enenitrile; 3-(3-ethoxy-4-methoxyphenyl)-3-(4-pyridyl)prop-2-enenitrile; 3-(3-ethoxy-4-methoxyphenyl)-3-(4-pyridyl)propanenitrile; 3-(3-cyclopentoxy-4-methoxyphenyl)-3-(4-pyridyl)prop-2-enenitrile; 3-(3-cyclopentoxy-4-methoxyphenyl)-3-(4-pyridyl)propanenitrile; 4-(3,4-dimethoxyphenyl)-4-(4-methoxy-3-prop-1-enylphenyl)but-3-en-2-one; 4-(3,4-dimethoxyphenyl)-4-(4-methoxy-3-prop-1-enylphenyl)but-3-en-2-one; 4,4-bis-(3,4-dimethoxyphenyl)butan-2-one; 4-(3,4-dimethoxyphenyl)-4-(3-ethoxy-4-methoxyphenyl)butan-2-one; 4-(3,4-dimethoxyphenyl)-4-(3-(cyclopentylidenemethyl)-4-methoxyphenyl)butan-2-one; 4-(3,4-dimethoxyphenyl)-4-(4-methoxy-3-prop-1-enylphenyl)butan-2-one; 4,4-bis-(3-ethoxy-4-methoxyphenyl)but-3-en-2-one; 3-(3,4-dimethoxyphenyl)-3-(3-(cyclopentylidenemethyl)-4-methoxyphenyl)prop-2-enenitrile; 3-(3-(cyclopentylidenemethyl)-4-methoxyphenyl)-3-phenyl-prop-2-enenitrile; 1-(3,4-dimethoxyphenyl)-1-(3-ethoxy-4-methoxyphenyl)pentan-3-one; 1-(3,4-dimethoxyphenyl)-1-(3-ethoxy-4-methoxyphenyl)pent-1-en-3-one; 1,1-bis-(3,4-dimethoxyphenyl)pentan-3-one; 3-(3,4-dimethoxyphenyl)-3-(3-(cyclopentylidenemethyl)-4-methoxyphenyl)prop-2-enenitrile; 3-(3-(cyclopentylidenemethyl)-4-methoxyphenyl)-3-phenyl-propanenitrile; 3,3-bis-(3-(cyclopentylidenemethyl)-4-methoxyphenyl)propanenitrile; 3,3-bis-(3-(cyclopentylidenemethyl)-4-methoxyphenyl)prop-2-enenitrile; 3-(3,4-dimethoxyphenyl)-3-(3-(cyclopentylidenemethyl)-4-methoxyphenyl)prop-2-enamide; 3-(3-(cyclopentylidenemethyl)-4-methoxyphenyl-3-phenyl propanamide; 3,3-bis-(3-(cyclopentylidenemethyl)-4-methoxyphenyl)propanamide; 3,3-bis-(3-(cyclopentylidenemethyl)-4-methoxyphenyl)prop-2-enamide; 3-(3,4-dimethoxyphenyl)-3-(3-ethoxy-4-methoxyphenyl)prop-2-enamide; 3,3-bis-(3-ethoxy-4-methoxyphenyl)prop-2-enamide; 3,3-bis-(3,4-dimethoxyphenyl)prop-2-enamide; 3,3-bis-(3-ethoxy-4-methoxyphenyl)propanamide; 3,3-bis-(3,4-dimethoxyphenyl)propanamide; 4-(3,4-dimethoxyphenyl)-4-(4-methoxy-3-exo-norbornyloxyphenyl)but-3-en-2-o ne; 3-(3,4-dimethoxyphenyl)-3-(4-methoxy-3-exo-norbornyloxyphenyl)prop-2-enenitrile; 3-(3,4-dimethoxyphenyl)-3-(3,4-methylenedioxyphenyl)prop-2-enenitrile; 3-(4-aminophenyl)-3-(3,4-dimethoxyphenyl)prop-2-enenitrile; 3-(4-aminophenyl)-3-(3-ethoxy-4-dimethoxyphenyl)prop-2-enenitrile; 3-(3,4-dimethoxyphenyl)-3-(3-ethoxy-4-methoxyphenyl)acrylonitrile; 3-(3,4-dimethoxyphenyl)-3-phenylacetate; 3-phenyl-3-(3'-ethoxy-4-methoxyphenyl)acrylamide; 1-(3,4-dimethoxyphenyl)-1-phenylprop-1-ene; 1-(3,4-dimethoxyphenyl)-1-(3-ethoxy-4-methoxyphenyl)prop-1-ene; 1-(3,4-dimethoxyphenyl)-1-(3-ethoxy-4-methoxyphenyl)but-1-ene; 3-(3-ethoxy-4-methoxyphenyl)-3-phenylacrylonitrile; 3-(3-ethoxy-4-methoxyphenyl)-3-phenylpropionitrle; 3-(3,4-dimethxyphenyl)-3-(3',5'-dimethoxyphenyl)-acrylonitrile; 3-(3,4-dimethoxyphenyl)-3-(3'-nitrophenyl)acrylonitrile; 3-(3'-aminophenyl)-3-(3,4-dimethoxyphenyl)acrylonitrile; 3,4-dimethoxy-3'-aminobenzophenone; 3-(3,4-dimethoxyphenyl)-3-(4-nitrophenyl)acrylonitrile; 3-(4-aminophenyl)-3-(3,4-dimethoxyphenyl)acrylonitrile; 3,4-dimethoxy-4'aminobenzophenone; 3-(3,4-dimethoxyphenyl)-3-(4-methylphenyl)acrylonitrile; 3-(4-biphenylyl)-3-(3,4-dimethoxyphenyl)acrylonitrile; 3-(3,4-dimethoxyphenyl)-3-(4'-fluorophenyl)acrylonitrile; 3-(3,4-dimethoxyphenyl)-3-naphth-2-ylacrylonitrile; 3-(3,4-dimethoxyphenyl)-3-(3,4-methylenedioxyphenyl)acrylonitrile; 3-(3,4-dimethoxyphenyl)-3-pyridine-4-ylacrylonitrile; 3-(3,4-dimethoxyphenyl)-3-pyridin-2-ylacrylonitrile; 3-(3,4-dimethoxyphenyl)-3-(2-furyl)acrylonitrile; 3-(3,4-diethylphenyl)-3-phenylacrylonitrile; 3-(3,4-diethylphenyl)-3-(3,4-dimethoxyphenyl)acrylonitrile; 4-(3-ethoxy-4-methoxyphenyl)-4-phenyl-3-butan-2-one; 3-(3,4-dimethoxyphenyl)-3-(naphth-1-yl)acrylonitrile; 3-(3,4-dimethoxyphenyl)-3-(2,5-dichlorophenyl)acrylonitrile; 2',6',3,4-tetramethoxybenzophenone; and pharmaceutically acceptable salts, solvates and hydrates thereof.

In a particular embodiment, the invention encompasses compounds that inhibit or reduce tubulin polymerization and/or stability. In a specific embodiment, the invention encompasses compounds that inhibit or reduce tubulin polymerization or stability and inhibit or reduce the expression one or more activities of tumor necrosis factor-α (TNF-α). In another embodiment, the invention encompasses compounds that inhibit or reduce tubulin polymerization or stability and inhibit or reduce the expression of one or more activities of PDE4. In another embodiment, the invention encompasses compounds of formula I that inhibit or reduce tubulin polymerization or stability, inhibit or reduce the expression of one or more activities of TNF-α, and inhibit or reduce the expression of one or more activities of PDE4. In yet another embodiment, the invention encompasses compounds that arrest the cell cycle in $G_2$/M phase.

As discussed above, certain compounds of the invention may contain one or more chiral atoms. Thus, the invention encompasses all stereoisomers (i.e., geometric isomers) including conformational and configurational (e.g., enantiomers, diastereoisomers, and mixtures thereof). In one embodiment, the invention includes the racemic or either the R- or S-enantiomers of all the compounds described herein. The enantiomers may each be provided in a form substantially free of the other enantiomer (e.g., at least 75% free (w/w), at least 90% free (w/w) or at least 99% free (w/w)) or as mixtures (e.g., racemic mixtures).

The compounds of the invention also contain olefins which, if asymmetrically substituted, can exist in both the E and Z or cis and trans configurations. Thus, the invention encompasses both the E and Z and cis and trans olefin isomers of these compounds. For example, a compound whose structure is depicted as:

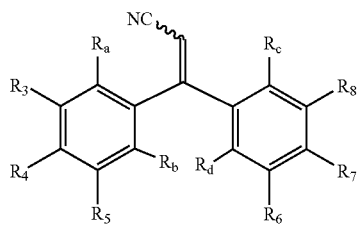

is understood to encompass both the E and Z olefin isomers having the structures:

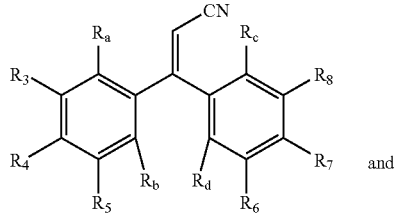

and

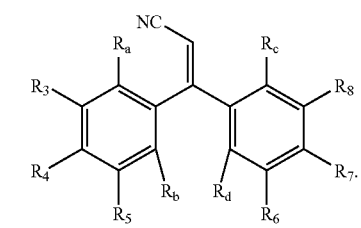

4.1 Methods for Making Compounds of the Invention

Compounds of the invention can be made using conventional organic syntheses. By way of example and not limitation, a compound of the invention having the formula I supra may be prepared as outlined in Schemes 1-4.

Scheme 1 shows how compounds of formula I can be made using a Friedel-Crafts acylation process.

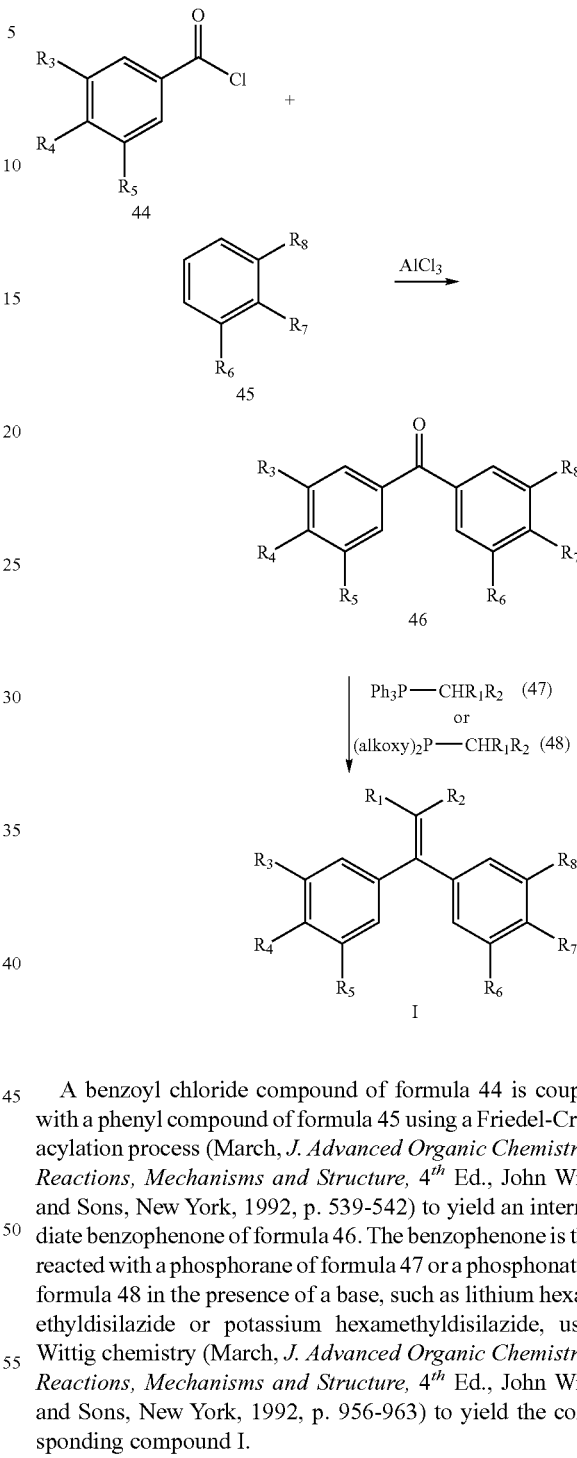

A benzoyl chloride compound of formula 44 is coupled with a phenyl compound of formula 45 using a Friedel-Crafts acylation process (March, *J. Advanced Organic Chemistry—Reactions, Mechanisms and Structure*, 4$^{th}$ Ed., John Wiley and Sons, New York, 1992, p. 539-542) to yield an intermediate benzophenone of formula 46. The benzophenone is then reacted with a phosphorane of formula 47 or a phosphonate of formula 48 in the presence of a base, such as lithium hexamethyldisilazide or potassium hexamethyldisilazide, using Wittig chemistry (March, *J. Advanced Organic Chemistry—Reactions, Mechanisms and Structure*, 4$^{th}$ Ed., John Wiley and Sons, New York, 1992, p. 956-963) to yield the corresponding compound I.

In one embodiment, the base used in the Wittig reaction is LHMDS.

In another embodiment, the base used in Wittig reaction is KHMDS.

General Procedure A—Fridel-Crafts Acylation

To a 0.5 to 1.0 M solution of a phenyl compound of formula 45 (about 1 eq) in methylene chloride at 0° C. is added aluminum trichloride (about 1 eq). To the resulting mixture is added a benzoyl chloride of formula 44 (about 1 eq) and the reaction is allowed to warm to room temperature. The reaction mixture is then diluted with methylene chloride, washed using water (3×), dried over magnesium sulfate, filtered and concentrated in vacuo to afford a crude residue. The crude residue is purified using flash column chromatography (hexane/EtOAc) to provide a compound of formula 46.

General Procedure B—Wittig Reaction

To a 0.5 to 1.0 M solution of a phosphorane of formula 47 or a phosphonate of formula 48 (about 1 eq) in THF at 0° C. is added KHMDS (about 1.5 eq). The resulting mixture is allowed to warm to room temperature and is then stirred for an additional time of about 15 minutes to about 1 hour, after which time am approximately 1.0 M solution of a benzophenone of formula 46 (about 1.5 eq) in THF is added and the resulting mixture is heated at reflux for about 4 hours to about 36 hours while being monitored using TLC. The reaction is allowed to cool to room temperature and is then concentrated in vacuo to provide a crude residue which is purified using flash column chromatography (hexane/EtOAc) to provide a compound of formula I.

Scheme 2 shows how compounds of formula I can be prepared using Grignard chemistry.

(PCC), pyridinium dichromate (PDC), Jones Reagent, Dess-Martin periodinane, $MnO_2$ and tetra-n-propylperruthenate (TPAP).

In a preferred embodiment the oxidizing agent is PCC.

General Procedure C—Grignard Reaction

To an approximately 0.5M solution of magnesium turnings (about 1.2 eq) in THF is slowly added about one-fourth of the volume of an approximately 0.5M solution of a bromobenzene compound of formula 43 (about 1.2 eq) in THF. The resulting mixture is heated to reflux for about 30 minutes, then the heat source is removed and the remainder of the bromobenzene compound of formula 43 is added dropwise. The resulting mixture is heated to reflux for about 5 hours to about 24 hours, then allowed to cool to room temperature and stirred for about 18 hours at room temperature. The resulting solution is then added to an approximately 0.5 M solution of a benzaldehyde compound of formula 44 in THF at about 0° C. at a rate such that the reaction temperature does not exceed 15° C. during the addition. After the addition is complete, the resulting reaction is allowed to stir for about 12 hours to about 24 hours at room temperature and is then cooled to about 0° C. and quenched with saturated aqueous ammonium chloride. The resulting mixture is extracted using EtOAc (3×) and the combined organic extracts are washed with water (3×), brine, dried over magnesium sulfate and concentrated in vacuo to

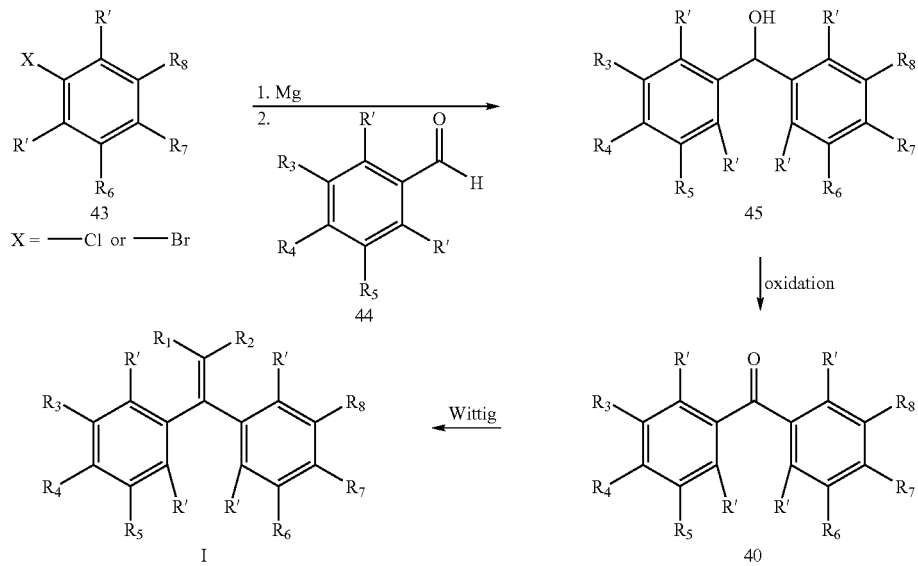

Scheme 2

A bromo- or chlorobenzene of formula 43 is reacted with magnesium to make the corresponding Grignard reagent which is then reacted with a benzaldehyde of formula 44 to provide a diphenyl hydroxy compound of formula 45. Hydroxy compound 45 is then treated with an oxidizing agent to provide an intermediate benzophenone compound of formula 40 which is reacted with an appropriate phosphorane 47 or phosphonate 48, as depicted in Scheme 1 herein above, in a Wittig reaction to provide a compound of formula I.

Suitable oxidizing agents useful in the conversion of a compound of formula 45 to a compound of formula 40 include, but are not limited to pyridinium chlorochromate provide a crude residue which is purified using flash column chromatography (hexane/EtOAc eluent) to provide a hydroxy compound of formula 45.

General Procedure D—Oxidation of a Hydroxy Compound of Formula 45

To an approximately 0.5M solution of a hydroxy compound of formula 45 (about 1 eq) in methylene chloride is added pyridinium chlorochromate (about 1.5 eq) and celite (about 100 mg per 1 mmol of a hydroxy compound of formula 45) and the resulting mixture is allowed to stir for about 6 hours to about 24 hours. The reaction mixture is filtered, the resulting filtercake is washed using methylene chloride and the filtrate and washings are combined and concentrated in vacuo to afford a crude residue which is purified using flash column chromatography to provide a benzophenone compound of formula 40 which can be transformed to a compound of formula I using General Procedure B as described herein above.

Scheme 3 shows the synthesis of compounds of formula I via the palladium catalyzed coupling of a styrene and a bromobenzene.

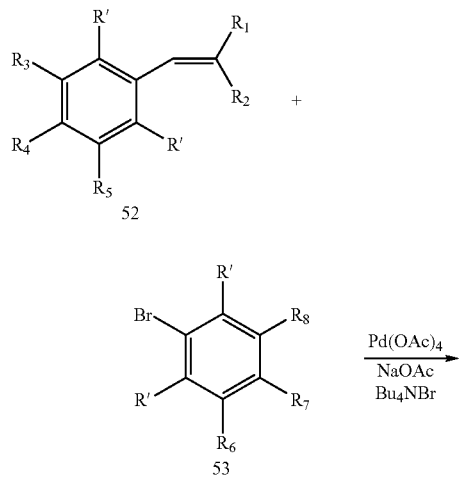

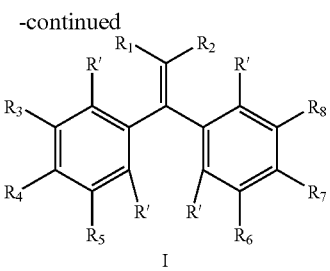

General Procedure E—Palladium-catalyzed Coupling of a Styrene and a Bromobenzene To a suspension of a styrene compound of formula 52 (about 1 eq), a bromobenzene compound of formula 53 (about 1.5 eq), sodium acetate (about 1.7 eq) and tetra-n-butyl ammonium bromide (about 1.1 eq) in DMF is added an approximately 0.5M suspension of Pd(OAc)$_4$ (about 0.03 eq) in DMF. The resulting mixture is heated to 60° C. and allowed to stir at this temperature for about 6 hours to about 18 hours and is then cooled to room temperature and poured into a mixture of water:EtOAc (3:1). The organic phase was collected and the aqueous phase was washed using EtOAc (3×). The combined organic extracts were washed sequentially with water and brine, then dried over magnesium sulfate, filtered and concentrated in vacuo to provide a crude residue which was purified using flash column chromatography to provide a compound of formula I.

Scheme 4 shows methodology useful for making a compound of formula I using phenyllithium intermediates.

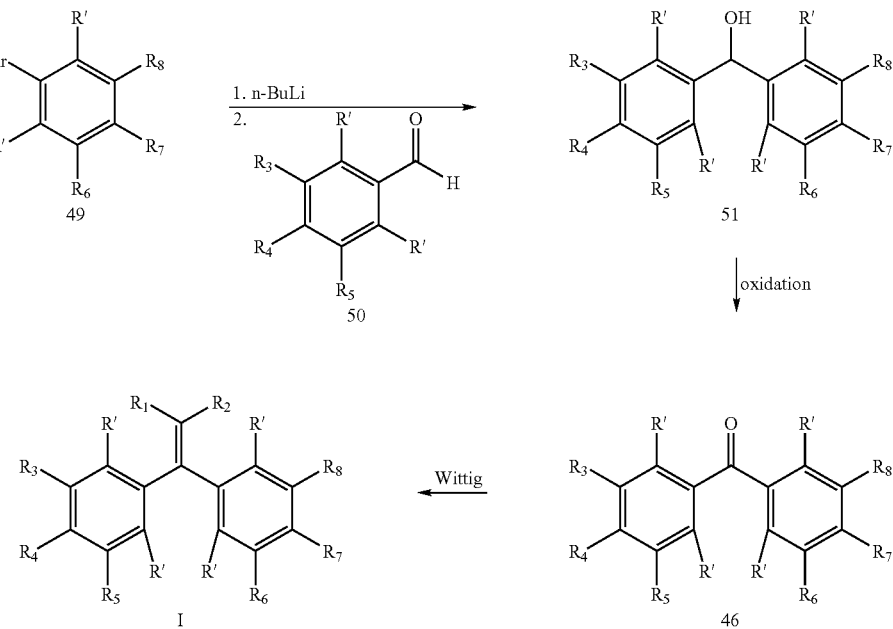

A bromobenzene of formula 49 is reacted with n-butyllithium to make the corresponding intermediate organolithium reagent which is then reacted with a benzaldehyde of formula 50 to provide a diphenyl hydroxy compound of formula 51. Hydroxy compound 51 is then treated with an oxidizing agent to provide an intermediate benzophenone compound of formula 46 which is reacted with an appropriate phosphorane 47 or phosphonate 48, as depicted in Scheme 1 herein above, in a Wittig reaction to provide a compound of formula I.

Suitable oxidizing agents useful in the conversion of a compound of formula 51 to a compound of formula 46 include, but are not limited to pyridinium chlorochromate (PCC), pyridinium dichromate (PDC), Jones Reagent, Dess-Martin periodinane, $MnO_2$ and tetra-n-propylperruthenate (TPAP).

In a preferred embodiment the oxidizing agent is PCC.

It will be obvious to one of ordinary skill in the art of organic chemistry how to prepare the scope of the compounds of the invention using the methodology depicted in Schemes 1-4 and by simple chemical transformations upon the products obtained using the methodology of Schemes 1-4.

Compounds of the invention can also be prepared using the procedures set forth in PCT International Publication No. WO 98/06692, published Feb. 19, 1998 (see, e.g., page 10, line 25 to page 11, line 3 and Examples 1-30) and U.S. Pat. No. 5,929,117, issued Jul. 22, 1999 (see, e.g., column 7, line 57 to column 8, line 14 and Examples 1-34), each of which is incorporated by reference herein in its entirety.

Once synthesized, a compound of the invention can be isolated from chemical precursors or other chemicals using standard purification techniques such as, for example, chromatography (e.g., flash column chromatography and HPLC), asymmetric methods of synthesis, recrystallization and differential solubility.

4.2 Agents Useful in Combination with Compounds of the Invention

The present invention provides methods for preventing, managing, treating, or ameliorating disorders (e.g., proliferative disorders, disorders associated with or characterized by aberrant angiogenesis, disorders prevented, managed or treated by inhibiting or reducing PDE4 expression and/or activity or inhibiting or reducing tubulin polymerization and/or stability, or inflammatory disorders) comprising administering to a subject in need thereof or one or more compounds of the invention and one or more therapies (e.g., one or more prophylactic or therapeutic agents) other than compounds of the invention.

The present invention also provides compositions comprising one or more compounds of the invention and one or more prophylactic or therapeutic agents other than compounds of the invention and methods of preventing, managing, treating, or ameliorating a proliferative disorder or an inflammatory disorder utilizing said compositions. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, RNAi, triple helices and nucleotide sequences encoding biologically active proteins, polypeptides or peptides), antibodies, synthetic or natural inorganic molecules, mimetic agents, and synthetic or natural organic molecules.

Any agent which is known to be useful, or which has been used or is currently being used for the prevention, management, treatment, or amelioration of a disorder (e.g., a proliferative disorder, disorders characterized by or associated with aberrant angiogenesis, proliferative disorders, inflammatory disorders and disorders prevented, managed, treated or ameliorated by inhibiting PDE4, or by reducing or inhibiting tubulin polymerization or stability, or an inflammatory disorder) or one or more symptoms thereof can be used in combination with a compound of the invention in accordance with the invention described herein. See, e.g., Gilman et al., Goodman and Gilman's: The Pharmacological Basis of Therapeutics, Tenth Ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W. B. Saunders, Philadelphia, 1996 for information regarding prophylactic or therapeutic agents which have been or are currently being used for preventing, treating, managing, or ameliorating proliferative disorders or inflammatory disorders or one or more symptoms thereof. Examples of such agents include, but are not limited to, anti-inflammatory agents (e.g., corticosteroids (e.g., prednisone and hydrocortisone), glucocorticoids, steroids, nonsteriodal anti-inflammatory drugs (e.g., aspirin, ibuprofen, diclofenac, and COX-2 inhibitors), beta-agonists, anticholinergic agents and methyl xanthines), immunomodulatory agents, gold injections, sulphasalazine, penicillamine, antiangiogenic agents (e.g., angiostatin, TNF-α antagonists (e.g., anti-TNFα antibodies), and endostatin), anti-fibrotics, anti-emetic agents (e.g., metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron), opioids (e.g., morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene), hematopoietic colony stimulating factors (e.g., filgrastim, pegfilgrastim sargramostim, molgramostim and epoetin alfa), antiemetic agents (e.g., metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron), dapsone, psoralens (e.g., methoxalen and trioxsalen), antihistamines, anti-malarial agents (e.g., hydroxychloroquine), anti-viral agents, antibiotics (e.g., dactinomycin (formerly actinomycin), bleomycin, erythomycin, penicillin, mithramycin, and anthramycin (AMC)), vascular targeting agents (e.g., microtubulin destabilizing drugs, combretastatin A-4 disodium phosphate, ZD6126, AVE8062, Oxi 4503, TZT 1027 and DMXAA), IMiDs® and SelCIDs® (Celgene Corporation, New Jersey) (e.g., Revimid, Actimid, and those disclosed in U.S. Pat. Nos. 6,075,041; 5,877,200; 5,698,579; 5,703,098; 6,429,221; 5,736,570; 5,658,940; 5,728,845; 5,728,844; 6,262,101; 6,020,358; 5,929,117; 6,326,388; 6,281,230; 5,635,517;

5,798,368; 6,395,754; 5,955,476; 6,403,613; 6,380,239; and 6,458,810, each of which is incorporated herein by reference).

4.2.1 Immunodulatory Agents

Any immunomodulatory agent well-known to one of skill in the art may be used in the methods and compositions of the invention.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules, triple helices and nucleic acid molecules encoding immunomodulatory gene products), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, IL-23 TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, anti-IL-12 receptor antibodies, anti-IL-15 receptor antibodies and anti-IL-23 receptor antibodies), anti-cytokine antibodies (e.g., anti-IFN α antibodies, anti-IFN-β antibodies, anti-IFN-γ antibodies, anti-TNF-α antibodies, anti-IL-1β, antibodies, anti-IL-2 antibodies, anti-IL-4 antibodies, anti-IL-6 antibodies, anti-IL-8 antibodies (e.g., ABX-IL-8 (Abgenix)), anti-IL-9 antibodies, anti-IL-10 antibodies, anti-IL-12 antibodies and anti-IL-23 antibodies). In a specific embodiment, a cytokine receptor modulator is IL-4, IL-10, or a fragment thereof. In another embodiment, a cytokine receptor modulator is an anti-IL-1β antibody, anti-IL-6 antibody, anti-IL-12 receptor antibody, or anti-TNF-α antibody. In another embodiment, a cytokine receptor modulator is the extracellular domain of a TNF-α receptor or a fragment thereof. In certain embodiments, a cytokine receptor modulator is not a TNF-α antagonist.

4.2.2 Anti-Angiogenic Agents

Any anti-angiogenic agent well-known to one of skill in the art can be used in the compositions and methods of the invention. Non-limiting examples anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-α, nucleic acid molecules (e.g., antisense molecules or triple helices), organic molecules, inorganic molecules, and small molecules that reduce or inhibit angiogenesis. In particular, examples of anti-angiogenic agents, include, but are not limited to, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, anti-integrin $\alpha_v\beta_3$ antibodies, acid fibroblast growth factor (aFGF) antagonists, basic fibroblast growth factor (bFGF) antagonists, vascular endothelial growth factor (VEGF) antagonists (e.g., anti-VEGF antibodies), and VEGF receptor (VEGFR) antagonists (e.g., anti-VEGFR antibodies).

Examples of integrin $\alpha_v\beta_3$ antagonists include, but are not limited to, proteinaceous agents such as non-catalytic metalloproteinase fragments, RGD peptides, peptide mimetics, fusion proteins, disintegrins or derivatives or analogs thereof, and antibodies that immunospecifically bind to integrin $\alpha_v\beta_3$, nucleic acid molecules, organic molecules, and inorganic molecules. Non-limiting examples of antibodies that immunospecifically bind to integrin $\alpha_v\beta_3$ include 11D2 (Searle). Non-limiting examples of small molecule peptidometric integrin UvP3 antagonists include S836 (Searle) and S448 (Searle). Examples of disintegrins include, but are not limited to, Accutin. The invention also encompasses the use of any of the integrin $\alpha_v\beta_3$ antagonists disclosed in the following U.S. patents and International publications in the compositions and methods of the invention: U.S. Pat. Nos. 5,652,109; 5,652,110; 5,578,704; 5,149,780; 5,196,511; 5,204,445; 5,262,520; 5,306,620; 5,478,725; 5,498,694; 5,523,209; 5,578,704; 5,589,570; 5,652,109; 5,652,110; 5,693,612; 5,705,481; 5,753,230; 5,767,071; 5,770,565; 5,780,426; 5,817,457; 5,830,678; 5,849,692; 5,955,572; 5,985,278; 6,048,861; 6,090,944; 6,096,707; 6,130,231; 6,153,628; 6,160,099; and 6,171,58; and International Publication Nos. WO 95/22543; WO 98/33919; WO 00/78815; WO 00/31248; WO 98/46264; WO 98/40488; and WO 02/070007, each of which is incorporated herein by reference in its entirety.

In a specific embodiment of the invention, an anti-angiogenic agent is endostatin. Naturally occurring endostatin consists of the C-terminal ~180 amino acids of collagen XVIII (cDNAs encoding two splice forms of collagen XVIII have GenBank Accession Nos. AF18081 and AF18082). In another embodiment of the invention, an anti-angiogenic agent is a plasminogen fragment (the coding sequence for plasminogen can be found in GenBank Accession Nos. NM_000301 and A33096). Angiostatin peptides naturally include the four kringle domains of plasminogen, kringle 1 through kringle 4. It has been demonstrated that recombinant kringle 1, 2 and 3 possess the anti-angiogenic properties of the native peptide, whereas kringle 4 has no such activity (Cao et al., 1996, J. Biol. Chem. 271:29461-29467). Accordingly, the angiostatin peptides comprises at least one and preferably more than one kringle domain selected from the group consisting of kringle 1, kringle 2 and kringle 3. In a specific embodiment, the anti-angiogenic peptide is the 40 kDa isoform of the human angiostatin molecule, the 42 kDa isoform of the human angiostatin molecule, the 45 kDa isoform of the human angiostatin molecule, or a combination thereof. In another embodiment, an anti-angiogenic agent is the kringle 5 domain of plasminogen, which is a more potent inhibitor of angiogenesis than angiostatin (angiostatin comprises kringle domains 1-4). In another embodiment of the invention, an anti-angiogenic agent is antithrombin III. Antithrombin III, which is referred to hereinafter as antithrombin, comprises a heparin binding domain that tethers the protein to the vasculature walls, and an active site loop which interacts with thrombin. When antithrombin is tethered to heparin, the protein elicits a conformational change that allows the active loop to interact with thrombin, resulting in the proteolytic cleavage of said loop by thrombin. The proteolytic cleavage event results in another change of conformation of antithrombin, which (i) alters the interaction interface between thrombin and antithrombin and (ii) releases the complex from heparin (Carrell, 1999, Science 285:1861-1862, and references therein). O'Reilly et al. (1999, Science 285:1926-1928) have discovered that the cleaved antithrombin has potent anti-angiogenic activity. Accordingly, in one embodiment, an anti-angiogenic agent is the anti-angiogenic form of antithrombin. In another embodiment of the invention, an anti-angiogenic agent is the 40 kDa and/or 29 kDa proteolytic fragment of fibronectin.

In another embodiment of the invention, an anti-angiogenic agent is a urokinase plasminogen activator (uPA) receptor antagonist. In one mode of the embodiment, the antagonist is a dominant negative mutant of uPA (see, e.g., Crowley et al., 1993, Proc. Natl. Acad. Sci. USA 90:5021-5025). In another mode of the embodiment, the antagonist is a peptide antagonist or a fusion protein thereof (Goodson et al., 1994, Proc. Natl. Acad. Sci. USA 91:7129-7133). In yet another mode of the embodiment, the antagonist is a dominant negative soluble uPA receptor (Min et al., 1996, Cancer Res. 56:2428-2433). In another embodiment of the invention, an anti-angiogenic agent is the 16 kDa N-terminal fragment of prolactin, comprising approximately 120 amino acids, or a biologically active fragment thereof (the coding sequence for prolactin can be found in GenBank Accession No. NM_000948). In another embodiment of the invention, an anti-angiogenic agent is the 7.8 kDa platelet factor-4 fragment. In another embodiment of the invention, an anti-angiogenic agent is a small peptide corresponding to the anti-angiogenic 13 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, the small anti-angiogenic peptides of laminin, fibronectin, procollagen, or EGF, or small peptide antagonists of integrin $\alpha_v\beta_3$ or the VEGF receptor. In another embodiment, the small peptide comprises an RGD or NGR motif. In certain embodiments, an anti-angiogenic agent is a TNF-α antagonist. In other embodiments, an anti-angiogenic agent is not a TNF-α antagonist.

Nucleic acid molecules encoding proteins, polypeptides, or peptides with anti-angiogenic activity, or proteins, polypeptides or peptides with anti-angiogenic activity can be administered to a subject with a disorder (e.g., a disorder characterized by or associated with aberrant angiogenesis, a proliferative disorder, an inflammatory disorder or a disorder prevented, managed, treated or ameliorated by inhibiting PDE4, or by reducing or inhibiting tubulin polymerization or stability) in accordance with the methods of the invention. Further, nucleic acid molecules encoding derivatives, analogs, fragments, or variants of proteins, polypeptides, or peptides with anti-angiogenic activity, or derivatives, analogs, fragments, or variants of proteins, polypeptides, or peptides with anti-angiogenic activity can be administered to a subject with a disorder (e.g., a disorder characterized by or associated with aberrant angiogenesis, a proliferative disorder, an inflammatory disorder or a disorder prevented, managed, treated or ameliorated by inhibiting PDE4, or by reducing or inhibiting tubulin polymerization or stability) in accordance with the methods of the invention. Preferably, such derivatives, analogs, variants, and fragments retain the anti-angiogenic activity of the full-length, wild-type protein, polypeptide, or peptide.

Proteins, polypeptides, or peptides that can be used as anti-angiogenic agents can be produced by any technique well-known in the art or described herein. Proteins, polypeptides or peptides with anti-angiogenic activity can be engineered so as to increase the in vivo half-life of such proteins, polypeptides, or peptides utilizing techniques well-known in the art or described herein. Preferably, anti-angiogenic agents that are commercially available are used in the compositions and methods of the invention. The anti-angiogenic activity of an agent can be determined in vitro and/or in vivo by any technique well-known to one skilled in the art or described herein.

Anti-angiogenic agents and their dosages, routes of administration and recommended usage are known in the art and have been described in such literature as the *Physician's Desk Reference* (57$^{th}$ ed., 2003).

4.2.3 TNF-α Antagonists

Any TNF-α antagonist well-known to one of skill in the art can be used in the compositions and methods of the invention. Non-limiting examples of TNF-α antagonists include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-α, nucleic acid molecules (e.g., antisense molecules or triple helices), organic molecules, inorganic molecules, and small molecules that block, reduce, inhibit or neutralize a function, an activity and/or the expression of TNF-α. In various embodiments, a TNF-α antagonist reduces the function, activity and/or expression of TNF-α by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

Examples of antibodies that immunospecifically bind to TNF-α include, but are not limited to, infliximab (REMICADE®; Centacor), D2E7 (Abbott Laboratories/Knoll Pharmaceuticals Co., Mt. Olive, N.J.), CDP571 which is also known as HUMICADE™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379). The present invention also encompasses the use of the antibodies that immunospecifically bind to TNF-α disclosed in the following U.S. patents in the compositions and methods of the invention: U.S. Pat. Nos. 5,136,021; 5,147,638; 5,223,395; 5,231,024; 5,334,380; 5,360,716; 5,426,181; 5,436,154; 5,610,279; 5,644,034; 5,656,272; 5,658,746; 5,698,195; 5,736,138; 5,741,488; 5,808,029; 5,919,452; 5,958,412; 5,959,087; 5,968,741; 5,994,510; 6,036,978; 6,114,517; and 6,171,787; each of which are herein incorporated by reference in their entirety. Examples of soluble TNF-α receptors include, but are not limited to, sTNF-R1 (Amgen), etanercept (ENBREL™; Immunex) and its rat homolog RENBREL™, soluble inhibitors of TNF-α derived from TNFrI, TNFrII (Kohno et al., 1990, Proc. Natl. Acad. Sci. USA 87:8331-

8335), and TNF-α Inh (Seckinger et al., 1990, Proc. Natl. Acad. Sci. USA 87:5188-5192).

In one embodiment, a TNF-α antagonist used in the compositions and methods of the invention is a soluble TNF-α receptor. In a specific embodiment, a TNF-α antagonist used in the compositions and methods of the invention is etanercept (ENBREL™; Immunex) or a fragment, derivative or analog thereof. In another embodiment, a TNF-α antagonist used in the compositions and methods of the invention is an antibody that immunospecifically binds to TNF-α. In a specific embodiment, a TNF-α antagonist used in the compositions and methods of the invention is infliximab (REMICADE®; Centacor) a derivative, analog or antigen-binding fragment thereof.

Other TNF-α antagonists encompassed by the invention include, but are not limited to, IL-10, which is known to block TNF-α production via interferon γ-activated macrophages (Oswald et al. 1992, Proc. Natl. Acad. Sci. USA 89:8676-8680), TNFR-IgG (Ashkenazi et al., 1991, Proc. Natl. Acad. Sci. USA 88:10535-10539), the murine product TBP-1 (Serono/Yeda), the vaccine CytoTAb (Protherics), antisense molecule 104838 (ISIS), the peptide RDP-58 (SangStat), thalidomide (Celgene), CDC-801 (Celgene), DPC-333 (Dupont), VX-745 (Vertex), AGIX-4207 (AtheroGenics), ITF-2357 (Italfarmaco), NPI-13021-31 (Nereus), SCIO-469 (Scios), TACE targeter (Immunix/AHP), CLX-120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), and anti-p38 MAPK agents by Uriach.

TNF-α antagonists and their dosages, routes of administration and recommended usage are known in the art and have been described in such literature as the *Physician's Desk Reference* (57$^{th}$ ed., 2003).

4.2.4 Anti-Inflammatory Agents

Anti-inflammatory agents have exhibited success in treatment of proliferative disorders or inflammatory disorders and are now a common and a standard treatment for such disorders as well as others. Any anti-inflammatory therapy (e.g., an anti-inflammatory agent) well-known to one of skill in the art can be used in the compositions and methods of the invention. Non-limiting examples of anti-inflammatory agents include non-steroidal anti-inflammatory drugs (NSAIDs), steroidal anti-inflammatory drugs, beta-agonists, anticholingeric agents, antihistamines (e.g., ethanolamines, ethylenediamines, piperazines, and phenothiazine), and methyl xanthines. Examples of NSAIDs include, but are not limited to, aspirin, ibuprofen, salicylates, acetominophen, celecoxib (CELEBREX™), diclofenac (VOLTAREN™), etodolac (LODINE™), fenoprofen (NALFON™), indomethacin (INDOCIN™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

Anti-inflammatory agents and their dosages, routes of administration and recommended usage are known in the art and have been described in such literature as the *Physician's Desk Reference* (57 wt ed., 2003).

4.2.5 Anti-Cancer Agents

Any therapy (e.g., any prophylactic or therapeutic agent) which is known to be useful, has been used, or is currently being used for the prevention, treatment, management, or amelioration of one or more symptoms associated with a proliferative disorder, such as cancer can be used in compositions and method of the invention. Therapeutic or prophylactic agents include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies.

In certain embodiments, the anti-cancer agent is an immunomodulatory agent such as a chemotherapeutic agent. In other embodiments, the anti-cancer agent is not an immunomodulatory agent. In specific embodiments, the anti-cancer agent is an anti-angiogenic agent. In other embodiments, the anti-cancer agent is not an anti-angiogenic agent.

Examples of anti-cancer agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin-2 (including recombinant interleukin 2, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epothilone A; epothilone B; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MWF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl-lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

In more particular embodiments, the present invention also comprises the administration of a compound of the invention in combination with the administration of one or more therapies such as, but not limited to anti-cancer agents such as those disclosed in Table 2, preferably for the treatment of breast, ovary, melanoma, prostate, colon and lung cancers.

TABLE 2

| Therapeutic Agent | Dose/Administration/Formulation | | |
|---|---|---|---|
| Doxorubicin hydrochloride (Adriamycin RDF ® and Adriamycin PFS ®) | Intravenous | 60-75 mg/m² on Day 1 | 21 day intervals |
| Epirubicin hydrochloride (Ellence ™) | Intravenous | 100-120 mg/m² on Day 1 of each cycle or divided equally and given on Days 1-8 of the cycle | 3-4 week cycles |
| Fluorouracil | Intravenous | How supplied: 5 mL and 10 mL vials (containing 250 and 500 mg fluorouracil respectively) | |
| Docetaxel (Taxotere ®) | Intravenous | 60-100 mg/m² over 1 hour | Once every 3 weeks |
| Paclitaxel (Taxol ®) | Intravenous | 175 mg/m² over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | Intravenous or intramuscular injection | How supplied: 350 mg vial | Dosage is unclear from text. PDR 3610 |
| luprolide acetate (Lupron ®) | Single subcutaneous injection | 1 mg (0.2 mL or 20 unit mark) | Once a day |
| Flutamide (Eulexin ®) | Oral (capsule) | 250 mg (capsules contain 125 mg flutamide each) | 3 times a day at 8 hour intervals (total daily dosage 750 mg) |
| Nilutamide (Nilandron ®) | Oral (tablet) | 300 mg or 150 mg (tablets contain 50 or 150 mg nilutamide each) | 300 mg once a day for 30 days followed by 150 mg once a day |
| Bicalutamide (Casodex ®) | Oral (tablet) | 50 mg (tablets contain 50 mg bicalutamide each) | Once a day |
| Progesterone | Injection | USP in sesame oil 50 mg/mL | |
| Ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated. | |
| Estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | |
| Dacarbazine (DTIC-Dome ®) | Intravenous | 2-4.5 mg/kg | Once a day for 10 days. May be repeated at 4 week intervals |
| Polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |

TABLE 2-continued

| Therapeutic Agent | | Dose/Administration/Formulation | |
|---|---|---|---|
| Cisplatin | Injection | [n/a in PDR 861] How supplied: solution of 1 mg/mL in multi-dose vials of 50 mL and 100 mL | |
| Mitomycin | Injection | supplied in 5 mg and 20 mg vials (containing 5 mg and 20 mg mitomycin) | |
| gemcitabine HCl (Gemzar ®) | Intravenous | For NSCLC-2 schedules have been investigated and the optimum schedule has not been determined 4 week schedule- administration intravenously at 1000 mg/m$^2$ over 30 minutes on 3 week schedule- Gemzar administered intravenously at 1250 mg/m$^2$ over 30 minutes | 4 week schedule- Days 1, 8 and 15 of each 28-day cycle. Cisplatin intravenously at 100 mg/m$^2$ on day 1 after the infusion of Gemzar. 3 week schedule- Days 1 and 8 of each 21 day cycle. Cisplatin at dosage of 100 mg/m$^2$ administered intravenously after administration of Gemzar on day 1. |
| Carboplatin (Paraplatin ®) | Intravenous | Single agent therapy: 360 mg/m$^2$ I.V. on day 1 (infusion lasting 15 minutes or longer) Other dosage calculations: Combination therapy with cyclophosphamide, Dose adjustment recommendations, Formula dosing, etc. | Every 4 weeks |
| Ifosamide (Ifex ®) | Intravenous | 1.2 g/m$^2$ daily | 5 consecutive days Repeat every 3 weeks or after recovery from hematologic toxicity |
| Topotecan hydrochloride (Hycamtin ®) | Intravenous | 1.5 mg/m$^2$ by intravenous infusion over 30 minutes daily | 5 consecutive days, starting on day 1 of 21 day course |

In specific embodiments, radiation therapy comprising the use of x-rays, gamma rays and other sources of radiation to destroy the cancer cells is used in combination with the antibodies of the invention. In preferred embodiments, the radiation treatment is administered as external beam radiation or teletherapy, wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physician's Desk Reference* (57$^{th}$ ed., 2003).

4.2.6 Antibiotics

Antibiotics well known to one of skill in the art can be used in the compositions and methods of the invention. Non-limiting examples of antibiotics include penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine.

Antibiotics and their dosages, routes of administration and recommended usage are known in the art and have been described in such literature as the *Physician's Desk Reference* (57$^{th}$ ed., 2003).

4.2.7 Antiviral Agents

Any anti-viral agent well-known to one of skill in the art can be used in the compositions and the methods of the invention. Non-limiting examples of anti-viral agents include proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

Antiviral agents and their dosages, routes of administration and recommended usage are known in the art and have been described in such literature as the *Physician's Desk Reference* (56$^{th}$ ed., 2002).

4.2.8 Vascular Targeting Agents

Any vascular targeting agent well-known to one of skill in the art can be used in the compositions and methods of the invention (see, e.g., Thorpe, P. E., *Clin. Can. Res.* 10:415-427 (2004), incorporated herein by reference in its entirety).

Non-limiting examples of vascular targeting agents include small molecule vascular targeting agents (e.g., microtubulin destabilizing drugs, combretastatin A-4 disodium phosphate, ZD6126, AVE8062, Oxi 4503, TZT 1027 and DMXAA) and ligand-based vascular targeting agents including, but not limited to, fusion proteins (e.g., vascular endothelial growth factor linked to the plant toxin gelonin), immunotoxins (e.g., monoclonal antibodies to endoglin conjugated to ricin A), antibodies linked to cytokines and liposomally encapsulated drugs.

In one embodiment, a ligand-based vascular targeting agent is comprised of any ligand that binds selectively to a component of a tumor blood vessel, which is linked (e.g., by a chemical cross-linker or peptide bond) to an agent capable of occluding a tumor blood vessel. Examples of ligands that bind selectively to a component of a tumor blood vessel include, but are not limited to, an antibody or peptide directed against a marker that is selectively up-regulated on tumor tissue endothelial cells compared to normal tissue endothelial cells. Example of markers that are selectively up-regulated on tumor tissue endothelial cells compared to normal tissue endothelial cells include, but are not limited to, cell adhesion molecules induced by inflammatory mediators (e.g., interleukin (IL)-1) and molecules associated with prothrombotic changes that occur on tumor vascular endothelium. Examples of agents capable of occluding a tumor blood vessel include, but are not limited to, coagulation-inducing proteins (e.g., tissue factor), toxins (e.g., diphtheria toxin, ricin, gelonin), cytotoxic agents (e.g., doxorubicin, neocarzinostatin), cytokines (e.g., interleukin-2, interleukin-12, tumor necrosis factor-α), apoptosis-induction agents (e.g., RAF-1 gene, mitochondrial-membrane disrupting peptide), radioisotopes (e.g., iodine-131, actinium-225, bismuth-213) and liposomally encapsulated effectors (e.g., arabinofuranosylcytosine derivatives).

Vascular targeting agents and their dosages, routes of administration and recommended usage are known in the art and have been described in such literature as the *Physician's Desk Reference* ($57^{th}$ ed., 2003).

4.3 Uses of Compounds of the Invention

The present invention is directed to therapies which involve administering one of more compounds of the invention, or compositions comprising said compounds to a subject, preferably a human subject, for preventing, treating, managing, or ameliorating disease or disorder or one or more symptoms thereof. In one embodiment, the invention provides a method of preventing, treating, managing, or ameliorating a disease or disorder or one or more symptoms thereof, said method comprising administering to a subject in need thereof a dose of a prophylactically or therapeutically effective amount of one or more compounds of the invention.

The invention also provides methods of preventing, treating, managing, or ameliorating a disease or disorder or one or more symptoms thereof, said methods comprising administering to a subject in need thereof one or more of compounds of the invention and one or more therapies (e.g., one or more prophylactic or therapeutic agents) that are currently being used, have been used, or are known to be useful in the prevention, treatment or amelioration of one or more symptoms associated with said disease or disorder. The prophylactic or therapeutic agents of the combination therapies of the invention can be administered sequentially or concurrently. In a specific embodiment, the combination therapies of the invention comprise one or more compounds and at least one other therapy (e.g., another prophylactic or therapeutic agent) which has the same mechanism of action as said compounds. In another specific embodiment, the combination therapies of the invention comprise one or more compounds of the invention and at least one other therapy (e.g., another prophylactic or therapeutic agent) which has a different mechanism of action than said compounds. In certain embodiments, the combination therapies of the present invention improve the prophylactic or therapeutic effect of one or more compounds of the invention by functioning together with compounds to have an additive or synergistic effect. In certain embodiments, the combination therapies of the present invention reduce the side effects associated with therapies (e.g., prophylactic or therapeutic agents).

The prophylactic or therapeutic agents of the combination therapies can be administered to a subject, preferably a human subject, in the same pharmaceutical composition. In alternative embodiments, the prophylactic or therapeutic agents of the combination therapies can be administered concurrently to a subject in separate pharmaceutical compositions. The prophylactic or therapeutic agents may be administered to a subject by the same or different routes of administration.

In a specific embodiment, a pharmaceutical composition comprising one or more compounds of the invention is administered to a subject, preferably a human, to prevent, treat, manage, or ameliorate one or more symptoms associated with a disease or disorder. In accordance with the invention, pharmaceutical compositions of the invention may also comprise one or more prophylactic or therapeutic agents which are currently being used, have been used, or are known to be useful in the prevention, treatment or amelioration of one or more symptoms associated with a disease or disorder.

Diseases and disorders which can be prevented, treated, managed, or ameliorated by administering an effective amount of one or more compounds of the invention include, but are not limited to, disorders characterized by or associated with aberrant angiogenesis, central nervous system disorders, proliferative disorders, inflammatory disorders, autoimmune disorders, disorders prevented, managed, treated or ameliorated by vascular inhibition (e.g., blocking angiogenesis through vascular inhibition) and disorders prevented, managed, treated or ameliorated by inhibiting and/or reducing the expression and/or activity of PDE4, or by inhibiting or reducing tubulin polymerization or stability. Examples of disorders characterized or associated with angiogenesis include, but are not limited to, proliferative disorders, such as cancer. Examples of disorders prevented, managed, treated or ameliorated by the inhibition or reduction in the expression and/or activity of PDE4 include, but are not limited to, inflammatory disorders such as asthma, inflammation, chronic or acute obstructive pulmonary disease, chronic or acute pulmonary inflammatory disease, inflammatory bowel disease, Crohn's Disease, Bechet's Disease, HSP, colitis, and inflammation due to reperfusion. Examples of disorders prevented, managed, treated or ameliorated by the inhibition or reduction of tubulin polymerization or stability include, but are not limited to, proliferative disorders such as cancer and noncancerous disorders such as psoriasis and fibrosis.

In a specific embodiment, the invention provides methods for preventing, managing, treating or ameliorating disorders prevented, managed, treated or ameliorated by vascular inhibition (e.g., blocking angiogenesis through vascular inhibition), disorders prevented, managed, treated or ameliorated by inhibiting and/or reducing the expression and/or activity of PDE4, or by inhibiting or reducing tubulin polymerization or stability, cancers refractory to current therapy or cancers which are or have become multi-drug resistant, comprising administering to a patient in need thereof an effective amount of one of more compounds of formula I or formula X, or pharmaceutically acceptable salts, solvates or hydrates thereof.

In one embodiment, the cancer is refractory to treatment with colchicine, a taxane or a vinca alkaloid.

In another specific embodiment, the invention provides methods for preventing, managing, treating or ameliorating disorders prevented, managed, treated or ameliorated by vascular inhibition (e.g., blocking angiogenesis through vascular inhibition), disorders prevented, managed, treated or ameliorated by inhibiting and/or reducing the expression and/or activity of PDE4, or by inhibiting or reducing tubulin polymerization or stability, cancers refractory to current therapy or cancers which are or have become multi-drug resistant, comprising administering to a patient in need thereof an effective amount of one of more of the following compounds: 3,3-bis-(3,4-dimethoxyphenyl)acrylonitrile, 3,3-bis-(3-ethoxy-4-methoxyphenyl)acrylonitrile, methyl 3,3-bis-(3-ethoxy-4-methoxyphenyl)-propenoate, methyl 3-(3-ethoxy-4-methoxyphenyl)-3-phenylpropenoate, 3-(3-propoxy-4-methoxyphenyl)-3-phenylacrylonitrile, 3-(3-ethoxy-4-methoxyphenyl)-3-phenylacrylonitrile, 3,3-bis-(3-cyclopentoxy-4-methoxyphenyl)-acrylonitrile, methyl 3-(3-cyclopentoxy-4-methoxyphenyl)-3-phenylpropenoate, 3-(3-cyclopentoxy-4-methoxyphenyl)-3-phenylacrylonitrile, 3-(3-cyclopentoxy-4-methoxyphenyl)-3-phenylpropene, 1-(3-cyclopentoxy-4-methoxyphenyl)-1-phenylpropane, 3-(3-cyclopentoxy-4-methoxyphenyl)-3-phenylpropanenitrile, methyl 3-(3-cyclopentoxy-4-methoxyphenyl)-3-phenylpropanoate, 3-(3-ethoxy-4-methoxyphenyl)-3-phenylpropanenitrile, methyl 3-(3-ethoxy-4-methoxyphenyl)-3-phenylpropanoate, 3,3-bis-(3,4-dimethoxyphenyl)propanenitrile, 3,3-bis-(3-ethoxy-4-methoxyphenyl)propanenitrile, 3-(3,4-dimethoxyphenyl)-3-phenylacrylonitrile, 3-(3-ethoxy-4-methoxyphenyl)-3-naphthylpropanenitrile, 3-(3,4-dimethoxyphenyl)-3-phenylpropanenitrile; 3-(3,4-dimethoxyphenyl)-3-(3-ethoxy-4-methoxyphenyl)propanenitrile, 4,4-bis-(3,4-dimethoxyphenyl)but-3-en-2-one; 4-(3,4-dimethoxyphenyl)-4-(3-ethoxy-4-methoxyphenyl)but-3-en-2-one; 4-(3,4-dimethoxyphenyl)-4-phenylbut-3-en-2-one; 4-(3,4-dimethoxyphenyl)-4-(3-cyclopentoxy-4-methoxyphenyl)but-3-en-2-one; 4-(3,4-dimethoxyphenyl)-4-(3-indan2-yloxy-4-methoxyphenyl)but-3-en-2-one; 4-(3-ethoxy-4-methoxyphenyl)-4-(4-pyridyl)but-3-en-2-one; 4-(3-ethoxy-4-methoxyphenyl)-4-(4-pyridyl)butan-2-one; 4-(3-cyclopentoxy-4-methoxyphenyl)-4-(4-pyridyl)but-3-en-2-one; 4-(3-cyclopentoxy-4-methoxyphenyl)-4-(4-pyridyl)butan-2-one; methyl 3-(3-cyclopentoxy-4-methoxyphenyl)-3-(4-pyridyl)prop-2-enoate; methyl 3-(3-ethoxy-4-methoxyphenyl)-3-(4-pyridyl)prop-2-enoate; methyl 3-(3-ethoxy-4-methoxyphenyl)-3-(4-pyridyl)propanoate; 4-(3-ethoxy-4-methoxyphenyl)-4-(2-furyl)but-3-en-2-one; 3-(3-ethoxy-4-methoxyphenyl)-3-(2-furyl)prop-2-enenitrile; 3-(3-ethoxy-4-methoxyphenyl)-3-(4-pyridyl)prop-2-enenitrile; 3-(3-ethoxy-4-methoxyphenyl)-3-(4-pyridyl)propanenitrile; 3-(3-cyclopentoxy-4-methoxyphenyl)-3-(4-pyridyl)prop-2-enenitrile; 3-(3-cyclopentoxy-4-methoxyphenyl)-3-(4-pyridyl)propanenitrile; 4-(3,4-dimethoxyphenyl)-4-(4-methoxy-3-prop-1-enylphenyl)but-3-en-2-one; 4-(3,4-dimethoxyphenyl)-4-(4-methoxy-3-prop-1-enylphenyl)but-3-en-2-one; 4,4-bis-(3,4-dimethoxyphenyl)butan-2-one; 4-(3,4-dimethoxyphenyl)-4-(3-ethoxy-4-methoxyphenyl)butan-2-one; 4-(3,4-dimethoxyphenyl)-4-(3-(cyclopentylidenemethyl)-4-methoxyphenyl)butan-2-one; 4-(3,4-dimethoxyphenyl)-4-(4-methoxy-3-prop-1-enylphenyl)butan-2-one; 4,4-bis-(3-ethoxy-4-methoxyphenyl)but-3-en-2-one; 3-(3,4-dimethoxyphenyl)-3-(3-(cyclopentylidenemethyl)-4-methoxyphenyl)prop-2-enenitrile; 3-(3-(cyclopentylidenemethyl)-4-methoxyphenyl)-3-phenyl-prop-2-enenitrile; 1-(3,4-dimethoxyphenyl)-1-(3-ethoxy-4-methoxyphenyl)pentan-3-one; 1-(3,4-dimethoxyphenyl)-1-(3-ethoxy-4-methoxyphenyl)pent-1-en-3-one; 1,1-bis-(3,4-dimethoxyphenyl)pentan-3-one; 3-(3,4-dimethoxyphenyl)-3-(3-(cyclopentylidenemethyl)-4-methoxyphenyl)prop-2-enenitrile; 3-(3-(cyclopentylidenemethyl)-4-methoxyphenyl)-3-phenyl-propanenitrile; 3,3-bis-(3-(cyclopentylidenemethyl)-4-methoxyphenyl)propanenitrile; 3,3-bis-(3-(cyclopentylidenemethyl)-4-methoxyphenyl)prop-2-enenitrile; 3-(3,4-dimethoxyphenyl)-3-(3-(cyclopentylidenemethyl)-4-methoxyphenyl)prop-2-enamide; 3-(3-(cyclopentylidenemethyl)-4-methoxyphenyl-3-phenyl)propanamide; 3,3-bis-(3-(cyclopentylidenemethyl)-4-methoxyphenyl)propanamide; 3,3-bis-(3-(cyclopentylidenemethyl)-4-methoxyphenyl)prop-2-enamide; 3-(3,4-dimethoxyphenyl)-3-(3-ethoxy-4-methoxyphenyl)prop-2-enamide; 3,3-bis-(3-ethoxy-4-methoxyphenyl)prop-2-enamide; 3,3-bis-(3,4-dimethoxyphenyl)prop-2-enamide; 3,3-bis-(3-ethoxy-4-methoxyphenyl)propanamide; 3,3-bis-(3,4-dimethoxyphenyl)propanamide; 4-(3,4-dimethoxyphenyl)-4-(4-methoxy-3-exo-norbornyloxyphenyl)but-3-en-2-o ne; 3-(3,4-dimethoxyphenyl)-3-(4-methoxy-3-exo-norbornyloxyphenyl)prop-2-enenitrile; 3-(3,4-dimethoxyphenyl)-3-(3,4-methylenedioxyphenyl)prop-2-enenitrile; 3-(4-aminophenyl)-3-(3,4-dimethoxyphenyl)prop-2-enenitrile; 3-(4-aminophenyl)-3-(3-ethoxy-4-dimethoxyphenyl)prop-2-enenitrile; 3-(3,4-dimethoxyphenyl)-3-(3-ethoxy-4-methoxyphenyl)acrylonitrile; 3-(3,4-dimethoxyphenyl)-3-phenylacetate; 3-phenyl-3-(3'-ethoxy-4-methoxyphenyl)acrylamide; 1-(3,4-dimethoxyphenyl)-1-phenylprop-1-ene; 1-(3,4-dimethoxyphenyl)-1-(3-ethoxy-4-methoxyphenyl)prop-1-ene; 1-(3,4-dimethoxyphenyl)-1-(3-ethoxy-4-methoxyphenyl)but-1-ene; 3-(3-ethoxy-4-methoxyphenyl)-3-phenylacrylonitrile; 3-(3-ethoxy-4-methoxyphenyl)-3-phenylpropionitirle; 3-(3,4-dimethxyphenyl)-3-(3',5'-dimethoxyphenyl)-acrylonitrile; 3-(3,4-dimethoxyphenyl)-3-(3'-nitrophenyl)acrylonitrile; 3-(3'-aminophenyl)-3-(3,4-dimethoxyphenyl)acrylonitrile; 3,4-dimethoxy-3'-aminobenzophenone; 3-(3,4-dimethoxyphenyl)-3-(4-nitrophenyl)acrylonitrile; 3-(4-aminophenyl)-3-(3,4-dimethoxyphenyl)acrylonitrile; 3,4-dimethoxy-4'aminobenzophenone; 3-(3,4-dimethoxyphenyl)-3-(4-methylphenyl)acrylonitrile; 3-(4-biphenylyl)-3-(3,4-dimethoxyphenyl)acrylonitrile; 3-(3,4-dimethoxyphenyl)-3-(4'-fluorophenyl)acrylonitrile; 3-(3,4-dimethoxyphenyl)-3-naphth-2-ylacrylonitrile; 3-(3,4-dimethoxyphenyl)-3-(3,4-methylenedioxyphenyl)acrylonitrile; 3-(3,4-dimethoxyphenyl)-3-pyridine-4-ylacrylonitrile; 3-(3,4-dimethoxyphenyl)-3-pyridin-2-ylacrylonitrile; 3-(3,4-dimethoxyphenyl)-3-(2-furyl)acrylonitrile; 3-(3,4-diethylphenyl)-3-phenylacrylonitrile; 3-(3,4-diethylphenyl)-3-(3,4-dimethoxyphenyl)acrylonitrile; 4-(3-ethoxy-4-methoxyphenyl)-4-phenyl-3-butan-2-one; 3-(3,4-dimethoxyphenyl)-3-(naphth-1-yl)acrylonitrile; 3-(3,4-dimethoxyphenyl)-3-(2,5-dichlorophenyl)acrylonitrile; 2',6',3,4-tetramethoxybenzophenone; or a pharmaceutically acceptable salt, solvate and hydrate thereof.

In one embodiment, 3,4-disubstituted compounds of the invention are preferred inhibitors of PDE4. In another embodiment, 3,4-dialkoxy substituted compounds of the invention are preferred inhibitors of PDE4. In another embodiment, 3,4-dimethoxy substituted compounds of the invention are preferred inhibitors of PDE4.

4.3.1 Proliferative Disorders

Compounds of the invention and compositions comprising said compounds can be used to prevent, treat, manage, or ameliorate a proliferative disorder (e.g., cancer) or one or more symptoms thereof. Without being bound by theory, in one embodiment, a compound of the invention binds to an $\alpha$- or $\beta$-tubulin subunit in a cancer or tumor cell and inhibits tubulin polymerization or stability, thereby disrupting the cancer or tumor cell's ability to replicate. In an alternative embodiment, a compound of the invention binds to an $\alpha$- or $\beta$-tubulin subunit in endothelial cells of a vascularized tumor and causes a change in the shape of these cells. The change in shape of these endothelial cells results in constriction of blood vessels that supply a tumor with blood and oxygen, thereby cause the tumor to shrink or die.

In one embodiment, a compound of the invention binds to an $\alpha$- or $\beta$-tubulin subunit in a tumor cell tumor cell or cancer cell. In another embodiment, a compound of the invention binds to an $\alpha$- or $\beta$-tubulin subunit in a endothelial cell in a vascularized tumor. In a specific embodiment, a compound of the invention is useful for preventing, managing, treating or ameliorating cancers that are sensitive to tubulin-binding agents. In another embodiment, a compound of the invention is useful for preventing, managing, treating or ameliorating cancers that are resistant to tubulin-binding agents.

In another embodiment, the present invention provides methods for inhibiting proliferation of a cancer cell or tumor cell comprising contacting the cancer cell or tumor cell with an effective amount of a compound of the invention. In one embodiment, the cancer cell or tumor cell is resistant to traditional cancer therapy. In another embodiment, the cancer cell or tumor cell is a multi-drug resistant cancer cell or tumor cell.

The present invention provides methods for preventing, treating, managing, or ameliorating one or more symptoms of a non-cancerous disorder associated with cellular hyperproliferation, particularly of epithelial cells (e.g., as in asthma, COPD, pulmonary fibrosis, bronchial hyperresponsiveness, psoriasis, lymphoproliferative disorder, and seborrheic dermatitis), and endothelial cells (e.g., as in restenosis, hyperproliferative vascular disease, Behcet's Syndrome, atherosclerosis, and macular degeneration), said methods comprising administering to a subject in need thereof one or more compounds of the invention. The present invention also provides methods for preventing, managing, treating, or ameliorating a non-cancerous disorder associated with cellular hyperproliferation, said methods comprising of administering to a subject in need thereof one or more compounds of the invention and one or more other therapies (e.g., one or more other prophylactic or therapeutic agents) useful for the prevention, treatment, management, or amelioration of said disorder.

In a specific embodiment, the invention provides methods for preventing, managing, treating, or ameliorating a non-cancerous disorder associated with cellular hyperproliferation (e.g., Behcet's Syndrome, sarcoidosis, keloids, pulmonary fibrosis, macular degeneration and renal fibrosis) or one or more symptoms thereof, said methods comprising of administering to a subject in need thereof a prophylactically or therapeutically effective amount of one or more compounds of the invention. In another embodiment, the invention provides methods for preventing, managing, treating, or ameliorating a non-cancerous disorder associated with cellular hyperproliferation (e.g., Behcet's Syndrome, sarcoidosis, keloids, pulmonary fibrosis, renal and fibrosis) or one or more symptoms thereof, said methods comprising of administering to a subject in need thereof a prophylactically or therapeutically effective amount of one or more compounds of the invention and a prophylactically or therapeutically effective amount of one or more other therapies (e.g., one or more prophylactic or therapeutic agents).

The invention encompasses methods for preventing, treating, managing, or ameliorating one or more symptoms of a disorder associated with cellular hyperproliferation in a subject refractory to conventional therapies for such disorder, said methods comprising administering to subject a dose of a prophylactically or therapeutically effective amount of one or more compounds of the invention. The present invention also provides methods for preventing, managing, treating, or ameliorating a non-cancerous disorder associated with cellular hyperproliferation in a subject refractory to conventional therapies for such disorder, said methods comprising of administering to a subject in need thereof one or more compounds of the invention and one or more other therapies (e.g., one or more other prophylactic or therapeutic agents) useful for the prevention, treatment, management, or amelioration of said disorder.

The present invention provides methods for preventing, treating, managing, or ameliorating cancer or one or more symptoms thereof, said methods comprising administering one or more compounds of the invention to a subject in need thereof. The invention also provides methods for preventing, treating, managing, or ameliorating cancer in which one or more compounds of the invention are administered in combination with one or more other therapies (e.g., prophylactic or therapeutic agents) useful for the prevention, treatment, management, or amelioration of cancer or a secondary condition.

In a specific embodiment, the invention provides a method of preventing, treating, managing, or ameliorating cancer or one or more symptoms thereof, said method comprising administering to a subject in need thereof a dose of a prophylactically or therapeutically effective amount of one or more compounds of the invention. In another embodiment, the invention provides a method of preventing, treating, managing, or ameliorating cancer or one or more symptoms thereof, said method comprising administering to a subject in need thereof a dose of a prophylactically or therapeutically effective amount of one or more compounds of the invention and a dose of a prophylactically or therapeutically effective amount of one or more therapies (e.g., one or more prophylactic or therapeutic agents) useful for the prevention, treatment, management, or amelioration of cancer, or a secondary condition (e.g., a viral, bacterial, or fungal infection).

The compounds of the invention are particularly useful as vascular targeting agents. Without being bound by theory, it is thought that the compounds of the invention are effective anti-tumor agents due to their ability to occlude blood vessels (e.g., pre-existing blood vessels) of tumors resulting in tumor cell death from ischemia and hemorrhagic necrosis. Thus, the compounds of the invention are useful for destroying or disrupting the vascular system of a tumor.

The compounds of the invention are particularly effective as vascular targeting agents against vessels in the interior of the tumor and, accordingly, are can be synergistically used in combination with anti-tumor agents which are effective against peripheral tumor cells (e.g., anti-angiogenic agents). Also without being limited by theory, due to their ability to target tumor cell vasculature, the compounds of the invention are particularly effective against tumor cells in locations distant from blood vessels where drug penetration is poor. Such tumor cells are more likely to become resistant to radiation and drug therapy. Thus, the compounds of the invention are particularly effective against tumors and tumor cells which are or have become resistant to traditional cancer therapies.

In one embodiment, the present invention provides a method for targeting, blocking or destroying the function of tumor vasculature, said method comprising contacting a tumor with an effective amount of a compound of the invention.

In another embodiment, the present invention provides a method for targeting, blocking or destroying the endothelium of tumor vessels, said method comprising contacting a tumor with an effective amount of a compound of the invention.

In another embodiment, the present invention provides a method for occluding pre-existing blood vessels of a tumor, said method comprising contacting a tumor with an effective amount of a compound of the invention.

In another embodiment, the present invention provides a method for killing a tumor cell, said method comprising contacting a tumor cell with an effective amount of a compound of the invention.

In another embodiment, the present invention provides a method for causing acute vascular collapse in a tumor cell, said method comprising contacting a tumor cell with an effective amount of a compound of the invention.

In another embodiment, the present invention provides a method for blocking angiogenesis through vascular inhibition, said method comprising contacting a cell with an effective amount of a compound of the invention.

In another embodiment, the present invention provides a method of inhibiting tumor growth through vascular inhibition, said method comprising administering to a subject in need thereof an effective amount of a compound of the invention.

Without being limited by theory, it is thought that because the compounds of the invention have both vascular targeting activity, which is particularly effective against central tumor cells, and anti-angioenic activity, which is particulary effective against peripheral tumor cells, the compounds of the invention are particularly useful in eradicating the majority of a tumor and, in one embodiment, completely eradicating a tumor. Accordingly, the compounds of the invention are particularly active against tumors due to the synergistic effect of their dual activity as both vascular targeting agents and anti-angiogenic agents.

The compounds of the invention can be used in an in vitro or ex vivo fashion for the management, treatment or amelioration of certain cancers, including, but not limited to leukemias and lymphomas, such treatment involving autologous stem cell transplants. This can involve a multi-step process in which the subject's autologous hematopoietic stem cells are harvested and purged of all cancer cells, the patient's remaining bone-marrow cell population is then eradicated via the administration of a high dose of a compound of the invention with or without accompanying high dose radiation therapy, and the stem cell graft is infused back into the subject. Supportive care is then provided while bone marrow function is restored and the subject recovers.

One or more of the compounds of the invention may be used as a first, second, third, fourth or fifth line of cancer treatment. The invention provides methods for preventing, treating, managing, or ameliorating cancer or one or more symptoms thereof in a subject refractory to conventional therapies for such a cancer, said methods comprising administering to said subject a dose of a prophylactically or therapeutically effective amount of one or more compounds of the invention. A cancer may be determined to be refractory to a therapy means when at least some significant portion of the cancer cells are not killed or their cell division arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory when the number of cancer cells has not been significantly reduced, or has increased after treatment.

The invention provides methods for preventing, managing, treating or ameliorating cancer or one or more symptoms thereof in a subject refractory to existing single agent therapies for such a cancer, said methods comprising administering to said subject a dose of a prophylactically or therapeutically effective amount of one or more compounds of the invention and a dose of a prophylactically or therapeutically effective amount of one or more therapies (e.g., one or more prophylactic or therapeutic agents) useful for the prevention, treatment, management, or amelioration of cancer or a secondary condition. The invention also provides methods for preventing, treating, managing, or ameliorating cancer or a secondary condition by administering one or more compounds of the invention in combination with any other therapy(ies) (e.g., radiation therapy, chemotherapy or surgery) to patients who have proven refractory to other treatments but are no longer on this therapy(ies).

In a specific embodiment, the invention provides methods for preventing, managing, treating or ameliorating cancer refractory to colchicine, paclitaxel, docetaxel and/or vinblastine and/or other vinca alkaloids or one or more symptoms thereof, said methods comprising administering to a subject in need thereof a dose of a prophylactically or therapeutically effective amount of one or more compounds of the invention. In another embodiment, the invention provides methods for preventing, managing, treating or ameliorating cancer refractory to colchicine, paclitaxel, docetaxel and/or vinblastine or one or more symptoms thereof, said methods comprising administering to a subject in need thereof a dose of a prophylactically or therapeutically effective amount of one or more compounds of the invention and a dose of a prophylactically or therapeutically effective amount of one or more other therapies. In accordance with this embodiment, the other therapies may be a chemotherapeutic agent, an immunomodulatory agent, an anti-angiogenic agent, radiation therapy or surgery.

The invention provides methods for the prevention, treatment, management, or amelioration of a patient having cancer and immunosuppressed by reason of having previously undergone other cancer therapies. The invention also provides alternative methods for the prevention, treatment, management, or amelioration of cancer where chemotherapy, radiation therapy, hormonal therapy, and/or biological therapy/immunotherapy has proven or may prove too toxic, i.e., results in unacceptable or unbearable side effects, for the subject being treated. Further, the invention provides methods for preventing the recurrence of cancer in patients that have been treated and have no disease activity by administering one or more compounds of the invention.

Cancers that can be prevented, managed, treated or ameliorated in accordance with the methods of the invention include, but are not limited to, neoplasms, tumors (malignant and benign) and metastases, or any disease or disorder characterized by uncontrolled cell growth. The cancer may be a primary or metastatic cancer. Specific examples of cancers that can be prevented, managed, treated or ameliorated in accordance with the methods of the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or urerer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

In a specific embodiment, the cancer that is being prevented, managed, treated or ameliorated in accordance with the method of the invention is prostate cancer, breast cancer, bone cancer, melanoma, lung cancer and ovarian cancer. In another embodiment, the cancer that is being prevented, managed, treated or ameliorated in accordance with the methods of the invention are metastatic tumors including, but not limited to, tumors that have or may metastasize to the bone (non-limiting examples are prostate, breast and lung cancers that have metastasized or have the potential to metastasize to the bone), tumors that have or may metastasize to the lung, tumors that have or may metastasize to the brain, and tumors that have or may metastasize to other organs or tissues of a subject. In another embodiment, the cancer that is being prevented, managed, treated or ameliorated in accordance with the method of the invention is not associated with TNF-α expression and/or activity.

4.3.2 Inflammatory Disorders

One or more compounds of the invention and compositions comprising of said compounds can be used to prevent, treat, manage, or ameliorate an inflammatory disorder or one or more symptoms thereof. Compounds of the invention or compositions comprising said compounds may also be administered in combination with one or more other therapies (e.g., one or more other prophylactic or therapeutic agents) useful for the prevention, treatment, management, or amelioration of an inflammatory disorder or one or more symptoms thereof.

In a specific embodiment, the invention provides a method of preventing, treating, managing, or ameliorating an inflammatory disorder or one or more symptoms thereof, said method comprising administering to a subject in need thereof a dose of a prophylactically or therapeutically effective amount one or more compounds of the invention. In another embodiment, the invention provides a method of preventing, treating, managing, or ameliorating an inflammatory disorder or one or more symptoms thereof, said method comprising administering to a subject in need thereof a dose of a prophylactically or therapeutically effective amount of one or more of compounds of the invention and a dose of a prophylactically or therapeutically effective amount of one or more other therapies (e.g., one or more other prophylactic or therapeutic agents).

The invention provides methods for preventing, managing, treating or ameliorating an inflammatory disorder or one or more symptoms thereof in a subject refractory to conventional therapies (e.g., methotrexate and a TNF-α antagonist (e.g., REMICADE™ or ENBREL™)) for such an inflammatory disorder, said methods comprising administering to said subject a dose of a prophylactically or therapeutically effective amount of one or more compounds of the invention. The invention also provides methods for preventing, treating, managing, or ameliorating an inflammatory disorder or one or more symptoms thereof in a subject refractory to existing single agent therapies for such an inflammatory disorder, said methods comprising administering to said subject a dose of a prophylactically or therapeutically effective amount of one or more compounds of the invention and a dose of a prophylactically or therapeutically effective amount of one or more other therapies (e.g., one or more other prophylactic or therapeutic agents). The invention also provides methods for preventing, treating, managing, or ameliorating an inflammatory disorder by administering one or more compounds of the invention in combination with any other therapy(ies) to patients who have proven refractory to other treatments but are no longer on this therapy(ies). The invention also provides alternative methods for the prevention, treatment, management, or amelioration of an inflammatory disorder where another therapy has proven or may prove too toxic, i.e., results in unacceptable or unbearable side effects, for the subject being treated. Further, the invention provides methods for preventing the recurrence of an inflammatory disorder in patients that have been treated and have no disease activity by administering one or more compounds of the invention.

Examples of the inflammatory disorders which can be prevented, managed, treated, or ameliorated in accordance with the methods of the invention, include, but are not limited to, asthma, allergic disorders, inflammatory disorders characterized by type-1 mediated inflammation, inflammatory disorders characterized by type-2 mediated inflammation, fibrotic disease (e.g., pulmonary fibrosis), psoraisis, multiple sclerosis, systemic lupus erythrematosis, chronic obstructive pulmonary disease (COPD), encephilitis, inflammatory bowel disease (e.g., Crohn's disease and ulcerative colitis), ischemic reperfusion injury, Gout, Behcet's disease, septic shock, undifferentiated spondyloarthropathy, undifferentiated arthropathy, arthritis, rheumatoid arthritis (juvenile and adult), osteoarthritis, psoriatic arthritis, inflammatory osteolysis, sepsis, meningitis, and chronic inflammation resulting from chronic viral or bacteria infections. In a specific embodiment, the inflammatory disorder which is prevented, treated, managed, or ameliorated in accordance with the methods of the invention is an inflammatory disorder characterized as a type 2-mediated inflammation. Type 2-mediated inflammation is characterized by eosinophilic and basophilic tissue infiltration and/or extensive mast cell degranulation, a process dependent on cross-linking of surface-bound IgE. In another embodiment, the inflammatory disorder which is prevented, treated, managed, or ameliorated in accordance with the methods of the invention is asthma, Behcet's disease, arthritis, chronic obstructive pulmonary disease (COPD), pulmonary fibrosis, renal fibrosis, Gout or allergic disorders.

In a specific embodiment, an effective amount of one or more compounds of the invention is administered to a subject in combination with an effective amount of one or more therapies (e.g., prophylactic or therapeutic agents) useful in preventing, treating, managing, or ameliorating asthma or one or more symptoms thereof. Non-limiting examples of such therapies include, but are not limited to, adrenergic stimulants (e.g., catecholamines (e.g., epinephrine, isoproterenol, and isoetharine), resorcinols (e.g., metaproterenol, terbutaline, and fenoterol), saligenins (e.g. salbutamol)), anticholinergics (e.g., atropine sulfate, atropine methylnitrate, and ipratropium bromide (ATROVENT™)), beta2-agonists (e.g. abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), corticosteroids (e.g., methlyprednisolone (MEDROL™), prednisone (PREDNISONE™ and DELTASONE™), and prednisolone (PRELONE™, PEDIAPRED™)), glucocorticoids (e.g. oral steroids or other systemic or oral steroids, and inhaled glucocoritcoids), other steroids, immunosuppressant agents (e.g. methotrexate and gold salts), leukotriene modifiers (e.g., montelukast (SINGULAIR™), zafirlukast (ACCOLATE™), and zileuton (ZYFLO™)), mast cell stabilizers (e.g., cromolyn sodium (INTAL™) and nedocromil sodium (TILADE™)), methylxanthines (e.g., theophylline (UNIPHYL™, THEO-DUR™, SLO-BID™, AND TEHO-42™)), and mucolytic agents (e.g., acetylcysteine)).

In a specific embodiment, an effective amount of one or more compounds of the invention is administered to a subject in combination with an effective amount of one or more therapies (e.g., prophylactic or therapeutic agents) useful in preventing, treating, managing, or ameliorating allergies or one or more symptoms thereof. Non-limiting examples of therapies include antimediator drugs (e.g., antihistamine, see Table 3), corticosteroids, decongestants, sympathomimetic drugs (e.g., α-adrenergic and β-adrenergic drugs), theophylline and its derivatives, glucocorticoids, and immunotherapies (e.g., repeated long-term injection of allergen, short course desensitization, and venom immunotherapy).

TABLE 3

| $H_1$ Antihistamines | |
|---|---|
| Chemical class and representative drugs | Usual daily dosage |
| Ethanolamine | |
| Diphehydramine | 25-50 mg every 4-6 hours |
| Clemastine | 0.34-2.68 mg every 12 hours |
| Ethylenediamine | |
| Tripelennamine | 25-50 mg every 4-6 hours |

TABLE 3-continued

H₁ Antihistamines

| Chemical class and representative drugs | Usual daily dosage |
|---|---|
| Alkylamine | |
| Brompheniramine | 4 mg every 4-6 hours; or 8-12 mg of SR form every 8-12 hour |
| Chlorpheniramine | 4 mg every 4-6 hours; or 8-12 mg of SR form every 8-12 hour |
| Triprolidine (1.25 mg/5 ml) | 2.5 mg every 4-6 hours |
| Phenothiazine | |
| Promethazine | 25 mg at bedtime |
| Piperazine | |
| Hydroxyzine | 25 mg every 6-8 hours |
| Piperidines | |
| Astemizole (nonsedating) | 10 mg/d |
| Azatadine | 1-2 mg every 12 hours |
| Cetirzine | 10 mg/d |
| Cyproheptadine | 4 mg every 6-8 hour |
| Fexofenadine (nonsedating) | 60 mg every 12 hours |
| Loratidine (nonsedating) | 10 mg every 24 hours |

In a specific embodiment, an effective amount of one or more compounds of the invention is administered to a subject in combination with an effective amount of one or more therapies (e.g., prophylactic or therapeutic agents) useful in preventing, treating, managing, or ameliorating COPD or one or more symptoms thereof. Non-limiting examples of such therapies include, but are not limited to, bronchodilators (e.g. short-acting $\beta_2$-adrenergic agonist (e.g., albuterol, pirbuterol, terbutaline, and metaproterenol), long-acting $\beta_2$-adrenergic agonists (e.g., oral sustained-release albuterol and inhaled salmeterol), anticholinergics (e.g., ipratropium bromide), and theophylline and its derivatives (therapeutic range for theophylline is preferably 10-20 μg/mL)), glucocorticoids, exogenous $\alpha_1$AT (e.g., $\alpha_1$AT derived from pooled human plasma administered intravenously in a weekly dose of 60 mg/kg), oxygen, lung transplantation, lung volume reduction surgery, endotracheal intubation, ventilation support, yearly influenza vaccine and pneumococcal vaccination with 23-valent polysaccharide, exercise, and smoking cessation.

In a specific embodiment, an effective amount of one or more compounds of the invention is administered to a subject in combination with an effect amount of one or more therapies (e.g., prophylactic or therapeutic agents) useful in preventing, treating, managing, or ameliorating pulmonary fibrosis or one or more symptoms thereof. Non-limiting examples of such therapies include, oxygen, corticosteroids (e.g., daily administration of prednisone beginning at 1-1.5 mg/kg/d (up to 100 mg/d) for six weeks and tapering slowly over 3-6 months to a minimum maintenance dose of 0.25 mg/kg/d), cytotoxic drugs (e.g., cyclophosphamide at 100-120 mg orally once daily and azathioprine at 3 mg/kg up to 200 mg orally once daily), bronchodilators (e.g., short- and long-acting $\beta_2$-adrenergic agonists, anticholinergics, and theophylline and its derivatives), and antihistamines (e.g., diphenhydramine and doxylamine).

Anti-inflammatory therapies and their dosages, routes of administration and recommended usage are known in the art and have been described in such literature as the *Physician's Desk Reference* (57th ed., 2003).

4.3.3 Central Nervous System Disorders

One or more compounds of the invention and compositions comprising of said compounds can be used to prevent, treat, manage, or ameliorate a central nervous system disorder or one or more symptoms thereof. Compounds of the invention or compositions comprising said compounds may also be administered in combination with one or more other therapies (e.g., one or more other prophylactic or therapeutic agents) useful for the prevention, treatment, management, or amelioration of a central nervous system disorder or one or more symptoms thereof.

Central nervous system disorders include, but are not limited to, Parkinson's disease; bradykinesia; muscle rigidity; parkinsonian tremor; parkinsonian gait; motion freezing; depression; defective long-term memory, Rubinstein-Taybi syndrome (RTS); dementia; sleep disorders; postural instability; hypokinetic disorders; inflammation; synuclein disorders; multiple system artrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease; Alzheimer disease with parkinsonism; genetic disorders that can have parkinsonian features; Wilson disease; Hallervorden-Spatz disease; Chediak-Hagashi disease; SCA-3 spinocerebellar ataxia; X-linked dystonia parkinsonism; Huntington disease; prion disease; hyperkinetic disorders; chorea; ballismus; dystonia tremors; Amyotrophic Lateral Sclerosis (ALS); CNS trauma and myoclonus.

In particular embodiments of the invention, a compound of the invention is used, administered, or formulated with one or more second active ingredients to treat, prevent or manage central nervous system disorders. Examples of the second active ingredients include but are not limited to dopamine agonists, Levodopa, compounds used to augment Levodopa therapy such as monoamine oxidase inhibitors (MAO) and catechol-O-methyltransferase inhibitors (COMT), amantadine, anticholinergics, antiemetics, and other standard therapies for central nervous system disorders. In another example, the second active ingredients are anti-inflammatory agents, including, but not limited to, nonsteroidal anti-inflammatory drugs (NSAIDs), Methotrexate, Leflunomide, antimalarial drugs and sulfasalazine, gold salts, glucocorticoids, immunosuppresive agents, and other standard therapies for central nervous system disorders.

4.4 Compositions and Methods for Administering Therapies

The present invention provides compositions for the treatment, prophylaxis, and amelioration of disorders characterized by or associated with aberrant angiogenesis, proliferative disorders, inflammatory disorders and disorders prevented, managed, treated or ameliorated by the inhibition or reduction in expression and/or activity of PDE4 or the inhibition or reduction in tubulin polymerization or stability. In a specific embodiment, a composition comprises one or more compounds of the invention, or a pharmaceutically acceptable salt, solvate, or hydrate thereof. In another embodiment, a composition of the invention comprises one or more prophylactic or therapeutic agents other than a compound of the invention, or a pharmaceutically acceptable salt, solvate or hydrate thereof, said prophylactic or therapeutic agents known to be useful for, or having been or currently being used in the prevention, treatment, management, or amelioration of a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability) or one or more symptoms thereof. In another embodiment, a composition of the invention comprises one or more compounds of the invention, or a pharmaceutically acceptable salt, solvate, or hydrate thereof, and one or more prophylactic or therapeutic agents, said prophylactic or therapeutic agents known to useful, or having been or currently being used in the prevention, treatment or amelioration of a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability) or one or more symptoms thereof.

In a specific embodiment, a composition comprises one or more compounds of the invention, or a pharmaceutically acceptable salt, solvate, or hydrate thereof, and one or more immunomodulatory agents. In another embodiment, a composition comprises one or more compounds of the invention, or a pharmaceutically acceptable salt, solvate, or hydrate thereof, and one or more anti-angiogenic agents, wherein the anti-angiogenic agents are not a compounds of the invention. In another embodiment, a composition comprises one or more compounds of the invention, or a pharmaceutically acceptable salt, solvate, or hydrate thereof, and one or more anti-inflammatory agents, wherein the anti-inflammatory agents are not compounds of the invention. In another embodiment, a composition comprises one or more compounds of the invention, or a pharmaceutically acceptable salt, solvate, or hydrate thereof, and one or more anti-cancer agents, wherein the anti-cancer agents are not compounds of the invention. In accordance with this embodiment, the anti-cancer agent may or may not be an immunomodulatory agent or an anti-angiogenic agent. In another embodiment, a composition comprises one or more compounds of the invention, or a pharmaceutically acceptable salt, solvate, or hydrate thereof, and one or more anti-viral agents. In another embodiment, a composition comprising one or more compounds of the invention, or a pharmaceutically acceptable salt, solvate, or hydrate thereof, or one or more antibiotics. In yet another embodiment, a composition comprises one or more compounds of the invention, or a pharmaceutically acceptable salt, solvate, or hydrate thereof, and any combination of one, two, three, or more of each of the following prophylactic or therapeutic agents: an immunomodulatory agent, an anti-angiogenic agent, an anti-cancer agent other than an immunomodulatory agent or anti-angiogenic agent, an anti-inflammatory agent, an anti-viral agent, or an anti-bacterial agent (e.g., an antibiotic).

In a preferred embodiment, a composition of the invention is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of the invention, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose-free compositions of the invention can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the pharmaceutical compositions or single unit dosage forms are sterile and in suitable form for administration to a subject, preferably an animal subject, more preferably a mammalian subject, and most preferably a human subject.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocane to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disorder may contain larger amounts of one or more of the active ingredients it comprises than a dosage form used in the chronic treatment of the same disease. Also, the therapeutically effective dosage form may vary among different types of cancer. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Typical dosage forms of the invention comprise a compound of the invention, or a pharmaceutically acceptable salt, solvate or hydrate thereof lie within the range of from about 1 mg to about 1000 mg per day, given as a single once-a-day dose in the morning but preferably as divided doses throughout the day taken with food.

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pregelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.4.4 Transdermal, Topical & Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5 Dosage & Frequency of Administration

The amount of the compound or composition of the invention which will be effective in the prevention, treatment, management, or amelioration of a disorder (e.g., a disorder characterized by or associated with aberrant angiogensis, a proliferative disorder, an inflammatory disorder or a disorder prevented, managed, treated or ameliorated by inhibiting or reducing PDE4 or inhibiting or reducing tubulin polymerization or stability, or by reducing or inhibiting tubulin polymerization or stability), or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the *Physician's Desk Reference* (57th ed., 2003).

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In general, the recommended daily dose range of a compound of the invention for the conditions described herein lie within the range of from about 0.01 mg to about 1000 mg per day, given as a single once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention administered to prevent, treat, manage, or ameliorate a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than compounds of the invention, which have been or are currently being used to prevent, treat, manage, or ameliorate a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof can be used in the combination therapies of the invention. Preferably, dosages lower than those which have been or are currently being used to prevent, treat, manage, or ameliorate a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof are used in the combination therapies of the invention. The recommended dosages of agents currently used for the prevention, treatment, management, or amelioration of a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof can obtained from any reference in the art including, but not limited to, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR) 57$^{th}$ Ed., 2003, Medical Economics Co., Inc., Montvale, N.J., which are incorporated herein by reference in its entirety.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies (e.g., prophylactic or therapeutic agents) are administered within the same patent visit.

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing, treating, managing, or ameliorating a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every 3 days, preferably, once every 4 days, once every 5 days, once every 6 days, once every 7 days, once every 8 days, once every 10 days, once every two weeks, once every three weeks, or once a month.

The present invention provides methods of preventing, treating, managing, or preventing a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof, said method comprising: (a) administering to a subject in need thereof one or more doses of a prophylactically or therapeutically effective amount of one or more compounds of the invention; and (b) monitoring the mean absolute lymphocyte count in said subject after administration of a certain number of doses of the said compounds of the invention. Moreover, preferably, said certain number of doses is 1, 2, 3, 4, 5, 6, 7, 8, 9, 10 or 12 of a prophylactically or therapeutically effective amount of the one or more compounds of the invention.

In a specific embodiment, the invention provides a method of preventing, treating, managing, or ameliorating a disorder (e.g., a disorder characterized by or associated with aberrant angiogensis, a proliferative disorder, an inflammatory disorder or a disorder prevented, managed, treated or ameliorated by inhibiting PDE4, or by reducing or inhibiting tubulin polymerization or stability), or one or more symptoms thereof, said method comprising: (a) administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention; and (b) administering one or more subsequent doses to said subject when the mean absolute lymphocyte count in said subject is at least approximately 500 cells/mm$^3$, preferably at least approximately 600 cells/mm$^3$, at least approximately 700 cells/mm$^3$, at least approximately 750 cells/mm$^3$, at least approximately 800 cells/mm$^3$, at least approximately 850 cells/mm$^3$, or at least approximately 900 cells/mm$^3$.

4.5 Biological Asssays

The anti-cancer activity of the pharmaceutical compositions and compounds of the invention can be determined using any suitable animal model, including, but not limited to, SCID mice with a tumor or injected with malignant cells. Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumors (see, e.g., Ghaneh et al., 2001, Gene Ther 8(3): 199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

The anti-inflammatory activity of the pharmaceutical compositions and compounds of the invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the pharmaceutical compositions and compounds of the invention. The following are illustrative assays provided as examples and not by limitation.

The principal animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety.

The anti-inflammatory activity of the pharmaceutical compositions and compounds of the invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," Inflammation, 24(2): 141-155, (2000). Also commonly used are zymosan-induced inflammation animal models as known and described in the art.

The anti-inflammatory activity of the pharmaceutical compositions and compounds of the invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test pharmaceutical composition or compound of the invention is expressed as the percent inhibition of the increase in hind paw weight of the test group relative to the vehicle dosed control group.

In a specific embodiment of the invention where the experimental animal model used is adjuvant-induced arthritis rat model, body weight can be measured relative to a control group to determine the anti-inflammatory activity of the pharmaceutical compositions and compounds of the invention. Alternatively, the efficacy of the pharmaceutical compositions and compounds of the invention can be assessed using assays that determine bone loss. Animal models such as ovariectomy-induced bone resorption mice, rat and rabbit models are known in the art for obtaining dynamic parameters for bone formation. Using methods such as those described by Yositake et al. or Yamamoto et al., bone volume is measured in vivo by microcomputed tomography analysis and bone histomorphometry analysis. Yoshitake et al., "Osteopontin-Deficient Mice Are Resistant to Ovariectomy-Induced Bone Resorption," Proc. Natl. Acad. Sci. 96:8156-8160, (1999); Yamamoto et al., "The Integrin Ligand Echistatin Prevents Bone Loss in Ovariectomized Mice and Rats," Endocrinology 139(3): 1411-1419, (1998), both incorporated herein by reference in their entirety.

Additionally, animal models for inflammatory bowel disease can also be used to assess the efficacy of the pharmaceutical compositions and compounds of the invention (Kim et al., 1992, Scand. J. Gastroenterol. 27:529-537; Strober, 1985, Dig. Dis. Sci. 30(12 Suppl):3S-10S). Ulcerative colitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for asthma can also be used to assess the efficacy of the pharmaceutical compositions and compounds of the invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (Cohn et al., 1997, J. Exp. Med. 186 1737-1747).

Animal models for psoriasis can also be used to assess the efficacy of the pharmaceutical compositions and compounds of the invention. Animal models for psoriasis have been developed (see, e.g., Schon, 1999, J. Invest. Dermatol. 112: 405-410).

Further, any assays known to those skilled in the art can be used to evaluate the prophylactic and/or therapeutic utility of the pharmaceutical compositions and compounds of the invention for the disorders disclosed herein.

The effect of the pharmaceutical compositions and compounds of the invention on peripheral blood lymphocyte counts can be monitored/assessed using standard techniques known to one of skill in the art. Peripheral blood lymphocytes counts in a subject can be determined by, e.g., obtaining a sample of peripheral blood from said subject, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in subject can be determined by, e.g., separating the lymphocytes from other components of peripheral blood such as plasma using, e.g., a use of Ficoll-Hypaque (Pharmacia) gradient centrifugation, labeling the T-cells with an antibody directed to a T-cell antigen such as CD3, CD4, and CD8 which is conjugated to FITC or phycoerythrin, and measuring the number of T-cells by FACS.

The toxicity and/or efficacy of the pharmaceutical compositions and compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical compositions and compounds of the invention that exhibit large therapeutic indices are preferred. While pharmaceutical compositions and compounds of the invention that exhibit toxic side effects may be used, care should be taken to design a delivery system that targets such compositions and compounds to the site of affected tissue in order to minimize potential damage to uninfected cells and, thereby, reduce side effects.

The data obtained from the cell culture assays and animal studies can be used in formulating a range of dosage of the pharmaceutical compositions and compounds of the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography (HPLC) and radioimmunoassay (RIA). The pharmacokinetics of a prophylactic or therapeutic can be determined, e.g., by measuring parameters such as peak plasma level ($C_{max}$), area under the curve (AUC, which is measured by plotting plasma concentration of the agent versus time, and reflects bioavailability), half-life of the compound ($t_{1/2}$), and time at maximum concentration.

Efficacy in preventing or treating a proliferative disorder such as cancer may be demonstrated, e.g., by detecting the ability of the pharmaceutical compositions and compounds of the invention to reduce one or more symptoms of the proliferative disorder, to reduce the proliferation of cancerous cells, to reduce the spread of cancerous cells, or to reduce the size of a tumor. Efficacy in preventing or treating an inflammatory disorder may be demonstrated, e.g., by detecting the ability of the pharmaceutical compositions and compounds of the invention to reduce one or more symptoms of the inflammatory disorder, to decrease T cell activation, to decrease T cell proliferation, to modulate one or more cytokine profiles, to reduce cytokine production, to reduce inflammation of a joint, organ or tissue or to improve quality of life. Changes in inflammatory disease activity may be assessed through tender and swollen joint counts, patient and physician global scores for pain and disease activity, and the ESR/CRP. Progression of structural joint damage may be assessed by quantitative scoring of X-rays of hands, wrists, and feet (Sharp method). Changes in functional status in humans with inflammatory disorders may be evaluated using the Health Assessment Questionnaire (HAQ), and quality of life changes are assessed with the SF-36.

4.6 EXAMPLES

4.6.1 Biological Assays

Compounds of the invention can be assayed using the examples set forth below. General chemicals, as well as tubulin inhibitors Taxol, vinblastine, and colchicine can be purchased from Sigma (St. Louis, Mo.). All compounds are dissolved in 100% DMSO before further dilution in cell culture media. Final DMSO concentrations are kept at a constant 0.1% for all samples, including controls, unless otherwise stated. Streptavidin-coated yttrium SPA beads are obtained from Amersham Pharmacia Biotech (Piscataway, N.J.). [$^3$H] colchicine is available from New England Nuclear (Boston, Mass.), and [$^3$H]Taxol and [$^3$H]vinblastine were from Morevek Biochemicals (Brea, Calif.). Purified tubulin and biotinylated microtubule associated protein-free bovine brain tubulin are available from Cytoskeleton, Inc. (Denver, Colo.).

The human tumor cell lines HT29 (colon adenocarcinoma, HTB-38), HT-144 (melanoma, HTB-63), HCT 116 (colorectal carcinoma, CCL-247), A549 (NSCLC, CCL 185), NIH: OVCAR-3 (ovary adenocarcinoma, HTB-161), PC-3 (prostate adenocarcinoma, CRL-1435), HCT-15 (colorectal adenocarcinoma, CCL-225), MCF-7 (breast adenocarcinoma, HTB-22), MES-SA (uterine sarcoma, CRL-1976), MES-SA/MX2 (CRL-2274), MES-SA/Dx5 (CRL-1977), are available from American Type Culture Collection (Manassas, Va.). MCF-7/ADR is provided by the Signal Research Division of Celgene Corporation. All cell lines are cultivated at 37° C., 5% $CO_2$ in medium as published or as stated on ATCC information sheets. The detailed characteristics of human parental MCF-7, MES-SA cell lines as well as the multidrug-resistant, P-gp 170-overexpressing MCF-7/ADR, MES-SA/MX2, MES-SA/Dx5, HCT-15 cell lines have been reported (see Shan, J., Mason, J. M., Yuan, L., Barcia, M., Porti, D., Calabro, A., Budman, D., Vinciguerra, V., and Xu, H. Rab6c, "A new member of the rab gene family, is involved in drug resistance in MCF7/AdrR cells", Gene 257:67-75 (2000)). HUVEC is provided by the Cellular Therapeutic Division of Celgene Corporation. PBMC from normal donors is obtained by Ficoll-Hypaque (Pharmacia, Piscataway, N.J.) density centrifugation.

4.6.1.1 Cell Proliferation Assay

Cell proliferation is assessed in cancer cell lines, HUVEC and human PBMC by [$^3$H]thymidine incorporation assay. Briefly, cells are seeded on 96-well microtiter plates 24 hours before addition of compound to allow them to adhere to plates. Each compound is tested at serial dilutions in triplicate. Following compound treatment, the cells are incubated at 37° C. for additional 72 hours. [$^3$H]thymidine (1 µCi in 20 µl medium) is added to each well for the last 6 hours of incubation time. The cells are then harvested for detection of tritium incorporation with a TopCount® Microplate Scintillation Counter (Packard Instrument Company, Meriden, Conn.). $IC_{50}$ is calculated from nonlinear regression analysis using GraphPad Prism® program (San Diego, Calif.).

4.6.1.2 Flow Cytometric Analysis

For cell cycle analysis, cells are harvested following treatment with test agents for 24 h, and stained with propidium iodide (PI), per instruction of Cycle Test Plus DNA Reagent Kits from Becton Dickinson (San Jose, Calif.). Samples are examined using FACS Calibur instrument (Becton Dickinson, San Jose, Calif.). Cell cycle distribution is analyzed with CellQuest™ v3.1 acquisition software and the ModFit™ v2.0 program.

For apoptosis analysis, cells are treated with test agents for 48 h and then harvested. Double staining for FITC-Annexin V binding and for DNA using PI is performed as described before (see Zhang, L. H. and Longley, R. E., "Induction of apoptosis in mouse thymocytes by microcolin A and its synthetic analog", Life Sci, 64:1013-1028 (1999)).

4.6.1.3 Tubulin Polymerization or Stability Assay

The polymerization or stability of purified tubulin is monitored using the CytoDYNAMIX™ Screen (Cytoskeleton, Denver, Colo.). This assay uses a 96-well assay plate format with 200 µg of lyophilized purified tubulin in each well. The tubulin is reconstituted with ice-cold 180 µl polymerization or stability buffer (80 mM PIPES, 1 mM $MgCl_2$, 1 mM EGTA) containing test compounds, or vehicle control DMSO. The assay is conducted at 37° C. in a temperature-controlled microtiter plate reader. Tubulin polymerization or stability is monitored spectrophotometrically by the change in absorbance at 340 nm. The absorbance is measured at 1-min intervals for 60 min, using a PowerWave™ HT microplate reader (Bio-Tek Instruments, Highland Park, Vt.).

4.6.1.4 Immunofluorescence Microscopy

Detection of α-tubulin in A549 cells by immunofluorescence is done as described before (see Isbrucker, R. A., Gunasekera, S. P., and Longley, R. E, "Structure-activity relationship studies of discodermolide and its semisynthetic acetylated analogs on microtubule function and cytotoxicity", Cancer Chemother. Pharmacol., 48:29-36 (2001)). Briefly, cells are treated with test compounds for 24 h, washed with PBS. Cells are then fixed and permeabilized with warm PBS buffer containing 3.7% formaldehyde and 1% Triton-X for 30 min. After washing cells twice with PBS and saturation with 1% mouse blocking serum in PBS for 30 min, staining is performed with an anti-α-tubulin-FITC antibody (Sigma) alone or in the presence of 100 µg/ml of propidium iodide. Cells are observed under an epifluorescence microscope (Nikon Instruments, Melville, N.Y.) and imaged with a CCD camera using Image-Pro™ (Media Cybernetics, Silver Spring, Md.).

4.6.1.5 Tubulin Competition-Binding SPA Assay

The tubulin-binding assay is performed as previously reported (see Tahir, S. K., Kovar, P., Rosenberg, S. H., and Ng, S. C., "Rapid colchicine competition-binding scintillation proximity assay using biotin-labeled tubulin", Biotechniques, 29:156-160 (2000)) using biotin-labeled tubulin, streptavidin-coated yttrium SPA beads, and [$^3$H]-labeled ligands ([$^3$H]colchicine, [$^3$H]Taxol, or [$^3$H]vinblastine). Briefly, the binding mixture includes 0.08 µM [$^3$H]-labeled ligand, 1 mM GTP, and 0.5 µg of biotinylated tubulin in 100-µl of assay buffer containing 80 mM PIPES pH 6.9, 1 mM $MgCl_2$, 1 mM EGTA, and 5% glycerol. The test compound and [$^3$H]I-labeled ligand are added before tubulin. After incubation at 37° C. for 2 h, 20 µl of SPA beads (80 µg in the assay buffer) are added. After further incubation for 30 min under agitation at room temperature, the SPA beads are allowed to settle down for 45 min, and scintillation counting is done on the TopCount® Microplate Scintillation Counter.

4.6.1.6 Caspase Assay

Caspase activity is determined per instructions from the assay kit supplier (R&D systems, Minneapolis, Minn.). Briefly, cells are collected and centrifuged at 250×g for 10 minutes, following drug treatment. Cell pellets are lysed using lysis buffer. Cell lysates are incubated on ice for 10 minutes and then centrifuged at 10,000×g for 1 minute. The enzymatic reaction for caspase activity is carried out in 96 well microtiter plates. 50 µl of lysate containing 200 µg of total protein, 50 µl of 2× reaction buffer and 5 µl of caspase specific peptide substrates (DEVD, IETD or LEHD conjugated to p-nitroanaline for caspase-3, -8.-9 respectively) are mixed. The mixtures are incubated at 37° C. for 2 hours before $A_{405nm}$ is read using the microplate reader. The results are expressed as fold change in caspase activity of drug-treated cells over the vehicle control cells.

4.6.1.7 Immunoblot Analysis of Cell Cycle Regulatory Proteins

Cancer cells are treated with a compound of the invention or 0.1% DMSO for 24 h. Cells are trypsinized and spun down for 6 seconds in a microfuge and immediately lysed in 0.1 ml lysis buffer containing 10 mM Tris-HCl pH 8.0, 10 mM EDTA, 150 mM NaCl, 1% NP-40, 0.5% SDS, 1 mM DTT, 1 mM $Na_3VO_4$, plus Complete protease inhibitor cocktail (Roche Applied Science, Indianapolis, Ind.), then spun through a Qiashredder™ (Qiagen, Valencia, Calif.) for 1 minute and frozen on dry ice. Samples are diluted with 3×SDS sample buffer (New England Biolabs, Beverly, Mass.) and boiled 5 minutes. Approximately 30 µl of this mixture is loaded per lane on Tris-Glycine polyacrylamide gels (Invitrogen, Carlsbad, Calif.), electrophoresed, and transferred to PVDF membranes (Invitrogen). PVDF membranes are blocked for 1 hour at room temperature in PBS containing 0.05% Tween-20 and 5% non-fat milk powder, then blotted overnight at 4° C. with antibodies against either MPM-2 (Upstate Biotechnology, Lake Placid, N.Y.), Bcl-2, Cdc2, p53, p21 or Cdc25C (Santa Cruz Biotechnology, Santa Cruz, Calif.). Membranes are washed and incubated with HRPO conjugated anti-rabbit or anti-mouse IgG (Santa Cruz Biotechnology, Santa Cruz, Calif.) (1:10.00 dilution) for 60 minutes at room temperature, washed 3 times, then developed using the ECL Plus chemiluminescent detection system (Amersham Biosciences, Piscataway, N.J.).

4.6.1.8 PBMC Culture and ELISA for TNF-α

PBMC are prepared by density centrifugation on Ficoll-Hypaque. PBMC, re-suspended at $1\times10^6$/ml in complete RPMI-1640 medium/10% fetal calf serum, are stimulated with LPS (1 µg/ml; *Escherichia coli* serotype 0127:B8; Sigma) in 24-well plates by incubation at 37° C. in 5% $CO_2$ for 24 h±compounds (0.1-100 µM). Cell-free supernatants are collected and stored in aliquots at −70° C. until assayed by ELISA. Supernatants are assayed for TNF-α using an assay procedure and reagents provided by R&D Systems (Minneapolis, Minn.).

4.6.1.9 PDE4 Assay

PDE purification from U937 cells is performed as described previously (see Marriott, J. B., Westby, M., Cookson, S., Guckian, M., Goodbourn, S., Muller, G., Shire, M. G., Stirling, D., and Dalgleish, A. G., "CC-3052: A water-soluble analog of thalidomide and potent inhibitor of activation-induced TNF-alpha production", J. Immunol., 161:4236-4243 (1998)). Briefly, cells ($1\times10^9$) are washed in PBS and lysed in cold homogenization buffer (20 mM Tris-HCl, pH 7.1, 3 mM 2-mercaptoenthanol, 1 mM $MgCl_2$, 0.1 mM EGTA, 1 µM PMSF, 1 µg/ml leupeptin). Following homogenization, the supernatant is collected by centrifugation and loaded onto a Sephacryl S-200 column equilibrated in homogenization buffer. PDE is eluted in homogenization buffer and rolipram-sensitive fractions pooled and stored in aliquots. PDE activity is assayed by a procedure described by Di Santo and Heaslip (DiSanto, M. E. and Heaslip, R. J., "Identification and stabilization of large molecular weight PDE-IVs from U937 cells", Biochem. Biophys. Res. Commun., 197:1126-1131 (1993)) and in the presence of varying concentrations of compounds, 50 mM Tris-HCl, pH 7.5, 5 mM $MgCl_2$, and 1 µM cAMP (of which 1% was [$^3$H]cAMP). The amount of extract used is predetermined to ensure that reactions are within the linear range and consumed <15% of the total substrate. Reactions are performed at 30° C. for 30 min and terminated by boiling for 2 min. The samples are then chilled and treated with snake venom (1 mg/ml) at 30° C. for 15 min. Unused substrate is removed by addition of 200 µl AG1-X8 resin (Bio-Rad, Richmond, Calif.) for 15 min. Samples are then spun at 3000 rpm for 5 min, and 50 µl of the aqueous phase is taken for counting. Each data point is conducted in duplicate with activity expressed as percentage of control. $IC_{50}$ is determined from dose-response curves derived from three independent experiments.

4.6.1.10 Human Tumor Xenograft Model

CB17 SCID mice (6-8 weeks old, female) are maintained in microisolator cages under sterile conditions. HCT-116 (colon cancer) cells suspended in sterile PBS are injected subcutaneously into mice ($2\times10^6$ cells/mouse). On day 6, tumors of all mice are measured with a digital caliper and volumes calculated with a formula of $W^2\times L/2$ [W=width (short axis); L=Length (long axis)]. Mice bearing tumor size ranging between 75-125 mm$^3$ are pooled together and randomly distributed into cages. The mice are then ear tagged and cages were randomly assigned to treatment groups. On day 7, the tumors are measured and considered as starting volumes, the mice are then administered i.p. with either vehicle control (N-methyl-2 pyrrolidone: PEG400: saline at ratio of 1:9:10), CC-5079 (5 and 25 mg/kg) or positive control Camptosar™ (10 mg/kg). Tumor sizes are determined at intervals indicated.

4.6.1.11 Cell Adhesion Assay

HUVECs are seeded on 24 well culture plates and incubated for 2 days to allow formation of a confluent monolayer. Cancerous cells or a cancer cell line such as LS-180 human colon adenocarcinoma cells are labeled with 5 µM Calcein-AM for 30 min. Calcein-AM labeled LS-180 cells are added into each well of the HUVEC culture and incubated for 10 min at 37° C. TNF-α (80 ng/ml) is then added and the culture is incubated for an additional 110 min. Non-adherent cells are removed by washing with PBS. The fluorescence intensity of adherent LS-180 cell in each individual well is measured by a fluorescent plate reader set at excitation 485/20 nm and emission at 530/25 nm.

4.6.1.12 Cell Migration and Invasion Assay

Cell migration and invasion are determined using an assay based on the BD BioCoast Angiogenesis System (BD Biosciences, Bedford, Mass.). The fluorescence blocking membrane of the insert is a 3 micron pore size PET filter which has been coated either with BD Matrigel basement matrix (for invasion assay) or without Matrigel matrix (for migration assay). HUVECs (250 µl/well) in culture medium without serum are added to the top chamber and a compound of the invention is added to bottom wells containing medium (750 µl/well) with VEGF as a chemo-attractant. Cells are then incubated for 22 h at 37° C. After incubation, cells are stained with Calcein AM for measurement of fluorescence.

4.6.1.13 Angiogenesis Assay

The effect of a compound of the invention on angiogenesis is assessed using fresh human umbilical cords collected by trained medical personnel. The cords are transported directly to the laboratory within about three hours and umbilical cords and vessel lumens are rinsed with chilled basal nutrient medium. The artery is removed from the cord using mechanical means, forceps and small surgical scissors in an aseptic field. The vessel is cleaned of connective tissue and vessel rings are cut cross-wise in a length of 1 mm. The rings are placed into EGM-2 medium (Clonetics Corp), in a 50 ml conical bottom tube and transported at 4° C. to Celgene corporation. Six-well tissue culture plates are covered with 250 µl of Matrigel and allowed to gel for 30-45 min at 37° C., 5% $CO_2$. The vessel rings are rinsed in EGM-w medium and placed on the Matrigel coated wells, covered with additional 250 µl Matrigel, and allowed to gel for 30-45 min at 37° C. The vessels are cultured for 24 hours in 4 ml of EGM-2 to allow the tissue to adapt to its new environment. After 24 hours incubation, the rings are treated either with 0.1% DMSO as control, or different concentrations of a compound of the invention. Culture medium is changed twice per week for total of three weeks. The effects of the compound of the invention are compared with DMSO treated vessel rings. The results are analyzed using image-proplus software.

4.6.2 Synthesis of Illustrative Compounds of the Invention

4.6.2.1 3-(2,3-Dihydro-benzo[1,4]dioxin-6-yl)-3-(3,5-dimethoxy-phenyl)-acrylonitrile

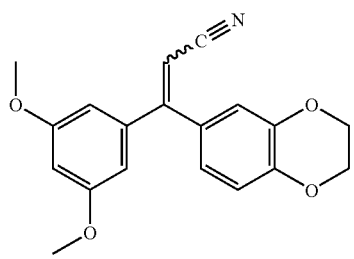

A solution of 6-bromo-2,3-dihydrobenzo[1,4]dioxine (1.09 g, 5.07 mmol) in anhydrous THF (10 ml) was cooled to −78° C., evacuated and refilled with nitrogen for ten cycles. To this clear solution was slowly added n-butyl lithium (2.03 ml, 5.07 mmol) and stirred for 30 min. Then a solution of 3,5-dimethoxybenzaldehyde (0.77 g, 4.61 mmol) in anhydrous THF (10 ml) was added via a syringe. The mixture was stirred at −78° C. under nitrogen for 4 h then quenched with 2-propanol (2.10 ml, 27.65 mmol) and stirred overnight. To the orange colored mixture was added 30 ml of water and extracted with ether (3×60 ml). The combined ether extracts was washed with water (2×60 ml), dried over MgSO$_4$, filtered and concentrated in vacuo to an oil, which was purified via flash column chromatography (10% EtOAc in hexane gradient to 40% EtOAc in hexane in about 40 min.) to give (2,3-dihydro-benzo[1,4]dioxin-6-yl)-(3,5-dimethoxy-phenyl)-methanol as a light brown oil (1.27 g, 91%), HPLC purity was 93.4% at 3.45 min. (50/50 ACN/0.1% H$_3$PO$_4$): $^1$HNMR (CDCl$_3$) δ 6.88-6.79 (m, 3H, Ar), 6.54 (d, J=2 Hz, 2H, Ar), 6.35 (t, J=2 Hz, 1H, Ar), 5.65 (d, J=3 Hz, 1H, CH), 4.22 (m, 4H, 2CH$_2$), 3.77 (s, 6H, OCH$_3$), 2.25 (d, J=3 Hz, 1H, OH). The product was carried over to the next step.

To a stirred solution of (2,3-dihydrobenzo[1,4]dioxin-6-yl)-(3,5-dimethoxyphenyl)-methanol (1.15 g, 3.80 mmol) in CH$_2$Cl$_2$ (20 ml) at rt was added activated MnO$_2$ powder (1.65 g, 19 mmol) and kept adding 2~3 equivalents of MnO$_2$ every 3~5 h until HPLC showed at least 98% conversion occurred. The black suspension was filtered through a Celite pad, concentrated in vacuo to give (2,3-dihydro-benzo[1,4]dioxin-6-yl)-(3,5-dimethoxy-phenyl)-methanone as an oil (1.06 g, 93%): $^1$HNMR (CDCl$_3$) δ 7.42 (d, J=1 Hz, 1H, Ar), 7.38 (dd, J=1.88, 8 Hz, 1H, Ar), 6.92 (d, J=8 Hz, 1H, Ar), 6.88 (d, J=2 Hz, 2H, Ar), 6.64 (t, J=2 Hz, 1H, Ar), 4.36-4.29 (m, 4H, 2CH$_2$), 3.82 (s, 6H, OCH$_3$). The product was carried over to the next step.

To a stirred solution of cyanomethylphosphonic acid diethyl ester (1.08 ml, 6.86 mmol) in anhydrous THF (10 ml) in an ice bath was added lithium bis-(trimethylsilyl) amide (1.0 M solution in THF, 6.86 ml, 6.86 mmol) slowly. The mixture was stirred at rt for 40 min, before a solution of (2,3-dihydrobenzo[1,4]dioxin-6-yl)-(3,5-dimethoxyphenyl) methanone (1.03 g, 3.43 mmol) in anhydrous THF (20 ml) was added. The mixture was refluxed overnight. The solution was poured into ice water (20 ml) and the two phases were separated. The THF phase was evaporated and combined with the aqueous phase, which were then extracted with CH$_2$Cl$_2$ (2×40 ml), washed with water (50 ml), dried over MgSO$_4$, filtered and concentrated in vacuo to an oil, which was purified via flash column chromatography 5% EtOAc in hexane gradient to 25% EtOAc in hexane) to give 3-(2,3-dihydro-benzo[1,4]dioxin-6-yl)-3-(3,5-dimethoxy-phenyl)-acrylonitrile as an oil (0.98 g, 88%): $^1$H NMR (DMSO-d$_6$) δ 6.99-6.79 (m, 3H, Ar), 6.65-6.62 (2ts, 1H, Ar), 6.46-6.44 (2ds, 2H, Ar), 6.25 (s, 0.47H, double bond proton of one isomer), 6.20 (s, 0.54H, double bond proton of the other isomer), 4.33-4.24 (m, 4H, 2CH$_2$), 3.76 (s, 3H, OCH$_3$), 3.74 (s, 3H, OCH$_3$); $^{13}$C NMR (DMSO-d$_6$) δ 179.5, 160.8, 160.7, 145.7, 144.8, 143.3, 143.0, 140.3, 139.1, 130.4, 129.7, 122.5, 121.7, 118.2, 118.1, 117.9, 117.2, 117.1, 116.6, 107.1, 106.7, 101.8, 100.9, 95.4, 94.3, 64.4, 64.2, 64.0, 64.0, 55.4, 54.9; Anal. Calcd. For C$_{19}$H$_{17}$NO$_4$ (+0.05H$_2$O): C, 69.40; H, 5.26; N, 4.24. Found: C, 69.19; H, 5.11; N, 4.25.

4.6.2.2 2E and 2Z 3-(2,3-Dihydro-benzo[1,4]dioxin-6-yl)-3-(3,5-dimethoxy-phenyl)-acrylonitrile

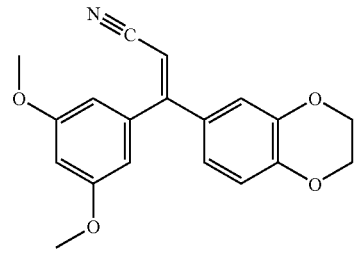

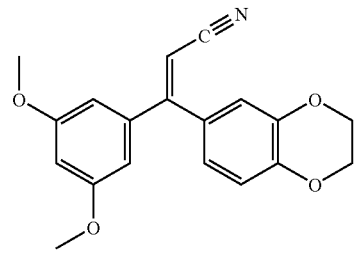

About 0.7 g of oily 3-(2,3-dihydro-benzo[1,4]dioxin-6-yl)-3-(3,5-dimethoxy-phenyl)-acrylonitrile was purified via Prep HPLC using 40% acetonitrile/60% water (90 min. run) to give 2E and 2Z isomers (about 200 mg white solid each isomer).

2E  3-(2,3-Dihydro-benzo[1,4]dioxin-6-yl)-3-(3,5-dimethoxy-phenyl)-acrylonitrile: HPLC purity was 98.03% at 4.76 min (60/40 ACN/H$_2$O). mp, 93-95° C.; $^1$HNMR (DMSO-d$_6$) δ 6.93 (d, J=2 Hz, 1H, Ar), 6.89 (d, J=8 Hz, 1H, Ar), 6.81 (dd, J=1.95, 8 Hz, 1H, Ar), 6.64 (t, J=2 Hz, 1H, Ar), 6.44 (d, J=2 Hz, 2H, Ar), 6.24 (s, 1H, double bond proton), 4.29-4.24 (m, 4H, CH$_2$), 3.76 (s, 6H, OCH$_3$); $^{13}$C NMR (DMSO-d$_6$) δ 160.7, 160.4, 145.7, 143.3, 139.1, 130.4, 121.7, 118.2, 117.2, 116.6, 107.1, 100.9, 94.3, 64.4, 64.0, 55.4; Anal. Calcd. for C$_{19}$H$_{17}$NO$_4$ (+0.05H$_2$O): C, 70.38; H, 5.32; N, 4.32. Found: C, 70.12; H, 5.29; N, 4.36. The absolute structure was determined via NOE.

2Z  3-(2,3-Dihydro-benzo[1,4]dioxin-6-yl)-3-(3,5-dimethoxy-phenyl)-acrylonitrile: HPLC purity was 97.39% at 5.22 min (60/40 ACN/H$_2$O). mp, 100-102° C.; $^1$HNMR (DMSO-d$_6$) δ 6.97 (d, J=8 Hz, 1H, Ar), 6.89 (d, J=1 Hz, 1H, Ar), 6.82 (dd, J=2.09, 8 Hz, 1H, Ar), 6.62 (t, J=2 Hz, 1H, Ar), 6.45 (d, J=2 Hz, 2H, Ar), 6.20 (s, 1H, double bond H), 4.33-

4.28 (m, 4H, CH$_2$), 3.73 (s, 6H, OCH$_3$); $^{13}$C NMR (DMSO-d$_6$) δ 160.8, 160.4, 144.8, 143.0, 140.3, 129.7, 122.6, 118.2, 117.9, 117.1, 106.8, 101.8, 95.5, 64.3, 64.0, 55.4; Anal. Calcd. for C$_{19}$H$_{17}$NO$_4$ (+0.25H$_2$O): C, 69.61; H, 5.38; N, 4.27; Found: C, 69.64; H, 5.40; N, 4.42. The absolute structure was determined via NOE.

4.6.2.3 3-(3,5-Dimethoxy-phenyl)-3-(3-hydroxy-4-methoxy-phenyl)-acrylonitrile

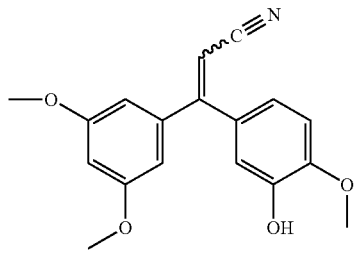

Ethyldiisopropylamine (1.72 ml, 9.85 mmol) was added to a solution of 5-bromo-2-methoxy-phenol (0.80 g, 3.94 mmol) in DMF (10 ml) at rt. The clear, colorless solution was stirred for 5 min. followed by addition of tert-butylchlorodimethylsilane (0.71 g, 4.73 mmol). The reaction was complete in about two hours. Distilled water (~6 ml) was added to the clear solution, stirred for 10 min., added ether (50 ml) and sat. NaHCO$_3$ (10 ml), stirred for 30 min. The ether portion was separated and the aqueous phase was extracted with ether (2×50 ml). The combined ether phases were washed with water (100 ml), brine (60 ml), dried over MgSO$_4$, filtered and concentrated to an oil, which was further purified by flash column chromatography [100% hexane with 0.5% triethylamine gradient to 30% EtOAc in hexane with 0.5% Et$_3$N] to give (5-bromo-2-methoxy-phenoxy)-tert-butyl-dimethyl-silane as an oil (0.59 g, 99%), HPLC purity 99.5% at 1.43 min. (90/10 ACN/0.1% H$_3$PO$_4$): $^1$H NMR (DMSO-d$_6$) δ 7.04-6.97 (m, 2H, Ar), 6.71 (d, J=8 Hz, Ar), 3.78 (s, 3H, single OCH$_3$), 0.99 (s, 9H, 3OCH$_3$), 0.16 (s, 6H, 2OCH$_3$). The product was carried over to the next step.

(5-Bromo-2-methoxyphenoxy)-tert-butyldimethylsilane (0.98 g, 3.09 mmol), n-butyl lithium (1.24 ml, 3.09 mmol), and 3,5-dimethoxybenzaldehyde (0.47 g, 2.81 mmol) were treated in the same manner as described above for the synthesis of (2,3-dihydrobenzo[1,4]dioxin-6-yl)-(3,5-dimethoxyphenyl)methanol. The crude material was purified via flash column chromatography (5% EtOAc in hexane gradient to 30% EtOAc in hexane in about 40 min.) to give [3-(tert-butyl-dimethyl-silanyloxy)-4-methoxy-phenyl]-(3,5-dimethoxyphenyl)-methanol as an oil (0.79 g, 69%), HPLC purity was 98.3% at 2.55 min. (90/10 ACN/0.1% H$_3$PO$_4$): $^1$HNMR (CDCl$_3$) δ 6.92-6.78 (m, 3H, Ar), 6.53 (d, J=2 Hz, 2H, Ar), 6.35 (t, J=2 Hz, 1H, Ar), 5.66 (d, J=3 Hz, 1H, CH), 3.78 (s, 3H, single OCH$_3$), 3.76 (s, 6H, 2OCH$_3$), 2.15 (d, J=3 Hz, 1H, OH), 0.97 (s, 9H, 3OCH$_3$), 0.13 (s, 6H, 2OCH$_3$). The product was carried over to the next step.

[3-(tert-Butyldimethylsilanyloxy)-4-methoxyphenyl]-(3,5-dimethoxyphenyl)methanol (0.78 g, 1.93 mmol) and activated MnO2 powder (1.33 g, 15 mmol) were treated in the same manner as described above for the synthesis of (2,3-dihydrobenzo[1,4]dioxin-6-yl)-(3,5-dimethoxyphenyl)methanone. The product [3-(tert-butyl-dimethyl-silanyloxy)-4-methoxy-phenyl]-(3,5-dimethoxy-phenyl)-methanone was an oil (0.82 g, 100%): $^1$HNMR (CDCl$_3$) δ 7.47-7.40 (m, 2H, Ar), 6.90-6.86 (m, 3H, Ar), 6.65 (t, J=2 Hz, 1H, Ar), 3.88 (s, 3H, OCH3), 3.82 (s, 6H, 2OCH3), 0.99 (s, 9H, 3OCH3), 0.18 (s, 6H, 2OCH3). The product was carried over to the next step.

[3-(tert-butyldimethylsilanyloxy)-4-methoxyphenyl]-(3,5-dimethoxyphenyl) methanone (0.74 g, 1.84 mmol), cyanomethylphosphonic acid diethyl ester (0.58 ml, 3.68 mmol) in anhydrous THF (10 ml), and lithium bis(trimethylsilyl)amide (1.0 M solution in THF, 3.70 ml, 3.68 mmol) were treated in the same manner as described above for the synthesis of 3-(2,3-dihydrobenzo[1,4]dioxin-6-yl)-3-(3,5-dimethoxyphenyl)-acrylonitrile. The crude was purified via flash column chromatography (100% hexane gradient to 20% EtOAc in hexane in about 40 min.) to give 3-[3-(tert-butyl-dimethyl-silanyloxy)-4-methoxy-phenyl]-3-(3,5-dimethoxy-phenyl)-acrylonitrile as an clear colorless oil (0.58 g, 74%): $^1$HNMR (CDCl$_3$) δ 7.09-6.78 (m, 3H, Ar), 6.53-6.51 (m, 2H, Ar), 6.41 (d, J=2 Hz, 1H, Ar), 5.60 (s, 1H, CH), 3.86-3.76 (multiple singlets, 9H), 0.97 (s, 9H, 3OCH$_3$), 0.14 (s, 6H, 2OCH$_3$). The product was carried over to the next step.

Tetrabutylammonium fluoride (1.0 M solution in THF, 1.49 ml, 1.49 mmol) was added at rt to a stirred solution of 3-[3-(tert-butyldimethylsilanyloxy)-4-methoxyphenyl]-3-(3,5-dimethoxyphenyl)acrylonitrile (0.53 g, 1.25 mmol) in THF (15 ml). The colorless clear solution immediately turned into brown/red wine color. The reaction should be done within one hour. Ice water (10 ml) was poured into the reddish solution, followed by addition of ether (50 ml). The mixture was washed with water (2×80 ml), dried over MgSO$_4$, filtered and concentrated to a yellow oil, which was lyophilized to give 3-(3,5-dimethoxy-phenyl)-3-(3-hydroxy-4-methoxy-phenyl)-acrylonitrile as a foamy solid (0.35 g, 90%): mp, 43-45° C.; $^1$HNMR (DMSO-d$_6$) δ 9.36 (s, 1H, OH group of one isomer), 9.28 (s, 1H, OH group of the other isomer), 7.07 (d, J=8 Hz, 1H, Ar), 7.00 (d, J=8 Hz, 1H, Ar), 6.91-6.82 (m, 4H, Ar), 6.69-6.65 (m, 2H, Ar), 6.49 (t, J=2 Hz, 4H, Ar), 6.19 (s, 1H, double bond proton of one isomer), 6.17 (s, 1H, double bond proton of the other isomer), 3.87 (s, 3H, OCH$_3$), 3.84 (s, 3H, OCH$_3$), 3.81 (s, 6H, 2OCH$_3$), 3.78 (s, 6H, 2OCH$_3$), isomer ratio based on $^1$HNMR was 45%: 55%; $^{13}$C NMR (CDCl$_3$) δ 162.8, 162.6, 160.8, 160.8, 148.7, 148.2, 145.7, 145.5, 141.4, 139.1, 131.9, 130.2, 122.3, 121.3, 118.2, 118.1, 116.0, 114.4, 110.4, 110.4, 107.8, 107.1, 102.2, 94.2, 93.5, 56.2, 56.1, 55.6; Anal. Calcd. For C$_{18}$H$_{17}$NO$_4$: C, 69.12; H, 5.53; N, 4.48. Found: C, 68.76; H, 5.69; N, 4.22.

4.6.2.4 3-Benzo[1,3]dioxol-5-yl-3-(3,5-dimethoxy-phenyl)-acrylonitrile

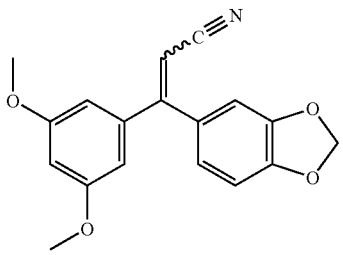

1-Bromo-3,5-dimethoxybenzene (0.47 g, 3.14 mmol), benzo[1,3]dioxole-5-carbaldehyde (0.75 g, 3.46 mmol), and n-butyl lithium (1.38 ml, 3.46 mmol) were treated in the same manner as described above for the synthesis of (2,3-dihydrobenzo[1,4]dioxin-6-yl)-(3,5-dimethoxyphenyl)methanol. The crude was purified via flash column chromatography (5% EtOAc in hexane gradient to 30% EtOAc in hexane in about 40 min.) to give Benzo[1,3]dioxol-5-yl-(3,5-dimethoxy-phenyl)-methanol as an off-white oil (0.73 g, 81%): ¹HNMR (CDCl₃) δ6.87-6.83 (m, 2H, Ar), 6.77-6.74 (m, 1H, Ar), 6.53 (d, J=2 Hz, 2H, Ar), 6.36 (t, J=2 Hz, 1H), 5.93 (m, 2H, CH₂), 5.68 (d, J=3 Hz, 1H, CHOH), 3.77 (s, 6H, 2OCH₃), 2.15 (d, J=3 Hz, 1H, OH). The product was carried over to the next step.

Benzo[1,3]dioxol-5-yl-(3,5-dimethoxyphenyl)methanol (0.72 g, 2.43 mmol) and activated MnO₂ powder (3.4 g, 39 mmol) were treated in the same manner as described above for the synthesis of (2,3-dihydrobenzo[1,4]dioxin-6-yl)-(3,5-dimethoxyphenyl) methanone. The product benzo[1,3]dioxol-5-yl-(3,5-dimethoxy-phenyl)-methanone was an off-white solid (0.64 g, 92%): ¹HNMR (CDCl₃) δ 7.43-7.38 (m, 2H, Ar), 6.88-6.84 (m, 3H, Ar), 6.65 (t, J=2 Hz, 1H, Ar), 6.07 (s, 2H, CH₂), 3.83 (s, 6H, 2OCH₃). The product was carried over to the next step.

Benzo[1,3]dioxol-5-yl-(3,5-dimethoxyphenyl)methanone (0.63 g, 2.20 mmol), cyanomethylphosphonic acid diethyl ester (0.69 ml, 4.40 mmol) in anhydrous THF (10 ml), and lithium bis(trimethylsilyl)amide (1.0 M solution in THF, 4.40 ml, 4.40 mmol) were treated in the same manner as described above for the synthesis of 3-(2,3-dihydrobenzo-[1,4]dioxin-6-yl)-3-(3,5-dimethoxyphenyl)acrylonitrile. The crude material was purified via flash column chromatography (5% EtOAc in hexane gradient to 30% EtOAc in hexane in about 40 min.) to give a light brown oil, which was lyophilized to give benzo[1,3]dioxol-5-yl-(3,5-dimethoxy-phenyl)-methanone as a solid (0.64 g, 94%): mp, 147-149° C.; ¹HNMR (DMSO-d₆) δ 7.11 (d, J=1 Hz, 1H, Ar), 7.04 (d, J=7 Hz, 1H, Ar), 6.95-6.92 (m, 2H, Ar), 6.87 (dd, J=1.7, 7 Hz, 1H, Ar), 6.73 (dd, J=1 Hz and 8 Hz, 1H, Ar), 6.65-6.62 (m, 2H, Ar), 6.47-6.45 (m, 4H, Ar), 6.25 (s, 1H, double bond proton of one isomer), 6.24 (s, 1H, double bond proton of the other isomer), 6.12 (s, 2H, CH₂ of one isomer), 6.09 (s, 2H, CH₂ of the other isomer), 3.76 (s, 3H, OCH₃), 3.73 (s, 3H, OCH₃), isomer ratio based on ¹HNMR was 44%: 56%; ¹³C NMR (DMSO-d₆) δ 161.1, 160.9, 160.4, 149.4, 148.5, 147.9, 147.3, 140.2, 139.2, 131.4, 130.5, 123.8, 123.7, 118.2, 118.2, 109.3, 108.3, 108.2, 107.3, 107.1, 106.7, 101.9, 101.8, 101.7, 10.0, 95.8, 94.4, 55.4, 55.4; Anal. Calcd. For C₁₈H₁₅NO₄: C, 69.89; H, 4.89; N, 4.53. Found: C, 69.90; H, 4.70; N, 4.52.

4.6.2.5 3,3-Bis-(3,5-dimethoxy-phenyl) acrylonitrile

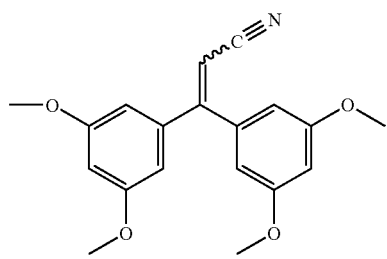

3,5-Dimethoxybenzaldehyde (0.84 g, 5.03 mmol), 1-bromo-3,5-dimethoxybenzene (1.20 g, 5.53 mmol), and n-butyl lithium (2.20 ml, 5.53 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 60% EtOAc in hexane in about 40 min.) to give Bis-(3,5-dimethoxy-phenyl)-methanol as an off-white solid (1.31 g, 86%): ¹HNMR (CDCl₃) δ6.55 (d, J=2 Hz, 4H, Ar), 6.36 (t, J=2 Hz, 2H, Ar), 5.67 (d, J=3 Hz, 1H, CHOH), 3.77 (s, 12H, 4OCH₃), 2.24 (d, J=3 Hz, 1H, OH). The product was carried over to the next step.

Bis-(3,5-dimethoxyphenyl)methanol (1.30 g, 4.27 mmol) and activated MnO₂ powder (1.86 g, 21 mmol) were treated in the same manner as described above for the synthesis of (2,3-dihydrobenzo[1,4]dioxin-6-yl)-(3,5-dimethoxyphenyl) methanone. The product bis-(3,5-dimethoxy-phenyl)methanone was an off-white solid (1.36 g, 100%): ¹HNMR (CDCl₃) δ 6.93 (d, J=2 Hz, 4H, Ar), 6.67 (t, J=2 Hz, 2H, Ar), 3.83 (s, 12H, 4OCH₃). The product was carried over to the next step.

Bis-(3,5-dimethoxyphenyl)methanone (1.29 g, 4.27 mmol), cyanomethylphosphonic acid diethyl ester (1.34 ml, 8.53 mmol) in anhydrous THF (10 ml), and lithium bis(trimethylsilyl)amide (1.0 M solution in THF, 8.53 ml, 8.53 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (5% EtOAc in hexane gradient to 40% EtOAc in hexane in about 45 min.) to give 3,3-bis-(3,5-dimethoxy-phenyl)-acrylonitrile as an off-white solid (1.06 g, 76%): mp, 149-151° C.; ¹HNMR (DMSO-d₆) δ 6.66-6.62 (m, 2H, Ar), 6.50-6.47 (m, 4H, Ar), 6.39 (s, 1H, double bond proton), 3.76 (s, 6H, 2OCH₃), 3.74 (s, 6H, 2OCH₃); ¹³C NMR (CDCl₃) δ 163.0, 160.9, 160.8, 140.8, 138.7, 117.7, 107.8, 106.9, 102.4, 102.2, 95.5, 55.6; Anal. Calcd. For C₁₉H₁₉NO₄: C, 70.14; H, 5.89; N, 4.30. Found: C, 69.93; H, 5.96; N, 4.18.

4.6.2.6 3-(2,5-Dimethoxy-phenyl)-3-(3,5-dimethoxyphenyl)-acrylonitrile

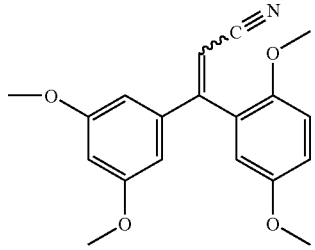

Aluminum chloride (3.76 g, 28.18 mmol) was added to a stirred mixture of 1,3-dimethoxybenzene (3.54 g, 25.62 mmol) in anhydrous methylene chloride (20 ml) in an ice bath. A solution of 3,5-dimethoxybenzoyl chloride (5.14 g, 25.62 mmol) in anhydrous methylene chloride (50 ml) was then added. The mixture was allowed to warm up to rt and refluxed overnight. After cooling down to rt, the mixture was poured to ice water (50 ml), stirred for 20 min., and extracted with methylene chloride (3×50 ml). The combined organic extracts was washed with sat. NaHCO₃ (3×50 ml), H₂O (2×50 ml), brine (50 ml), dried over MgSO₄, filtered and concentrated in vacuo to an oil, which was purified via flash column chromatography (10% EtOAc in hexane) to give (2,5-dimethoxy-phenyl)-(3,5-dimethoxy-phenyl)-methanone as a yellow oil (4.81 g, 62% as the major product); ¹HNMR (CDCl₃) δ 7.36 (d, J=8 Hz, 1H, Ar), 6.93 (d, J=2 Hz, 2H, Ar), 6.63 (t, J=2 Hz, 1H, Ar), 6.55 (d, J=2 Hz, 1H, Ar), 6.51 (m, 1H), 3.89 (s, 3H, OCH₃), 3.83 (s, 6H, 2OCH₃); ¹³C NMR (CDCl₃) δ 195.3, 163.4, 160.6, 159.8, 140.9, 132.2, 121.7, 107.7, 105.2, 104.6, 99.1, 55.8, 55.7, 55.6; Anal. Calcd. For C₁₇H₁₈O₅: C, 67.54; H, 6.00. Found: C, 67.50; H, 5.88. The product was carried over to the next step.

(2,5-dimethoxyphenyl)-(3,5-dimethoxyphenyl)methanone (1.25 g, 4.13 mmol), cyanomethylphosphonic acid diethyl ester (1.30 ml, 8.26 mmol) in anhydrous THF (10 ml), and lithium bis(trimethylsilyl)amide (1.0 M solution in THF, 8.26 ml, 8.26 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (5% EtOAc in hexane gradient to 20% EtOAc in hexane in about 45 min.) to give an oil (1.27 g), which was further purified via PREP HPLC. The pure fractions were concentrated to give 3-(2,5-dimethoxy-phenyl)-3-(3,5-dimethoxyphenyl)-acrylonitrile as an oil (1.13 g, 84%); ¹HNMR (DMSO-d₆) δ 7.12-6.41 (m, 12H, Ar), 6.17 (s, 1H, double bond proton), 3.83-3.66 (multiple singlets, 24H, 8OCH₃); ¹³C NMR (CDCl₃) δ 162.4, 162.3, 160.9, 160.7, 160.1, 159.4, 159.3, 158.4, 141.3, 140.8, 133.3, 131.9, 120.4, 118.9, 118.5, 118.0, 107.2, 105.8, 104.9, 104.6, 101.9, 101.7, 99.4, 99.2, 96.7, 96.6, 55.8, 55.7, 55.6, 55.6; Anal. Calcd. For C₁₉H₁₉NO₄: C, 70.14; H, 5.89; N, 4.30. Found: C, 69.96; H, 5.67; N, 4.68.

4.6.2.7 3,3-Bis-(2,3-dihydro-benzo[1,4]dioxin-6-yl)-acrylonitrile

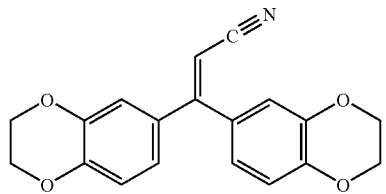

2,3-dihydrobenzo[1,4]dioxine-6-carbaldehyde (0.87 g, 5.28 mmol), 6-bromo-2,3-dihydrobenzo[1,4]dioxine (1.25 g, 5.81 mmol), and n-butyl lithium (2.33 ml, 5.81 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 40% EtOAc in hexane in about 40 min.) to give bis-(2,3-dihydro-benzo[1,4]dioxin-6-yl)-methanol as an oil (1.37 g, 86%): ¹HNMR (CDCl₃) δ6.87-6.82 (m, 6H, Ar), 5.63 (d, J=3 Hz, 1H, CHOH), 4.22 (s, 8H, 2CH₂CH₂), 2.19 (d, J=3 Hz, 1H, OH). The product was carried over to the next step.

Bis-(2,3-dihydrobenzo[1,4]dioxin-6-yl)methanol (1.32 g, 4.40 mmol) and activated MnO₂ powder (3.3 g, 38 mmol) were treated in the same manner as described above for the synthesis of (2,3-dihydrobenzo[1,4]dioxin-6-yl)-(3,5-dimethoxyphenyl)methanone. The product bis-(2,3-dihydrobenzo[1,4]dioxin-6-yl)methanone was an oil (1.25 g, 95%): ¹HNMR (CDCl₃) δ 7.37-6.90 (m, 6H, Ar), 4.36-4.27 (m, 8H, 2CH₂CH₂). The product was carried over to the next step.

Bis-(2,3-dihydrobenzo[1,4]dioxin-6-yl)methanone (1.12 g, 3.75 mmol), cyanomethylphosphonic acid diethyl ester (1.18 ml, 7.51 mmol) in anhydrous THF (10 ml), and lithium bis(trimethylsilyl)amide (1.0 M solution in THF, 7.51 ml, 7.51 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (5% EtOAc in hexane gradient to 40% EtOAc in hexane in about 40 min.) to give a foam, which was lyophilized to give 3,3-bis-(2,3-dihydro-benzo[1,4]dioxin-6-yl)-acrylonitrile as an light yellow solid (0.90 g, 75%): mp, 138-140° C.; ¹HNMR (DMSO-d₆) δ 6.98 (d, J=8 Hz, 1H, Ar), 6.91-6.77 (m, 5H, Ar), 6.08 (s, 1H, double bond proton), 4.33-4.24 (m, 4H, 2CH₂CH₂); ¹³C NMR (DMSO-d₆) δ 160.4, 145.6, 144.7, 143.2, 143.1, 131.2, 130.0, 122.5, 121.9, 118.6, 117.9, 117.2, 117.1, 116.9, 93.3, 64.3, 64.2, 64.0, 64.0. Anal. Calcd. For C₁₉H₁₅NO₄: C, 70.62; H, 4.74; N, 4.33. Found: C, 70.45; H, 4.67; N, 4.20.

4.6.2.8 3-(2,3-Dihydro-benzo[1,4]dioxin-6-yl)-3-(3,4-dimethoxy-phenyl)-acrylonitrile

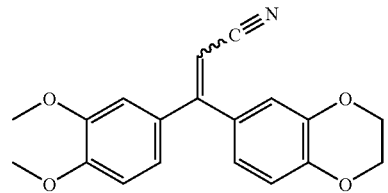

3,4-dimethoxybenzaldehyde (2.21 g, 13.32 mmol), 6-Bromo-2,3-dihydrobenzo[1,4]dioxine (3.15 g, 14.65 mmol), and n-butyl lithium (5.86 ml, 14.65 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 40% EtOAc in hexane in about 40 min.) to give (2,3-dihydrobenzo[1,4]dioxin-6-yl)-(3,4-dimethoxy-phenyl)-methanol as an oil (3.60 g, 89%): ¹HNMR (CDCl₃) δ6.93-6.80 (m, 6H, Ar), 5.70 (d, J=3 Hz, 1H, CHOH), 4.24 (s, 4H, CH₂CH₂), 3.86 (s, 6H, 2OCH₃), 2.14 (d, J=3 Hz, 1H, OH). The product was carried over to the next step.

(2,3-Dihydrobenzo[1,4]dioxin-6-yl)-(3,4-dimethoxyphenyl)methanol (3.60 g, 11.91 mmol) and activated MnO₂ powder (10 g, 115 mmol) were treated in the same manner as described above for the synthesis of (2,3-dihydrobenzo[1,4]dioxin-6-yl)-(3,5-dimethoxyphenyl)methanone. The oily product solidified to (2,3-dihydro-benzo[1,4]dioxin-6-yl)-(3,4-dimethoxy-phenyl)methanone as a solid at rt (3.02 g, 85%): ¹HNMR (CDCl₃) δ 7.44-7.27 (m, 4H, Ar), 6.95-6.88 (m, 2H, Ar), 4.36-4.28 (m, 4H, CH₂CH₂), 3.96 (s, 3H, OCH₃), 3.94 (s, 3H, OCH₃). The product was carried over to the next step.

(2,3-dihydrobenzo[1,4]dioxin-6-yl)-(3,4-dimethoxyphenyl)methanone (3.01 g, 10.02 mmol), cyanomethylphosphonic acid diethyl ester (3.15 ml, 20.05 mmol) in anhydrous THF (20 ml), and lithium bis(trimethylsilyl)amide (1.0 M solution in THF, 20.05 ml, 20.05 mmol) were treated in the same manner as described above for the synthesis of 3-(2,3-dihydrobenzo[1,4]dioxin-6-yl)-3-(3,5-dimethoxyphenyl) acrylonitrile. The crude material was purified via flash column chromatography (5% EtOAc in hexane gradient to 40% EtOAc in hexane in about 40 min.) to give an oil, which was lyophilized to give 3-(2,3-dihydro-benzo[1,4]dioxin-6-yl)-3-(3,4-dimethoxy-phenyl)-acrylonitrile as an light yellow foam (2.80 g, 86%): ¹HNMR (DMSO-d₆) δ 7.09-6.69 (m, 6H, Ar), 6.15 (s, 0.49H, double bond proton of one isomer), 6.09 (s, 0.45H, double bond proton of the other isomer), 4.33-4.25 (m, 4H, 2CH₂CH₂), 3.83-3.74 (multiple singlets, 2OCH₃); ¹³C NMR (DMSO-d₆) δ 161.0, 160.9, 150.9, 150.0, 148.6, 148.3, 145.6, 144.7, 143.2, 143.0, 131.3, 130.5, 130.1, 129.2, 122.6, 122.4, 122.3, 122.0, 118.7, 118.7, 118.0, 117.2, 117.1, 117.0, 112.7, 111.4, 111.2, 111.1, 93.1, 93.0, 64.3, 64.2, 64.0, 64.0, 55.6, 55.5. Anal. Calcd. For $C_{19}H_{17}NO_4$ (+0.45$H_2O$): C, 68.85; H, 5.44; N, 4.23. Found: C, 68.69; H, 5.31; N, 4.04.

4.6.2.9 3,3-Bis-benzo[1,3]dioxol-5-yl-acrylonitrile

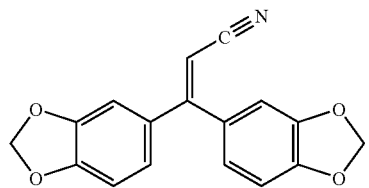

Benzo[1,3]dioxole-5-carbaldehyde (1.80 g, 11.96 mmol), 5-bromobenzo[1,3]dioxole (2.65 g, 13.16 mmol), and n-butyl lithium (5.26 ml, 13.16 mmol) were treated in the same manner as described above for the synthesis of (2,3-dihydrobenzo[1,4]dioxin-6-yl)-(3,5-dimethoxyphenyl)methanol. The crude material was purified via flash column chromatography (5% EtOAc in hexane gradient to 40% EtOAc in hexane in about 40 min.) to give bis-benzo[1,3]dioxol-5-yl-methanol as a light brown oil (2.69 g, 83%): $^1$HNMR (CDCl$_3$) δ 6.86-6.74 (m, 6H, Ar), 5.93 (s, 4H, 2CH$_2$), 5.68 (d, J=3 Hz, 1H, CHOH), 2.16 (d, J=3 Hz, 1H, OH). The product was carried over to the next step.

Bis-benzo[1,3]dioxol-5-yl-methanol (2.66 g, 9.77 mmol) and activated MnO$_2$ powder (9.5 g, 109 mmol) were treated in the same manner as described above for the synthesis of (2,3-dihydrobenzo[1,4]dioxin-6-yl)-(3,5-dimethoxyphenyl)methanone. The product bis-benzo[1,3]dioxol-5-yl-methanone was an off-white solid (2.41 g, 91%): $^1$HNMR (CDCl$_3$) δ 7.34 (d, J=8 Hz, 2H, Ar), 7.30 (d, J=1 Hz, 2H, Ar), 6.86 (d, J=7 Hz, 2H, Ar), 6.06 (s, 4H, 2CH$_2$). The product was carried over to the next step.

Bis-benzo[1,3]dioxol-5-yl-methanone (2.41 g, 8.92 mmol), cyanomethylphosphonic acid diethyl ester (2.81 ml, 17.84 mmol) in anhydrous THF (10 ml), and lithium bis(trimethylsilyl)amide (1.0 M solution in THF, 17.84 ml, 17.84 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (10% EtOAc in hexane gradient to 50% EtOAc in hexane in about 40 min.) to give 3,3-bis-benzo[1,3]dioxol-5-yl-acrylonitrile as an off-white solid (2.11 g, 81%): mp. 126-128° C.; $^1$HNMR (DMSO-d$_6$) δ 7.07-7.03 (2 ds, J=1.84 and J=8 Hz, 2H, Ar), 6.94 (d, J=8 Hz, 1H, Ar), 6.90 (d, J=1 Hz, 1H, Ar), 6.86 (dd, J=1.76 and J =7 Hz, 1H, Ar), 6.74 (dd, J=1.82 and J=8 Hz, 1H, Ar), 6.13 (s, 1H, double bond proton), 6.12 (s, 2H, CH$_2$), 6.10 (s, 2H, CH$_2$); $^{13}$C NMR (DMSO-d$_6$) δ 160.8, 149.4, 148.4, 147.8, 147.3, 132.2, 130.9, 123.8, 123.6, 118.5, 109.4, 108.4, 108.2, 107.7, 101.8, 101.6, 93.8. Anal. Calcd. For $C_{17}H_{11}NO_4$: C, 69.62; H, 3.78; N, 4.78. Found: C, 68.43; H, 3.97; N, 4.37.

4.6.2.10 3-(2,3-Dihydro-benzo[1,4]dioxin-6-yl)-3-(3-ethoxy-4-methoxy-phenyl)-acrylonitrile

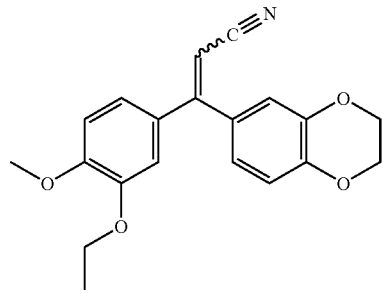

3-ethoxy-4-methoxybenzaldehyde (0.92 g, 5.12 mmol), 6-bromo-2,3-dihydro-benzo[1,4]dioxine (1.21 g, 5.63 mmol), and n-butyl lithium (2.25 ml, 5.63 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 40% EtOAc in hexane in about 40 min.) to give (2,3-dihydrobenzo[1,4]dioxin-6-yl)-(3-ethoxy-4-methoxy-phenyl)-methanol as a yellow solid (0.91 g, 56%): $^1$HNMR (CDCl$_3$) δ 6.92-6.80 (m, 6H, Ar), 5.68 (d, J=3 Hz, 1H, CHOH), 4.23 (s, 4H, 2CH2), 4.07 (q, J=6.90, 14 Hz, 2H, CH2CH3), 3.85 (s, 3H, OCH3), 2.13 (d, J=2 Hz, 1H, OH), 1.44 (t, J=7 Hz, 3H, CH2CH3). The product was carried over to the next step.

(2,3-Dihydrobenzo[1,4]dioxin-6-yl)-(3-ethoxy-4-methoxyphenyl)methanol (0.91 g, 2.88 mmol) and activated MnO2 powder (5.2 g, 60 mmol) were treated in the same manner as described above for the synthesis of (2,3-dihydrobenzo[1,4]dioxin-6-yl)-(3,5-dimethoxyphenyl)methanone. The product (2,3-dihydro-benzo[1,4]dioxin-6-yl)(3-ethoxy-4-methoxy-phenyl)methanone was a solid (0.86 g, 95%): $^1$HNMR (CDCl$_3$) δ 7.42 (d, J=1 Hz, 1H, Ar), 7.39-7.31 (m, 3H, Ar), 6.93 (d, J=8 Hz, 1H, Ar), 6.89 (d, J=8 Hz, 1H, Ar), 4.35-4.29 (m, 4H, 2CH2), 4.16 (q, J=6.91, 14 Hz, 2H, CH2CH3), 3.95 (s, 3H, OCH3), 1.49 (t, J=6 Hz, 3H, CH2CH3). The product was carried over to the next step.

(2,3-Dihydrobenzo[1,4]dioxin-6-yl)-(3-ethoxy-4-methoxyphenyl)methanone (0.83 g, 2.64 mmol), cyanomethylphosphonic acid diethyl ester (0.83 ml, 5.28 mmol) in anhydrous THF (20 ml), and lithium bis(trimethylsilyl)amide (1.0 M solution in THF, 5.28 ml, 5.28 mmol) were treated in the same manner as described above for the synthesis of 3-(2,3-dihydrobenzo[1,4]dioxin-6-yl)-3-(3,5-dimethoxyphenyl) acrylonitrile. The crude material was purified via flash column chromatography (10% EtOAc in hexane gradient to 40% EtOAc in hexane in about 40 min.) to give a foam, which was lyophilized to give 3-(2,3-Dihydro-benzo[1,4]dioxin-6-yl)-3-(3-ethoxy-4-methoxy-phenyl)-acrylonitrile as a waxy oil (0.70 g, 78%): $^1$HNMR (DMSO-d$_6$) δ 7.09-6.73 (m, 6H, Ar), 6.12 (s, 0.5H, double bond proton of one isomer), 6.07 (s, 0.5H, double bond proton of the other isomer), 4.33-4.25 (m, 4H, CH2CH2 for the two isomers), 4.05-3.97 (m, 2H, CH2CH3), 3.83 (s, 1.5H, OCH3 of one isomer), 3.79 (s, 1.5H, OCH3 of the other isomer), 1.31 (t, J=6 Hz, 3H, CH2CH3); $^{13}$C NMR (DMSO-d$_6$) δ 161.0, 160.8, 151.0, 150.1, 147.8, 147.4, 145.5, 144.7, 143.2, 143.0, 131.3, 130.5, 130.1, 129.2, 122.6, 122.3, 120.0, 118.8, 118.7, 118.0, 117.1, 117.1, 117.0, 113.7, 112.1, 111.5, 111.3, 93.0, 92.9, 64.3, 64.2, 64.0, 64.0, 63.8, 55.5, 55.5, 14.6, 14.6. Anal. Calcd. For C20H19NO4 (+0.45H2O): C, 70.08; H, 5.76; N, 4.09. Found: C, 69.91; H, 5.54; N, 4.13.

4.6.2.11 3-(3,5-Dimethoxy-phenyl)-3-(2,3,4-trimethoxy-phenyl)-acrylonitrile

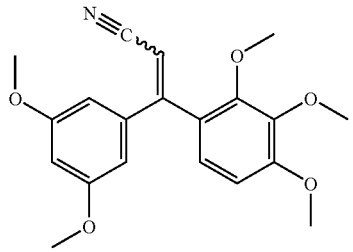

3,5-Dimethoxybenzoyl chloride (5.19 g, 25.87 mmol), 1,2,3-trimethoxybenzene (4.35 g, 25.87 mmol) in anhydrous methylene chloride (40 ml), and aluminum chloride (3.79 g, 28.45 mmol) were treated in the same manner as described above for the synthesis of (2,5-dimethoxy-phenyl)-(3,5-dimethoxy-phenyl)-methanone. The crude material was purified via flash column chromatography (20% EtOAc in hexane) to give (3,5-dimethoxy-phenyl)-(2-hydroxy-3,4-dimethoxy-phenyl)-methanone as a yellow solid (4.15 g, 50%); $^1$HNMR (CDCl$_3$) δ 12.36 (s, 1H, OH), 7.42 (d, J=9 Hz, 1H, Ar), 6.75 (d, J=2 Hz, 2H, Ar), 6.64 (t, J=2 Hz, 1H, Ar), 6.47 (d, J=9 Hz, 1H, Ar), 3.94 (s, 6H, 2OCH$_3$), 3.84 (s, 6H, 2OCH$_3$); $^{13}$C NMR (CDCl$_3$) δ 200.4, 160.7, 158.9, 158.0, 140.1, 136.9, 130.3, 114.6, 107.0, 103.8, 102.9, 60.9, 56.3, 55.7; Anal. Calcd. For C$_{17}$H$_8$O$_6$: C, 64.14; H, 5.70. Found: C, 64.29; H, 5.42; N, <0.05. The product was carried over to the next step.

To a mixture of (3,5-dimethoxyphenyl)-(2-hydroxy-3,4-dimethoxyphenyl)methanone (1.59 g, 5.00 mmol) in DMF (25 ml) was added iodomethane (0.62 ml, 10.00 mmol), and powdered Na$_2$CO$_3$ (1.06 g, 10.00 mmol) at rt. The suspension was stirred at ~35° C. overnight. DMF was evaporated in vacuo and to the residue was added CH$_2$Cl$_2$ (100 ml) and washed with H$_2$O (3×80 ml). The white salt was filtered and the solution was washed with 5 N KOH (4×80 ml), H$_2$O (1×80 ml), dried over MgSO$_4$ and concentrated to a brown oil, which was purified via flash column chromatography (20% EtOAc in hexane) to give (3,5-dimethoxy-phenyl)-(2,3,4-trimethoxy-phenyl)methanone as a clear oil (1.49 g, 90%): $^1$HNMR (CDCl$_3$) δ 7.12 (d, J=8 Hz, 1H, Ar), 6.94 (d, J=2 Hz, 2H, Ar), 6.71 (d, J=8 Hz, 1H, Ar), 6.65 (t, J=2 Hz, 1H, Ar), 3.93 (s, 3H, OCH$_3$), 3.89 (s, 3H, OCH$_3$), 3.81 (s, 6H, 2OCH$_3$), 3.79 (s, 3H, OCH$_3$); $^{13}$C NMR (CDCl$_3$) δ 195.2, 160.7, 156.3, 152.9, 142.2, 140.5, 126.6, 125.1, 107.7, 106.8, 105.4, 62.0, 61.1, 56.3, 55.7; Anal. Calcd. For C$_{18}$H$_{20}$O$_6$: C, 65.05; H, 6.07. Found: C, 64.93; H, 6.09. The product was carried over to the next step.

(3,5-Dimethoxyphenyl)-(2,3,4-trimethoxyphenyl)methanone (1.15 g, 3.46 mmol), cyanomethylphosphonic acid diethyl ester (1.09 ml, 6.92 mmol) in anhydrous THF (8 ml), and lithium bis(trimethylsilyl)amide (1.0 M solution in THF, 6.92 ml, 6.92 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (20% EtOAc in hexane) to give 3-(3,5-dimethoxy-phenyl)-3-(2,3,4-trimethoxy-phenyl)-acrylonitrile as a pink oil (1.20 g, 98%): $^1$HNMR (DMSO-d$_6$) δ 7.00-6.84 (m, 2H, Ar), 6.62-6.59 (m, 1H, Ar), 6.45 (d, J=2 Hz, 2H, Ar), 6.01 (s, 0.51H, double bond proton), 3.87-3.44 (multiple singlets, 15H, 5OCH$_3$); $^{13}$C NMR (CDCl$_3$) δ 160.9, 160.8, 160.7, 160.2, 155.5, 155.4, 152.5, 151.8, 142.7, 142.6, 141.4, 140.5, 126.2, 125.8, 125.4, 124.1, 118.0, 117.8, 107.2, 107.0, 105.7, 102.0, 101.9, 96.8, 96.6, 61.1, 61.0, 60.9, 56.2, 55.7, 55.6; Anal. Calcd. For C$_{20}$H$_{21}$NO$_5$: C, 67.59; H, 5.96; N, 3.94. Found: C, 67.53; H, 5.84; N, 3.88.

4.6.2.12 Phosphoric Acid mono-{5-[2-cyano-1-(3,5-dimethoxy-phenyl)-vinyl]-2-methoxy-phenyl}ester

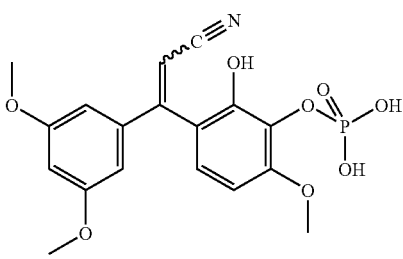

To a pre-died flask containing a stirred solution of 3-(3,5-dimethoxyphenyl)-3-(3-hydroxy-4-methoxyphenyl)acrylonitrile (0.98 g, 3.15 mmol) in anhydrous CH$_2$Cl$_2$ (25 ml) was added POCl$_3$ (0.88 ml, 9.44 mmol) at 0° C. The mixture was stirred for 5 min. followed by addition of Et$_3$N (1.32 ml, 9.44 mmol) and stirred at rt overnight. H$_2$O (25 ml) was poured into the solution and stirred for 20 min. followed by the extraction with CH$_2$Cl$_2$ (3×50 ml). The combined CH$_2$Cl$_2$ extracts was washed with 0.1 N HCl (1×100 ml), dried over MgSO4, filtered and concentrated to an oil, which was further purified via preparative HPLC to give Phosphoric acid mono-{5-[2-cyano-1-(3,5-dimethoxy-phenyl)-vinyl]-2-methoxy-phenyl}ester as a white solid (0.65 g, 53%): $^1$HNMR (DMSO-d$_6$) δ 11.17 (s, 1H, OH), 8.47 (s, 1H, OH), 7.56-6.34 (m, 10H, Ar), 5.65-5.26 (m, 2H, double bond protons), 3.89-3.67 (multiple singlets, 18H, 6OCH$_3$). $^{13}$C NMR (DMSO-d$_6$) δ 161.9, 161.2, 160.9, 160.3, 157.5, 156.4, 153.5, 152.8, 145.7, 143.6, 142.4, 141.5, 129.2, 127.8, 126.4, 122.1, 119.0, 118.8, 110.2, 109.0, 107.7, 105.0, 103.9, 98.8, 97.6, 69.1, 65.0, 64.9, 56.2, 55.7; LC/MS: 392 for (M+1)$^{+1}$ for positive ion mass and 390 for (M−1)$^{−1}$ for negative ion mass.

4.6.2.13 3-(2,3,4-Trimethoxy-phenyl)-3-(3,4,5-trimethoxy-phenyl)-acrylonitrile

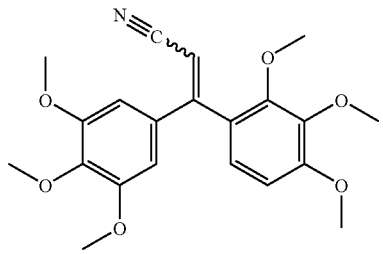

3,4,5-Trimethoxybenzoyl chloride (11.07 g, 48.0 mmol), 1,2,3-trimethoxybenzene (8.07 g, 48.0 mmol) in anhydrous methylene chloride (60 ml), and aluminum chloride (7.04 g, 52.8 mmol) were treated in the same manner as described above for the synthesis of (2,5-dimethoxy-phenyl)-(3,5-dimethoxy-phenyl)methanone. The crude material was purified via flash column chromatography (25% EtOAc in hexane) to give (2-hydroxy-3,4-dimethoxy-phenyl)-(3,4,5-trimethoxy-phenyl)-methanone as a yellow solid (9.44 g, 54%); mp, 135-137° C.: $^1$HNMR (DMSO-d$_6$) δ 11.39 (s, 1H, OH), 7.35 (d, J=8 Hz, 1H, Ar), 6.97 (s, 2H, Ar), 6.70 (d, J=9 Hz, 1H, Ar), 3.89 (s, 3H, OCH$_3$), 3.81 (s, 6H, 2OCH$_3$), 3.76 (s, 3H, OCH$_3$), 3.74 (s, 3H, OCH$_3$); $^{13}$C NMR (DMSO-d$_6$) δ 197.5, 157.6, 154.6, 152.5, 140.8, 136.0, 132.9, 128.7, 115.8, 106.7, 103.6, 60.1, 60.0, 56.0; Anal. Calcd. For C$_{18}$H$_{20}$O$_7$: C, 62.06; H, 5.79. Found: C, 62.05; H, 5.55. The product was carried over to the next step.

(2-hydroxy-3,4-dimethoxyphenyl)-(3,4,5-trimethoxyphenyl)methanone (4.44 g, 12.75 mmol), iodomethane (1.59 ml, 25.51 mmol), and Na$_2$CO$_3$ (2.7 g, 25.51 mmol) were treated in the same manner as described above for the synthesis of (3,5-Dimethoxy-phenyl)-(2,3,4-trimethoxy-phenyl)-methanone. The crude material was purified via flash column chromatography (20% EtOAc in hexane) to give (2,3,4-trimethoxy-phenyl)-(3,4,5-trimethoxy-phenyl)-methanone as an off-white solid (3.88 g, 84%); mp, 122-124° C.: $^1$HNMR (CDCl$_3$) δ 7.11 (d, J=8 Hz, 1H, Ar), 7.08 (s, 2H, Ar), 6.73 (d, J=8 Hz, 1H, Ar), 3.94 (s, 6H, 2OCH$_3$), 3.91 (s, 3H, OCH$_3$), 3.86 (s, 6H, 2OCH$_3$), 3.81 (s, 3H, OCH$_3$); $^{13}$C NMR (DMSO-d$_6$) δ 194.4, 156.1, 152.9, 152.7, 142.6, 142.3, 133.5, 126.5, 124.9, 107.6, 106.8, 62.1, 61.1, 56.4, 56.3; Anal. Calcd. For C$_{19}$H$_{22}$O$_7$: C, 62.98; H, 6.12. Found: C, 63.14; H, 6.13. The product was carried over to the next step.

(2,3,4-trimethoxyphenyl)-(3,4,5-trimethoxyphenyl) methanone (2.87 g, 7.92 mmol), cyanomethylphosphonic acid diethyl ester (2.50 ml, 15.84 mmol) in anhydrous THF (15 ml), and lithium bis(trimethylsilyl)amide (1.0 M solution in THF, 15.84 ml, 15.84 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (20% EtOAc in hexane) to give 3-(2,3,4-trimethoxy-phenyl)-3-(3,4,5-trimethoxy-phenyl)-acrylonitrile as an off-white solid (2.32 g, 76%); mp, 125-127° C.: $^1$HNMR (DMSO-d$_6$) δ 7.01-6.85 (m, 2H, Ar), 6.63-6.61 (m, 2H, Ar), 5.95 (s, 1H, double bond proton), 3.87-3.32 (multiple singlets, 18H, 6OCH$_3$); $^{13}$C NMR (CDCl$_3$) δ 160.6, 160.2, 155.5, 153.3, 153.1, 152.4, 151.8, 142.6, 139.5, 134.7, 133.8, 126.2, 125.8, 125.4, 118.4, 118.0, 107.2, 107.1, 106.4, 106.1, 104.8, 95.9, 61.2, 61.1, 61.0, 61.0, 56.4, 56.4, 56.2; Anal. Calcd. For C$_{21}$H$_{23}$NO$_6$ (+0.05H$_2$O): C, 65.29; H, 6.03; N, 3.63. Found: C, 64.90; H, 5.94; N, 3.55.

4.6.2.14 3-(2,3-Dimethoxy-phenyl)-3-(3,5-dimethoxy-phenyl)-acrylonitrile 2,3-Dimethoxybenzaldehyde (0.84 g, 5.03 mmol), 1-bromo-3,5-dimethoxybenzene (1.20 g, 5.53 mmol), and n-butyl lithium (2.20 ml, 5.53 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 50% EtOAc in hexane in about 40 min.) to give (2,3-dimethoxy-phenyl)-(3,5-dimethoxy-phenyl)-methanol as a greenish yellow oil (1.36 g, 89%): $^1$HNMR (CDCl$_3$) δ 7.08-7.01 (m, 1H, Ar), 6.93-6.85 (m, 2H, Ar), 6.57 (d, J=2 Hz, 2H, Ar), 6.35 (t, J=2 Hz, 1H, Ar), 5.94 (d, J=6 Hz, 1H, CHOH), 3.86 (s, 3H, OCH$_3$), 3.76 (s, 6H, 2OCH$_3$), 3.66 (s, 3H, OCH$_3$), 3.05 (d, J=6 Hz, 1H, OH). The product was carried over to the next step.

(2,3-Dimethoxyphenyl)-(3,5-dimethoxyphenyl)methanol (1.25 g, 4.11 mmol), and activated MnO$_2$ powder (2.86 g, 32.9 mmol) were treated in the same manner as described above for the synthesis of (2,3-dihydrobenzo[1,4]dioxin-6-yl)-(3,5-dimethoxyphenyl)methanone. The product (2,3-Dimethoxy-phenyl)-(3,5-dimethoxy-phenyl)-methanone was an off-white solid (1.21 g, 98%): $^1$HNMR (CDCl$_3$) δ 7.14-7.02 (m, 2H, Ar), 6.97 (d, J=2 Hz, 2H, Ar), 6.89 (dd, J=2, 7 Hz, 1H, Ar), 6.66 (t, J=2 Hz, 1H, Ar), 3.91 (s, 3H, OCH$_3$), 3.80 (s, 6H, 2OCH$_3$), 3.75 (s, 3H, OCH$_3$). The product was carried over to the next step.

(2,3-Dimethoxyphenyl)-(3,5-dimethoxyphenyl)methanone (1.19 g, 3.94 mmol), cyanomethylphosphonic acid diethyl ester (1.24 ml, 7.87 mmol) in anhydrous THF (20 ml), and lithium bis(trimethylsilyl)amide (1.0 M solution in THF, 7.9 ml, 7.87 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (5% EtOAc in hexane gradient to 20% EtOAc in hexane in about 40 min.) to give 3-(2,3-Dimethoxy-phenyl)-3-(3,5-dimethoxy-phenyl)-acrylonitrile as a clear light pink oil (1.16 g, 91%): $^1$HNMR (DMSO-d$_6$) δ 7.21-7.08 (m, 2H, Ar), 6.83-6.79 (m, 1H, Ar), 6.62-6.56 (m, 1H, Ar), 6.47-6.46 (m, 2H, Ar), 6.00 (s, 1H, double bond proton), 3.86-3.72 (multiple singlets, 12H, 4OCH$_3$); $^{13}$C NMR (CDCl$_3$) δ 161.0, 160.9, 160.7, 160.4, 153.2, 153.1, 147.3, 146.7, 140.5, 140.1, 133.9, 131.7, 124.3, 124.0, 122.5, 122.2, 117.7, 117.5, 114.1, 107.0, 105.7, 102.0, 101.9, 97.8, 97.2, 60.9, 60.7, 56.1, 56.0, 55.7, 55.6; Anal. Calcd. For C$_{19}$H$_{19}$NO$_4$: C, 73.20; H, 5.80; N, 4.74. Found: C, 73.10; H, 5.72; N, 4.68.

4.6.2.15 3-(2,5-Dimethoxy-phenyl)-3-(3,5-dimethoxy-phenyl)-acrylonitrile

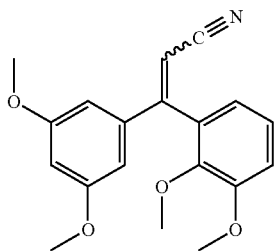

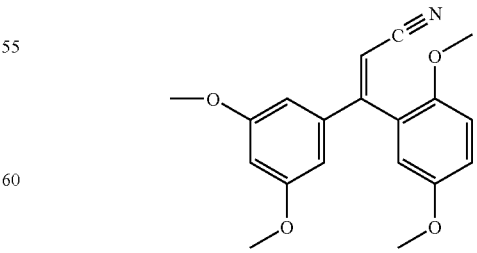

3,5-Dimethoxybenzoyl chloride (2.00 g, 9.99 mmol), 1,4-dimethoxybenzene (1.38 g, 9.99 mmol) in anhydrous methylene chloride (10 ml), and aluminum chloride (1.46 g, 10.99 mmol) were treated in the same manner as described above for the synthesis of (2,5-dimethoxy-phenyl)-(3,5-dimethoxyphenyl)-methanone. The crude material was purified via flash column chromatography (10% EtOAc in hexane gradient to 60% EtOAc in hexane in 40 min.) to give (2,5-dimethoxyphenyl)-(3,5-dimethoxy-phenyl)-methanone as a yellowish green oil (1.00 g, 33%); $^1$HNMR (CDCl$_3$) δ 7.02-6.88 (m, 5H, Ar), 6.66 (t, J=2 Hz, 1H, Ar), 3.81 (s, 6H, 2OCH$_3$), 3.78 (s, 3H, OCH$_3$), 3.69 (s, 3H, OCH$_3$). The product was carried over to the next step.

(2,5-dimethoxyphenyl)-(3,5-dimethoxyphenyl)methanone (0.92 g, 3.04 mmol), cyanomethylphosphonic acid diethyl ester (0.96 ml, 6.09 mmol) in anhydrous THF (15 ml), and lithium bis(trimethylsilyl)amide (1.0 M solution in THF, 6.09 ml, 6.09 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (10% EtOAc in hexane gradient to 25% EtOAc in hexane in about 20 min.) to give a brown oil, which was lyophilized to give 3-(2,5-dimethoxy-phenyl)-3-(3,5-dimethoxy-phenyl)-acrylonitrile as a light yellow solid (0.88 g, 89%): δ $^1$HNMR (CDCl$_3$) δ 6.94-6.43 (m, 12H, Ar), 5.89 (s, 0.65H, double proton of one isomer), 5.87 (s, 0.84H, double proton of the other isomer), 3.83-3.67 (multiple singlets, 24H, 8OCH$_3$). The product was a mixture of two isomers with the ratio of 43.6%:56.4%; $^{13}$C NMR (CDCl$_3$) δ 161.0, 160.7, 159.9, 159.8, 153.6, 153.5, 151.9, 151.2, 140.3, 140.0, 128.9, 126.9, 117.9, 117.5, 117.3, 116.3, 116.2, 115.8, 113.2, 107.0, 105.8, 102.0, 102.0, 98.3, 97.4, 56.5, 56.0, 56.0, 55.6, 55.6; Anal. Calcd. For C$_{19}$H$_{19}$NO$_4$: C, 70.14; H, 5.89; N, 4.30. Found: C, 69.78; H, 5.77; N, 4.20.

4.6.2.16
3-(3,5-Dimethoxy-phenyl)-3-phenyl-acrylonitrile

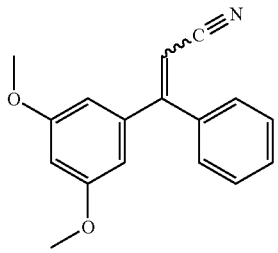

3,5-Dimethoxybenzaldehyde (2.50 g, 15.04 mmol), bromobenzene (2.60 g, 16.55 mmol), and n-butyl lithium (33.10 ml, 13.24 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 20% EtOAc in hexane in about 30 min.) to give (3,5-Dimethoxy-phenyl)-phenyl-methanol as a light yellow oil (3.14 g, 85%). HPLC purity was 83% at 3.01 min. (50/50 ACN/0.1% H$_3$PO$_4$). $^1$HNMR (CDCl$_3$) δ 7.39-7.25 (m, 4H, Ar), 6.54 (d, J=2 Hz, 2H, Ar), 6.50-6.34(m, 2H, Ar), 5.74 (d, J=3 Hz, 1H, CHOH), 3.75 (s, 6H, 2OCH$_3$), 2.34 (d, J=3 Hz, 1H, OH). The product was carried over to the next step.

(3,5-Dimethoxyphenyl)phenylmethanol (0.50 g, 2.05 mmol) and activated MnO$_2$ powder (0.89 g, 10.25 mmol) were treated in the same manner as described above for the synthesis of (2,3-dihydrobenzo[1,4]dioxin-6-yl)-(3,5-dimethoxyphenyl)-methanone. The product (3,5-Dimethoxy-phenyl)-phenyl-methanone was an oil (0.34 g, 69%), HPLC purity was 99% at 6.25 min. (50/50 ACN/0.1% H$_3$PO$_4$). $^1$HNMR (CDCl$_3$) δ 7.83-7.79 (m, 2H, Ar), 7.61-7.55 (m, 1H, Ar) 7.50-7.44 (m, 2H, Ar), 6.92 (d, J=2 Hz, 2H, Ar), 6.67 (t, J=2 Hz, 1H, Ar), 3.82 (s, 6H, 2OCH$_3$). The product was carried over to the next step.

(3,5-Dimethoxyphenyl)phenylmethanone (0.34 g, 1.40 mmol), lithium bis (trimethylsilyl)amide (1.0 M solution in THF, 2.81 ml, 2.81 mmol), and cyanomethylphosphonic acid diethyl ester (0.44 ml, 2.81 mmol) in anhydrous THF (5 ml) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (10% EtOAc in hexane) to give 3-(3,5-dimethoxy-phenyl)-3-phenyl-acrylonitrile as an oil (0.33 g, 89%): $^1$HNMR (DMSO-d$_6$) δ 7.55-7.35 (m, 5H, Ar), 6.67-6.62 (2ts, 1H, Ar), 6.48-6.45 (2ds, 2H, Ar), 6.39 (s, 0.57H, double bond proton of one isomer), 6.34 (s, 0.43H, double bond proton of the other isomer), 3.76 (s, 3H, OCH$_3$), 3.73 (s, 3H, OCH$_3$); $^{13}$C NMR (CDCl$_3$) δ 163.2, 163.1, 160.9, 160.9, 141.2, 138.9, 138.7, 137.0, 130.6, 130.2, 129.7, 128.8, 128.6, 128.5, 117.9, 117.8, 107.8, 107.0, 102.3, 102.2, 95.3, 95.1, 55.7, 55.6; Anal. Calcd. For C$_{17}$H$_{15}$NO$_2$ (+0.03H$_2$O): C, 76.80; H, 5.71; N, 5.27. Found: C, 76.41; H, 5.40; N, 5.18.

4.6.2.17 3-(3,5-Dimethoxy-phenyl)-3-(2-methoxyphenyl)-acrylonitrile

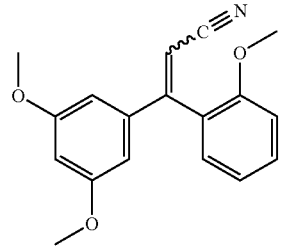

2-Methoxybenzaldehyde (0.81 g, 5.95 mmol), 1-bromo-3,5-dimethoxybenzene (1.42 g, 6.54 mmol), and n-butyl lithium (2.62 ml, 6.54 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 40% EtOAc in hexane in about 40 min.) to give (3,5-dimethoxy-phenyl)-(2-methoxy-phenyl)-methanol as a greenish oil (1.38 g, 85%): $^1$HNMR (CDCl$_3$) δ7.30-7.18 (m, 2H, Ar), 6.96-6.88 (m, 2H, Ar), 6.57 (d, J=1 Hz, 2H, Ar), 6.36 (t, J=2 Hz, 1H, Ar), 5.99 (d, J=5 Hz, 1H, CHOH), 3.84 (s, 3H, OCH$_3$), 3.77 (s, 6H, 2OCH$_3$), 3.04 (d, J=5 Hz, 1H, OH). The product was carried over to the next step.

(3,5-Dimethoxy-phenyl)-(2-methoxy-phenyl)-methanol (1.30 g, 4.74 mmol), and activated MnO$_2$ powder (3.75 g, 43 mmol) were treated in the same manner as described above for the synthesis of (2,3-dihydrobenzo[1,4]dioxin-6-yl)-(3,5-dimethoxyphenyl)methanone. The product (3,5-Dimethoxy-phenyl)-(2-methoxy-phenyl)-methanone was an oil (1.23 g, 95%): $^1$HNMR (CDCl$_3$) δ7.49-7.42 (m, 1H, Ar), 7.34-7.31 (m, 1H, Ar), 7.05-6.96 (m, 4H, Ar), 6.65 (t, J=2 Hz, 1H, Ar), 3.80 (s, 6H, 2OCH$_3$), 3.75 (s, 3H, OCH$_3$). The product was carried over to the next step.

(3,5-Dimethoxyphenyl)-(2-methoxyphenyl)methanone (1.22 g, 4.48 mmol), cyanomethylphosphonic acid diethyl ester (1.41 ml, 8.96 mmol) in anhydrous THF (30 ml), and lithium bis(trimethylsilyl)amide (1.0 M solution in THF, 9.00 ml, 9.00 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (10% EtOAc in hexane gradient to 30% EtOAc in hexane in about 30 min.) to give 3-(3,5-Dimethoxy-phenyl)-3-(2-methoxyphenyl)-acrylonitrile as an off-white solid (0.93 g, 70%); mp, 82-84° C.: $^1$HNMR (CDCl$_3$) δ7.39-6.90 (m, 8H, Ar), 6.57 (d, J=2 Hz, 2H, Ar), 6.51-6.48 (m, 2H, Ar), 6.42 (d, J=2 Hz, 2H, Ar), 5.89 (s, 2H, double bond protons of the two isomers), 3.78 (s, 6H, 2OCH$_3$), 3.75 (s, 6H, 2OCH$_3$), 3.74 (s, 6H, 2OCH$_3$); $^{13}$C NMR (CDCl$_3$) δ 160.9, 160.7, 160.2, 159.9; 157.7, 140.6, 140.3, 131.6, 131.2, 130.9, 128.0, 126.2, 120.9, 120.7, 118.0, 117.6, 111.8, 107.1, 105.8, 101.9, 98.0, 97.3, 55.8, 55.6, 55.6; Anal. Calcd. For C$_{18}$H$_{17}$NO$_3$: C, 73.20; H, 5.80; N, 4.74. Found: C, 73.08; H, 5.85; N, 4.78.

4.6.2.18 3-(3,5-Dimethoxy-phenyl)-3-(2,2,3,3-tetrafluoro-2,3-dihydro-benzo[1,4]dioxin-5-yl)-acrylonitrile

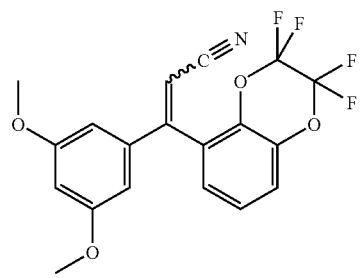

6-Bromo-2,2,3,3-tetrafluoro-2,3-dihydrobenzo[1,4]dioxine (1.50 g, 5.23 mmol), 3,5-dimethoxybenzaldehyde (0.79 g, 4.75 mmol), and n-butyl lithium (2.09 ml, 5.23 mmol) were treated in the same manner as described above for the synthesis of (2,3-dihydrobenzo[1,4]dioxin-6-yl)-(3,5-dimethoxyphenyl)methanol. The crude material was purified via flash column chromatography (5% EtOAc in hexane gradient to 30% EtOAc in hexane in about 40 min.) to give (3,5-Dimethoxy-phenyl)-(2,2,3,3-tetrafluoro-2,3-dihydro-benzo[1,4]dioxin-5-yl)-methanol as an oil (0.47 g, 26%): $^1$HNMR (CDCl$_3$) δ7.37 (dd, J=1, 7 Hz, 1H, Ar), 7.17 (t, J=8 Hz, 1H, Ar), 7.06 (dd, J=1, 8 Hz, 1H, Ar), 6.57 (d, J=2 Hz, 2H, Ar), 6.38 (t, J=2 Hz, 1H, Ar), 6.12 (d, J=3 Hz, 1H, CHOH), 3.77 (s, 6H, 2OCH$_3$), 2.36 (d, J =3 Hz, 1H, OH). The product was carried over to the next step.

(3,5-Dimethoxyphenyl)-(2,2,3,3-tetrafluoro-2,3-dihydrobenzo[1,4]dioxin-5-yl)methanol (5233-15-C, 0.45 g, 1.20 mmol), and activated MnO$_2$ powder (2.42 g, 28 mmol) were treated in the same manner as described above for the synthesis of (2,3-dihydrobenzo[1,4]dioxin-6-yl)-(3,5-dimethoxyphenyl)methanone. The product (3,5-dimethoxy-phenyl)-(2,2,3,3-tetrafluoro-2,3-dihydro-benzo[1,4]dioxin-5-yl)-methanone was an oil (0.43 g, 96%): $^1$HNMR (CDCl$_3$) δ7.32-7.27 (m, 3H, Ar), 6.94 (d, J=2 Hz, 2H, Ar), 6.72 (t, J=2 Hz, 1H, Ar), 3.82 (s, 6H, 2OCH$_3$). The product was carried over to the next step.

(3,5-Dimethoxyphenyl)-(2,2,3,3-tetrafluoro-2,3-dihydrobenzo[1,4]dioxin-5-yl)methanone (0.42 g, 1.13 mmol), cyanomethylphosphonic acid diethyl ester (0.36 ml, 2.26 mmol) in anhydrous THF (10 ml), and lithium bis(trimethylsilyl)amide (1.0 M solution in THF, 2.26 ml, 2.26 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (5% EtOAc in hexane gradient to 25% EtOAc in hexane in about 30 min.) to give 3-(3,5-dimethoxy-phenyl)-3-(2,2,3,3-tetrafluoro-2,3-dihydro-benzo[1,4]dioxin-5-yl)-acrylonitrile as an oil (0.42 g, 94%): $^1$HNMR (DMSO-d$_6$) δ7.70-7.35 (m, 6H, Ar), 6.86 (s, 0.32H, double bond proton of one isomer), 6.68-6.66 (m, 2H, Ar), 6.53 (d, J=2 Hz, 1.3H, Ar), 6.48 (d, J=1 Hz, 0.7H, Ar), 6.27 (s, 0.62H, double bond proton of the other isomer), 3.74 (s, 6H, 2OCH$_3$); $^{13}$C NMR (DMSO-d$_6$) δ 160.7, 160.5, 155.0, 153.8, 138.0, 137.3, 136.7, 133.7, 128.7, 128.7, 127.8, 127.5, 126.8, 126.7, 126.5, 119.5, 119.3, 117.1, 116.9, 106.2, 105.3, 102.5, 101.8, 101.1, 100.6, 55.4, 55.4; Anal. Calcd. For C$_{19}$H$_{13}$F$_4$NO$_4$: C, 57.73; H, 3.31; N, 3.54; F, 19.22. Found: C, 57.62; H, 3.34; N, 3.49; F, 19.17.

4.6.2.19 3-(3-Benzyloxy-phenyl)-3-(3,5-dimethoxyphenyl)-acrylonitrile

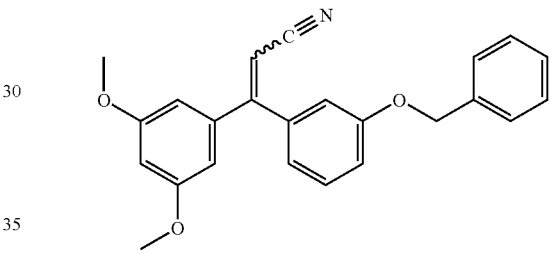

To a stirred solution of bromomethylbenzene (24.39 g, 143 mmol), 3-bromophenol (24.92 g, 144 mmol) in acetone (20 ml) was added potassium carbonate (59.72 g, 430 mmol). The suspension was refluxed overnight and then evaporated. To the residue was added H$_2$O (100 ml) and extracted with EtOAc (3×80 ml). The combined EtOAc extracts were back washed with Na$_2$CO$_3$ and then dried over MgSO$_4$, filtered and evaporated to get an off-white solid, which was purified via flash column chromatography (10% CH$_2$Cl$_2$ in hexane) to give 1-benzyloxy-3-bromo-benzene as a white solid (10 g, 67%): $^1$HNMR (DMSO-d$_6$) δ7.46-7.00 (m, 9H, Ar), 5.12 (s, 2H, CH$_2$). The product was carried over to the next step.

1-Benzyloxy-3-bromobenzene (10.56 g, 40.13 mmol), 3,5-dimethoxybenzaldehyde (7.34 g, 44.14 mmol), and n-butyl lithium (17.66 ml, 44.14 mmol) were treated in the same manner as described above for the synthesis of (2,3-dihydrobenzo[1,4]dioxin-6-yl)-(3,5-dimethoxyphenyl)methanol. The crude material was purified via flash column chromatography (10% EtOAc in hexane gradient to 40% EtOAc in hexane in about 40 min.) to give (3-Benzyloxy-phenyl)-(3,5-dimethoxy-phenyl)-methanol as an oil (11.54 g, 82%): $^1$HNMR (CDCl$_3$) δ7.43-7.21 (m, 6H, Ar), 7.04-6.85 (m, 3H, Ar), 6.54 (d, J=2 Hz, 2H, Ar), 6.36 (t, J=2 Hz, 1H, Ar), 5.72 (d, J=3 Hz, 1H, CHOH), 5.04 (s, 2H, CH$_2$), 3.76 (s, 6H, 2OCH$_3$), 2.21 (d, J=3 Hz, 1H, OH). The product was carried over to the next step.

(3-Benzyloxyphenyl)-(3,5-dimethoxyphenyl)methanol (11.51 g, 32.85 mmol), and activated MnO$_2$ powder (30 g, 345 mmol) were treated in the same manner as described above for the synthesis of (2,3-dihydrobenzo[1,4]dioxin-6-yl)-(3,5-dimethoxyphenyl)methanone. The product (3-benzyloxy-phenyl)-(3,5-dimethoxy-phenyl)methanone was a clear oil (10.67 g, 93%): $^1$HNMR (CDCl$_3$) δ7.45-7.33 (m, 8H, Ar), 7.22-7.17 (m, 1H, Ar), 6.92 (d, J=2 Hz, 2H, Ar), 6.67 (t, J=2 Hz, 1H, Ar), 5.11 (s, 2H, CH$_2$), 3.82 (s, 6H, 2OCH$_3$). The product was carried over to the next step.

(3-Benzyloxyphenyl)-(3,5-dimethoxyphenyl)methanone (10.66 g, 30.60 mmol), cyanomethylphosphonic acid diethyl ester (9.63 ml, 61.19 mmol) in anhydrous THF (10 ml), and lithium bis(trimethylsilyl)amide (1.0 M solution in THF, 61.20 ml, 61.19 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography (5% EtOAc in hexane gradient to 30% EtOAc in hexane in about 40 min.) to give 3-(3-benzyloxy-phenyl)-3-(3,5-dimethoxy-phenyl)-acrylonitrile as a white solid (9.82 g, 86%): $^1$HNMR (DMSO-d$_6$) δ7.47-7.31 (m, 6H, Ar), 7.20-6.88 (m, 3H, Ar), 6.66-6.62 (2ts, 1H, Ar), 6.46 (d, J=2 Hz, 2H, Ar), 6.40 (s, 0.5H, double bond proton of one isomer), 6.38 (s, 0.5H, double bond proton of the other isomer), 5.12 (s, 1H, halfCH$_2$), 5.11 (s, 1H, halfCH$_2$), 3.76 (s, 3H, OCH$_3$), 3.73 (s, 3H, OCH$_3$); $^{13}$C NMR (DMSO-d$_6$) δ 161.2, 160.4, 158.4, 158.2, 139.6, 138.9, 138.8, 138.3, 136.7, 129.8, 128.4, 127.9, 127.8, 121.5, 120.8, 117.9, 117.9, 116.8, 116.0, 115.5, 114.4, 107.1, 106.5, 101.9, 101.1, 96.8, 96.5, 69.4, 55.4, 53.6; Anal. Calcd. For C$_{24}$H$_{21}$NO$_3$: C, 77.61; H, 5.70; N, 3.77. Found: C, 77.39; H, 5.70; N, 3.69.

4.6.2.20 3-(3,5-Dimethoxy-phenyl)-3-(3,4,5-trimethoxy-phenyl)-acrylonitrile

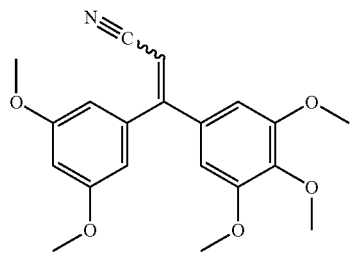

(3,5-Dimethoxy-phenyl)-(3,4,5-trimethoxy-phenyl)-methanone (0.55 g, 1.7 mmol), cyanomethylphosphonic acid diethyl ester (0.52 ml, 3.3 mmol) in anhydrous THF (20 ml), and potassium bis-(trimethylsilyl)amide (0.66 g, 3.3 mmol) were treated in the same manner as described above for the synthesis of 3-(2,3-dihydro-benzo[1,4]dioxin-6-yl)-3-(3,5-dimethoxy-phenyl)-acrylonitrile. The crude material was purified by flash column chromatography to give a solid (450 mg, 81%): mp, 135-137° C.; $^1$H NMR (DMSO-d$_6$) δ 6.67-6.63 (m, 3H), 6.51 (d, J=1 Hz, 2H), 6.36-6.33 (m, 1H), 3.77-3.71 (m, 15H); $^{13}$C NMR (DMSO-d$_6$) δ 161.33, 161.16, 160.38, 160.29, 152.70, 152.65, 139.73, 139.63, 138.73, 138.59, 132.82, 132.09, 118.14, 118.05, 107.24, 106.82, 106.62, 106.01, 102.36, 96.32, 95.77, 60.11, 56.06, 55.39; Anal. Calcd. For C$_{20}$H$_{21}$NO$_5$: C, 67.59; H, 5.96; N, 3.94. Found: C, 67.44; H, 5.73; N, 3.77.

4.6.2.21 3-(3-Amino-4-methoxy-phenyl)-3-(3,4-dimethoxy-phenyl)-acrylonitrile (E and Z Isomers)

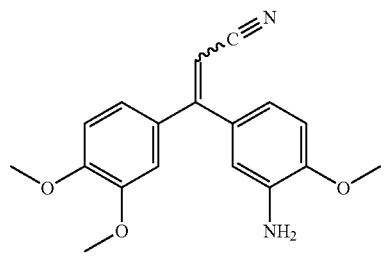

Grignard reagent was prepared in an oven-dried three necked flask outfitted with a reflux condenser, dropping funnel, and magnetic stirrer. Approximately 3 mL of a solution of 3,4-bromoveratrole (3.5 g, 15.9 mmol) in THF (10 mL) was added to a mixture of magnesium turnings (0.4 g, 15.9 mmol) in THF (5 mL) with a small piece of iodine. As soon as the solution became colorless (heating sometimes necessary), the remaining 3,4-bromoveratrole solution was added dropwise to the solution under mild reflux. The resulting mixture was refluxed for 3 h then cooled to room temperature for 30 min. The (3,4-dimethoxyphenyl)magnesium bromide was then added slowly to a stirred solution of 4-methoxy-3-nitro-benzaldehyde (2.4 g, 13.3 mmol) in THF (10 mL) at 0° C. After complete addition, the solution was allowed to stir at room temperature for 1 h. The mixture was cooled to 0° C. and quenched with saturated NH$_4$Cl solution (40 mL). The aqueous layer was extracted with EtOAc (3×20 mL). The combined organic layers were washed with water (2×30 mL), brine (30 mL) and dried (MgSO$_4$). Solvent was removed and residue was purified by flash chromatography (silica gel, CH$_2$Cl$_2$:EtOAc 9:1) to give (4-methoxy-3-nitro-phenyl)-(3,4-dimethoxy-phenyl)-methanol as an oil (2.6 g, 63%): $^1$H NMR (CDCl$_3$) δ 7.89 (d, J=2 Hz, 1H), 7.54-7.49 (dd, J=2, 8 Hz, 1H), 7.05 (d, J=8 Hz, 1H), 6.88-6.81 (m, 3H), 5.78 (d, J=3 Hz, 1H), 3.94 (s, 3H), 3.87 (s, 3H), 3.85 (s, 3H), 2.38 (d, J=3 Hz, 1H).

Pyridinium chlorochromate (2.6 g, 12.2 mmol) and Celite (1 g) was added to a stirred solution of (4-methoxy-3-nitrophenyl)-(3,4-dimethoxy-phenyl)-methanol (2.6 g, 8.1 mmol) in CH$_2$Cl$_2$ (100 mL). The mixture was stirred for 4 h at room temperature then filtered through Celite. The filtrate was washed with water (2×40 mL), brine (40 mL) and dried (MgSO$_4$). Solvent was removed and the residue was purified by flash chromatography (silica gel, CH$_2$Cl$_2$:EtOAc 95:5) to give (4-methoxy-3-nitro-phenyl)-(3,4-dimethoxy-phenyl)-methanone (2.0 g, 76%): $^1$H NMR (CDCl$_3$) δ 8.29 (d, J=2 Hz, 1H), 8.07-8.03 (dd, J=2, 8 Hz, 1H), 7.34 (d, J=1 Hz, 1H), 7.35-7.26 (dd, J=2, 8 Hz, 1H), 7.21 (d, J=8 Hz, 1H), 6.94 (d, J=8 Hz, 1H), 4.06 (s, 3H), 3.98 (s, 3H), 3.95 (s, 3H); $^{13}$C NMR (CDCl$_3$) δ 192.10, 155.48, 153.34, 149.29, 139.01, 135.57, 130.35, 129.49, 127.60, 124.94, 113.14, 111.98, 109.96, 56.86, 56.13, 56.07.

Lithium bis(trimethylsilyl)amide (7.2 mL, 7.2 mmol) was added slowly to a stirred solution of diethyl cyanomethylphosphate (1.2 g, 6.6 mmol) in THF (15 mL) at 4-6° C. The resulting solution was stirred at room temperature for 40 min. then added to a stirred mixture of (4-methoxy-3-nitro-phenyl)-(3,4-dimethoxy-phenyl)-methanone (1.9 g, 6.0 mmol) in THF (25 mL). The resulting mixture was stirred at room temperature overnight. The reaction mixture was quenched with water (40 mL) and extracted with $CH_2Cl_2$ (3×30 mL). The combined organic extracts were washed with water (2×40 mL), brine (40 mL) and dried ($MgSO_4$). Solvent was removed and the residue was purified by flash chromatography (silica gel, Hexane: $CH_2Cl_2$ 5:95) to give a mixture of isomers of 3-(4-methoxy-3-nitro-phenyl)-3-(3,4-dimethoxy-phenyl)-acrylonitrile (1.8 g, 88%) as a yellow solid: $^1H$ NMR ($CDCl_3$) δ 7.86-7.50 (m, 2H), 7.27-6.79 (m, 4H), 5.69 (5.61) (s, 1H), 4.04 (4.01) (s, 3H), 3.95 (3.92) (s, 3H), 3.88 (3.85) (s, 3H); $^{13}C$ NMR ($CDCl_3$) δ 159.93, 153.94 (154.14), 151.61 (151.04), 149.20 (148.92), 139.92, 135.31 (133.97), 130.50 (131.57), 129.32 (128.33), 127.10 (125.72), 122.25 (123.10), 117.78 113.54 (112.43), 111.03 (110.87), 93.72 (93.93), 56.78 (56.73), 56.09, 56.04 (55.97).

A mixture of 3-(4-methoxy-3-nitro-phenyl)-3-(3,4-dimethoxy-phenyl)-acrylonitrile (1.8 g, 5.3 mmol) and 10% Pd/C (0.2 g) in EtOAc (100 mL) was hydrogenated at 50 psi of hydrogen overnight. The reaction mixture was filtered through Celite and the filtrate was concentrated. The crude product was purified by flash chromatography (silica gel, $CH_2Cl_2$:EtOAc 9:1) to give a mixture of isomers of 3-(3-amino-4-methoxy-phenyl)-3-(3,4-dimethoxy-phenyl)-acrylonitrile (0.9 g, 54%) as a yellow solid: mp 99-101° C.; $^1H$ NMR ($CDCl_3$) δ 7.06-8.65 (m, 6H), 5.52 (5.51) (s, 1H), 3.93-3.86 (m, 9H), 3.82 (s, 2H); $^{13}C$ NMR ($CDCl_3$) δ 162.89, 150.90 (150.10), 149.12 (148.68), 148.72 (148.51), 135.94 (136.13), 132.17 (131.99), 129.84, 122.15 (123.10), 120.66 (119.66), 118.81 (118.73), 115.93 (114.57), 111.45 (112.81), 110.66 (109.79), 91.54 (91.49), 77.20, 56.03, 55.96, 55.90, (55.56, 55.49); Anal Calcd for $C_{18}H_{18}N_2O_3+0.1H_2O$: C, 69.26; H, 5.88; N, 8.97. Found: C, 68.88; H, 5.81; N, 8.78.

Acetyl chloride (0.1 mL, 1.6 mmol) was added to a stirred solution of 3-(3-amino-4-methoxy-phenyl)-3-(3,4-dimethoxy-phenyl)-acrylonitrile (0.4 g, 1.2 mmol) in THF (20 mL). The solution was refluxed for 30 min then cooled to room temperature. The reaction mixture was quenched with methanol (0.5 mL) and concentrated. The residue was stirred with hexane (20 mL) to afford a mixture of isomers of N-{5-[2-cyano-1-(3,4-dimethoxy-phenyl)-vinyl]-2-methoxy-phenyl}-acetamide (0.3 g, 81%) as a yellow solid: mp 139-141° C.; $^1H$ NMR ($CDCl_3$) δ 8.48 (8.35) (d, J=1 Hz, 1H), 7.75 (s, 1H), 7.21-6.80 (m, 5H), 5.60 (5.59) (s, 1H), 3.94-3.83 (m, 9H), 2.20 (2.17) (s, 3H); $^3C$ NMR ($CDCl_3$) δ 168.26 (168.08), 162.54 (162.25), 151.10 (150.45), 149.35 (148.94), 148.82 (148.56), 131.99 (131.48), 129.88 (129.52), 127.79 (127.50), 125.40 (124.81), 123.07 (122.21), 121.24 (119.56), 118.60 (118.50), 112.78 (111.25), 110.74 (110.69), 109.56 (109.51), 92.53 (92.31), 56.01, 55.97, 55.86 (55.80), 15.55 (24.81); Anal Calcd for $C_{20}H_{20}N_2O_4+0.06H_2O$: C, 67.96; H, 5.74; N, 7.93. Found: C, 67.66; H, 5.88; N, 7.82.

4.6.2.22 N-{5-[2-Cyano-1-(3,4-dimethoxy-phenyl)-vinyl]-2-methoxy-phenyl}-acetamide (E and Z Isomers)

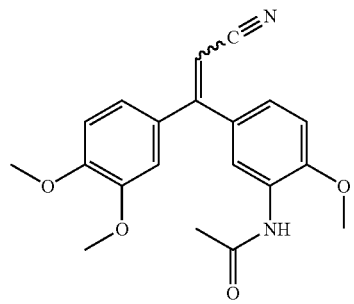

Acetyl chloride (0.1 mL, 1.6 mmol) was added to a stirred solution of 3-(3-amino-4-methoxy-phenyl)-3-(3,4-dimethoxy-phenyl)-acrylonitrile (0.4 g, 1.2 mmol) in THF (20 mL). The solution was refluxed for 30 min then cooled to room temperature. The reaction mixture was quenched with methanol (0.5 mL) and concentrated. The residue was stirred with hexane (20 mL) to afford a mixture of isomers of N-{5-[2-cyano-1-(3,4-dimethoxy-phenyl)-vinyl]-2-methoxy-phenyl}-acetamide (0.3 g, 81%) as a yellow solid: mp 139-141° C.; $^1H$ NMR ($CDCl_3$) δ 8.48 (8.35) (d, J=1 Hz, 1H), 7.75 (s, 1H), 7.21-6.80 (m, 5H), 5.60 (5.59) (s, 1H), 3.94-3.83 (m, 9H), 2.20 (2.17) (s, 3H); $^{13}C$ NMR ($CDCl_3$) δ 168.26 (168.08), 162.54 (162.25), 151.10 (150.45), 149.35 (148.94), 148.82 (148.56), 131.99 (131.48), 129.88 (129.52), 127.79 (127.50), 125.40 (124.81), 123.07 (122.21), 121.24 (119.56), 118.60 (118.50), 112.78 (111.25), 110.74 (110.69), 109.56 (109.51), 92.53 (92.31), 56.01, 55.97, 55.86 (55.80), 15.55 (24.81); Anal Calcd for $C_{20}H_{20}N_2O_4+0.06H_2O$: C, 67.96; H, 5.74; N, 7.93. Found: C, 67.66; H, 5.88; N, 7.82.

4.6.2.23 3-(3-Amino-4-methoxy-phenyl)-3-(3,4,5-trimethoxy-phenyl)-acrylonitrile (E and Z Isomers)

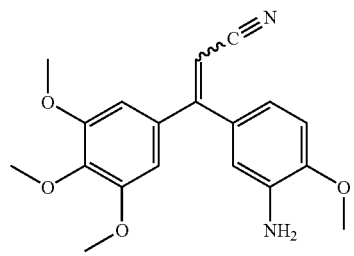

(4-Methoxy-3-nitro-phenyl)-(3,4,5-trimethoxy-phenyl)-methanol was prepared analogously to (4-methoxy-3-nitro-phenyl)-3-(3,4-dimethoxy-phenyl)-methanol using 3,4,5-tromethoxybromobenzene (4.4 g, 17.8 mmol), magnesium turning (0.4 g, 17.8 mmol) and 4-methoxy-3-nitro-benzaldehyde (2.7 g, 14.4 mmol). The crude product was purified by flash chromatography (silica gel, $CH_2Cl_2$:EtOAc 9:1) to afford (4-methoxy-3-nitro-phenyl)-(3,4,5-trimethoxy-phenyl0-methanol (2.4 g, 46%): $^1H$ NMR ($CDCl_3$) δ 7.88 (d, J=2 Hz, 1H), 7.53-7.49 (dd, J=2, 8 Hz, 1H), 7.05 (d J=8 Hz, 1H), 6.54 (s, 2H), 5.72 (d, J=3 Hz, 1H), 3.94 (s, 3H), 3.91 (s, 3H), 3.81 (s, 6H), 3.02 (d, J=3 Hz, 1H).

(4-Methoxy-3-nitro-phenyl)-(3,4,5-trimethoxy-phenyl)-methanone was prepared analogously to (4-methoxy-3-nitro-phenyl)-(3,4-dimethoxy-phenyl)-methanone using (4-methoxy-3-nitro-phenyl)-(3,4,5-trimethoxy-phenyl)-methanol (2.4 g, 6.9 mmol) and pyridinium chlorochromate (2.2 g, 10.3 mmol). The crude product was purified by flash chromatography (silica gel, $CH_2Cl_2$:EtOAc 95:5) to afford (4-methoxy-3-nitro-phenyl)-(3,4,5-trimethoxy-phenyl)-methanone (1.3 g, 55%) as a white solid: $^1$H NMR ($CDCl_3$) δ 8.34 (d, J=2 Hz, 1H), 8.10-8.06 (dd, J=2, 8 Hz, 1H), 7.22 (d, J=8 Hz, 1H), 7.01 (s, 2H), 4.07 (s, 3H), 3.95 (s, 3H), 3.87 (s, 3H).

3-(4-Methoxy-3-nitro-phenyl)-3-(3,4,5-trimethoxy-phenyl)-acrylonitrile was prepared analogously to 3-(4-methoxy-3-nitro-phenyl)-3-(3,4-dimethoxy-phenyl)-acrylonitrile using 3-(4-methoxy-3-nitro-phenyl)-3-(3,4,5-trimethoxy-phenyl)-methanone (1.3 g, 3.7 mmol), lithium bis(trimethylsilyl)amide (4.5 mL, 4.5 mmol) and diethyl cyanomethylphosphate (0.7 g, 4.1 mmol). The crude product was purified by flash chromatography (silica gel, $CH_2Cl_2$:EtOAc 95:5) to afford a 1:1 mixture of isomers of 3-(4-methoxy-3-nitro-phenyl)-3-(3,4,5-trimethoxy-phenyl)-acrylonitrile (0.9 g, 65%): $^1$H NMR ($CDCl_3$) δ 7.88-7.85 (m, 1H), 7.83-7.48 (dd, J=2, 8 Hz, 1H), 7.22-7.12 (d, J=8 Hz, 1H), 6.46 (6.63) (s, 2H), 5.70 (5.66) (s, 1H), 4.04 (4.01) (s, 3H), 3.90 (3.93) (s, 3H), 3.81 (3.84) (s,6H).

3-(3-Amino-4-methoxy-phenyl)-3-(3,4,5-trimethoxy-phenyl)-acrylonitrile was prepared analogously to 3-(3-amino-4-methoxy-phenyl)-3-(3,4-dimethoxy-phenyl)-acrylonitrile using 3-(4-methoxy-3-nitro-phenyl)-3-(3,4,5-trimethoxy-phenyl)-acrylonitrile (0.9 g, 2.4 mmol) and 10% Pd/C (0.1 g). The crude product was purified by flash chromatography (silica gel, $CH_2Cl_2$:EtOAc 85:15) to afford a mixture of isomers of 3-(3-amino-4-methoxy-phenyl)-3-(3,4,5-trimethoxy-phenyl)-acrylonitrile (0.3 g, 41%) as a yellow solid: mp 97-99° C.; $^1$H NMR ($CDCl_3$) δ 6.87-6.51 (m, 5H), 5.75 (5.51) (s, 1H), 3.91-3.80 (m, 14H); $^{13}$C NMR ($CDCl_3$) δ 163.04 (163.13), 152.97 (152.89), 149.22 (148.80), 1139.26 (139.85), 136.19 (135.96), 132.58 (135.12), 131.52 (129.53), 119.53 (120.75), 114.38 (115.88), 109.83 (109.77), 107.20 (106.21), 92.10 (92.56), 60.91, 56.25, 55.56, 55.49; Anal Calcd for $C_{19}H_{20}N_2O_4$: C, 67.05; H, 5.92; N, 8.23. Found: C, 67.08; H, 6.08; N, 7.94.

4.6.2.24 3-(2-Amino-5-methoxy-phenyl)-3-(3,4,5-trimethoxy-phenyl)-acrylonitrile (E and Z Isomers)

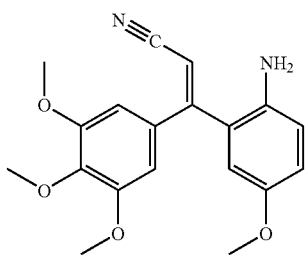

(5-Methoxy-2-nitro-phenyl)-(3,4,5-trimethoxy-phenyl)-methanol was prepared analogously to (4-methoxy-3-nitro-phenyl)-(3,4-dimethoxy-phenyl)-methanol using 3,4,5-trimethoxy-bromobenzene (4.6 g, 18.5 mmol), magnesium turning (0.5 g, 18.5 mmol) and 5-methoxy-2-nitro-benzaldehyde (2.8 g, 15.5 mmol). The crude product was purified by flash chromatography (silica gel, $CH_2Cl_2$:EtOAc 9:1) to afford (5-methoxy-2-nitro-phenyl)-(3,4,5-trimethoxy-phenyl)-methanol (2.9 g, 53%); $^1$H NMR ($CDCl_3$) δ 8.08 (d, J=9 Hz, 1H), 7.20 (d, J=2 Hz, 1H), 6.91-6.87 (dd, J=3, 9 Hz, 1H), 6.57 (s, 2H), 6.45 (d, J=4 Hz, 1H), 3.88 (s, 3H), 3.82 (s, 3H), 3.80 (s, 6H), 3.04 (d, J=4 Hz, 1H).

(5-Methoxy-2-nitro-phenyl)-(3,4,5-trimethoxy-phenyl)-methanone was prepared analogously to (4-methoxy-3-nitro-phenyl)-(3,4-dimethoxy-phenyl)-methanone using (5-methoxy-2-nitro-phenyl)-(3,4,5-trimethoxy-phenyl)-methanol (2.9 g, 8.2 mmol) and pyridinium chlorochromate (2.6 g, 12.2 mmol). The crude product was purified by flash chromatography (silica gel, $CH_2Cl_2$:EtOAc 95:5) to afford (5-methoxy-2-nitro-phenyl)-(3,4,5-trimethoxy-phenyl)-methanone (2.2 g, 76%) as a white solid: $^1$H NMR ($CDCl_3$) δ 8.22 (d, J=9 Hz, 1H), 7.11-7.06 (dd, J=3, 9 Hz, 1H), 7.00 (s, 2H), 6.89 (d, J=2 Hz, 1H), 3.93 (s, 3H), 3.92 (s, 3H), 3.82 (s, 6H); $^{13}$C NMR ($CDCl_3$) δ 191.95, 164.01, 153.25, 143.37, 139.57, 138.57, 130.85, 126.93, 115.30, 113.49, 106.78, 60.93, 56.32, 56.25.

3-(5-Methoxy-2-nitro-phenyl)-3-(3,4,5-trimethoxy-phenyl)-acrylonitrile was prepared analogously to 3-(4-methoxy-3-nitro-phenyl)-3-(3,4-dimethoxy-phenyl)-acrylonitrile using (5-methoxy-2-nitro-phenyl)-(3,4,5-trimethoxy-phenyl)-methanone (2.2 g, 6.2 mmol), lithium bis(trimethylsilyl)amide (9.3 mL, 9.3 mmol) and diethyl cyanomethylphosphate (1.6 g, 9.3 mmol). The product was purified by flash chromatography (silica gel, Hexane:EtOAc 6:4) to afford mixture of isomers of 3-(5-methoxy-2-nitro-phenyl)-3-(3,4,5-trimethoxy-phenyl)-acrylonitrile (2.2 g, 93%): $^1$H NMR ($CDCl_3$) δ 8.12 (8.27) (d, J=9 Hz, 1H), 7.07-7.03 (dd, J=3, 9 Hz, H), 6.91 (6.97) (d, J=2 Hz, 1H), 6.68 (6.43) (s, 2H), 5.49 (5.89) (s, 1H), 3.96 (s, 3H), 3.87 (s, 3H), 3.79 (6H).

3-(2-Amino-5-methoxy-phenyl)-3-(3,4,5-trimethoxy-phenyl)-acrylonitrile was prepared analogously to 3-(3-amino-4-methoxy-phenyl)-3-(3,4-dimethoxy-phenyl)-acrylonitrile using 3-(5-methoxy-2-nitro-phenyl)-3-(3,4,5-trimethoxy-phenyl)-acrylonitrile (1.5 g, 4.0 mmol) and 10% Pd/C (0.2 g). The crude product was purified by flash chromatography (silica gel, $CH_2Cl_2$:EtOAc 85:15) to afford a single isomer of 3-(2-amino-5-methoxy-phenyl)-3-(3,4,5-trimethoxy-phenyl)-acrylonitrile (0.3 g, 25%) as a yellow solid: mp 132-134° C.; $^1$H NMR ($CDCl_3$) δ 6.87-6.82 (dd, J=3, 8 Hz, 1H), 6.81 (s, 2H), 6.68 (d, J=2 Hz, 1H), 6.64 (d, J=8.8 Ha, 1H), 5.58 (s, 1H), 3.90 (s, 3H), 3.83 (s, 6H), 3.77 (s, 3H), 3.28 (b, 2H); $^{13}$C NMR ($CDCl_3$) δ 161.09, 153.38, 152.40, 140.15, 138.26, 131.07, 125.44, 117.94, 117.84, 117.24, 115.55, 106.15, 96.46, 60.95, 55.79, 55.32; Anal Calcd for $C_{19}H_{20}N_2O_4$: C, 67.05; H, 5.92; N, 8.23. Found: C, 67.02; H, 6.02; N, 8.07.

4.6.2.25 3-(4-Methoxy-3-nitro-phenyl)-3-(3,5-dimethoxy-phenyl)-acrylonitrile (E and Z Isomers)

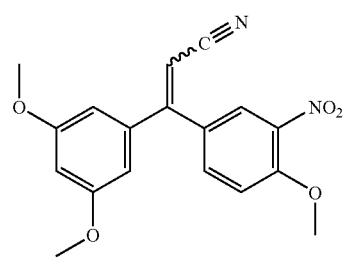

(4-Methoxy-3-nitro-phenyl)-(3,5-dimethoxy-phenyl)-methanol was prepared analogously to 3-(4-methoxy-3-nitro-phenyl)-(3,4-dimethoxy-phenyl)-methanol using 3,5- dimethoxy-bromobenzene (5.0 g, 23.0 mmol), magnesium turning (0.6 g, 23.0 mmol) and 4-methoxy-3-nitro-benzaldehyde (3.5 g, 19.2 mmol). The crude product was purified by flash chromatography (silica gel, Hexane:EtOAc 1:1) to afford (4-methoxy-3-nitro-phenyl)-(3,5-dimethoxy-phenyl)-methanol (3.7 g, 60%) as an oil: $^1$H NMR (CDCl$_3$) δ 7.88 (s, 1H), 7.54-7.50 (dd, J=2, 8 Hz, 1H), 7.04 (d, J=8 Hz, 1H), 6.38 (d, J=1 Hz, 1H), 5.72 (d, J=3 Hz, 1H), 3.93 (s, 3H), 3.76 (s, 6H), 2.45 (d, 2 Hz, 1H).

(4-Methoxy-3-nitro-phenyl)-(3,5-dimethoxy-phenyl)-methanone was prepared analogously to (4-methoxy-3-nitro-phenyl)-(3,4-dimethoxy-phenyl)-methanone using (4-methoxy-3-nitro-phenyl)-(3,5-dimethoxy-phenyl)-methanol (3.7 g, 11.5 mmol) and pyridinium chlorochromate (3.7 g, 17.0 mmol). The crude product was purified by flash chromatography (silica gel, CH$_2$Cl$_2$:EtOAc 9:1) to afford (4-methoxy-3-nitro-phenyl)-(3,5-dimethoxy-phenyl)-methanone (3.0 g, 82%) as a white solid: $^1$H NMR (CDCl$_3$) δ 8.33 (d, J=2 Hz, 1H), 8.09 (d, J=9.1 Ha, 1H), 7.20-7.15 (dd, J=3, 8 Hz, 1H), 6.84 (d, J=2 Hz, 2H), 6.69 (m, 1H), 4.06 (s, 3H), 3.83 (s, 6H).

3-(4-Methoxy-3-nitro-phenyl)-3-(3,5-dimethoxy-phenyl)-acrylonitrile (E and Z isomers) were prepared analogously to 3-(4-methoxy-3-nitro-phenyl)-3-(3,4-dimethoxy-phenyl)-acrylonitrile using (4-methoxy-3-nitro-phenyl)-(3,5-dimethoxy-phenyl)-methanone (3.0 g, 9.5 mmol), lithium bis(trimethylsilyl)amide (10.4 mL, 10.4 mmol) and diethyl cyanomethylphosphate (1.9 g, 10.4 mmol). The crude product was purified by flash chromatography (silica gel, Hexane:CH$_2$Cl$_2$ 1:9) to afford mixture of isomers of 3-(4-methoxy-3-nitro-phenyl)-3-(3,5-dimethoxy-phenyl)-acrylonitrile (2.9 g, 91%) as a yellow solid: mp 122-124° C.; $^1$H NMR (CDCl$_3$) δ 7.85-7.78 (m, 1H), 7.20 (d, J=8 Hz, 1H), 7.10 (d, J=8 Hz, 1H), 6.57-6.54 (m, 1H), 6.51 (d, J=2 Hz, 1H), 6.37 (d, J=2 Hz, 1H), 5.75 (s, 1H), 4.03 (4.00) (s, 3H), 3.80 (3.77) (s, 6H); $^{13}$C NMR (CDCl$_3$) δ 161.04, 160.98, 160.26, 154.04, 135.18, 133.75, 130.90, 129.05, 127.10, 125.40, 113.61, 113.55, 56.80, 56.75, 55.53; Anal Calcd for C$_{18}$H$_{16}$N$_2$O$_5$: C, 63.53; H, 4.74; N, 8.23. Found: C, 63.35; H, 4.50; N, 8.19.

4.6.2.26 3-(3-Amino-4-methoxy-phenyl)-3-(3,5-dimethoxy-phenyl)-acrylonitrile (E and Z Isomers)

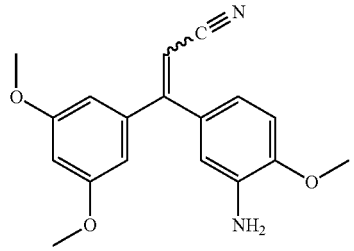

3-(3-Amino-4-methoxy-phenyl)-3-(3,5-dimethoxy-phenyl)-acrylonitrile (E and Z isomers) was prepared analogously to 3-(4-amino-3-methoxy-phenyl)-3-(3,4,5-trimethoxy-phenyl)-acrylonitrile using 3-(4-methoxy-3-nitro-phenyl)-3-(3,5-dimethoxy-phenyl)-acrylonitrile (1.5 g, 4.4 mmol) and tin chloride dihydrate (5.4 g, 23.0 mmol). The crude product was purified by flash chromatography (silica gel, Hexane:EtOAc 75:25) to afford mixture of isomers of 3-(3-amino-4-methoxy-phenyl)-3-(3,5-dimethoxy-phenyl)-acrylonitrile (0.8 g, 54%) as a yellow solid: mp 93-95° C.; $^1$H NMR (CDCl$_3$) δ 6.82-6.42 (m, 6H), 5.54 (s, 1H), 3.89 (3.87) (s, 3H), 3.87-3.70 (b, 2H), 3.79 (3.73) (s, 6H); $^{13}$C NMR (CDCl$_3$) δ 163.14, 162.93, 160.60, 160.55, 149.22, 148.78, 141.73, 139.25, 136.17, 135.95, 131.24, 129.54, 120.67, 119.36, 115.82, 114.23, 109.86, 109.80, 107.64, 107.00, 101.97, 101.92, 93.36, 92.65, 55.57, 55.46; Anal Calcd for C$_{18}$H$_{18}$N$_2$O$_3$: C, 69.66; H, 5.85; N, 9.03. Found: C, 69.60; H, 5.58; N, 8.88.

4.6.2.27 N-{5-[2-Cyano-1-(3,5-dimethoxy-phenyl)-vinyl]-2-methoxy}-acetamide (E and Z Isomers)

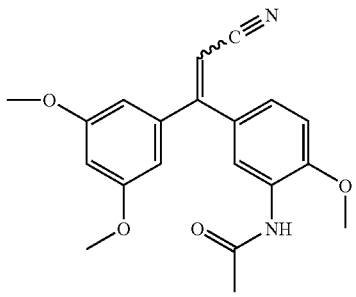

Acetyl chloride (0.2 mL, 2.6 mmol) was added to a stirred solution of 3-(3-amino-4-methoxy-phenyl)-3-(3,5-dimethoxy-phenyl)acrylonitrile (0.4 g, 1.3 mmol) in THF (20 mL). The solution was refluxed for 30 min then cooled to room temperature. The reaction mixture was quenched with methanol (0.5 mL) and concentrated. The crude product was purified by flash chromatography (silica gel, Hexane:EtOAc 1:1) to afford a mixture of isomers of N-{5-[2-cyano-1-(3,5-dimethoxy-phenyl)-vinyl]-2-methoxy}-acetamide (0.3 g, 62%) as a white solid: mp 163-165° C.; $^1$H NMR (CDCl$_3$) δ 9.28 (s, 1H), 7.93 (s, 1H), 7.17 (m, 2H), 6.62 (s, 1H), 6.46 (d, J=1 Hz, 2H), 6.22 (6.14) (s, 1H), 3.91 (s, 3H), 3.76 (s, 6H), 2.06 (s, 3H); $^{13}$C NMR (CDCl$_3$) δ 168.67, 161.28, 160.34, 150.52, 140.25, 128.54, 127.28, 125.48, 122.49, 118.27, 110.86, 106.68, 101.99, 95.35, 55.84, 55.37, 23.81; Anal Calcd for C$_{20}$H$_{20}$N$_2$O$_4$: C, 68.17; H, 5.72; N, 7.95. Found: C, 68.03; H, 5.54; N, 7.85.

4.6.2.28 4-Amino-N-{5-[2-cyano-1-(3,4,5-trimethoxy-phenyl)-vinyl]-2-methoxy-phenyl}butyramide Hydrochloride (E and Z Isomers)

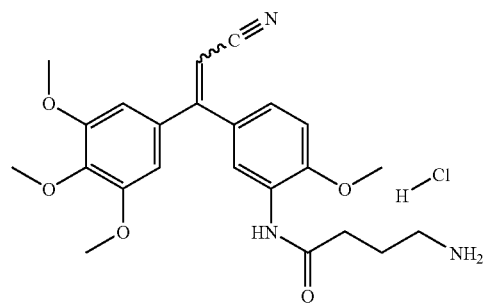

N-BOC-γ-Aminobutyric acid (0.5 g, 2.4 mmol) was added to a stirred solution of 3-(3-amino-4-methoxy-phenyl)-3-(3,4,5-trimethoxy-phenyl)-acrylonitrile (0.7 g, 2.0 mmol), dicyclohexylcarbodiimide (0.5 g, 2.4 mmol) and 1-hydroxybenzotriazole (0.4 g, 3.0 mmol) in DMF (10 mL). The mixture was stirred at room temperature for 2 days. Ethyl acetate (15 mL) was added and the mixture was filtered. The filtrate was diluted with EtOAc (50 mL) and was washed with water (3×30 mL), brine (30 mL) and dried (MgSO$_4$). Solvent was removed and the residue was purified by flash chromatography (silica gel, CH$_2$Cl$_2$: EtOAc 9:1) to afford mixture of isomers of N-BOC-4-amino-N-{5-[2-cyano-1-(3,4,5-trimethoxy-phenyl)-vinyl]-2-methoxy-phenyl}-butyramide (0.6 g, 57%): $^1$H NMR (CDCl$_3$) δ 8.00 (b,1H), 7.23-6.84 (m,3H), 6.51 (6.65) (s, 2H), 5.60 (5.66) (s, 1H), 4.71 (b, 1H), 3.95 (3.92 (s, 3H), 3.91 (3.92) (s, 3H), 3.80 (3.83) (s, 6H), 3.24-3.19 (m, 2H), 2.46-2.39 (m, 2H), 1.94-1.82 (m, 2H), 1.42 (s, 9H).

A solution of 4N HCl/dioxane (2.0 mL) was added to a stirred solution of N-BOC-4-amino-N-{5-[2-cyano-1-(3,4,5-trimethoxy-phenyl)-vinyl]-2-methoxy-phenyl}-butyramide (0.6g, 1.1 mmol) in CH$_2$Cl$_2$ (10 mL). The solution was stirred at room temperature overnight. Ether (10 mL) was added and the mixture was stirred for 2 h. The slurry was filtered and washed with ether to give mixture of isomers of 4-amino-N-{5-[2-cyano-1-(3,4,5-trimethoxy-phenyl)-vinyl]-2-methoxy-phenyl}butyramide hydrochloride (0.5 g, 90%) as a white solid: mp 168-170° C.; $^1$H NMR (DMSO-d$_6$) δ 9.35 (s, 1H), 8.06 (b, 3H), 7.93 (s, 1H), 7.25-7.09 (m, 2H), 6.67 (6.65) (s, 2H), 6.23 (6.10) (s, 1H), 3.92 (3.88) (s, 3H), 3.76-3.71 (m, 9H), 2.79 (t, J=7 Hz, 2H), 2.50-2.45 (m, 2H), 1.86-1.77 (m, 2H); $^{13}$C NMR (DMSO-d$_6$) δ 170.66 (173.68), 161.15 (161.31), 152.65 (152.61), 151.91 (150.90), 139.46 (138.52), 133.52 (132.25), 129.63 (128.44), 127.01 (126.89), 125.25 (126.04), 123.18 (122.66), 118.57 (118.53), 111.22 (110.93), 106.96 (106.25), 94.36 (93.45), 66.32, 60.12, 56.00 (55.87), 38.29 (38.13), 32.74 (30.49), 23.05 (22.46), Anal Calcd for C$_{23}$H$_{28}$N$_3$O$_5$Cl +1.0H$_2$O: C, 57.56; H, 6.30; N, 8.75; Cl, 7.39. Found: C, 57.72; H, 6.18; N, 8.80; Cl, 8.28.

4.6.2.29 2-Amino-N-{5-[2-cyano-1-(3,4,5-trimethoxy-phenyl)-vinyl]-2-methoxy-phenyl}-acetamide Hydrochloride (E and Z Isomers)

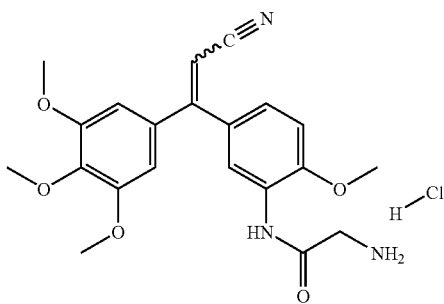

N-BOC-glycine (0.5 g, 2.8 mmol) was added to a stirred solution of 3-(3-amino-4-methyoxy-phenyl)-3-(3,4,5-trimethoxy-phenyl)acrylonitrile (0.8 g, 2.4 mmol), dicyclohexylcarbodiimide (0.6 g, 2.8 mmol) and 1-hydroxybenzotriazole (0.5 g, 3.5 mmol) in DMF (15 mL). The mixture was stirred at room temperature for 2 days. Ethyl acetate (15 mL) was added and the mixture was filtered. The filtrate was diluted with EtOAc (50 mL) and was washed with water (3×30 mL), brine (30 mL) and dried (MgSO$_4$). Solvent was removed and the residue was purified by flash chromatography (silica gel, CH$_2$Cl$_2$:EtOAc 9:1) to afford mixture of isomers of N-BOC-2-amino-N-{5-[2-cyano-1-(3,4,5-trimethoxy-phenyl)-vinyl]-2-methoxy-phenyl}-acetamide (0.9 g, 75%): $^1$H NMR (CDCl$_3$) δ 8.42-8.39 (m, 2H), 6.97-6.85 (m, 1H), 6.50 (6.65) (s, 2H), 5.61 (5.65) (s, 1H), 3.94-3.80 (m, 14H), 1.48 (s, 9H).

A solution of 4N HCl/dioxane (2.0 mL) was added to a stirred solution of N-BOC-2-amino-N-{5-[2-cyano-1-(3,4,5-trimethoxy-phenyl)-vinyl]-2-methoxy-phenyl}-acetamide (0.9 g, 1.8 mmol) in CH$_2$Cl$_2$ (10 mL). The solution was stirred overnight. Ether (10 mL) was added and the mixture was stirred for 2 h. The slurry was filtered and washed with ether to give mixture of isomers of 2-amino-N-{5-[2-cyano-1-(3, 4,5-trimethoxy-phenyl)-vinyl]-2-methoxy-phenyl}-acetamide hydrochloride (0.7 g, 89%) as a white solid: mp 192-194° C.; $^1$H NMR (DMSO-d$_6$) δ 9.94 (9.90) (s, 1H), 8.27 (b, 3H), 7.79 (7.88) (s, 1H), 7.31-7.20 (m, 2H), 6.65 (6.68) (s, 2H), 6.23 (6.13) (s, 1H), 3.94-3.71 (m, 14H); $^{13}$C NMR (DMSO-d$_6$) δ 165.30 161.02 (161.22), 152.65, 150.83 (151.62), 139.41 (138.43), 133.62 (132.29), 128.58 (129.80), 126.15 (126.52), 125.22, 123.01 (122.55), 118.48, 111.20 (111.58), 106.27 (106.88), 94.43 (93.66), 66.33, 60.12, 56.00 (55.96), 40.92; Anal Calcd for C$_{21}$H$_{24}$N$_3$O$_5$Cl+0.75H$_2$O: C, 56.38; H, 5.74; N, 9.39; Cl, 7.92. Found: C, 56.22; H, 5.76; N, 9.13; Cl, 7.75.

4.6.2.30 2-Amino-N-{5-[2-cyano-1-(3,4,5-trimethoxy-phenyl)-vinyl]-2-methoxy-phenyl}-propionamide Hydrochloride (E and Z Isomers)

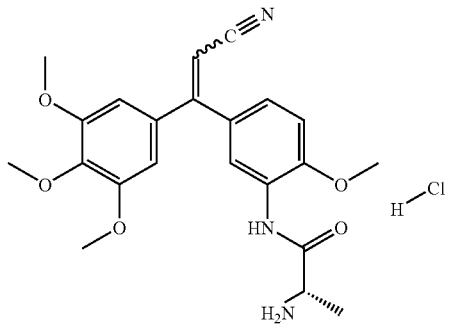

N-BOC-L-Alanine (0.5 g, 2.7 mmol) was added to a stirred solution of 3-(3-amino-4-methoxy-phenyl)-3-(3,4,5-trimethoxy-phenyl)-acrylonitrile (0.8 g, 2.2 mmol), dicyclohexylcarbodiimide (0.6 g, 2.7 mmol) and 1-hydroxybenzotriazole (0.5 g, 3.4 mmol) in DMF (15 mL). The mixture was stirred at room temperature for 2 days. Ethyl acetate (15 mL) was added and the mixture was filtered. The filtrate was diluted with EtOAc (50 mL) and was washed with water (3×30 mL), brine (30 mL) and dried (MgSO$_4$). Solvent was removed and the residue was purified by flash chromatography (silica gel, CH$_2$Cl$_2$:EtOAc 9:1) to afford mixture of isomers of N-BOC-2-amino-N-{5-[2-cyano-1-(3,4,5-trimethoxy-phenyl)-vinyl]-2-methoxy-phenyl}-propionamide (0.8 g, 72%): $^1$H NMR (CDCl$_3$) δ 8.55 (b, 1H), 8.40 (s, 1 h), 7.25-6.85 (m, 2H), 6.50 (6.55) (s, 2H), 5.61 (5.66 (s, 1H), 5.04 (d, J=7 Hz, 1H), 4.33 (b, 1H), 3.94-3.80 (m, 12H), 1.47-1.41 (m, 12H).

A solution of 4N HCl/dioxane (2.0 mL) was added to a stirred solution of N-BOC-2-amino-N-{5-[2-cyano-1-(3,4,5-trimethoxy-phenyl)-vinyl]-2-methoxy-phenyl}-propionamide (0.8 g, 1.6 mmol) in CH$_2$Cl$_2$ (20 mL). The mixture was stirred at room temperature overnight. Ether (35 mL) was added and the mixture was stirred for 2 h. The slurry was filtered and was washed with ether to give mixture of isomers of 2-amino-N-{5-[2-cyano-1-(3,4,5-trimethoxy-phenyl)-vinyl]-2-methoxy-phenyl}-propionamide hydrochloride (0.6 g, 76%) as a white solid: mp 180-182° C.; $^1$H NMR (DMSO-$d_6$) δ 9.98 (9.93) (s, 1H), 8.36 (b, 3H), 7.89-7.84 (m, 1H), 7.40-7.16 (m, 2H), 6.65 (6.68) (s, 2H), 6.25 (6.14) (s, 1H), 4.21-4.16 (m, 1H), 3.94 (3.91) (s, 3H), 3.76-3.70 (m, 9H), 1.44-1.33 (m, 3H); $^{13}$C NMR (DMSO-$d_6$) δ 168.84, 160.92 (161.14), 152.65, 151.31 (152.05), 139.42 (138.45), 133.55 (132.24), 128.52 (129.77), 126.88 (126.09), 25.96 (125.61), 123.61 (122.97), 118.51 (118.47), 111.26 (111.60), 106.28 (106.91), 94.45 (93.67), 60.32, 60.15 (60.12), 56.11 (56.00), 48.59, 17.40; Anal Calcd for $C_{22}H_{26}N_3O_5Cl+1.2H_2O$: C, 56.28; H, 6.10; N, 8.95; Cl, 7.55. Found: C, 55.98; H, 6.07; N, 9.07; Cl, 7.81.

4.6.2.31 4-Amino-N-{5-[2-cyano-1-(3-ethoxy-4-methoxy-phenyl)-vinyl]-2-methoxy-phenyl}-butyramide Hydrochloride (E and Z Isomers)

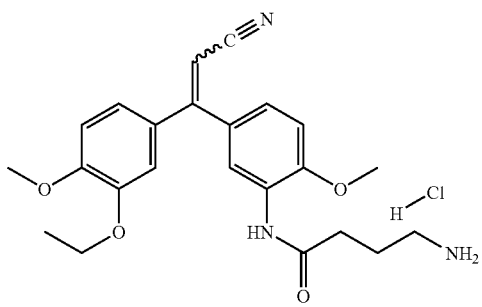

N-BOC-γ-aminobutyric acid (0.6 g, 3.0 mmol) was added to stirred solution of 3-(3-amino-4-methoxy-phenyl)-3-(3-ethoxy-4-methoxy-phenyl)-acrylonitrile (0.8 g, 2.5 mmol), dicyclohexylcarbodiimide (0.6 g, 3.0 mmol) and 1-hydroxybenzotriazole (0.5 g, 3.7 mmol) in DMF (15 mL). The resulting mixture was stirred at room temperature for 2 days. Ethyl acetate (15 mL) was added and the mixture was filtered. The filtrate was diluted with EtOAc (50 mL) and was washed with water (3×30 mL), brine (30 mL) and dried (MgSO$_4$). Solvent was removed and the residue was purified by flash chromatography (silica gel, CH$_2$Cl$_2$:EtOAc 9:1) to afford N-BOC-4-amino-N-{5-[2-cyano-1-(3-ethoxy-4-methoxy-phenyl)-vinyl]-2-methoxy-phenyl}-butyramide (1.1 g, 89%): $^1$H NMR (CDCl$_3$) δ 7.95 (b, 1H), 7.32-6.81 (m, 6H), 5.57 (5.59) (s, 1H), 4.06-4.01 (q, 2H), 3.94 (3.91) (s,3H), 3.89 (s, 3H), 3.21-3.18 (m, 2H), 2.45-2.40 (m, 2H), 1.93-1.85 (m, 2H), 1.47-1.42 (t, 3H), 1.42 (s, 9H).

A solution of 4N HCl/dioxane (2 mL) was added to a stirred solution of N-BOC-4-amino-N-{5-[2-cyano-1-(3-ethoxy-4-methoxy-phenyl)-vinyl]-2-methoxy-phenyl}butyramide (1.1 g, 1.2 mmol) in CH$_2$Cl$_2$ (15 mL). The resulting mixture was stirred overnight. Ether (30 mL) was added and the mixture was stirred for 2 h. The slurry was filtered and washed with ether to afford mixture isomers of 4-amino-N-{5-[2-cyano-1-1 (3-ethoxy-4-methoxy-phenyl)-vinyl]-2-methoxy-phenyl}butyramide Hydrochloride (0.85 g, 88%) was a white solid: mp 162-164° C.; $^1$H NMR (DMSO-$d_6$) δ 9.30 (s, 1H), 8.03 (s, 3H), 7.95 (7.92 (s, 1H), 7.18-6.74 (m, 5H), 6.15 (5.97) (s, 1H), 4.02 (q, J=6 Hz, 2H), 3.943.92) (s, 3H), 3.79 (3.83) (s, 3), 2.81-2.75 (m, 2H), 2.53-2.45 (m, 2H), 1.88-1.79 (m, 2H), 1.31 (t, J =6 Hz, 3H); $^{13}$C NMR (DMSO-$d_6$) δ 170.62, 161.26 (161.47), 151.05 (151.66), 150.21. (150.47), 147.31 (147.77), 130.30 (130.45), 128.98 (129.17), 127.04 (126.71), 125.70 (125.21), 122.43 (122.21), 118.79 (118.72), 113.83 (112.19), 111.46 (111.13), 92.84 (92.56), 63.79 (63.74), 55.95 (55.87), 55.55 (55.48), 38.03, 32.76 (32.69), 23.01, 14.59 (14.56); Anal Calcd for $C_{23}H_{28}N_3O_4Cl+0.58H_2O$: C, 60.53; H, 6.44; N, 9.21; Cl, 7.77. Found: C, 60.27; H, 6.20; N, 9.90; Cl, 7.65.

4.6.2.32 2-Amino-N-{5-[2-cyano-1-(3-ethoxy-4-methoxy-phenyl)-vinyl]-2-methoxy-phenyl}-acetamide Hydrochloride (E and Z Isomers)

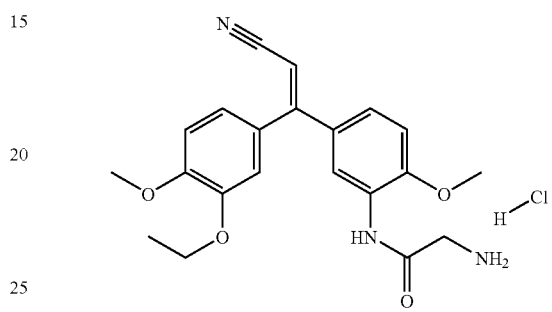

N-BOC-glycine (0.5 g, 3.0 mmol) was added to a stirred solution of 3-(3-amino-4-methoxy-phenyl)-3-(3-ethoxy-4-methoxy-phenyl)-acrylonitrile (0.8 g, 2.5 mmol), dicyclohexylcarbodiimide (0.6 g, 3.0 mmol) and 1-hydroxybenzotriaole (0.5 g, 3.7 mmol) in DMF (15 mL). The mixture was stirred at room temperature for 2 days. Ethyl acetate (15 mL) was added and the mixture was filtered. The filtrate was diluted with EtOAc (50 mL) and was washed with water (3×30 mL), brine (30 mL) and dried (MgSO$_4$). Solvent was removed and the residue was purified by flash chromatography (silica gel, CH$_2$Cl$_2$:EtOAc 9:1) to afford a mixture of isomers of N-BOC-2-amino-N-{5-[2-cyano-1-(3-ethoxy-4-methoxy-phenyl)-vinyl]-2-methoxy-phenyl}-acetamide (0.9 g, 75%): $^1$H NMR (CDCl$_3$) δ 8.47-8.37 (m, 2H), 7.01-6.80 (m, 5H), 5.58 (s, 1H), 5.20 (b, 1H), 4.12-4.07 (q, 2H), 3.98-3.89 (m, 6H), 1.94-1.89 (m, 1H), 1.73-1.67 (m, 1H), 1.48-1.43 (m, 12H).

A solution of 4N HCl/dioxane (3 mL) was added to a stirred solution of N-BOC-2-amino-N-{5-[2-cyano-1-1 (3-ethoxy-4-methoxy-phenyl)-vinyl]-2-methoxy-phenyl}-acetamide (1.1 g, 2.4 mmol) in CH$_2$Cl$_2$ (35 mL). The resulting solution was stirred at room temperature overnight. Ether (10 mL) was added and the mixture was stirred for 2 h. The slurry was filtered and was washed with ether to afford mixture isomers of E-2-amino-N-{5-[2-cyano-1-(3-ethoxy-4-methoxy-phenyl)-vinyl]-2-methoxy-phenyl}-acetamide hydrochloride (0.44 g, 44%) as a white solid: mp, 208-210° C.; $^1$H NMR (DMSO-$d_6$) δ 9.88 (s, 1H), 8.20 (b, 3H), 7.89 (d, J=1 Hz, 1H), 7.36-6.91 (m, 5H), 6.01 (s, 1H), 3.99 (q, J=7 Hz, 2H), 3.90 (s, 3H), 3.83 (s, 3H), 3.78 (s, 2H), 1.31 (t, J=6 Hz, 3H); $^{13}$C NMR (DMSO-$d_6$) δ 165.39, 161.37, 151.39, 150.15, 147.37, 130.45, 129.21, 126.22, 125.24, 122.36, 118.73, 113.75, 111.48, 92.81, 63.75, 56.06, 55.50, 40.97, 14.59; Anal Calcd for $C_{21}H_{24}N_3O_4Cl+1.4H_2O$: C, 56.92; H, 6.10; N, 9.48; Cl, 8.00. Found: C, 56.58; H, 5.85; N, 9.72; Cl, 8.47.

4.6.2.33 2-Amino-N-{5-[2-cyano-1-(3,4,5-trimethoxy-phenyl)-vinyl]-2-methoxy-phenyl}-3-hydroxy-propionamide Hydrochloride (E and Z Isomers)

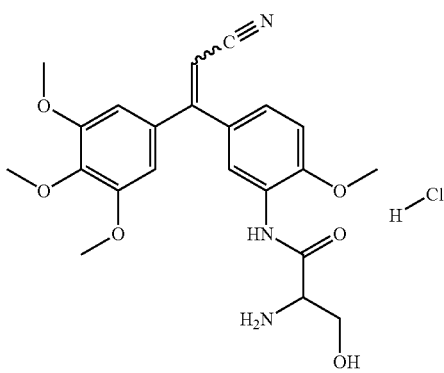

N-Fmco-O-t-Bu-L-Ser (1.1 g, 2.8 mmol) was added to a stirred solution of 3-(3-amino-4-methoxy-phenyl)-3-(3,4,5-trimethoxy-phenyl)-acrylonitrile (0.8 g, 2.4 mmol), dicyclohexylcarbodiimide (0.6 g, 2.8 mmol) and 1-hydroxybenzotriazole (0.5 g, 3.5 mmol) in DMF (15 mL). The mixture was stirred at room temperature for 2 days. Ethyl acetate (15 mL) was added and the mixture was filtered. The filtrate was diluted with EtOAc (50 mL) and was washed with water (3×40 mL), brine (40 mL) and dried (MgSO$_4$). Solvent was removed and the residue was purified by flash chromatograph (silica gel, Hexane:EtOAc 1:1) to afford N-Fomc-2-amino-N-{5-[2-cyano-1-(3,4,5-trimethoxy-phenyl)-vinyl]-2-methoxy-phenyl}-3-t-butoxy-propionamide (1.5 g, 89%).

A solution of N-Fmco-2-amino-N-{5-[2-cyano-1-(3,4,5-trimethoxy-phenyl)-vinyl]-2-methoxy-phenyl}-3-t-butoxy-propionamide (1.5 g, 2.1 mmol) and pyridine (2 mL) in CH$_2$Cl$_2$ (20 mL) was stirred for 2 h. The mixture was diluted with CH$_2$Cl$_2$ (40 mL) and was washed with water (2×30 mL), brine (30 mL) and dried (MgSO$_4$). Solvent was removed and the residue was purified by flash chromatography (silica gel, CH$_2$Cl$_2$:EtOAc 7:3) to afford 2-amino-N-{5-[2-cyano-1-(3,4,5-trimethoxy-phenyl)-vinyl]-2-methoxy-phenyl}-3-t-butoxy-propionamide (0.5 g, 53%): $^1$H NMR (CDCl$_3$) δ 8.48 (8.65) (s, 1H), 7.24-6.58 (m, 3H), 6.51 (6.66) (s, 2H), 5.60 (5.67) (s, 1H), 3.96-3.79 (m, 12H), 3.69-3.57 (m, 3H), 1.21 (1.19) (s, 9H).

A solution of 4N HCl/dioxane (1 mL) was added to a stirred solution of 2-amino-N-{5-[2-cyano-1-(3,4,5-trimethoxy-phenyl)-vinyl]-2-methoxy-phenyl}-3-t-butoxy-propionamide (0.5 g, 1.1 mmol) in CH$_2$Cl$_2$ (10 mL). The resulting mixture was stirred at room temperature for 1 day. Ether (20 mL) was added and the mixture was stirred for 2 h. The slurry was filtered and washed with ether to afford mixture isomers of 2-amino-N-{5-[2-cyano-1-(3,4,5-trimethoxy-phenyl)-vinyl]-2-methoxy-phenyl}-3-hydroxy-propionamide hydrochloride (0.4 g, 78%) as white solid: mp 151-153° C.; $^1$H NMR (DMSO-d$_6$) δ 9.89 (9.94) (s 1H), 8.31 (b, 3H), 7.98-7.95 (m, 1H), 7.39-7.16 (m, 2H), 6.68 (6.65)-(s, 2H), 6.12 (6.25) (s, 1H), 5.63 (b, 1H), 4.18 (b, 1H), 3.91 (d, J=8 Hz, 2H), 3.87-3.70 (m, 12H); $^{13}$C NMR (DMSO-d$_6$) δ 166.20, 161.24 (160.99), 152.62, 151.52 (150.82), 139.43 (138.36), 133.54 (132.24), 129.80 (128.56), 126.60 (126.29), 126.16 (125.31), 122.99 (122.32), 118.51 (118.47), 111.50 (111.16), 106.91 (106.26), 94.46 (93.64), 66.33, 60.33 (60.15), 56.15, 56.02, 54.43; Anal Calcd for C$_{22}$H$_{26}$N$_3$O$_6$Cl+ 0.2H$_2$O: C, 56.52; H, 5.69; N, 8.99; Cl, 7.58. Found: C, 56.29; H, 5.81; N, 8.63; Cl, 7.35.

4.6.2.34 3-(3,4-Bis-difluoromethoxy-phenyl)-3-(3,5-dimethoxy-phenyl)-acrylonitrile (E and Z Isomers)

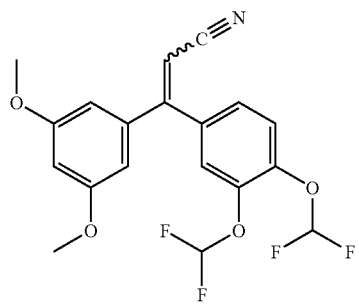

n-Butyl lithium (2.5 M, 3.7 mL) was added to s stirred solution of 3,5-dimethoxy-bromobenzene (2.0 g, 9.2 mmol) in THF (15 mL) at −65° C. After stirring for 30 min, a solution of 3,4-bis-difluoromethoxy-benzaldehyde (2.0 g, 8.4 mmol) in THF (15 mL) was added slowly. The resulting mixture was stirred at −65° C. for 6 h and then quenched with isopropanol (5 mL). Water (40 mL) was added and the mixture was extracted with ether (3×60 mL). The combined organic layers were washed with water (2×40 mL), brine (40 mL), and dried (MgSO$_4$). Solvent was removed and the residue was purified by flash chromatography (Silica gel, Hexane:EtOAc 7:3) to afford (3,4-bis-difluoromethoxy-phenyl)-(3,5-dimethoxy-phenyl)-methanol (1.3 g, 42%): $^1$H NMR (CDCl$_3$) δ 7.32 (m, 1H), 7.19 (m, 2H), 6.86-6.19 (m 5H), 5.69 (d, J=2 Hz, 1H), 3.76 (s, 6H), 2.47 (d, J=2 Hz, 1H).

A mixture of 3-(3,4-bis-difluoro-phenyl)-3-(3,5-dimethoxy-phenyl)-methanol (1.3 g, 3.3 mmol) and MnO$_2$ (2.3 g, 30 mmol) in CH$_2$Cl$_2$ (50 mL) was stirred at room temperature for 3 days. The mixture was filtered through Celite and the filtrate was concentrated. The crude product was purified by flash chromatography (Silica gel, Hexane:EtOAc 8:2) to afford (3,4-bis-difluoromethoxy-phenyl)-(3,5-dimethoxy-phenyl)-methanone (0.9 g, 76%): $^1$H NMR (CDCl$_3$) δ 7.75-7.68 (m, 2H), 7.36 (d, J=8 Hz, 1H), 6.88 (d, J=2 Hz, 2H), 6.69 (t, J=1 Hz, 1H), 6.63 (t, J=72 Hz, 1H), 6.59 (t, J=73 Hz, 1H), 3.80 (s, 6H).

Lithium bis-(trimethylsilyl)amide (1M, 3.0 mL) was added dropwise to a stirred solution of diethyl cyanomethylphosphate (0.5 g, 3.0 mmol) in THF (10 mL) at 5-8° C. The mixture was stirred at room temperature for 40 min. A solution of (3,4-bis-difluoromethoxy-phenyl)-(3,5-dimethoxy-phenyl)-methanone (0.9 g, 2.5 mmol) in THF (20 mL) was added and the mixture was stirred at room temperature for 17 h. The resulting mixture was poured into ice water (100 mL) and extracted with CH$_2$Cl$_2$ (3×50 mL). The combined organic layers were washed with water (2×40 mL), brine (40 mL) and dried (MgSO$_4$). Solvent was removed and the residue was purified by flash chromatography (Silica gel, Hexane:CH$_2$Cl$_2$ 4:6) to afford a mixture of isomers of 3-(3,4-bis-difluoromethxoy-phenyl)-3-(3,5-dimethoxy-phenyl)-acrylonitrile (0.6 g, 59%) as a white solid: mp 60-62° C.; $^1$H NMR (CDCl$_3$)

δ 7.35-7.22 (m, 3H), 6.90-6.20 (m, 5H), 5.76 (5.70) (s, 1H), 3.77 (3.80) (s, 6H); $^{13}$C NMR (CDCl$_3$) δ 160.98 (160.90), 160.65 (160.55), 143.60 (141.87), 139.92, 137.78 (137.06), 135.13, 127.99 (126.83), 123.70 (122.75), 121.84 (121.78), 117.25 (117.05), 115.68 (t, J=1047 Hz), 115.58 (t, J=1047 Hz), 106.80 (107.56), 102.51 (102.37), 96.29 (96.24); Anal Calcd for C$_{19}$H$_{15}$NO$_4$F$_4$: C, 75.44; H, 3.81; N, 3.53; F, 19.13. Found: C, 57.82; H, 3.61; N, 3.38; F, 19.39.

4.6.2.35 2-Amino-N-{5-[2-cyano-1-(3,5-dimethoxy-phenyl)-vinyl]-2-methoxyphenyl}-acetamide Hydrochloride (E and Z Isomers)

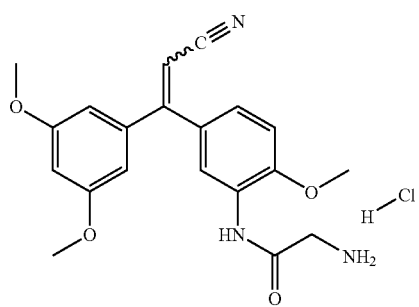

N-BOC-glycine (0.6 g, 3.5 mmol) was added to a stirred solution of 3-(3-amino-4-methoxy-phenyl)-3-(3,5-dimethoxy-phenyl)-acrylonitrile (0.9 g, 2.9 mmol), dicyclohexylcarbodiimide (0.7 g, 3.5 mmol) and 1-hydroxbenzotriazole (0.6 g, 4.3 mmol) in DMF (15 mL). The mixture was stirred at room temperature for 2 days. Ethyl acetate (20 mL) was added and the mixture was filtered. The filtrate was diluted with EtOAc (50 ml) and washed with water (3×30 mL), brine (2×30 mL) and dried (MgSO$_4$). Solvent was removed and the residue was purified by flash chromatography (Silica gel, CH$_2$Cl$_2$:EtOAc 9:1) to afford a mixture of isomers of N-BOC-2-amino-N-{5-[2-cyano-1-(3,5-dimethox-phenyl)-vinyl]-2-methoxy-phenyl}-acetamide (1.2 g, 89%): $^1$H NMR (CDCl$_3$) δ 8.52-8.36 (m, 2H), 7.27-6.83 (m, 2H), 6.53-6.41 (m, 3H), 5.64 (5.70) (s, 1H), 5.20 (b, 1H), 3.95-3.90 (m, 5H), 3.75 (3.79) (s, 6H), 1.48 (s, 9H).

A solution of 2N HCl/ether (5 mL) was added to a stirred solution of N-BOC-2-amino-N-{5-[2-cyano-1-(3,5-dimethoxy-phenyl)-vinyl]-2-methoxy-phenyl}-acetamide (1.2 g, 2.6 mmol) in CH$_2$Cl$_2$ (25 mL). The solution was stirred overnight. Ether (35 mL) was added and the mixture was stirred for 2 h. The slurry was filtered and washed with ether to afford a mixture of isomers of 2-amino-N-{5-[2-cyano-1-(3,5-dimethoxy-phenyl)-vinyl]-2-methoxy-phenyl}-acetamide hydrochloride (0.9 g, 81%) as a white solid: mp 167-169° C.; $^1$H NMR (DMSO-d$_6$) δ 9.94 (9.89) (s, 1H), 8.28 (b, 3H), 8.00 (7.89) (d, J=1 Hz, 1H), 7.39-7.15 (m, 2H), 6.62 (t, J=2 Hz, 1H), 6.48 (d, J=2 Hz, 2H), 6.25 (6.18) (s, 1H), 3.94-3.73 (m, 11H); $^{13}$C NMR (DMSO-d$_6$) δ 165.34, 161.05 (161.11), 160.35 (160.31), 150.62 (151.53), 140.26 (139.04), 128.69 (128.58), 126.30 (126.25), 124.92 (124.32), 122.48 (122.11), 118.22 (118.16), 111.21 (111.57), 106.71 (107.13), 101.96 (101.18), 95.49 (94.20), 55.98 (56.07), 55.39, 40.96 (40.89); Anal Calcd for C$_{20}$H$_{22}$N$_3$O$_4$Cl+0.3H$_2$O: C, 58.69; H, 5.57; N, 10.27; Cl, 8.66. Found: C, 58.43; H, 5.17; N, 10.50; Cl, 8.62.

4.6.2.36 2-Amino-N-{5-[2-cyano-1-(3,5-dimethoxy-phenyl)-vinyl]-2-methoxy-phenyl}-propionamide Hydrochloride (E and Z Isomers)

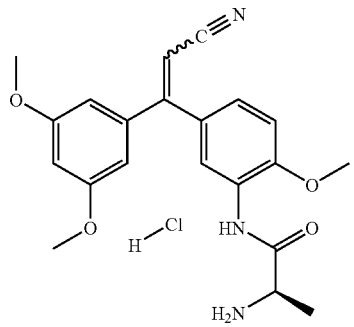

N-BOC-L-Alanine (0.7 g, 3.9 mmol) was added to a stirred solution of 3-(3-amino-4-methoxy-phenyl)-3-(3,5-dimethoxy-phenyl)-acrylonitrile (1.0 g, 3.2 mmol), dicyclohexylcarbodiimide (0.8 g, 3.9 mmol) and 1-hydroxybenzotriazole (0.7 g, 4.8 mmol) in DMF (15 mL). The mixture was stirred at room temperature for 2 days. Ethyl acetate (20 mL) and the mixture was filtered. The filtrate was diluted with EtOAc (50 mL) and washed with water (3×30 mL), brine (2×30 mL) and dried (MgSO$_4$). Solvent was removed and the residue was purified by flash chromatography (Silica gel, CH$_2$Cl$_2$:EtOAc 9:1) to afford a mixture of isomers of N-BOC-2-amino-N-{5-[2-cyano-1-(3,5-dimethoxy-phenyl)-vinyl]-2-methoxy-phenyl}-propionamide (1.2 g, 79%): $^1$H NMR (CDCl$_3$) δ 8.56-8.52 (m, 1H), 8.39 (s, 1H), 7.32-6.82 (m, 2H), 6.53-6.42 (m, 3H), 5.64 (5.71) (s, 1H), 5.00 (b, 1H), 4.32 (b, 1H), 3.93 (3.90) (s, 3H), 3.73 (3.79) (s, 6H), 1.47 (s, 9H), 1.43 (d, J=6 Hz, 3H).

A solution of 2N HCl/ether (5.0 mL) was added to a stirred solution of N-BOC-N-{5-[2-cyano-1-(3,5-dimethoxy-phenyl)-vinyl]-2-methoxy-phenyl}-propionamide (1.2 g, 2.5 mmol) in CH$_2$Cl$_2$ (20 mL). The mixture was stirred at room temperature for 2 days. Ether (30 mL) was added and the mixture was stirred for 2 h. The slurry was filtered and was washed with ether to afford a mixture of isomers of 2-amino-N-{5-[2-cyano-1-(3,5-dimethoxy-phenyl)-vinyl]-2-methoxy-phenyl}-propionamide hydrochloride (0.8 g, 80%) as a white solid: mp 231-233° C.; $^1$H NMR (DMSO-d$_6$) δ 9.97 (9.92) (s, 1H), 8.40 (b, 3H), 7.91 (7.86) (d, J=2 Hz, 1H), 7.38-7.15 (m, 2H), 6.64 (t, J=2 Hz, 1H), 6.48 (d, J=2 Hz, 2H), 6.26 (6.19) (s, 1H), 4.25-4.16 (q, J=6 Hz, 1H), 3.94 (3.90) (s, 3H), 3.76 (3.74) (s, 6H), 1.42 (1.40) (d, J=6 Hz, 3H); $^{13}$C NMR (DMSO-d$_6$) δ 168.85, 160.99, 160.36 (160.32), 151.12 (151.89), 140.21 (139.01), 128.65 (129.55), 126.22 (126.25), 125.33 (126.13), 123.08 (122.54), 118.20 (118.16), 111.28 (111.60), 106.70 (107.16), 102.00 (101.22), 95.56 (94.23), 56.12 (56.03), 55.39, 48.60 (53.67), 17.40; Anal Calcd for C$_{21}$H$_{24}$N$_3$O$_4$Cl+0.2H$_2$O: C, 59.84; H, 5.83; N, 9.97; Cl, 8.41. Found: C, 59.54; H, 5.62; N, 10.37; Cl 8.41.

4.6.2.37 3-(4-Amino-3-methoxy-phenyl)-3-(3,4,5-trimethoxy-phenyl)-acrylonitrile (E and Z Isomers)

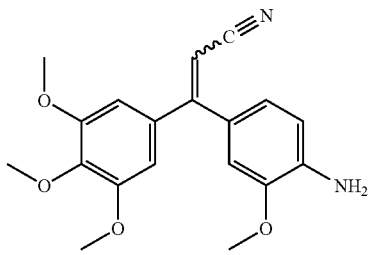

(3-Methoxy-4-nitro-phenyl)-(3,4,5-trimethoxy-phenyl)-methanol was prepared analogously to (4-methoxy-3-nitrophenyl)-(3,4,5-trimethoxy-phenyl)-methanol using 3,4,5-trimethoxy-bromobenzene (3.0 g, 12.1 mmol), magnesium turnings (1.0 g, 24.3 mmol) and 3-methoxy-4-nitro-benzaldehyde (1.8 g, 10.1 mmol). The crude product was purified by flash chromatography (silica gel, Hexane:EtOAc 7:3) to afford (3-methoxy-4-nitro-phenyl)-(3,4,5-trimethoxy-phenyl)-methanol (2.1 g, 60%): $^1$H NMR (CDCl$_3$) δ 7.82 (d, J=8 Hz, 1H), 7.23 (s, 1H), 6.97 (d, J=8 Hz, 1H), 6.54 (s, 2H), 5.76 (s, 1H), 4.76 (s, 1H), 3.96 (s, 3H), 3.85 (s, 9H).

A suspension of (3-methoxy-4-nitro-phenyl)-(3,4,5-trimethoxy-phenyl)-methanol (2.1 g, 6.1 mmol) and MnO$_2$ (6.0 g, 69 mmol) in CH$_2$Cl$_2$ (100 mL) was stirred at room temperature for 2 days. The mixture was filtered through Celite and the filtrate was concentrated. The crude product was purified by flash chromatography (silica gel, Hexane:EtOAc 7:3) to afford (3-methoxy-4-nitro-phenyl)-(3,4,5-trimethoxy-phenyl)-methanone (1.0 g, 48%): $^1$H NMR (CDCl$_3$) δ 7.90 (d, J=8 Hz, 1H), 7.50 (d, J=0 Hz, 1H), 7.37 (d, J=6 Hz, 1H), 7.05 (s, 2H), 4.02 (s, 3H), 3.96 (s, 3H), 3.88 (s, 6H).

3-(3-Methoxy-4-nitro-phenyl)-3-(3,4,5-trimethoxy-phenyl)-acrylonitrile (E and Z isomers) were prepared analogously to 3-(4-methoxy-3-nitro-phenyl)-3-(3,4-dimethoxyphenyl)-acrylonitrile using (3-methoxy-4-nitro-phenyl)-(3,4,5-trimethoxy-phenyl)-methanone (1.2 g, 3.5 mmol), lithium bis(trimethylsilyl)amide (3.9 ml, 3.9 mmol) and diethyl cyanomethylphosphate (0.7 g, 3.9 mmol). The crude product was purified by flash chromatography (silica gel, CH$_2$Cl$_2$) to afford mixture isomers of 3-(3-methoxy-4-nitro-phenyl)-3-(3,4,5-trimethoxy-phenyl)-acrylonitrile (0.9 g, 70%): $^1$H NMR (CDCl$_3$) δ 7.93 (dd, J=8.4 and 6 Hz, 1H), 7.06-6.96 (m, 2H), 6.65 (s, 1H), 6.46 (s, 2H), 5.80(5.71) (s, 1H), 4.00-3.81 (m, 12H).

A suspension of 3-(3-methoxy-4-nitro-phenyl)-3-(3,4,5-trimethoxy-phenyl)-acrylonitrile (0.9 g, 2.4 mmol) and tin chloride dihydrate (4.0 g, 17.7 mmol) in ethanol (25 mL) was heated at 70° C. for 1 h. The mixture was cooled and poured into ice (200 mL). The pH was made strongly alkaline by the addition of 10N NaOH. The mixture was extracted with EtOAc (5×50 mL) and the combined organic extracts were washed with water (40 mL), brine (40 mL), and dried (MgSO$_4$). Solvent was removed and the residue was purified by flash chromatography (silica gel, Hexane:EtOAc 1:13 to afford mixture isomers of 3-(4-amino-3-methoxy-phenyl)-3-(3,4,5-trimethoxy-phenyl)-acrylonitrile (0.4 g, 42%) as a yellow solid: mp 123-125° C.; $^1$H NMR (CDCl$_3$) δ 7.05-6.53 (m, 5H), 5.56(5.43) (s, 1H), 4.12 (s, 2H), 3.91-3.81 (m, 12H); $^{13}$C NMR (CDCl$_3$) δ 163.19, 163.09, 152.99, 152.93, 146.63, 139.82, 138.74, 135.43, 132.66, 128.33, 126.35, 124.12, 118.96, 113.76, 113.74, 111.99, 110.22, 107.35, 106.42, 91.14, 90.52, 60.94, 56.28, 56.25, 55.74, 55.59; Anal Calcd for C$_{19}$H$_{20}$N$_2$O$_4$: C, 67.05; H, 5.92; N, 8.23. Found: c, 66.92; H, 5.76; N, 8.10.

4.6.2.38 3,3-Bis-(3,4,5-trimethoxy-phenyl)-acrylonitrile

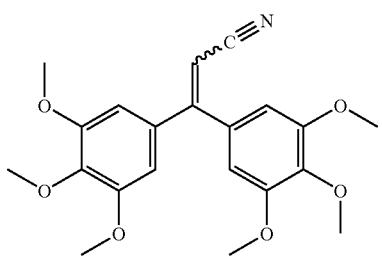

Bis-(3,4,5-trimethoxy-phenyl)-methanone (0.32 g, 0.88 mmol), cyanomethylphosphonic acid diethyl ester (0.28 ml, 0.31 mmol) in anhydrous THF (20 ml), and potassium bis(trimethylsilyl)amide (0.35 g, 1.8 mmol) were treated in the same manner as described above for the synthesis of 3-(2,3-dihydrobenzo[1,4]dioxin-6-yl)-3-(3,5-dimethoxyphenyl)acrylonitrile. The crude material was purified via flash column chromatography to give 3,3-Bis-(3,4,5-trimethoxy-phenyl)-acrylonitrile as a solid (0.25 g, 74%): mp, 146-148° C.; $^1$HNMR (DMSO-d$_6$) δ 6.69 (d, J=5 Hz, 4H, Ar), 6.32 (s, 1H, CH), 3.77-3.72 (m, 18H, 6OCH$_3$); $^{13}$C NMR (DMSO-d$_6$) δ 161.27, 152.69, 152.61, 139.60, 138.66, 133.06, 131.94, 118.43, 107.09, 106.23, 100.40, 95.21, 60.13, 60.10, 56.08, 56.07; Anal. Calcd. For C$_{21}$H$_{24}$NO$_6$: C, 65.44; H, 6.02; N, 3.63. Found: C, 65.08; H, 5.99; N, 3.45.

4.6.2.39 2-[(3,5-Dimethoxy-phenyl)-(3-methoxy-phenyl)-methylene]-malononitrile

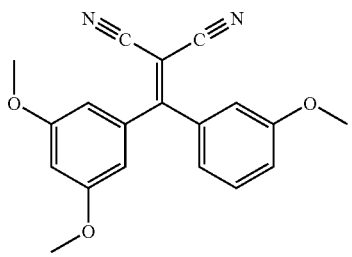

(3,5-dimethoxyphenyl)-(3-methoxyphenyl)methanone (0.31 g, 1.12 mmol), malononitrile (0.08 ml, 1.23 mmol), and aluminum oxide (0.57 g, 5.6 mmol) were mixed and heated in an oil bath at 160° C. overnight. After cooling down to r.t., the brown mixture was extracted with CH$_2$Cl$_2$ (50 ml), filtered through a Celite pad and concentrated to an oil, which was purified via flash column chromatography (5% EtOAc in hexane gradient to 20% EtOAc in hexane in about 40 min.) and lyophilized to give 2-[(3,5-dimethoxy-phenyl)-(3-methoxy-phenyl)-methylene]-malononitrile as a greenish solid (0.12 g, 34%): mp, 100-102° C.; $^1$HNMR (DMSO-d$_6$) δ 7.47 (t, J=8 Hz, 1H, Ar), 7.22 (dd, J=2.36, 8 Hz, 1H, Ar), 7.16 (t, J=1 Hz, 1H, Ar), 6.96 (d, J=7 Hz, 1H, Ar), 6.78 (t, J=2 Hz, 1H, Ar), 6.62 (d, J=2 Hz, 2H, Ar), 3.79 (s, 3H, OCH$_3$), 3.76 (s, 6H, 2OCH₃); ¹³C NMR (DMSO-d₆) δ 173.4, 160.3, 158.9, 137.5, 136.8, 130.1, 122.4, 118.0, 115.3, 114.1, 114.0, 108.1, 103.6, 82.9, 55.6, 55.5; Anal. Calcd. For C₁₉H₁₆N₂O₃: C, 71.24; H, 5.03; N, 8.74. Found: C, 71.10; H, 4.87; N, 8.59.

4.6.2.40 3-(3,5-Dimethoxy-phenyl)-3-(3-hydroxy-phenyl)-acrylonitrile

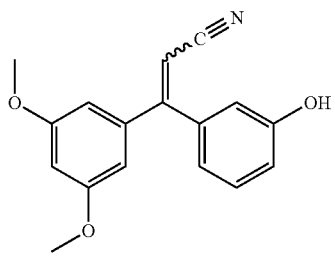

3-(3-Benzyloxyphenyl)-3-(3,5-dimethoxyphenyl)acrylonitrile (3.45 g), 20% palladium hydroxide on charcoal (0.103 g, 3% w.t.), cyclohexene (12 ml), and ethanol (24 ml) were heated to reflux overnight. The black suspension was cooled, filtered through a Celite pad, and concentrated to an oil, which was purified via flash column chromatography (5% EtOAc in hexane gradient to 30% EtOAc in hexane in about 30 min.) to give 3-(3,5-dimethoxy-phenyl)-3-(3-hydroxy-phenyl)-acrylonitrile as an off-white solid (1.66 g, 64%): mp, 127-129° C.; ¹HNMR (DMSO-d₆) δ 9.73 (s, 0.67H, OH of one isomer), 9.65 (s, 0.26H, OH of the other isomer), 7.33-7.23 (m, 1H, Ar), 6.92-6.62 (m, 4H, Ar), 6.46 (d, J=2 Hz, 2H, Ar), 6.32 (s, 0.73H, double bond proton of one isomer), 6.27 (s, 0.27H, double bond proton of the other isomer), 3.77 (s, 1.85H, 2OCH₃ of one isomer), 3.73 (s, 4.29H, 2OCH₃ of the other isomer), isomer ratio 27.6%:72.4%; ³C NMR (DMSO-d₆) δ 161.5, 160.4, 157.4, 157.2, 139.9, 138.7, 138.1, 129.7, 119.7, 118.7, 118.0, 117.5, 116.7, 115.7, 115.0, 107.1, 106.6, 101.8, 101.0, 96.3, 96.0, 55.4; Anal. Calcd. For C₁₇H₁₅NO₃: C, 72.58; H, 5.37; N, 4.98. Found: C, 72.40; H, 5.26; N, 4.85.

4.6.2.41 3-(3,5-Dimethoxy-phenyl)-3-(4-methoxy-phenyl)-acrylonitrile

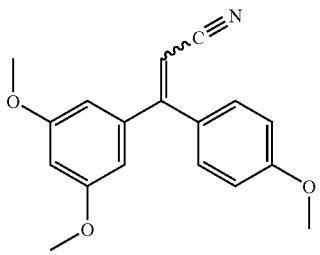

Aluminum chloride (2.20 g, 16.5 mmol) was added to a stirred mixture of anisole (1.63 ml, 15.0 mmol) in anhydrous methylene chloride (20 ml) in an ice bath. Then a solution of 3,5-dimethoxybenzoyl chloride (3.01 g, 15.0 mmol) in anhydrous methylene chloride (10 ml) was added. The mixture was allowed to warm up to rt, then refluxed overnight. After cooling down to rt, the mixture was poured to ice water (50 ml), stirred for 20 min., and extracted with methylene chloride (3-x 50 ml). The combined organic extracts were washed with sat. NaHCO₃ (3×50 ml), H₂O (2×50 ml), brine (50 ml), dried over MgSO₄, filtered and concentrated in vacuo to an oil, which was purified via flash column chromatography (10% EtOAc in hexane) to give (3,5-dimethoxy-phenyl)-(4-methoxy-phenyl)-methanone as a yellow solid (3.11 g, 76%): mp, 90-92° C.; ¹HNMR (CDCl₃) δ 7.85 (d, J=8.0 Hz, 2H, Ar), 6.96 (d, J=9.0 Hz, 2H, Ar), 6.88 (d, J=2.3 Hz, 2H, Ar), 6.65 (d, J=2.4 Hz, 1H, Ar), 3.89 (s, 3H, OCH₃), 3.83 (s, 6H, 2OCH₃). The product was carried over to the next step.

To a stirred solution of cyanomethylphosphonic acid diethyl ester (2.15 ml, 13.66 mmol) in anhydrous THF (10 ml) in an ice bath was added lithium bis(trimethylsilyl)amide (1.0 M solution in THF, 13.66 ml, 13.66 mmol) slowly. The mixture was stirred in rt for 40 min. To the mixture, a solution of (3,5-dimethoxyphenyl)-(4-methoxyphenyl)methanone (5193-23-B, 1.86 g, 6.83 mmol) in anhydrous THF (20 ml) was added. The mixture was refluxed overnight. The solution was poured into ice water (20 ml) and the two phases were separated. The THF phase was evaporated and combined with the aqueous phase, which were then extracted with CH₂Cl₂ (2×40 ml), washed with water (50 ml), dried over MgSO₄, filtered and concentrated in vacuo to an oil, which was purified via flash column chromatography (20% EtOAc in hexane) to give 3-(3,5-Dimethoxy-phenyl)-3-(4-methoxy-phenyl)-acrylonitrile as a yellow oil which was solidified slowly (1.97 g, 98%): mp, 79-81° C.; ¹HNMR (DMSO-d₆) δ 7.35-7.31 (m, 2H, Ar), 7.07-6.96 (m, 2H, Ar), 6.65-6.62 (m, 1H, Ar), 6.46-6.44 (m, 2H, Ar), 6.23 (s, 0.43H, double bond H of one isomer), 6.20 (s, 0.58H, double bond H of the other isomer), 3.82-3.68 (multiple singlets, 9H, OCH₃); ¹³C NMR (CDCl₃) δ 162.8, 162.6, 161.7, 161.3, 160.9, 160.8, 141.7, 139.2, 131.5, 131.0, 130.1, 129.3, 118.4, 118.2, 114.2, 114.0, 107.8, 107.2, 102.2, 102.1, 93.8, 93.0, 55.6, 55.5, 55.5; Anal. Calcd. for C₁₈H₁₇NO₃+0.05H₂O: C, 72.92; H, 5.89; N, 4.65. Found: C, 72.90; H, 5.52; N, 4.67.

4.6.2.42 3,3-Bis-(4-methoxy-phenyl)-acrylonitrile

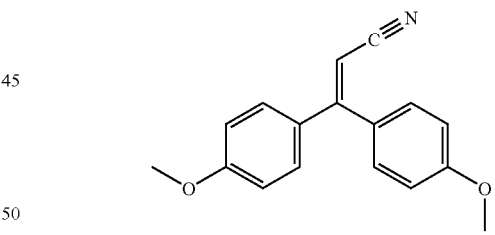

Bis-(4-methoxy-phenyl)-methanone (2.42 g, 10 mmol), cyano-methylphosphonic acid diethyl ester (1.6 ml, 10 mmol) in anhydrous THF (10 ml), and sodium hydride (0.48 g, 10 mmol) were treated in the same manner as described above for the synthesis of 3-(2,3-dihydrobenzo[1,4]dioxin-6-yl)-3-(3,5-dimethoxyphenyl)acrylonitrile. The crude material was purified by flash column chromatography to give 3,3-bis-(4-methoxy-phenyl)-acrylonitrile as a solid (1.84 g, 69%): ¹HNMR (CDCl₃) δ 7.39 (d, J=8.7 Hz, 1H, Ar), 7.25 (d, J=8.7 Hz, 1H, Ar), 6.95 (d, j=8.7 Hz, 1H, Ar), 6.88 (d, J=8.7 Hz, 1H, Ar), 5.54 (s, 1H, CH), 3.86, 3.83 (2s, 6H, CH₃); ¹³C NMR (CDCl₃) δ 162.3, 161.4, 160.9, 131.7, 131.3, 130.1, 129.5, 118.7, 113.9, 113.8, 91.5, 55.4, 55.3; Anal. Calcd. For C₁₇H₁₅NO₂: C, 76.94; H, 5.70; N, 5.27. Found: C, 76.83; H, 5.64; N, 5.17.

4.6.2.43 N-{4-[2-Cyano-1-(3-ethoxy-4-methoxy-phenyl)-vinyl]-phenyl}acetamide

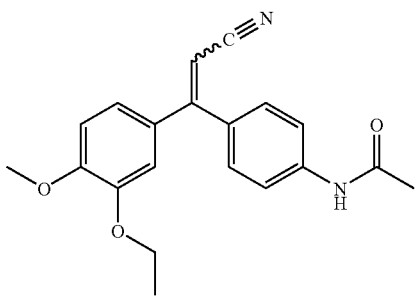

A mixture of 3-(3-ethoxy-4-methoxy-phenyl)-acrylonitrile (0.7 g, 3.2 mmol), N-(4-iodo-phenyl)-acetamide (1.4 g, 5.4 mmol), NaHCO$_3$ (1.1 g, 12.8 mmol), Bu$_4$NBr (1.2 g, 3.6 mmol) and Pd(OAc)$_2$ (0.04 g, 0.2 mmol) in DMF (15 mL) was heated at 70° C. for 2 days. The cooled mixture was poured into water (150 mL) and was extracted with EtOAc (3×50 mL). The combined organic extracts were washed with water (2×50 mL), brine (50 mL) and dried (MgSO$_4$). Solvent was removed and the residue was purified by flash chromatography (silica gel, CH$_2$Cl$_2$:EtOAc 9:1) to afford N-{4-[2-cyano-1-(3-ethoxy-4-methoxy-phenyl)-vinyl]-phenyl}acetamide (0.4 g, 32%): mp 175-177° C.; $^1$H NMR (CDCl$_3$) δ 7.51(d, J=8 Hz, 2H), 7.41 (s, 1H), 7.26 (d, J=9.0 Hz, 2H), 7.02-6.89 (m, 3H), 5.57 (s, 1H), 4.11-4.03 (q, J=7 Hz, 2H), 3.92 (s, 3H), 2.19 (s, 3H), 1.44 (t, J=7 Hz, 3H); $^{13}$C NMR (CDCl$_3$) δ 168.38, 162.14, 150.93, 147.96, 139.91, 134.84, 129.58, 129.30, 123.08, 119.34, 118.53, 114.06, 111.01, 92.49, 64.53, 55.96, 24.65, 14.66; Anal Calcd for C$_{20}$H$_{20}$N$_2$O$_3$: C, 71.46; H, 5.99; N, 8.33. Found: C, 71.46, 6.01; N, 8.25.

4.6.2.44 N-{5-[2-Cyano-1-(3-ethoxy-4-methoxy-phenyl)-vinyl]-2-methoxy-phenyl}-acetamide (E and Z Isomers)

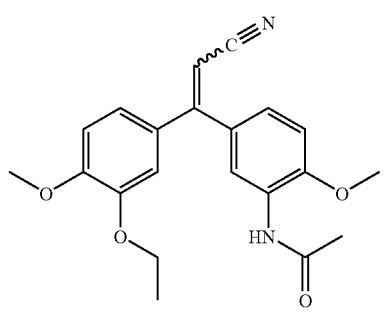

N-{5-[2-Cyano-1-(3-ethoxy-4-methoxy-phenyl)-vinyl]-2-methoxy-phenyl}-acetamide (E and Z isomers) were prepared analogously to N-{5-[2-cyano-1-(3,4-dimethoxy-phenyl)-vinyl]-2-methoxy-phenyl}-acetamide using 3-(3-amino-4-methoxy-phenyl)-3-(3-ethoxy-4-methoxy-phenyl)-acrylonitrile (0.4 g, 1.1 mmol) and acetyl chloride (1.1 mL). The crude product was slurried with hexane to give N-{5-[2-cyano-1-(3-ethoxy-4-methoxy-phenyl)-vinyl]-2-methoxy-phenyl}-acetamide (0.2 g, 41%) as a white solid: mp 155-157° C.; $^1$H NMR (CDCl$_3$) δ 9.25 (d, J=2 Hz, 1H), 7.90 (d, 13.5 Hz, 1H), 7.17-6.90 (m, 3H), 6.75 (d, J=1 Hz, 1H), 6.13 (s, 1H), 5.97 (s, 1H), 4.02-3.97 (m, 2H), 3.94-3.97 (m, 6H), 2.07 (d, J=7 Hz, 3H), 1.70 (t, 3H); $^{13}$C NMR (CDCl$_3$) δ 161.29, 151.18, 150.02, 147.76, 147.32, 130.47, 130.23, 129.18, 128.91, 127.26, 127.22, 122.40, 122.18, 118.77, 118.70, 113.81, 122.20, 111.43, 111.34, 111.04, 110.77, 92.73, 92.45, 63.76, 63.71, 55.87, 55.41, 23.80, 23.68, 14.57; Anal Calcd for C$_{21}$H$_{22}$N$_2$O$_4$: C, 68.84; H, 6.05; N, 7.65. Found: C, 68.94, 5.93; N, 7.53.

4.6.2.45 3-(3-Ethoxy-4-methoxy-phenyl)-3-(4-methoxy-3-pyrrol-1-Yl-phenyl)-acrylonitrile (E and Z Isomers)

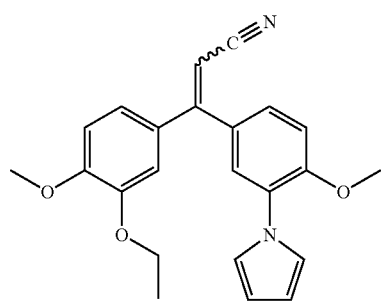

2,5-Dimethoxytetrahydrofuran (0.2 g, 1.7 mmol) was added to a stirred solution of 3-(3-amino-4-methoxy-phenyl)-3-(3-ethoxy-4-methoxy-phenyl)-acrylonitrile (0.5 g, 1.5 mmol) in acetic acid (10 mL). The reaction mixture was heated to reflux under nitrogen for one hour. The mixture was cooled down to room temperature. The mixture was stirred with EtOAc (100 mL) and saturated NaHCO$_3$ (40 mL) was added slowly. The EtOAc solution was washed with water (60 mL), brine (60 mL) and dried (MgSO$_4$). Solvent was removed and the residue was purified by flash chromatography (silica gel, Hexane:EtOAc 6:4) to afford mixture of isomers of 3-(3-ethoxy-4-methoxy-phenyl)-3-(4-methoxy-3-pyrrol-1-yl-phenyl)-acronitrile (0.4 g, 60%) as a white solid: mp 109-111° C.; $^1$H NMR (CDCl$_3$) δ 7.00 (m, 2H), 7.47-6.81 (m, 6H), 6.30 (m, 2H), 5.59 (5.57) (s, 1H), 4.05 (m, 2H), 3.91 (m, 6H), 1.45 (m, 3H); $^{13}$C NMR (CDCl$_3$) δ 161.67(161.61), 153.93 (154.35), 151.56(151.00), 148.27(148.00), 131.40(132.10), 129.83(130.06), 129.03(127.16), 125.93(127.93), 123.07, 122.21, 122.05(121.93), 118.52(118.43), 114.00, 112.01(112.06), 111.09(112.70), 109.15(109.28), 92.45, 64.56, 56.05(56.00), 14.69; Anal. Calcd for C$_{23}$H$_{22}$N$_2$O$_3$. Theoretical: C, 73.78; H, 5.92, N, 7.48. Found: C, 73.46; H, 5.71; N, 7.35.

4.6.2.46 2-Amino-N-{5-[2-cyano-1-(3-ethoxy-4-methoxy-phenyl)-vinyl]-2-methoxy-phenyl}-propionamide Hydrochloride (E and Z Isomers)

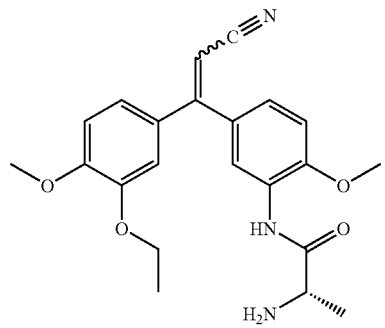

N-BOC-L-Alanine (1.1 g, 5.6 mmol) was added to a stirred solution of 3-(3-amino-4-methoxy-phenyl)-3-(3-ethoxy-4-methoxy-phenyl)-acrylonitrile (1.5 g, 4.6 mmol), dicyclohexyl carbodiimide (1.1 g, 5.6 mmol) and 1-hydroxybenzotriazole (0.9 g, 6.9 mmol) in DMF (30 mL). The mixture was stirred at room temperature for one day. Ethyl acetate (40 mL) was added and the mixture was filtered. The filtrate was diluted with ethyl acetate (50 mL) and washed with water (3×30 mL), brine (2×30 mL) and dried (MgSO$_4$). Solvent was removed and the residue was purified by flash chromatography (silica gel, CH$_2$Cl$_2$:EtOAc 9:1) to afford a mixture of isomers of N-BOC-2-amino-N-{5-[2-cyano-1-(3-ethoxy-4-methoxy-phenyl)-vinyl]-2-methoxy-phenyl}-propionamide (2.3 g, 98%): $^1$H NMR (CDCl$_3$) δ 8.52 (d, 1H), 8.37-7.23 (m, 6H), 5.58 (d, 1H), 5.00 (b, 1H), 4.33 (b, 1H), 4.04 (m, 2H), 3.91 (q, 6H), 1.40-1.47 (m, 15H).

A solution of 2N HCl/ether (8.8 mL) was added to a stirred solution of N-BOC-2-amino-N-{5-[2-cyano-1-(3-ethoxy-4-methoxy-phenyl)-vinyl]-2-methoxy-phenyl}-propionamide (2.1 g, 4.4 mmol) in CH$_2$Cl$_2$ (50 mL). The mixture was stirred at room temperature for 2 days. Ether (90 mL) was added and the mixture was stirred for 2 hours. The slurry was filtered and was washed with ether to afford a mixture of isomers of 2-amino-N-{5-[2-cyano-1-(3 ethoxy-4-methoxy-phenyl)-vinyl]-2-methoxy-phenyl}-propionamide hydrochloride (1.4 g, 74%) as a white solid: mp 207-209° C.; $^1$H NMR (DMSO-d$_6$) δ 9.94(9.90) (s, 1H), 8.31 (b, 1H), 7.92-6.75 (m, 6H), 6.16(6.02) (s, 1H), 4.19 (m, 1H), 3.99 (m, 2H), 3.94(3.91) (s, 3H), 3.79(3.83) (s, 3H), 1.41 (d, 3H), 1.31 (t, 3H); $^{13}$C NMR (DMSO-d$_6$) δ 168.81 161.04(161.31), 151.86(150.18), 151.06(150.94), 147.80(147.36), 130.48(130.43), 129.07(129.19), 126.61(125.64), 126.11, 123.09(122.88), 122.23(122.40), 118.69(118.75), 112.25(113.78), 114.48(111.55), 111.36(111.26), 93.02(92.85), 63.81(63.76), 56.04(56.13), 55.59(55.52), 48.62, 17.42, 14.62(14.59); Anal. Calcd for C$_{22}$H$_{26}$N$_3$O$_4$Cl+0.03H$_2$O; Theoretical: C, 61.10; H, 6.07; N, 9.72; Cl, 8.20. Found: C, 60.75; H, 5.84; N, 9.51; Cl, 8.33.

4.6.2.47 3-(3,5-Dimethoxy-phenyl)-3-(3-methoxy-phenyl)-acrylonitrile

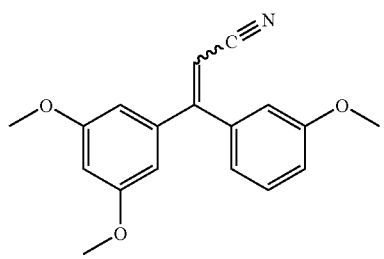

A solution of 1-bromo-3-methoxybenzene (2.48 g, 13.24 mmol) in anhydrous THF (10 ml) was cooled to −78° C., evacuated and refilled with nitrogen for ten cycles. To this clear solution was slowly added n-butyl lithium (5.30 ml, 13.24 mmol) and stirred for 30 min. Then a solution of 3,5-dimethoxybenzaldehyde (2.00 g, 12.04 mmol) in anhydrous THF (10 ml) was added via a syringe. The mixture was stirred at −78° C. under nitrogen for 4 h then quenched with 2-propanol (2.1 ml, 27 mmol) and stirred overnight. To the orange colored mixture was added 30 ml of water and extracted with ether (3×60 ml). The combined ether extracts was washed with water (2×60 ml), dried over MgSO$_4$, filtered and concentrated in vacuo to an oil, which was purified via flash column chromatography to give (3,5-dimethoxy-phenyl)-(3-methoxy-phenyl)-methanol as an off-white oil (2.69 g, 82%), HPLC purity was 98.3% at 2.81 min. (50/50 ACN/0.1% H$_3$PO$_4$): $^1$HNMR (CDCl$_3$) δ 7.26-7.29 (m, 1H, Ar), 6.95-6.92 (m, 2H, Ar), 6.81-6.77 (m, 1H, Ar), 6.53 (d, J=2 Hz, 2H, Ar), 6.34 (t, J=2 Hz, 1H), 5.68 (d, J=3 Hz, 1H, CH), 3.77 (s, 3H, single OCH$_3$ group), 3.74 (s, 6H, 2OCH$_3$ groups), 2.45 (d, J=3 Hz, 1H, OH). The product was carried over to the next step.

To a stirred solution of (3,5-dimethoxyphenyl)-(3-methoxyphenyl)methanol (2.47 g, 9.0 mmol) in CH$_2$Cl$_2$ (20 ml) at rt was added activated MnO$_2$ powder (3.91 g, 45 mmol) and kept adding 2~3 equivalents of MnO$_2$ every 3~5 h until HPLC showed at least 98% conversion occurred. The black suspension was filtered through a Celite pad, concentrated in vacuo to give (3,5-dimethoxy-phenyl)-(3-methoxy-phenyl)methanone was an oil (2.35 g, 92%): $^1$HNMR (CDCl$_3$) δ 7.38-7.35 (m, 3H, Ar), 7.15-7.13 (m, 1H, Ar), 6.93 (d, J=2 Hz, 2H, Ar), 6.67 (t, J=2 Hz, 1H, Ar), 3.86 (s, 3H, single OCH$_3$ group), 3.83 (s, 6H, 2OCH$_3$), 0.99 (s, 9H, 3OCH$_3$). The product was carried over to the next step.

To a stirred solution of cyanomethylphosphonic acid diethyl ester (1.18 ml, 7.49 mmol) in anhydrous THF (10 ml) in an ice bath was added lithium bis(trimethylsilyl)amide (1.0 M solution in THF, 7.49 ml, 7.49 mmol) slowly. The mixture was stirred in rt for 40 min, before a solution of (3,5-dimethoxyphenyl)-(3-methoxyphenyl)methanone (1.02 g, 3.75 mmol) in anhydrous THF (20 ml) was added. The mixture was refluxed overnight. The solution was poured into ice water (20 ml) and the two phases were separated. The THF phase was evaporated and combined with the aqueous phase, which were then extracted with CH$_2$Cl$_2$ (2×40 ml), washed with water (50 ml), dried over MgSO$_4$, filtered and concentrated in vacuo to an oil, which was purified via flash column chromatography to give 3-(3,5-dimethoxy-phenyl)-3-(3-methoxy-phenyl)-acrylonitrile as an off-white solid (1.06 g, 96%): mp, 81-83° C.; $^1$HNMR (DMSO-d$_6$) δ 7.46-7.30 (m, 2H, Ar), 7.11-6.85 (m, 6H, Ar), 6.66-6.62 (m, 2H, Ar), 6.47 (t, J=1 Hz, 4H, Ar), 6.39 (s, 1H, double bond proton of one isomer), 6.38 (s, 1H, double bond proton of the other isomer), 3.78-3.73 (multiple singlets, 18H, 6OCH$_3$), isomer ratio based on $^1$HNMR close to 48%:52%; $^{13}$C NMR (CDCl$_3$) δ 163.0, 163.0, 160.9, 160.8, 159.8, 159.6, 141.0, 140.1, 138.8, 138.2, 129.8, 129.7, 122.1, 121.0, 117.8, 117.8, 116.1, 115.9, 115.0, 114.3, 107.8, 107.0, 102.3, 122.1, 122.1, 121.0, 117.8, 117.8, 116.1, 115.9, 115.0, 114.3, 107.8, 107.0, 102.3, 102.2, 95.4, 95.4, 55.6, 55.6, 55.5; Anal. Calcd. For C$_{18}$H$_{17}$NO$_3$: C, 73.20; H, 5.80; N, 4.74. Found: C, 73.10; H, 5.72; N, 4.68.

4.6.2.48 3-(3,4-Dimethoxy-phenyl)-3-(4-methoxy-phenyl)-acrylonitrile

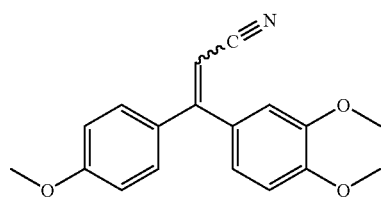

Aluminum chloride (2.15 g, 16.12 mmol) was added to a stirred mixture of 1,2-dimethoxybenzene (2.03 g, 14.65 mmol) in anhydrous methylene chloride (20 ml) in an ice bath. Then a solution of 4-methoxybenzoyl chloride (2.50 g, 14.65 mmol) in anhydrous methylene chloride (50 ml) was added. The mixture was allowed to warm up to rt. then refluxed overnight. After cooling down to rt, the mixture was poured to ice water (50 ml), stirred for 20 min., and extracted with methylene chloride (3×50 ml). The combined organic extracts were washed with sat. NaHCO₃ (3×50 ml), H₂O (2×50 ml), brine (50 ml), dried over MgSO₄, filtered and concentrated in vacuo to an oil, which was purified via flash column chromatography (10% EtOAc in hexane) to give (3,4-dimethoxy-phenyl)-(4-methoxy-phenyl)methanone as an off-white solid (3.66 g, 92%): ¹HNMR (CDCl₃) δ 7.80 (d, J=8 Hz, 2H, Ar), 7.44 (d, J=1 Hz, 12H, Ar), 7.37 (dd, J=1 Hz and 8 Hz, 1H, Ar), 6.97 (d, J=8 Hz, 2H, Ar), 6.90 (d, J=8 Hz, 1H), 3.96 (s, 3H, OCH₃), 3.94 (s, 3H, OCH₃), 3.89 (s, 3H, OCH₃). The product was carried over to the next step.

(3,4-dimethoxyphenyl)-(4-methoxyphenyl)methanone (2.00 g, 7.35 mmol), cyanomethylphosphonic acid diethyl ester (2.31 ml, 14.69 mmol) in anhydrous THF (10 ml), and lithium bis(trimethylsilyl)amide (1.0 M solution in THF, 14.69 ml, 14.69 mmol) were treated in the same manner as described above for the synthesis of 3-(3,5-dimethoxy-phenyl)-3-(3-methoxy-phenyl)-acrylonitrile. The crude was purified via flash column chromatography (5% EtOAc in hexane gradient to 30% EtOAc in hexane in about 40 min.) to give 3-(3,4-dimethoxy-phenyl)-3-(4-methoxy-phenyl)-acrylonitrile as a pink oil (2.08 g, 96%): ¹HNMR (DMSO-d₆) δ 7.34-6.7 (m, 7H, Ar), 6.14 (s, 0.50H, double bond proton of one isomer), 6.08 (s, 0.45H, double bond proton of the other isomer), 3.83-3.73 (multiple singlets, 9H, 3OCH₃); ¹³C NMR (CDCl₃) δ 162.6, 162.5, 161.6, 161.2, 151.2, 150.7, 149.0, 148.8, 132.2, 131.7, 131.5, 130.3, 129.8, 129.5, 123.2, 122.3, 118.8, 118.8, 114.1, 114.0, 112.9, 111.5, 110.9, 91.9, 91.8, 56.2, 56.1, 56.1, 55.5, 55.5; Anal. Calcd. For C₁₈H₁₇NO₃: C, 71.92; H, 6.19; N, 4.32 (+0.04H₂O). Found: C, 71.95; H, 6.04; N, 4.54.

4.6.2.49 3-(3,5-Dimethoxy-phenyl)-3-(3-ethoxy-4-methoxy-phenyl)-acrylonitrile

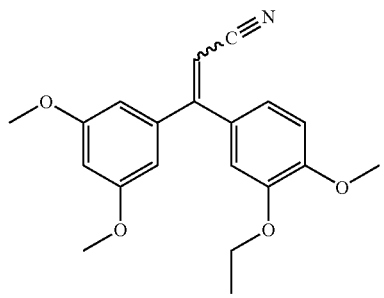

To a solution of 5-bromo-2-methoxyphenol (0.86 g, 4.24 mmol) in DMF (20 ml) was added iodoethane (0.68 ml, 8.47 mmol), and Na₂CO₃ (0.90 g, 8.47 mmol) at rt. The white suspension was stirred at 50° C. overnight. Water (100 ml) and EtOAc (100 ml) were poured into the mixture. The two phases were separated and the aqueous was extracted with EtOAc (2×50 ml). The combined organic phases were washed with water (100 ml), dried over MgSO₄ and concentrated to a clear oil, which quickly solidified to 4-bromo-2-ethoxy-1-methoxy-benzene as an off-white solid (0.68 g, 69%): ¹HNMR (CDCl₃) δ 7.04-6.97 (m, 2H, Ar), 6.74 (d, J=8 Hz, 1H, Ar), 4.07 (q, J=7 Hz, 2H, CH₂CH₃), 3.85 (s, 3H, OCH₃), 1.47 (t, J=7 Hz, 3H, CH₂CH₃). The product was carried over to the next step.

4-bromo-2-ethoxy-1-methoxybenzene (0.66 g, 2.86 mmol), n-butyl lithium (1.14 ml, 2.86 mmol), and 3,5-dimethoxybenzaldehyde (0.43 g, 2.60 mmol) were treated in the same manner as described above for the synthesis of 3-(3,5-dimethoxy-phenyl)-3-(3-methoxy-phenyl)-acryloni- trile. The crude was purified via flash column chromatography (20% EtOAc in hexane gradient to 50% EtOAc in hexane in about 40 min.) to give (3,5-dimethoxy-phenyl)-(3-ethoxy-4-methoxy-phenyl)-methanol as an off-white solid (0.66 g, 80%): ¹HNMR (CDCl₃) δ 6.92-6.80 (m, 3H, Ar), 6.54 (d, J=2 Hz, 2H, Ar), 6.36 (t, J=2 Hz, 1H, Ar), 5.70 (d, J=3 Hz, 1H, CHOH), 4.07 (q, J=6 Hz, 2H, CH₂CH₃), 3.85 (s, 3H, OCH₃), 3.76 (s, 6H, 2OCH₃), 2.19 (d, J=3 Hz, 1H, OH), 1.44 (t, J=7 Hz, 3H, CH₂CH₃). The product was carried over to the next step.

(3,5-dimethoxyphenyl)-(3-ethoxy-4-methoxyphenyl) methanol (0.65 g, 2.04 mmol) and activated MnO₂ powder (1.4 g, 16 mmol) were treated in the same manner as described above for the synthesis of 3-(3,5-dimethoxy-phenyl)-3-(3-methoxy-phenyl)-acrylonitrile. The product (3,5-dimethoxyphenyl)-(3-ethoxy-4-methoxy-phenyl)-methanone was an oil (0.65 g, 100%): ¹HNMR (CDCl₃) δ 7.49-7.39 (m, 2H, Ar), 6.91-6.87 (m, 3H, Ar), 6.65 (t, J=2 Hz, 1H, Ar), 4.17 (q, J=6 Hz, 2H, CH₂CH₃), 3.95 (s, 3H, single OCH₃ group), 3.83 (s, 6H, 2OCH₃), 1.50 (t, J=6 Hz, 3H, CH₂CH₃). The product was carried over to the next step.

(3,5-Dimethoxyphenyl)-(3-ethoxy-4-methoxyphenyl) methanone (0.63 g, 2.00 mmol), cyanomethylphosphonic acid diethyl ester (0.63 ml, 3.98 mmol) in anhydrous THF (10 ml), and lithium bis(trimethylsilyl)amide (1.0 M solution in THF, 3.98 ml, 3.98 mmol) were treated in the same manner as described above for the synthesis of 3-(3,5-dimethoxy-phenyl)-3-(3-methoxy-phenyl)-acrylonitrile. The crude was purified via flash column chromatography (5% EtOAc in hexane gradient to 40% EtOAc in hexane in about 40-min.) to give 3-(3,5-dimethoxy-phenyl)-3-(3-ethoxy-4-methoxy-phenyl)-acrylonitrile as an off-white solid (0.60 g, 89%): mp, 110-112° C.; ¹HNMR (CDCl₃) δ 7.04-6.82 (m, 3H, Ar), 6.55-6.43 (m, 3H, Ar), 5.65 (s, 0.50H, double bond proton of one isomer), 5.43 (s, 0.5H, double bond proton of the other isomer), 4.13-3.99 (m, 2H, CH₂CH₃ from the two isomers), 3.92 & 3.90 (s, 3H, single OCH₃ group from the two isomers), 3.80 & 3.77 (s, 6H, 2OCH₃ from the two isomers), 1.49-1.41 (two triplets, 3H, CH₂CH₃ from the two isomers); ¹³C NMR (CDCl₃) δ 162.9, 162.8, 160.9, 160.8, 151.7, 151.1, 148.3, 148.0, 141.6, 139.1, 131.2, 129.3, 123.3, 122.2, 118.2, 114.2, 112.7, 111.2, 111.1, 107.8, 107.2, 102.3, 102.2, 93.8, 93.2, 64.7, 56.2, 56.1, 55.7, 14.8; Anal. Calcd. For C₂₀H₂₁NO₄: C, 70.78; H, 6.24; N, 4.13. Found: C, 70.62; H, 6.25; N, 4.01.

4.6.2.50 (3,4-Dimethoxy-phenyl)-3-(3-methoxy-phenyl)-acrylonitrile

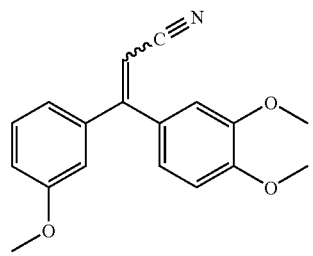

3-methoxybenzoyl chloride (2.06 ml, 14.65 mmol), 1,2-dimethoxybenzene (1.87 ml, 14.65 mmol) in anhydrous methylene chloride (25 ml), and aluminum chloride (2.15 g, 16.12 mmol) were treated in the same manner as described above for the synthesis of 3-(3,4-dimethoxy-phenyl)-3-(4-methoxy-phenyl)-acrylonitrile. The crude was purified via flash column chromatography (20% EtOAc in hexane) to give (3,4-dimethoxy-phenyl)-(3-methoxy-phenyl)-methanone as a yellow oil (4.39 g, 100%); ¹HNMR (CDCl₃) δ 7.50 (d, J=1 Hz, 1H, Ar), 7.42-7.30 (m, 4H, Ar), 7.14-7.09 (m, 1H, Ar), 6.90 (d, J=8 Hz, 1H, Ar), 3.96 (s, 3H, OCH₃), 3.95 (s, 6H, 2OCH₃), 3.86 (s, 3H, OCH₃); ¹³C NMR (CDCl₃) δ 195.4, 159.6, 153.1, 149.1, 139.7, 130.3, 129.2, 125.6, 122.5, 118.3, 114.4, 112.3, 109.9, 56.2, 56.2, 55.6; Anal. Calcd. For C₁₆H₁₆O₄: C, 70.58; H, 5.92. Found: C, 70.38; H, 5.99; N, <0.05. The product was carried over to the next step.

(3,4-Dimethoxyphenyl)-(3-methoxyphenyl)methanone (CC-15126, 5193-25-B, 2.00 g, 7.35 mmol), cyanomethylphosphonic acid diethyl ester (2.31 ml, 14.69 mmol) in anhydrous THF (10 ml), and lithium bis(trimethylsilyl)amide (1.0 M solution in THF, 14.69 ml, 14.69 mmol) were treated in the same manner as described above for the synthesis of 3-(3,5-dimethoxy-phenyl)-3-(3-methoxy-phenyl)-acrylonitrile. The crude was purified via flash column chromatography (20% EtOAc in hexane) to give 3-(3,4-dimethoxy-phenyl)-3-(3-methoxy-phenyl)-acrylonitrile as a pink oil (1.99 g, 92%): ¹HNMR (DMSO-d₆) δ 7.46-7.30 (m, 2H, Ar), 7.14-7.04 (m, 4H, Ar), 6.98-6.84 (m, 7H, Ar), 6.72-6.68 (m, 1H, Ar), 6.32 (s, 0.85H, double bond proton of one isomer), 6.20 (s, 0.97H, double bond proton of the other isomer), 3.83-3.73 (multiple singlets, 18H, 6OCH₃); ¹³C NMR (CDCl₃) δ 162.8, 162.7, 159.7, 159.6, 151.3, 150.8, 149.0, 148.8, 140.9, 138.6, 131.5, 129.7, 129., 129.5, 123.4, 122.3, 122.2, 121.3, 118.4, 118.2, 116.0, 115.9, 115.0, 114.5, 112.8, 111.2, 110.9, 110.9, 93.8, 93.3, 56.2, 56.1, 56.1, 55.5; Anal. Calcd. For C₁₈H₁₇NO₃: C, 72.20; H, 6.09; N, 4.43 (+0.04H₂O). Found: C, 72.33; H, 6.10; N, 4.60.

4.6.2.51 3,3-Bis-(3-methoxy-phenyl)-acrylonitrile

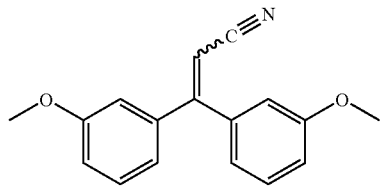

3-methoxybenzaldehyde (2.20 ml, 18.08 mmol), 1-bromo-3-methoxybenzene (2.52 ml, 19.89 mmol), and n-butyl lithium (7.96 ml, 19.89 mmol) were treated in the same manner as described above for the synthesis of 3-(3,5-dimethoxy-phenyl)-3-(3-methoxy-phenyl)-acrylonitrile. The crude was purified via flash column chromatography (10% EtOAc in hexane gradient to 25% EtOAc in hexane in about 40 min.) to give bis-(3-methoxy-phenyl)-methanol as a light yellow oil (4.45 g, 100%): ¹HNMR (CDCl₃) δ7.28-7.21 (m, 2H, Ar), 6.96-6.94 (m, 4H, Ar), 6.82-6.78 (m, 2H, Ar), 5.78 (d, J=3 Hz, 1H, CHOH), 3.78 (s, 6H, 2OCH₃ groups), 2.25 (d, J=3 Hz, 1H, OH). The product was carried over to the next step.

Bis-(3-methoxyphenyl)methanol (4.67 g, 19.12 mmol) and activated MnO₂ powder (5.7 g, 66 mmol) were treated in the same manner as described above for the synthesis of 3-(3,5-dimethoxy-phenyl)-3-(3-methoxy-phenyl)-acrylonitrile. The product bis-(3-methoxy-phenyl)-methanone was an oil (4.29 g, 92%): ¹HNMR (CDCl₃) δ7.46-7.32 (m, 2H, Ar), 7.11-7.02 (m, 4H, Ar), 6.93-6.89 (m, 2H, Ar), 5.83 (d, J=3 Hz, 1H, CHOH), 3.82 (s, 6H, 2OCH₃ groups), 2.30 (d, J=3 Hz, 1H, OH). The product was carried over to the next step.

Bis-(3-methoxyphenyl)methanone (1.23 g, 5.08 mmol), cyanomethylphosphonic acid diethyl ester (1.60 ml, 10.15 mmol) in anhydrous THF (10 ml), and lithium bis(trimethylsilyl)amide (1.0 M solution in THF, 10.15 ml, 10.15 mmol) were treated in the same manner as described above for the synthesis of 3-(3,5-dimethoxy-phenyl)-3-(3-methoxy-phenyl)-acrylonitrile. The crude was purified via flash column chromatography (10% EtOAc in hexane gradient to 25% EtOAc in hexane) to give 3,3-bis-(3=methoxy-phenyl)-acrylonitrile as a clear colorless oil (0.76 g, 56%): ¹HNMR (DMSO-d₆) δ 7.47-7.30 (two triplets, 2H, Ar), 7.12-7.04 (m, 2H, Ar), 6.98-6.82 (m, 4H, Ar), 6.38(s, 1H, double bond proton), 3.78 (s, 3H, OCH₃), 3.76 (s, 3H, OCH₃); ¹³C NMR (CDCl₃) δ 163.0, 159.8, 159.6, 140.3, 138.3, 129.8, 129.7, 122.1, 121.1, 117.9, 116.1, 115.9, 115.0, 114.4, 95.3, 55.5; Anal. Calcd. For C₁₇H₁₅NO₂: C, 76.96; H, 5.70; N, 5.28. Found: C, 76.65; H, 5.72; N, 5.15.

4.6.2.52 4-[1-(3,5-dimethoxyphenyl)prop-1-enyl]-1, 2-dimethoxybenzene

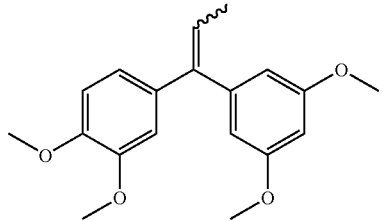

3,5-Dimethoxybenzoyl chloride (10.28 g, 51.24 mmol), 1,2-dimethoxybenzene (6.53 ml, 51.24 mmol), and aluminum chloride (7.52 g, 56.37 mmol) were treated in the same manner as described above for the synthesis of 3-(3,4-dimethoxy-phenyl)-3-(4-methoxy-phenyl)-acrylonitrile. The crude was purified via flash column chromatography (10% EtOAc in hexane gradient to 50% EtOAc in hexane in 50 min.) to give (3,4-dimethoxy-phenyl)-(3,5-dimethoxy-phenyl)-methanone as a light yellow solid (11.14 g, 72%); ¹HNMR (DMSO-d₆) δ 7.38-7.33 (m, 2H, Ar), 7.09 (d, J=8 Hz, 1H, Ar), 6.77 (s, 3H, OCH₃), 3.86 (s, 3H, OCH₃), 3.82 (s, 3H, OCH₃), 3.79 (s, 6H, 2OCH₃). The product was carried over to the next step.

(3,4-dimethoxyphenyl)-(3,5-dimethoxyphenyl)methanone (0.96 g, 3.18 mmol), (ethyl)triphenylphosphonium bromide (2.36 g, 6.35 mmol), and lithium bis(trimethylsilyl) amide (1.0 M solution in THF, 6.35 ml, 6.35 mmol) were treated in the same manner as described above for the synthesis of 3-(3,5-dimethoxy-phenyl)-3-(3-methoxy-phenyl)-acrylonitrile. The crude was purified via flash column chromatography (10% EtOAc in hexane gradient to 20% EtOAc in hexane in about 30 min.) to give 4-[1-(3,5-dimethoxyphenyl)prop-1-enyl]-1,2-dimethoxybenzene a light brown oil (0.97 g, 97%): ¹HNMR (CDCl₃) δ 6.89-6.83 (m, 2H, Ar), 6.76-6.68 (m, 4H, Ar), 6.43-6.39 (m, 3H, Ar), 6.36-6.34 (m, 3H,Ar), 6.20-6.03 (m, 2H, double bond protons), 3.91 (s, 3H, OCH₃), 3.86 (s, 3H, OCH₃), 3.83 (s, 6H, 2OCH₃), 3.78 (s, 6H, 2OCH₃), 3.74 (s, 6H, 2OCH₃), 1.78-1.74 (m, 6H, 2CH₃): ¹³C NMR (CDCl₃) δ 160.7, 160.6, 148.7, 148.7, 148.3, 148.0, 145.4, 142.3, 142.3, 142.2, 135.6, 132.5, 124.4, 122.8, 122.6, 119.9, 113.3, 111.0, 110.9, 110.3, 108.2, 105.8, 99.2, 99.0, 56.0, 56.0, 55.5, 55.4, 15.9, 15.8; Anal. Calcd. For C₁₉H₂₂O₄: C, 72.59; H, 7.05. Found: C, 72.43; H, 6.96.

4.6.2.53 3-(3,4-Diethyl-phenyl)-3-(3,4-dimethoxy-phenyl)-acrylonitrile

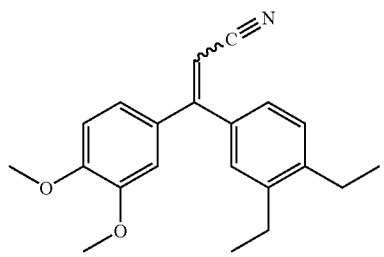

3,4-Dimethoxybenzoyl chloride (4.01 g, 20 mmol), 1,2-diethylbenzene (2.68 g, 20 mmol), and aluminum chloride (2.93 g, 22 mmol) were treated in the same manner as described above for the synthesis of 3-(3,4-dimethoxy-phenyl)-3-(4-methoxy-phenyl)-acrylonitrile. The crude was purified via flash column chromatography (10% EtOAc in hexane gradient to 20% EtOAc in hexane in 40 min.) to give (3,4-diethyl-phenyl)-(3,4-dimethoxy-phenyl)-methanone as an orange oil (2.45 g, 41%). The product was carried over without further purification to the next step.

(3,4-Diethylphenyl)-(3,4-dimethoxyphenyl)methanone (2.45 g, 8.21 mmol), lithium bis(trimethylsilyl)amide (1.0 M solution in THF, 18 ml, 18 mmol), and cyanomethylphosphonic acid diethyl ester (2.8 ml, 18 mmol) in anhydrous THF (40 ml) were treated in the same manner as described above for the synthesis of 3-(3,5-dimethoxy-phenyl)-3-(3-methoxy-phenyl)-acrylonitrile. The crude was purified via flash column chromatography (10% EtOAc in 1:1 mixture of hexane and $CH_2Cl_2$) to give a light brown oil (2.72 g), which was further purified via preparative HPLC to give 3-(3,4-diethyl-phenyl)-3-(3,4-dimethoxy-phenyl)-acrylonitrile as a white solid (0.34 g, 18%); mp, 129-131° C.: $^1$HNMR (DMSO-$d_6$) δ 7.29 (d, J=7 Hz, 1H, Ar), 7.18-7.10 (m, 3H, Ar), 6.97 (d, J=8 Hz, 1H, Ar), 6.71 (d, J=8 Hz, 1H, Ar), 6.20 (s, 1H, double bond proton), 3.78 (s, 3H, $OCH_3$), 3.76 (s, 3H, $OCH_3$), 2.73-2.61 (m, 4H, $2CH_2CH_3$), 1.25 (m, broad, 6H, $2CH_2CH_3$); $^{13}$C NMR (DMSO-$d_6$) δ 161.6, 150.9, 148.6, 143.0, 141.4, 134.7, 130.5, 129.0, 128.1, 126.9, 122.3, 118.7, 111.2, 111.0, 93.1, 55.6, 24.7, 24.6, 15.1, 14.8; Anal. Calcd. For $C_{21}H_{23}NO_2$: C, 78.47; H, 7.21; N, 4.36. Found: C, 78.26; H, 7.27; N, 4.40.

4.6.2.54 3-(3,4-Dimethoxy-phenyl)-3-(3,5-dimethoxy-phenyl)-acrylic Acid Methyl Ester

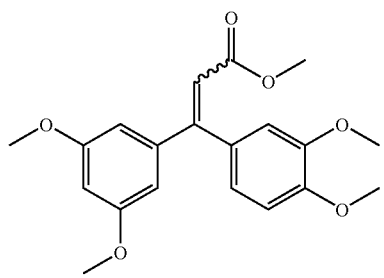

(3,4-dimethoxyphenyl)-(3,5-dimethoxyphenyl)methanone (0.50 g, 4.95 mmol), (diethoxyphosphoryl)acetic acid methyl ester (2.29 g, 9.90 mmol), and lithium bis(trimethylsilyl)amide (1.0 M solution in THF, 9.90 ml, 9.90 mmol) were treated in the same manner as described above for the synthesis of 3-(3,5-dimethoxy-phenyl)-3-(3-methoxy-phenyl)-acrylonitrile. The crude yellowish oil was purified via preparative HPLC to give 3-(3,4-dimethoxy-phenyl)-3-(3,5-dimethoxy-phenyl)-acrylic acid methyl ester as a light yellow oil (0.45 g, 25%): $^1$HNMR (CDCl$_3$) δ 6.89-6.72 (m, 2H, Ar), 6.49-6.36 (m, 4H, Ar), 6.28 (s, 1H, double bond proton), 3.92 (s, 3H, $OCH_3$), 3.82 (s, 3H, $OCH_3$), 3.75 (s, 6H, $2OCH_3$), 3.64 (s, 3H, $OCH_3$); Anal. Calcd. For $C_{20}H_{22}O_6$+1.06$H_2O$: C, 63.60; H, 6.45. Found: C, 63.22; H, 5.88.

4.6.2.55 3-(3,4-Dimethoxy-phenyl)-3-(3,5-dimethoxy-phenyl)-acrylic Acid

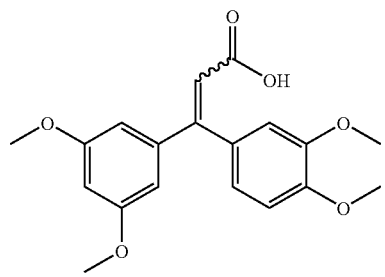

(3,4-Dimethoxyphenyl)-(3,5-dimethoxyphenyl)methanone (1.50 g, 4.95 mmol), (diethoxyphosphoryl)acetic acid methyl ester (2.29 g, 9.90 mmol), and lithium bis(trimethylsilyl)amide (1.0 M solution in THF, 9.90 ml, 9.90 mmol) were treated in the same manner as described above for the synthesis of 3-(3,5-dimethoxy-phenyl)-3-(3-methoxy-phenyl)-acrylonitrile. The crude yellowish oil was purified via preparative HPLC to give 3-(3,4-dimethoxy-phenyl)-3-(3,5-dimethoxy-phenyl)-acrylic acid ethyl ester as a light yellow oil (0.79 g, 43%): $^1$HNMR (CDCl$_3$) δ 6.89-6.72 (m, 2H, Ar), 6.48-6.45 (m, 4H, Ar), 6.28 (s, 1H, double bond proton), 4.09 (q, J=7 Hz, 2H, $CH_2CH_3$), 3.92 (s, 3H, $OCH_3$), 3.82 (s, 3H, $OCH_3$), 3.75 (s, 6H, $2OCH_3$), 1.16 (t, J=7 Hz, 3H, $CH_2CH_3$). The product was carried over to the next step.

3-(3,4-Dimethoxyphenyl)-3-(3,5-dimethoxyphenyl) acrylic acid ethyl ester (0.76 g, 2.05 mmol), potassium hydroxide (5 N, 8.10 ml, 20.52 mmol), methanol (6 ml), and $H_2O$ (1.5 ml) were mixed and stirred at rt for a couple of hours. The methanol was evaporated in vacuo leaving a clear solution, which was extracted with ether (2×60 ml) to get rid of the impurities. The aqueous phase was acidified with conc. HCl to pH around 2~3 to form a white precipitation, which was extracted with $CH_2Cl_2$ (2×100 ml), dried over $MgSO_4$, filtered and concentrated to give 3-(3,4-dimethoxy-phenyl)-3-(3,5-dimethoxy-phenyl)-acrylic acid as a foamy solid (0.69 g, 98%); mp, 90-92° C.: $^1$HNMR (CDCl$_3$) δ 6.90-6.75 (m, 4H, double bond protons and 2COOH), 6.50-6.24 (m, 12H, Ar), 3.92-3.75 (multiple singlets, 24H, 8$OCH_3$), isomer ratio based on $^1$HNMR close to 43%:57%; Anal. Calcd. For $C_{19}H_{20}O_6$: C, 66.27; H, 5.85. Found: C, 66.02; H, 5.81.

4.6.2.56 4-[1-(3,5-Dimethoxyphenyl)but-1-enyl]-1,2-dimethoxybenzene

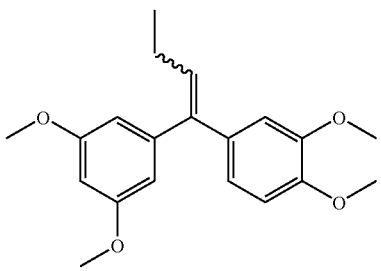

(3,4-Dimethoxyphenyl)-(3,5-dimethoxyphenyl)methanone (1.98 g, 6.54 mmol), propyltriphenylphosphonium bromide (5.04 g, 13.08 mmol), and lithium bis(trimethylsilyl)amide (1.0 M solution in THF, 13.08 ml, 13.08 mmol) were treated in the same manner as described above for the synthesis of 3-(3,5-dimethoxy-phenyl)-3-(3-methoxy-phenyl)-acrylonitrile. The crude yellowish solid was purified via flash column chromatography (10% EtOAc in hexane) to give a light brown oil (2.72 g), which was further purified via preparative HPLC to give 4-[1-(3,5-dimethoxyphenyl)but-1-enyl]-1,2-dimethoxybenzene as a colorless oil (2.11 g, 98%): $^1$HNMR (CDCl$_3$) δ 6.88-6.84 (m, 1H, Ar), 6.76-6.67 (m, 2H, Ar), 6.43-6.33 (m, 3H, Ar), 6.08-5.94 (m, 1H, double bond proton), 3.91-3.74 (multiple singlets, 12H, 4OCH$_3$), 3.73 (s, 3H, OCH$_3$), 2.16-2.04 (m, 2H, CH$_2$CH$_3$), 1.04 (t, J=7 Hz, 3H, CH$_2$CH$_3$); $^{13}$C NMR (CDCl$_3$) δ 160.7, 160.6, 148.7, 148.4, 148.1, 145.3, 142.5, 140.8, 140.7, 15.5, 132.8, 132.0, 130.3, 122.4, 120.0, 113.2, 110.9, 110.9, 110.3, 108.0, 105.8, 99.2, 99.0, 56.0, 55.4, 23.4, 23.4, 14.8, 14.7; Anal. Calcd. For C$_{20}$H$_{24}$O$_4$: C, 73.15; H, 7.37. Found: C, 72.98; H, 7.25.

4.6.2.57 4-(3,4-Dimethoxy-phenyl)-4-(3,5-dimethoxy-phenyl)-but-3-en-2-one

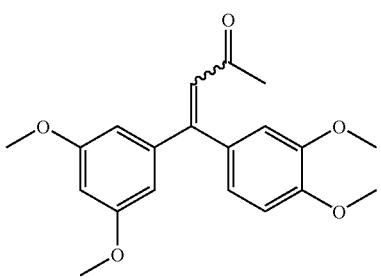

A suspension of Pd(OAc)$_2$ (67 mg, 0.30 mmol) in DMF (1 ml) was added to a stirred suspension of 4-(3,5-dimethoxyphenyl)-but-3-en-2-one (2.05 g, 9.96 mmol), 4-bromo-1,2-dimethoxybenzene (2.15 ml, 14.94 mmol), NaOAc (1.39 g, 16.94 mmol), and tetrabutylammonium bromide (3.53 g, 10.96 mmol) in DMF (19 ml). The suspension was heated at ~60° C. overnight. The mixture was then poured into EtOAc (50 ml) and H$_2$O (150 ml), followed by extraction with EtOAc (2×50 ml), washing with H$_2$O (2×50 ml), brine (50 ml) and drying over MgSO$_4$. The crude was purified flash column chromatography (10% EtOAc in hexane gradient to 25% EtOAc in hexane) to give 4-(3,4-dimethoxy-phenyl)-4-(3,5-dimethoxy-phenyl)-but-3-en-2-one as a gummy oil (0.49 g, 15%): $^1$HNMR (CDCl$_3$) δ 6.93-6.92 (m, 1H, Ar), 6.82-6.77 (m, 2H, Ar), 6.53-6.51 (m, 2H, Ar and double bond proton), 6.38 (d, J=2 Hz, 2H, Ar), 3.87 (s, 3H, OCH$_3$), 3.85 (s, 3H, OCH$_3$), 3.79 (s, 6H, 2OCH$_3$), 1.91 (s, 3H, CH$_3$); $^{13}$C NMR (CDCl$_3$) δ 160.9, 153.8, 150.7, 148.9, 141.1, 132.9, 126.5, 122.4, 113.2, 110.8, 100.9, 56.1, 55.8, 55.6, 55.4, 30.0; Anal. Calcd. For C$_{20}$H$_{22}$O$_5$: C, 70.16; H, 6.48. Found: C, 70.26; H, 6.37; N, <0.05.

4.6.2.58 3-(3,4-Dimethoxy-phenyl)-3-(3,5-dimethoxy-phenyl)propionitrile

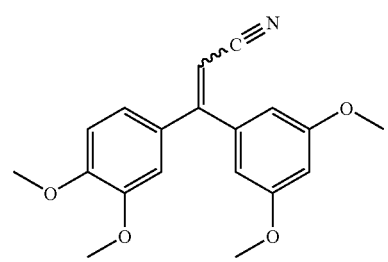

A solution of 3-(3,4-dimethoxyphenyl)-3-(3,5-dimethoxyphenyl)acrylonitrile (0.30 g, 0.92 mmol) in EtOAc (10 ml) was added to a mixture of 10% palladium on carbon (0.15 g, 50% w.t.) in EtOAc (20 ml). The mixture was then hydrogenated on a Parr-Shaker overnight. The suspension was filtered through a Celite pad, washed with EtOAc, and the solvent was evaporated to get an oil, which was further purified via flash column chromatography to give a light brown oil which solidified into 3-(3,4-dimethoxy-phenyl)-3-(3,5-dimethoxy-phenyl)-propionitrile as an off-white solid (0.20 g, 66%); mp, 121-123° C.: $^1$HNMR (CDCl$_3$) δ 6.82 (d, J=2 Hz, 2H, Ar), 6.72 (s, wide, 1H, Ar), 6.36 (s, wide, 3H, Ar), 4.24 (t, J=7 Hz, 1H, CHCH$_2$), 3.86 (s, 3H, OCH$_3$), 3.84 (s, 3H, OCH$_3$), 3.76 (s, 6H, 2OCH$_3$), 2.98 (d, J=7 Hz, 2H, CHCH$_2$); $^{13}$C NMR (CDCl$_3$) δ 161.2, 149.3, 148.5, 144.0, 133.6, 119.5, 118.6, 111.5, 111.3, 106.1, 98.8, 56.1, 56.1, 55.5, 47.0, 24.5; Anal. Calcd. For C$_{19}$H$_{21}$NO$_4$: C, 69.71; H, 6.47; N, 4.28. Found: C, 69.66; H, 6.42; N, 4.20.

4.6.2.59 3-(3,5-Dimethoxy-phenyl)-3-(4-hydroxy-3-methoxy-phenyl)-acrylonitrile

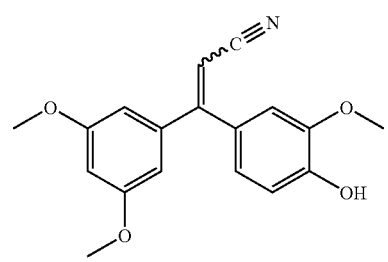

To a solution of 4-bromo-2-methoxyphenol (2.87 g, 14.13 mmol) in DMF (20 ml) was added ethyldiisopropylamine (6.15 ml, 35.32 mmol). The clear solution was stirred for 5 min. followed by addition of tert-butylchlorodimethylsilane (2.56 g, 16.95 mmol). The crude was purified via flash column chromatography (100% in hexane) to give (4-bromo-2-methoxy-phenoxy)-tert-butyl-dimethyl-silane as a clear oil (4.45 g, 99%): ¹HNMR (CDCl₃) δ 6.95 (s, wide, 1H, Ar), 6.92 (d, J=2 Hz, 1H, Ar), 6.71 (d, J=7 Hz, 1H, Ar), 3.79 (s, 3H, OCH₃), 0.98 (s, 9H, 3CH₃), 0.13 (s, 6H, 2CH₃). The product was carried over to the next step.

(4-bromo-2-methoxyphenoxy)-tert-butyldimethylsilane (4.37 g, 13.77 mmol), n-butyl lithium (5.51 ml, 13.77 mmol), and 3,5-dimethoxybenzaldehyde (2.08 g, 12.52 mmol) were treated in the same manner as described above for the synthesis of 3-(3,5-dimethoxy-phenyl)-3-(3-methoxy-phenyl)-acrylonitrile. The crude was purified via flash column chromatography (5% EtOAc in hexane gradient to 20% EtOAc in hexane in about 40 min.) to give [4-(tert-butyl-dimethyl-silanyloxy)-3-methoxy-phenyl]-(3,5-dimethoxy-phenyl)-methanol a clear oil (3.94 g, 78%): ¹HNMR (CDCl₃) δ 6.89 (s, wide, 1H, Ar), 6.78 (s, wide, 2H, Ar), 6.53 (d, J=2 Hz, 2H, Ar), 6.36 (t, J=2 Hz, 1H, Ar), 5.69 (d, J=3 Hz, 1H, CHOH), 3.77 (s, 3H, OCH₃), 3.76 (s, 6H, 2OCH₃), 2.19 (d, J=3 Hz, 1H, OH), 0.98 (s, 9H, 3CH₃), 0.14 (s, 6H, 2CH₃). The product was carried over to the next step.

[4-(tert-Butyldimethylsilanyloxy)-3-methoxyphenyl]-(3,5-dimethoxyphenyl)methanol (3.90 g, 9.64 mmol) and activated MnO₂ powder (8.1 g, 93 mmol) were treated in the same manner as described above for the synthesis of 3-(3,5-dimethoxy-phenyl)-3-(3-methoxy-phenyl)-acrylonitrile. The product [4-(tert-butyl-dimethyl-silanyloxy)-3-methoxyphenyl]-(3,5-dimethoxy-phenyl)-methanone was a light yellow oil (3.69 g, 95%): ¹HNMR (CDCl₃) δ 7.47 (d, J=1 Hz, 1H, Ar), 7.31 (dd, J=1 Hz and 7 Hz, 1H, Ar), 6.87 (m, 3H, Ar), 6.65 (t, J=2 Hz, 1H, Ar), 3.87 (s, 3H, single OCH₃ group), 3.83 (s, 6H, 2OCH₃), 1.01 (s, 9H, 3CH₃), 0.20 (s, 6H, 2CH₃). The product was carried over to the next step.

[4-(tert-Butyldimethylsilanyloxy)-3-methoxyphenyl]-(3,5-dimethoxyphenyl)methanone (3.64 g, 9.04 mmol), cyanomethylphosphonic acid diethyl ester (2.85 ml, 18.08 mmol) in anhydrous THF (10 ml), and lithium bis(trimethylsilyl)amide (1.0 M solution in THF, 18.08 ml, 18.08 mmol) were treated in the same manner as described above for the synthesis of 3-(3,5-dimethoxy-phenyl)-3-(3-methoxy-phenyl)-acrylonitrile. The crude was purified via flash column chromatography (5% EtOAc in hexane gradient to 20% EtOAc in hexane in about 30 min.) to give 3-[4-(tert-butyl-dimethyl-silanyloxy)-3-methoxy-phenyl]-3-(3,5-dimethoxy-phenyl)-acrylonitrile as a white solid (3.00 g, 78%). The product was carried over to the next step without further purification.

Tetrabutylammonium fluoride (1.0 M solution in THF, 5.55 ml, 5.55 mmol) was added at rt to a stirred solution of 3-[4-(tert-butyl-dimethyl-silanyloxy)-3-methoxy-phenyl]-3-(3,5-dimethoxy-phenyl)-acrylonitrile (1.97 g, 4.63 mmol) in THF (35 ml). The colorless clear solution immediately turned into brown/red wine color. The reaction should be done within one hour. Ice water (15 ml) was poured into the reddish solution, followed by addition of ether (80 ml). The mixture was washed with water (2×100 ml), dried over MgSO₄, filtered and concentrated to a yellow oil, which was lyophilized to give 3-(3,5-dimethoxy-phenyl)-3-(4-hydroxy-3-methoxy-phenyl)-acrylonitrile as a white gummy solid (1.26 g, 88%): mp, 120-122° C.; ¹HNMR (DMSO-d₆) δ 9.68 (s, 1H, OH group of one isomer), 9.60 (s, 1H, OH group of the other isomer), 7.11-6.61 (m, 8H, Ar), 6.49-6.46 (m, 4H, Ar), 6.23 (s, 1H, double bond proton of one isomer), 6.11 (s, 1H, double bond proton of the other isomer), 3.78-3.74 (multiple singlets, 18H, 6OCH₃), isomer ratio based on ¹HNMR was 49%:51%; ¹³C NMR (CDCl₃) δ 163.0, 162.9, 160.9, 160.8, 148.2, 147.7, 146.6, 146.3, 141.6, 139.2, 130.9, 128.9, 124.2, 122.9, 118.5, 118.2, 114.6, 114.5, 112.3, 110.6, 107.9, 107.2, 102.3, 102.2, 93.7, 93.1, 56.4, 56.2, 55.7, 55.6; Anal. Calcd. For C₁₈H₁₇NO₄: C, 69.44; H, 5.50; N, 4.50. Found: C, 69.24; H, 5.38; N, 4.27.

4.6.2.60 3-(3-Amino-4-methoxy-phenyl)-3-(3-ethoxy-4-methoxy-phenyl)-acrylonitrile (E and Z Isomers)

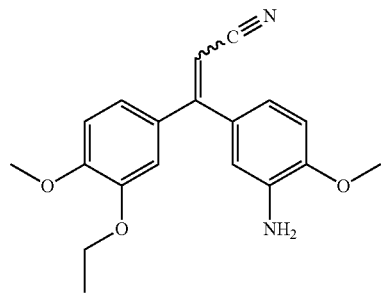

(4-Methoxy-3-nitro-phenyl)-(3-ethoxy-4-methoxy-phenyl)-methanol was prepared analogously to 3-(3-amino-4-methoxy-phenyl)-3-(3,4-dimethoxy-phenyl)-acrylonitrile using 3-ethoxy-4-methoxy-bromobenzene (7.6 g, 33 mmol), magnesium turning (0.8 g, 33 mmol) and 4-methoxy-3-nitro-benzaldehyde (5.0 g, 27.6 mmol). The crude product was purified by flash chromatography (silica gel, CH₂Cl₂:EtOAc 9:1) to afford (4-methoxy-3-nitro-phenyl)-(3-ethoxy-4-methoxy-phenyl)-methanol (3.9 g, 42%): ¹H NMR (CDCl₃) δ 7.88 (d, J=2 Hz, 1H), 7.53-7.49 (dd, J=3, 9 Hz, 1H), 7.05 (d, J=8 Hz, 1H), 6.84 (s, 3H), 5.75 (d, J=3 Hz, 1H), 4.01 (m, 2H), 3.94 (s, 3H), 3.86 (s, 3H), 2.30 (d, J=3 Hz, 1H), 1.44 (t, 3H).

(4-Methoxy-3-nitro-phenyl)-(3-ethoxy-4-methoxy-phenyl)-methanone was prepared analogously to 3-(3-amino-4-methoxy-phenyl)-3-(3,4-dimethoxy-phenyl)-acrylonitrile using (4-methoxy-3-nitro-phenyl)-(3-ethoxy-4-methoxy-phenyl)-methanol (3.9 g, 11.6 mmol) and pyridinium chlorochromate (3.7 g, 17.4 mmol). The crude product was purified by flash chromatography (silica gel, CH₂Cl₂:EtOAc 95:5) to afford (4-methoxy-3-nitro-phenyl)-(3-ethoxy-4-methoxy-phenyl)-methanone (3.4 g, 89%) as an orange solid: ¹H NMR (CDCl₃) δ 8.28 (d, J=2 Hz, 1H), 8.06-8.02 (dd, J=3, 8.7 Hz, 1H), 7.41 (d, J=1 Hz, 1H), 7.31-7.26 (dd, J=2, 8.4 Hz, 1H), 7.21 (d, J=8 Hz, 1H), 6.94 (d, J=8 Hz, 1H), 4.21-4.12 (q, J=7 Hz, 2H), 4.05 (s, 3H), 3.96 (s, 3H), 1.50 (t, J=6 Hz, 3H).

3-(4-Methoxy-3-nitro-phenyl)-3-(3-ethoxy-4-methoxy-phenyl)-acrylonitrile was prepared analogously to 3-(3-amino-4-methoxy-phenyl)-3-(3,4-dimethoxy-phenyl)-acrylonitrile using (4-methoxy-3-nitro-phenyl)-(3-ethoxy-4-methoxy-phenyl)-methanone (3.4 g, 10.3 mmol), lithium bis(trimethylsilyl)amide (11.3 mL, 11.3 mmol) and diethyl cyanomethylphosphate (2.0 g, 11.3 mmol). The crude product was purified by flash chromatography (silica gel, Hexane:CH₂Cl₂ 3:97) to afford a mixture of isomers of 3-(4-methoxy-3-nitro-phenyl)-3-(3-ethoxy-4-methoxy-phenyl)-acrylonitrile (3.4 g, 95%) as a yellow solid: ¹H NMR (CDCl₃) δ 7.85-7.77 (m, 1H), 7.54-6.78 (m, 5H), 5.67 (5.59) (s, 1H), 4.10-4.00 (m, 5H), 3.93 (s, 3H), 1.49-1.42 (m, 3H).

A suspension of 3-(4-methoxy-3-nitro-phenyl)-3-(3-ethoxy-4-methoxy-phenyl)-acrylonitrile (3.3 g, 9.7 mmol) and tin chloride dihydrate (11.6 g, 51.8 mmol) in ethanol (70 mL) was heated at 70° C. oil bath for 1 h then cooled to room temperature. The mixture was poured into ice (200 mL), and the pH was made strongly alkaline by the addition of 10N NaOH. The mixture was extracted with EtOAc (5×50 mL). The combined extracts were washed with water (40 mL), brine (40 mL) and dried (MgSO$_4$). Solvent was removed and the crude product was purified by flash chromatography (silica gel, Hexane:EtOAc 7:3) to afford mixture of isomers of 3-(3-amino-4-methoxy-phenyl)-3-(3-ethoxy-4-methoxy-phenyl)-acrylonitrile (1.1 g, 33%) as a yellow solid: mp 141-143° C.; $^1$H NMR (CDCl$_3$) δ 7.00-6.64 (m, 6H), 5.49 (d, 1H), 4.12-3.98 (m, 2H), 3.92-3.88 (m, 8H), 1.47-1.40 (m, 3H); $^{13}$C NMR (CDCl$_3$) δ 162.95, 151.23, 150.70, 146.70, 148.03, 147.81, 136.11, 135.93, 132.11, 129.90, 129.80, 123.07, 122.10, 120.72, 119.62, 118.89, 118.81, 115.99, 114.66, 114.23, 112.97, 110.90, 109.81, 55.59, 55.52, 14.67; Anal Calcd for C$_{19}$H$_{20}$N$_2$O$_3$: C, 70.35; H, 6.21; N, 8.64. Found: C, 70.25; H, 6.21; N, 8.46.

4.6.2.61 3-(4-Amino-3-methoxy-phenyl)-3-(3,4-dimethoxy-phenyl)-acrylonitrile (E and Z Isomers)

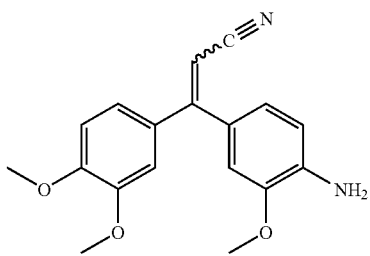

(3-Methoxy-4-nitro-phenyl)-(3,4-dimethoxy-phenyl)-methanol was prepared analogously to 3-(3-amino-4-methoxy-phenyl)-3-(3,4-dimethoxy-phenyl)-acrylonitrile using 3,4-bromoveratrole (2.5 g, 11.5 mmol), magnesium turning (0.3 g, 11.5 mmol) and 3-methoxy-4-nitro-benzaldehyde (1.5 g, 8.2 mmol). The crude product was purified by flash chromatography (silica gel, CH$_2$Cl$_2$:EtOAc 9:1) to afford (3-methoxy-4-nitro-phenyl)-(3,4-dimethoxy-phenyl)-methanol (1.9 g, 72%): $^1$H NMR (CDCl$_3$) δ 7.80 (d, J=8 Hz, 1H), 7.22 (s, 1H), 6.98-6.85 (m, 4H), 5.79 (d, J=2 Hz, 1H), 3.97 (s, 3H), 3.87 (s, 6H).

A suspension of (3-methoxy-4-nitro-phenyl)-(3,4-dimethoxy-phenyl)-methanol (1.9 g, 6.0 mmol) and MnO$_2$ (9.1 g, 104.7 mmol) in CH$_2$Cl$_2$ (100 mL) was stirred for 2 days. The mixture was filtered through Celite and the Celite was washed with CH$_2$Cl$_2$. The filtrate was concentrated and the residue was purified by flash chromatography (silica gel, CH$_2$Cl$_2$:EtOAc 95:5) to afford (3-methoxy-4-nitro-phenyl)-(3,4-dimethoxy-phenyl)-methanone (1.2 g, 64%) of yellow solid: $^1$H NMR (CDCl$_3$) δ 7.87 (d, J=8 Hz, 1H), 7.50-7.46 (dd, J=2, 5.7 Hz, 2H), 7.36-7.30 (m, 2H), 6.93 (d, J=8 Hz, 1H), 4.01 (s, 3H), 3.98 (s, 3H), 3.96 (s, 3H).

3-(3-Methoxy-4-nitro-phenyl)-3-(3,4-dimethoxy-phenyl)-acrylonitrile was prepared analogously to 3-(3-amino-4-methoxy-phenyl)-3-(3,4-dimethoxy-phenyl)-acrylonitrile using (3-methoxy-4-nitro-phenyl)-(3,4-diemthoxy-phenyl)-methanone (1.2 g, 3.8 mmol), lithium bis(trimethylsilyl)amide (4.2 mL, 4.2 mmol) and diethyl cyanomethylphosphate (0.7 g, 4.2 mmol). The crude product was purified by flash chromatography (silica gel, Hexane:EtOAc 1:1) to afford 3-(3-methoxy-4-nitro-phenyl)-3-(3,4-dimethoxy-phenyl)-acrylonitrile (1.2 g, 91%): $^1$H NMR (CDCl$_3$) δ 7.89 (d, J=8 Hz, 1H), 7.21 (d, J=1 Hz, 1H), 7.05 (dd, J=2, 8.4 Hz, 1H), 6.85 m, 3H), 5.79 (s, 1H), 3.98-3.86 (m 9H).

3-(4-Amino-3-methoxy-phenyl)-3-(3,4-diemthoxy-phenyl)-acrylonitrile was prepared analogously to 3-(3-amino-4-methoxy-phenyl)-3-(3-ethoxy-4-methoxy-phenyl)-acrylonitrile using 3-(3-methoxy-4-nitro-phenyl)-3-(3,4-dimethoxy-phenyl)-acrylonitrile (1.2 g, 3.4 mmol) and tin chloride dihydrate (4.2 g, 18.0 mmol). The crude product was purified by flash chromatography (silica gel, Hexane:EtOAc 7:3) to afford a mixture of isomers of 3-(4-amino-3-methoxy-phenyl)-3-(3,4-dimethoxy-phenyl)-acrylonitrile (0.7 g, 64%) as a yellow solid: mp 104-106° C.; $^1$H NMR (CDCl$_3$) δ 7.00-6.63 (m 6H), 5.52 (5.43)(s, 1H), 4.10 (s, 2H), 3.95-3.80 (m, 9H); $^{13}$C NMR (CDCl$_3$) δ 185.55, 183.98, 162.98, 150.83, 148.69, 148.52, 146.37, 138.97, 138.53, 135.76, 132.51, 129.30, 128.81, 123.95, 123.16, 122.80, 122.23, 119.17, 113.78, 112.93, 112.02, 111.81, 110.69, 110.37, 90.28, 90.18, 90.02, 55.97, 55.90, 55.54; Anal Calcd for C$_{18}$H$_{18}$N$_2$O$_3$: C, 69.66; H, 5.85; N, 9.03. Found: C, 69.59; H, 5.81; N, 8.95.

4.6.2.62 3-(4-Amino-3-methoxy-phenyl)-3-(3,5-dimethoxy-phenyl)-acrylonitrile (E and Z Isomers)

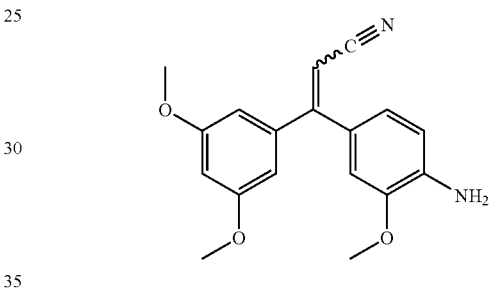

(3-Methoxy-4-nitro-phenyl)-(3,5-dimethoxy-phenyl)-methanol was prepared analogously to 3-(3-amino-4-methoxy-phenyl)-3-(3,4-dimethoxy-phenyl)-acrylonitrile using 3,5-dimethoxy-bromobenzene (4.4 g, 20.1 mmol), magnesium turning (1.0 g, 20.1 mmol) and 3-methoxy-4-nitro-benzaldehyde (3.0 g, 16.8 mmol) to afford (3-methoxy-4-nitro-phenyl)-(3,5-dimethoxy-phenyl)-methanol (3.9 g, 73%): $^1$H NMR (CDCl$_3$) δ 7.79 (d, J=8 Hz, 1H), 7.22 (s, 1H), 7.00-6.99 (dd, J=2, 9.1 Hz, 1H), 6.48 (d, J=2 Hz, 2H), 6.40 (d, J=2 Hz, 1H), 5.75 (d, J=3 Hz, 1H), 3.96 (s, 3H), 3.77 (s, 6H), 2.45 (d, J=2 Hz, 1H).

A suspension of (3-methoxy-4-nitro-phenyl)-(3,5-dimethoxy-phenyl)-methanol (3.9 g, 12.3 mmol) and MnO$_2$ (8.5 g, 98.4 mmol) in CH$_2$Cl$_2$ (100 mL) was stirred for 3 days. The mixture was filtered through Celite and the Celite was washed with CH$_2$Cl$_2$. The filtrate was concentrated to afford (3-methoxy-4-nitro-phenyl)-(3,5-dimethoxy-phenyl)-methanone (3.7 g, 94%): $^1$H NMR (CDCl$_3$) δ 7.85 (d, J=8 Hz, 1H), 7.52 (d, J=0.9 Hz, 1H), 7.39-7.35 (dd, J=2, 9.6 Hz, 1H), 6.89 (d, J=2 Hz, 2H), 6.71 (d, J=2 Hz, 1H), 4.01 (s, 3H), 3.83 (s, 6H).

3-(3-Methoxy-4-nitro-phenyl)-3-(3,5-dimethoxy-phenyl)-acrylonitrile (E and Z isomers) was prepared analogously to 3-(3-amino-4-methoxy-phenyl)-3-(3,4-dimethoxy-phenyl)-acrylonitrile using (3-methoxy-4-nitro-phenyl)-(3,5-dimethoxy-phenyl)-methanone (3.7 g, 11.5 mmol), lithium bis(trimethylsilyl)amide (12.7 mL, 12.7 mmol) and diethyl cyanomethylphosphate (2.5 g, 12.7 mmol) to afford mixture of isomers of 3-(3-methoxy-4-nitro-phenyl)-3-(3,5-dimethoxy-phenyl)-acrylonitrile (3.9 g, 99%): $^1$H NMR (CDCl$_3$) δ 7.91-7.82 (m, 1H), 7.26-7.22 (m, 1H), 7.04-6.98

(m, 2H), 6.59-6.53 (m, 2H), 6.38-6.37 (m, 1H), 5.85(5.77) (s, 1H), 4.00-3.91 (m, 3H), 3.83-3.78 (m 6H).

3-(4-Amino-3-methoxy-phenyl)-3-(3,5-dimethoxy-phenyl)-acrylonitrile was prepared analogously to 3-(3-amino-4-methoxy-phenyl)-3-(3-ethoxy-4-methoxy-phenyl)-acrylonitrile using 3-(3-methoxy-4-nitro-phenyl)-3-(3,5-dimethoxy-phenyl)-acrylonitrile (3.9 g, 11.5 mmol) and tin chloride dihydrate (12.8 g, 58.0 mmol) to afford mixture isomers of 3-(4-amino-3-methoxy-phenyl)-3-(3,5-dimethoxy-phenyl)-acrylonitrile (3.1 g, 84%) as a yellow solid: mp 114-116° c; $^1$H NMR (CDCl$_3$) δ 7.04-6.45 (m, 6H), 5.60(5.46) (s, 1H), 3.86-3.70 (m, 11H); $^{13}$C NMR (CDCl$_3$) δ 163.18, 162.98, 160.57, 146.32, 142.06, 139.34, 139.07, 138.57, 128.03, 126.37, 124.00, 122.74, 107.15, 102.02, 101.95, 91.86, 90.98, 55.69, 55.55; Anal Calcd for $C_{18}H_{18}N_2O_3$: C, 69.66; H, 5.85; N, 9.03. Found: C, 69.33; H, 5.67; 8.85.

4.6.2.63 3-(3-Cyclopentyloxy-4-methoxy-phenyl)-3-phenyl-acrylonitrile

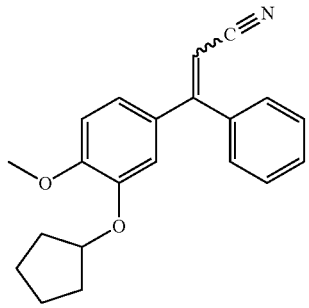

(3-Cyclopentyloxy-4-methoxy-phenyl)-phenyl-methanone (0.5 g, 1.7 mmol), cyanomethylphosphonic acid diethyl ester (0.3 ml, 1.9 mmol) in anhydrous THF (10 ml), and lithium bis(trimethylsilyl)amide (1.3 M solution in THF, 1.4 ml, 1.9 mmol) were treated in the same manner as described above for the synthesis of 3-(3,5-dimethoxy-phenyl)-3-(3-methoxy-phenyl)-acrylonitrile. The crude was purified by flash column chromatography to give 3-(3-cyclopentyloxy-4-methoxy-phenyl)-3-phenyl-acrylonitrile as a solid (0.41 g, 76%): mp, 90.6-93° C.; $^1$H NMR (CDCl$_3$) δ 7.54-7.24 (m, 10H), 7.05-6.73 (m, 6H), 5.66 (s, 1H), 5.60 (s, 1H), 4.81-4.62 (m, 2H), 3.89 (s, 3H), 3.87 (s, 3H), 2.00-1.45 (m, 16H); $^{13}$C NMR (CDCl$_3$) δ 162.8, 162.8, 152.2, 151.6, 147.4, 147.3, 139.5, 137.2, 130.2, 129.9, 129.6, 129.3, 128.7, 128.5, 128.4, 123.0, 121.8, 118.4, 118.3, 116.1, 114.8, 111.3, 93.2, 92.7, 80.6, 56.0, 32.8, 32.7, 24.1, 24.0; Anal. Calcd. For $C_{21}H_{21}NO_2$: C, 78.97; H, 6.63; N, 4.39. Found: C, 78.85; H, 6.59; N, 4.31.

4.6.2.64 3-(3,4-Dimethoxy-phenyl)-3-(3,4,5-trimethoxy-phenyl)-acrylonitrile

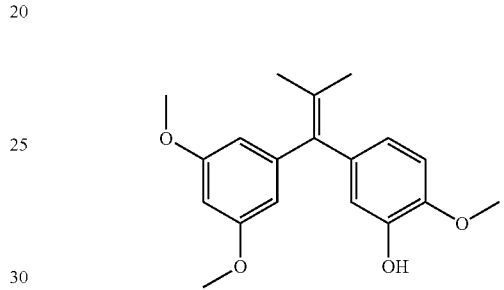

(3,4-Dimethoxy-phenyl)-(3,4,5-trimethoxy-phenyl)-methanone (3.3 g, 10 mmol), cyanomethylphosphonic acid diethyl ester (2.4 ml, 15 mmol) in anhydrous THF (50 ml), and potassium bis(trimethylsilyl)amide (3.0 g, 15 mmol) were treated in the same manner as described above for the synthesis of 3-(3,5-dimethoxy-phenyl)-3-(3-methoxy-phenyl)-acrylonitrile. The crude was purified by flash column chromatography to give 3-(3,4-dimethoxy-phenyl)-3-(3,4,5-trimethoxy-phenyl)-acrylonitrile as a solid (2.7 g, 77%): mp, 119-121° C.; $^1$H NMR (DMSO-d$_6$) 07.14-7.07 (m, 1H), 7.00-6.77 (m, 2H), 6.66 (d, J=3 Hz, 2H), 6.25 (s, 0.5H), 6.19 (s, 0.5H), 3.84-3.71 (m, 15H); $^{13}$C NMR (DMSO-d$_6$) 161.38, 161.31, 152.65, 150.99, 150.14, 148.64, 148.18, 139.44, 138.44, 133.69, 132.47, 130.01, 128.88, 122.66, 122.43, 118.66, 118.62, 112.75, 111.31, 111.22, 110.94, 106.88, 106.27, 94.23, 93.53, 60.08, 56.02, 55.98, 55.60, 55.55, 55.48; Anal. Calcd. For C20H21NO5: C, 67.59; H, 5.96; N, 3.94. Found: C, 67.66; H, 5.98; N, 3.88.

4.6.2.65 5-[1-(3,5-Dimethoxy-phenyl)-2-methyl-propenyl]-2-methoxy-phenol

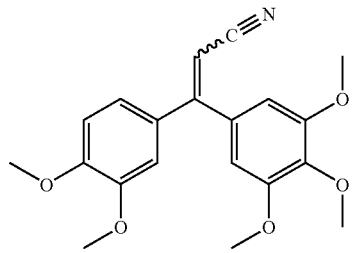

A solution of (5-bromo-2-methoxy-phenoxy)-tert-butyl-dimethyl-silane (12.7 g, 40.0 mmol) in THF (80 mL) was cooled to −78° C. under nitrogen, and a solution of t-butyl-lithium in pentane (51.7 mL, 1.7 M, 88.0 mmol) was added dropwise over the course of 1 h, maintaining the temperature below −70° C. throughout the addition. The mixture was stirred at −78° C. for 1 h following completion of the addition, and then a solution of 3,5-dimethoxybenzaldehyde (9.97 g, 60.0 mmol) in THF (10 mL) was added. The mixture was stirred for 1 h at −78° C., and was then quenched by the addition of 3 mL sat. NH$_4$Cl solution. The mixture was warmed to room temperature and evaporated under vacuum, and the residue was dissolved in CH$_2$Cl$_2$ (150 mL) and washed with water (3×150 mL), dried (MgSO$_4$), evaporated, and the residue was chromatographed using hexanes-ethyl acetate gradient, eluting [3-(tert-butyl-dimethyl-silanyloxy)-4-methoxy-phenyl]-(3,5-dimethoxy-phenyl)-methanol at 30:70 ethyl acetate-hexanes as an oil (13.1 g, 81% yield): $^1$H NMR (CDCl$_3$) δ 0.13 (s, 6H, 2SiCH$_3$), 0.97 (s, 9H, SiC(CH$_3$)$_3$), 2.15 (d, J=3.6 Hz, 1H, OH), 3.76 (s, 6H, 2OCH$_3$), 3.78 (s, 3H, OCH$_3$), 5.66 (d, J=3.6 Hz, 1H, CH), 6.35 (t, J=2.2 Hz, 1H, Ar), 6.53 (d, J=2.2 Hz, 2H, Ar), 6.79 (d, 1H, J=8.0 Hz, Ar), 6.87-6.90 (m, 2H, Ar).

To a solution of [3-(tert-butyl-dimethyl-silanyloxy)-4-methoxy-phenyl]-(3,5-dimethoxy-phenyl)-methanol (13.1 g, 32.4 mmol) in CH$_2$Cl$_2$ (330 mL) was added manganese dioxide (13.0 g, 150.0 mmol), and the mixture was stirred at ambient temperature for 8 h. Manganese dioxide (13.0 g, 150.0 mmol) was again added, and stirring proceeded for an additional 16 h. The mixture was filtered through Celite, and the sicciate was washed with CH$_2$Cl$_2$ (50 mL). The filtrate was evaporated, providing [3-(tert-butyl-dimethyl-silanyloxy)-4-methoxy-phenyl]-(3,5-dimethoxy-phenyl)-methanone as an oil (12.9 g, 99% yield): $^1$H NMR (CDCl$_3$) δ 0.18 (s, 6H, 2SiCH$_3$), 1.00 (s, 9H, SiC(CH$_3$)$_3$), 3.83 (s, 6H, 2OCH$_3$), 3.89 (s, 3H, OCH$_3$), 6.65 (t, J=2.4 Hz, 1H, Ar), 6.86-6.90 (m, 3H, Ar), 7.39-7.47 (m, 2H, Ar).

A suspension of isopropyltriphenylphosphonium iodide (2.60 g, 6.0 mmol) in THF (20 mL) was cooled to 0° C., and then a solution of lithium bis(trimethylsilyl)amide in THF (5.0 mL, 20%, 6.0 mmol) was added dropwise, over the course of 5 min. The mixture was stirred at 0° C. under nitrogen for 1 h, during which time a bright red solution formed. Then a solution of [3-(tert-butyl-dimethyl-silanyloxy)-4-methoxy-phenyl]-(3,5-dimethoxy-phenyl)-methanone (1.20 g, 3.0 mmol) in THF (20 mL) was added, and the resulting mixture was stirred at 0° C. for 30 min, and was then allowed to warm to ambient temperature. The mixture stirred at room temperature for 3 h to allow the reaction to proceed to completion. The reaction was quenched by the addition of 2 mL H$_2$O, and the solvent was removed under vacuum. The residue was dissolved in CH$_2$Cl$_2$ (75 mL) and washed with water (3×75 mL), dried (MgSO$_4$), and evaporated, and the residue was chromatographed using hexanes-ethyl acetate gradient, eluting the product at 10:90 ethyl acetate-hexanes as an oil (0.95 g, 74% yield). The above product (0.85 g, 2.05 mmol) was dissolved in THF (20 mL), and a solution of tetrabutylammonium fluoride (2.4 mL, 1.0 M, 2.4 mmol) was added. The resulting mixture was stirred at ambient temperature for 16 h. Water (20 mL) was added, and the mixture was extracted with diethyl ether (2×50 mL). The organic phases were washed with water (2×100 mL) dried (MgSO$_4$), and evaporated, and the residue was chromatographed using hexanes-ethyl acetate gradient, eluting 5-[1-(3,5-dimethoxyphenyl)-2-methyl-propenyl]-2-methoxy-phenol at 25:75 ethyl acetate-hexanes as an oil (0.6 g, 96% yield): $^1$H NMR (CDCl$_3$) δ 1.77 (s, 3H, =C—CH$_3$), 1.80 (s, 3H, =C—CH$_3$), 3.75 (s, 6H, 2OCH$_3$), 3.86(s, 3H, OCH$_3$), 5.53 (s, 1H, OH), 6.28-6.32 (m, 3H, Ar), 6.63 (dd, J=8.3, 2.0 Hz, 1H, Ar), 6.74-6.78 (m, 2H, Ar); $^{13}$C NMR (CDCl$_3$) δ 22.3, 22.5, 55.3, 55.9, 98.1, 107.9, 110.1, 116.0, 121.3, 130.7, 136.4, 136.5, 144.9, 145.6, 160.3; Anal. Calcd for C$_{19}$H$_{22}$O$_4$: C, 72.59; H, 7.05; N, 0.00. Found: C, 72.59; H, 7.10; N, <0.05.

4.6.2.66 5-[1-(3,5-Dimethoxy-phenyl)-vinyl]-2-methoxy-phenol

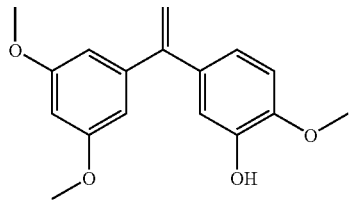

A suspension of methyltriphenylphosphonium bromide (2.14 g, 6.0 mmol) in THF (20 mL) was cooled to 0° C., and then a solution of lithium bis(trimethylsilyl)amide in THF (5.0 mL, 20%, 6.0 mmol) was added dropwise, over the course of 5 min. The mixture was stirred at 0° C. under nitrogen for 1 h, during which time a bright yellow solution formed. Then a solution of [3-(tert-butyl-dimethyl-silanyloxy)-4-methoxy-phenyl]-(3,5-dimethoxy-phenyl)-methanone (1.20 g, 3.0 mmol) in THF (20 mL) was added, and the resulting mixture was stirred at 0° C. for 30 min, and was then allowed to warm to ambient temperature. The reaction was quenched by the addition of 2 mL H$_2$O, and the solvent was removed under vacuum. The residue was dissolved in CH$_2$Cl$_2$ (75 mL) and washed with water (3×75 mL), dried (MgSO$_4$), and evaporated, and the residue was chromatographed using hexanes-ethyl acetate gradient, eluting the product at 10:90 ethyl acetate-hexanes as an oil (1.01 g, 84% yield).

The product from above (0.6 g, 1.5 mmol) was dissolved in THF (20 mL), and a solution of tetrabutylammonium fluoride (1.8 mL, 1.0 M, 1.8 mmol) was added. The resulting mixture was stirred at ambient temperature for 16 h. Water (20 mL) was added, and the mixture was extracted with diethyl ether (2×50 mL). The organic phases were washed with water (2×100 mL) dried (MgSO$_4$), and evaporated, and the residue was chromatographed using hexanes-ethyl acetate gradient, eluting 5-[1-(3,5-dimethoxy-phenyl)-vinyl]-2-methoxy-phenol at 25:75 ethyl acetate-hexanes as an oil (0.4 g, 93% yield): $^1$H NMR (CDCl$_3$) δ 3.78 (s, 6H, 2OCH$_3$), 3.88 (s, 3H, OCH$_3$), 5.36 (d, J=1.1, 1H, =CH), 5.41 (d, J=1.1 Hz, 1H, =CH), 5.72 (s, 1H, OH), 6.46 (t, J=2.1 Hz, 1H, Ar), 6.52 (d, J=2.1 Hz, 2H, Ar), 6.77-6.83 (m, 2H, Ar), 6.99 (d, J=2.0 Hz, 1H, Ar); $^{13}$C NMR (CDCl$_3$) δ 55.3, 55.9, 99.8, 106.7, 110.2, 113.3, 114.5, 120.2, 134.6, 143.9, 145.2, 146.4, 149.5, 160.5; Anal. Calcd for C$_{17}$H$_{18}$O$_4$+0.1H$_2$O: C, 70.87; H, 6.37; N, 0.00. Found: C, 70.77; H, 6.17; N, <0.05.

4.6.2.67 (E/Z) 5-[1-(3,5-Dimethoxy-phenyl)-propenyl]-2-methoxy-phenol

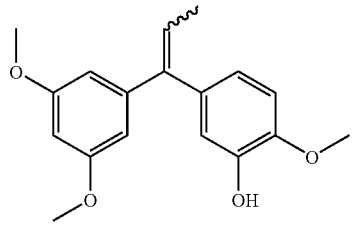

A suspension of ethyltriphenylphosphonium bromide (2.23 g, 6.0 mmol) in THF (20 mL) was cooled to 0° C., and then a solution of lithium bis(trimethylsilyl)amide in THF (5.0 mL, 20%, 6.0 mmol) was added dropwise, over the course of 5 min. The mixture was stirred at 0° C. under nitrogen for 1 h, during which time a bright orange solution formed. Then a solution of [3-(tert-butyl-dimethyl-silanyloxy)-4-methoxy-phenyl]-(3,5-dimethoxy-phenyl)-methanone (1.20 g, 3.0 mmol) in THF (20 mL) was added, and the resulting mixture was stirred at 0° C. for 30 min, and was then allowed to warm to ambient temperature. The reaction was quenched by the addition of 2 mL H$_2$O, and the solvent was removed under vacuum. The residue was dissolved in CH$_2$Cl$_2$ (75 mL) and washed with water (3×75 mL), dried (MgSO$_4$), and evaporated, and the residue was chromatographed using hexanes-ethyl acetate gradient, eluting the product at 10:90 ethyl acetate-hexanes as an oil (1.1 g, 89% yield).

The product from above (1.0 g, 2.4 mmol) was dissolved in THF (20 mL), and a solution of tetrabutylammonium fluoride (2.9 mL, 1.0 M, 2.9 mmol) was added. The resulting mixture was stirred at ambient temperature for 16 h. Water (20 mL) was added, and the mixture was extracted with diethyl ether (2×50 mL). The organic phases were washed with water (2×100 mL) dried (MgSO$_4$), and evaporated, and the residue was chromatographed using hexanes-ethyl acetate gradient, eluting (E/Z) 5-[1-(3,5-dimethoxy-phenyl)-propenyl]-2-methoxy-phenol at 25:75 ethyl acetate-hexanes as an oil (0.7 g, 97% yield): $^1$H NMR (CDCl$_3$) δ 1.71-1.78 (m, 3H, =C—CH$_3$), 3.75-3.91 (m, 9H, 2OCH$_3$), 5.50-5.57 (m, 1H, OH), 6.05-6.13 (m, 1H, =CH), 6.31-6.41 (m, 3H, Ar), 6.63-

6.77 (m, 2H, Ar), 6.82-6.88 (m, 1H, Ar); $^{13}$C NMR (CDCl$_3$) δ 15.6, 15.7, 55.3, 55.9, 56.0, 98.7, 99.0, 105.7, 108.0, 110.2, 110.3, 113.2, 116.3, 118.8, 121.8, 122.7, 124.2, 133.1, 136.1, 141.9, 142.2, 145.1, 145.4, 145.4, 145.6, 160.4, 160.6; Anal. Calcd for C$_{18}$H$_{20}$O$_4$: C, 71.98; H, 6.71; N, 0.00. Found: C, 71.72; H, 6.48; N, <0.05.

4.6.2.68 5-[1-(3-Ethoxy-4-methoxy-phenyl)-vinyl]-2-methoxy-phenol

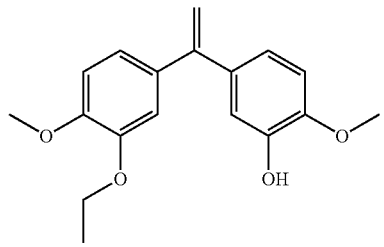

A solution of (5-bromo-2-methoxy-phenoxy)-tert-butyl-dimethyl-silane (6.3 g, 19.9 mmol) in THF (50 mL) was cooled to −78° C. under nitrogen, and a solution of t-butyl-lithium in pentane (26.0 mL, 1.7 M, 44.0 mmol) was added dropwise over the course of 1 h, maintaining the temperature below −70° C. throughout the addition. The mixture was stirred at −78° C. for 1 h following completion of the addition, and then a solution of 3-ethoxy-4-methoxybenzaldehyde (5.4 g, 30.0 mmol) in THF (10 mL) was added. The mixture was stirred for 1 h at −78° C., and was then quenched by the addition of 2 mL sat. NH$_4$Cl solution. The mixture was warmed to room temperature and evaporated under vacuum, and the residue was dissolved in CH$_2$Cl$_2$ (200 mL) and washed with water (3×200 mL), dried (MgSO$_4$), and evaporated, and the residue was chromatographed using hexanes-ethyl acetate gradient, eluting [3-(tert-butyl-dimethyl-silanyloxy)-4-methoxy-phenyl]-(3-ethoxy-4-methoxy-phenyl)-methanol at 25:75 ethyl acetate-hexanes as an oil (6.7 g, 81% yield): $^1$H NMR (CDCl$_3$) δ 0.13 (s, 6H, 2SiCH$_3$), 0.97 (s, 9H, SiC(CH$_3$)$_3$), 1.43 (t, J=6.9 Hz, 3H, OCH$_2$CH$_3$), 2.11 (d, J=3.5 Hz, 1H, OH), 3.79 (s, 3H, OCH$_3$), 3.85 (s, 3H, OCH$_3$), 4.05 (q, J=6.9 Hz, 2H, OCH$_2$CH$_3$), 5.69 (d, J=3.5 Hz, 1H, CH), 6.81-6.90 (m, 6H, Ar).

To a solution of [3-(tert-butyl-dimethyl-silanyloxy)-4-methoxy-phenyl]-(3-ethoxy-4-methoxy-phenyl)-methanol (6.5 g, 15.6 mmol) in CH$_2$Cl$_2$ (200 mL) was added manganese dioxide (2.65 g, 26.1 mmol), and the mixture was stirred at ambient temperature for 16 h. Manganese dioxide (2.65 g, 26.1 mmol) was again added, and stirring proceeded for an additional 7 h. The mixture was filtered through Celite, and the sicciate was washed with CH$_2$Cl$_2$ (50 mL). The filtrate was evaporated, providing [3-(tert-butyl-dimethyl-silanyloxy)-4-methoxy-phenyl]-(3-ethoxy-4-methoxy-phenyl)-methanone as an oil (6.2 g, 96% yield): $^1$H NMR (CDCl$_3$) δ 0.17 (s, 6H, 2SiCH$_3$), 1.00 (s, 9H, SiC(CH$_3$)$_3$), 1.49 (t, J=7.0 Hz, 3H, OCH$_2$CH$_3$), 3.89 (s, 3H, OCH$_3$), 3.95 (s, 3H, OCH$_3$), 4.16 (q, J=7.0 Hz, 2H, OCH$_2$CH$_3$), 6.87-6.92 (m, 2H, Ar), 7.33-7.43 (m, 4H, Ar).

A suspension of methyltriphenylphosphonium bromide (2.14 g, 6.0 mmol) in THF (20 mL) was cooled to 0° C., and then a solution of lithium bis(trimethylsilyl)amide in THF (5.0 mL, 20%, 6.0 mmol) was added dropwise, over the course of 5 min. The mixture was stirred at 0° C. under nitrogen for 1 h, during which time a bright yellow solution formed. Then a solution of [3-(tert-butyl-dimethyl-silanyloxy)-4-methoxy-phenyl]-(3-ethoxy-4-methoxy-phenyl)-methanone (1.25 g, 3.0 mmol) in THF (20 mL) was added, and the resulting mixture was stirred at 0° C. for 30 min, and was then allowed to warm to ambient temperature. The reaction was quenched by the addition of 2 mL H$_2$O, and the solvent was removed under vacuum. The residue was dissolved in CH$_2$Cl$_2$ (75 mL) and washed with water (3×75 mL), dried (MgSO$_4$), and evaporated, and the residue was chromatographed using hexanes-ethyl acetate gradient, eluting the product at 10:90 ethyl acetate-hexanes as an oil, (1.1 g, 88% yield). The above product (1.1 g, 2.7 mmol) was dissolved in THF (20 mL), and a solution of tetrabutylammonium fluoride (3.3 mL, 1.0 M, 3.3 mmol) was added. The resulting mixture was stirred at ambient temperature for 16 h. Water (20 mL) was added, and the mixture was extracted with diethyl ether (2×50 mL). The organic phases were washed with water (2×100 mL) dried (MgSO$_4$), and evaporated, and the residue was chromatographed using hexanes-ethyl acetate gradient, eluting 5-[1-(3-ethoxy-4-methoxy-phenyl)-vinyl]-2-methoxy-phenol at 30:70 ethyl acetate-hexanes (0.65 g, 83% yield): mp 99-101° C.; $^1$H NMR (CDCl$_3$) δ 1.42 (t, J=7.0 Hz, 3H, OCH$_2$CH$_3$), 3.89 (s, 3H, OCH$_3$), 3.91 (s, 3H, OCH$_3$), 4.06 (q, J=7.0 Hz, 2H, OCH$_2$CH$_3$), 5.29 (d, J=1.2 Hz, 1H, =CH), 5.32 (d, J=1.2 Hz, 1H, =CH), 5.60 (s, 1H, OH), 6.78-6.98 (m, 6H, Ar); $^{13}$C NMR (CDCl$_3$) δ 14.8, 55.9, 56.0, 64.3, 110.1, 111.0, 112.1, 113.1, 114.6, 120.2, 121.0, 134.5, 135.2, 145.2, 145.3, 147.8, 149.1, 149.2; Anal. Calcd for C$_{18}$H$_{20}$O$_4$: C, 71.98; H, 6.71; N, 0.00. Found: C, 71.90; H, 6.74; N, <0.05.

4.6.2.69 (E/Z) 3-(3-Ethoxy-4-methoxy-phenyl)-3-(3-hydroxy-4-methoxy-phenyl)-acrylonitrile

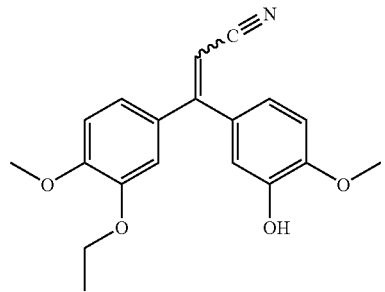

A solution of diethyl(cyanomethyl)phosphonate (0.53 g, 3.0 mmol) in THF (20 mL) was cooled to 0° C., and then a solution of lithium bis(trimethylsilyl)amide in THF (2.5 mL, 20%, 3.0 mmol) was added dropwise, over the course of 5 min. The mixture was stirred at 0° C. under nitrogen for 1 h. Then a solution of [3-(tert-butyl-dimethyl-silanyloxy)-4-methoxy-phenyl]-(3-ethoxy-4-methoxy-phenyl)-methanone (0.63 g, 1.5 mmol) in THF (20 mL) was added, and the resulting mixture was stirred at 0° C. for 30 min, and was then allowed to warm to ambient temperature, and was then heated to reflux with stirring for 4 h. The reaction was quenched by the addition of 2 mL H$_2$O, and the solvent was removed under vacuum. The residue was dissolved in CH$_2$Cl$_2$ (75 mL) and washed with water (3×75 mL), dried (MgSO$_4$), and evaporated, and the residue was chromatographed using hexanes-ethyl acetate gradient, eluting the product at 20:80 ethyl acetate-hexanes as an oil (0.61 g, 93% yield).

The product from above (0.61 g, 1.4 mmol) was dissolved in THF (20 mL), and a solution of tetrabutylammonium fluoride (1.7 mL, 1.0 M, 1.7 mmol) was added. The resulting mixture was stirred at ambient temperature for 16 h. Water (20 mL) was added, and the mixture was extracted with diethyl ether (2×50 mL). The organic phases were washed with water (2×100 mL) dried (MgSO$_4$), and evaporated, and the residue was chromatographed using hexanes-ethyl acetate gradient, eluting (E/Z) 3-(3-ethoxy-4-methoxy-phenyl)-3-(3-hydroxy-4-methoxy-phenyl)-acrylonitrile at 40:60 ethyl acetate-hexanes (0.4 g, 89% yield): mp 63-65° C.; $^1$H NMR (CDCl$_3$) δ 1.40-1.47 (m, 3H, OCH$_2$CH$_3$), 3.89-3.94 (m, 6H, 2OCH$_3$), 3.98-4.12 (m, 2H, OCH$_2$CH$_3$), 5.53-5.55 (m, 1H, =CH), 5.68 (m, OH), 6.80-7.09 (m, 6H, Ar); $^{13}$C NMR (CDCl$_3$) δ 14.7, 55.9, 56.0, 64.5, 92.0, 110.2, 111.0, 112.8, 114.1, 114.7, 116.0, 118.6, 118.7, 121.4, 122.1, 122.2, 123.1, 129.5, 130.4, 131.7, 132.5, 145.3, 145.5, 145.5, 147.9, 148.0, 148.1, 148.4, 150.8, 151.4, 162.4; Anal. Calcd for C$_{19}$H$_{19}$NO$_4$: C, 70.14; H, 5.89; N, 4.31. Found: C, 69.93; H, 5.84; N, 4.06.

4.6.2.70 5-[1-(3-Ethoxy-4-methoxy-phenyl)-2,2-difluoro-vinyl]-2-methoxy-phenol

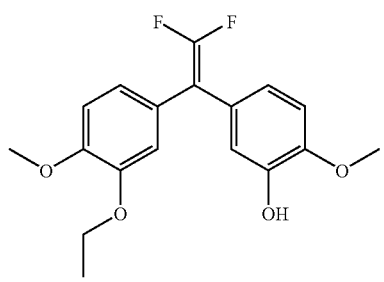

A solution of diethyl(difluoromethyl)phosphonate (1.13 g, 6.0 mmol) in THF (20 mL) was cooled to −78° C., and then a solution of lithium bis(trimethylsilyl)amide in THF (5.0 mL, 20%, 6.0 mmol) was added dropwise, over the course of 5 min. The mixture was stirred at −78° C. under nitrogen for 30 min. Then a solution of [3-(tert-butyl-dimethyl-silanyloxy)-4-methoxy-phenyl]-(3-ethoxy-4-methoxy-phenyl)-methanone (1.25 g, 3.0 mmol) in THF (20 mL) was added. After 15 min, the reaction flask was removed from the cooling bath and was heated to reflux for 1 h, and was then cooled to room temperature. The reaction was quenched by the addition of 2 mL H$_2$O, and the solvent was removed under vacuum. The residue was dissolved in CH$_2$Cl$_2$ (75 mL) and washed with water (3×75 mL), dried (MgSO$_4$), and evaporated, and the residue was chromatographed using hexanes-ethyl acetate gradient, eluting the product at 20:80 ethyl acetate-hexanes as an oil (0.84 g, 62% yield).

The product from above (0.80 g, 1.8 mmol) was dissolved in THF (20 mL), and a solution of tetrabutylammonium fluoride (2.2 mL, 1.0 M, 2.2 mmol) was added. The resulting mixture was stirred at ambient temperature for 16 h. Water (20 mL) was added, and the mixture was extracted with diethyl ether (2×50 mL). The organic phases were washed with water (2×100 mL) dried (MgSO$_4$), and evaporated, and the residue was chromatographed using hexanes-ethyl acetate gradient, eluting 5-[1-(3-ethoxy-4-methoxy-phenyl)-2,2-difluoro-vinyl]-2-methoxy-phenol at 30:70 ethyl acetate-hexanes (0.5 g, 83% yield): mp 74-76° C.; $^1$H NMR (CDCl$_3$) δ 1.43 (t, J=7.0 Hz, 3H, OCH$_2$CH$_3$), 3.88 (s, 3H, OCH$_3$), 3.90 (s, 3H, OCH$_3$), 4.03 (q, J=7.0 Hz, 2H, OCH$_2$CH$_3$), 5.57 (s, 1H, OH), 6.74-6.86 (m, 6H, Ar); $^{13}$C NMR (CDCl$_3$) δ 14.7, 55.9, 64.3, 110.3, 111.2, 114.3, 115.7, 115.8, 121.4, 121.5, 121.5, 122.2, 122.3, 122.3, 1.26.8, 145.3, 145.9, 148.0, 148.7, 153.5; Anal. Calcd for C$_{18}$H$_{18}$F$_2$O$_4$: C, 64.28; H, 5.39; N, 0.00. Found: C, 64.27; H, 5.46; N, <0.05.

4.6.2.71 (E/Z) 2-Amino-N-{5-[2-cyano-1-(3-ethoxy-4-methoxy-phenyl)-vinyl]-2-methoxy-phenyl}-acetamide; Hydrochloride

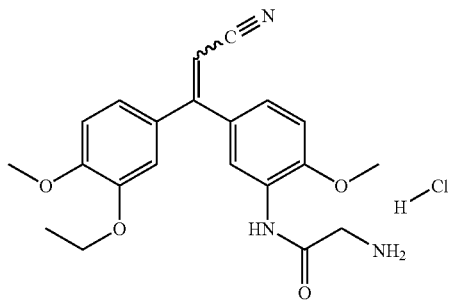

Grignard reagent was prepared in an oven-dried three necked flask outfitted with a reflux condenser, dropping funnel, and magnetic stirrer. Approximately ¼ of a solution of (3-ethoxy-4-methoxy-bromo)-benzene (10 g, 43.3 mmol) in anhydrous THF (60 mL) was added to a mixture of magnesium turnings (1.05 g, 43.3 mmol) in THF (10 mL) with a small piece of iodine. As soon as the solution became colorless (heating sometimes necessary), the remaining (3-ethoxy-4-methoxy-bromo)-benzene solution was added dropwise to the reaction mixture under mild reflux, over 30 min. The resulting mixture was refluxed for 3 h then cooled to room temperature for 30 min. The (3-ethoxy-4-methoxy-phenyl) magnesium bromide was then added slowly to a stirred solution of 4-methoxy-3-nitro-benzaldehyde (6.53 g, 36.1 mmol) in THF (60 mL) at 0° C. After complete addition, the reaction mixture was stirred at cold for 10 min and then at room temperature for 2 h. The solution was cooled to 0° C. and quenched with saturated NH$_4$Cl solution (90 mL). The aqueous layer was extracted with ether (3×90 mL). The combined organic layers were washed with water (2×120 mL), brine (120 mL) and dried (MgSO$_4$). Removal of solvent gave the crude (3-ethoxy-4-methoxy-phenyl)-(4-methoxy-3-nitrophenyl)-methanol, which was used in the next step without further purification.

MnO$_2$ (18 g, 210 mmol, 5 equivalent) was added to a stirred solution of the crude (3-ethoxy-4-methoxy-phenyl)-(4-methoxy-3-nitro-phenyl)-methanol in CH$_2$Cl$_2$ (100 mL). The reaction mixture was stirred at room temperature for 2 days and MnO$_2$ [6 equivalent (3×2 eq.)] was added during this period of time. The reaction mixture was then filtered through celite and washed with CH$_2$Cl$_2$ (3×60 mL). Removal of solvent from the filtrate and chromatography (Silica Gel) gave (3-ethoxy-4-methoxy-phenyl)-(4-methoxy-3-nitro-phenyl)-methanone as a solid (8.74 g, 73% yield): $^1$H NMR (CDCl$_3$) δ 1.47-1.53 (t, J=7.1 Hz, 3H, CH$_3$), 3.97 (s, 3H, OCH$_3$), 4.06 (s, 3H, OCH$_3$), 4.13-4.21 (q, J=6.9, 14.0 Hz, 2H, CH$_2$), 6.91-6.94 (d, J=8.3 Hz, 1H, Ar), 7.17-7.21 (d, J=8.7 Hz, 1H, Ar), 7.30-7.35 (dd, J=2.1, 8.5 Hz, 1H, Ar), 7.42 (d, J=1.9 Hz, 1H, Ar), 8.03-8.07 (dd, J=2.3, 8.7 Hz, 1H, Ar), 8.29 (d, J=2.0 Hz, 1H, Ar).

Lithium bis(trimethylsilyl)amide (11.4 mL, 11.4 mmol) was added dropwise to a stirred solution of diethylcyanomethyl phosphonate (2.03 g, 11.4 mmol) in anhydrous THF (20 mL) at 0° C. After 10 min at cold, the reaction mixture was stirred at room temperature for 40 min. The Wittig reagent was then added dropwise to a stirred suspension of (3-ethoxy-4-methoxy-phenyl)-(4-methoxy-3-nitro-phenyl)-methanone (3.16 g, 9.5 mmol) in THF (30 mL) at 0° C. The reaction mixture was stirred at room temperature overnight. The solution was poured into ice water (100 mL) and extracted with CH$_2$Cl$_2$ (3×50 mL). The combined organic layers were washed with water (2×40 mL), brine (40 mL) and dried (MgSO$_4$). Removal of solvent and chromatography (Silica Gel) gave a mixture of (E/Z) 3-(3-ethoxy-4-methoxy-phenyl)-3-(4-methoxy-3-nitro-phenyl)-acrylonitrile as a solid (3.01 g, 89% yield): $^1$H NMR (CDCl$_3$) δ 1.43-1.49 (m, 6H, 2CH$_3$), 3.92-3.94 (2s, 6H, 2OCH$_3$), 4.01-4.04 (2s, 6H, 2OCH$_3$), 4.00-4.13 (m, 4H, 2CH$_2$), 5.59-5.67 (2s, 2H, 2CH), 6.78-7.85 (m, 12H, Ar).

SnCl$_2$.2H$_2$O (22.83 g, 101.2 mmol) was added to a stirred suspension of (E/Z) 3-(3-ethoxy-4-methoxy-phenyl)-3-(4-methoxy-3-nitro-phenyl) -acrylonitrile (6.52 g, 18.4 mmol) in ethanol (200 proof, 60 mL) and ethyl acetate (30 mL). The reaction mixture was heated at 70° C. for 1 h. The solution was cooled down to room temperature, poured into ice (170 g), and basified with 10 N NaOH (75 mL) to pH ~12. The aqueous layer was extracted with ethyl acetate (5×60 mL). The combined organic layers were washed with water (60 mL), brine (50 mL) and dried (MgSO$_4$). Removal of solvent and chromatography (Silica Gel) gave a mixture of (E/Z) 3-(3-amino-4-methoxy-phenyl)-3-(3-ethoxy-4-methoxy-phenyl)-acrylonitrile as a solid (4.39 g, 74% yield): $^1$H NMR (CDCl$_3$) δ 1.41-1.48 (m, 6H, 2CH$_3$), 3.85-3.92 (m, 16H, 4OCH$_3$+2NH$_2$), 3.98-4.12 (m, 4H, 2CH$_2$), 5.50-5.51 (2s, 2H, 2CH), 6.65-7.04 (m, 12H, Ar); $^{13}$C NMR (CDCl$_3$) δ 14.65, 55.49, 55.56, 55.93, 55.98, 64.46, 91.34, 91.40, 109.77, 110.86, 112.91, 114.17, 114.63, 115.96, 118.80, 118.88, 119.60, 120.68, 122.08, 123.04, 129.77, 129.86, 132.08, 135.92, 136.09, 147.77, 147.99, 148.67, 149.10, 150.65, 151.19, 162.94.

A mixture of (E/Z) 3-(3-amino-4-methoxy-phenyl)-3-(3-ethoxy-4-methoxy-phenyl)-acrylonitrile (1.50 g, 4.6 mmol), 1,3-dicyclohexylcarbodiimide (1.14 g, 5.6 mmol) and 1-hydroxybenzotriazole (0.94 g, 6.9 mmol) in dry DMF (30 mL) was stirred at room temperature for 5 min. N-BOC-glycine (0.97 g, 5.6 mmol) was then added in solid form. The reaction mixture was stirred at room temperature overnight. Ethyl acetate (30 mL) was added and the mixture was filtered. The filtrate was concentrated and the residue was dissolved in ethyl acetate (120 mL). The organic layer was washed with water (5×60 mL), brine (60 mL) and dried (MgSO$_4$). Removal of solvent and chromatography (Silica Gel) gave a mixture of (E/Z) ({5-[2-cyano-1-(3-ethoxy-4-methoxy-phenyl)-vinyl]-2-methoxy-phenylcarbamoyl}-methyl)-carbamic acid tert-butyl ester as a solid (1.83 g, 82% yield): $^1$H NMR (CDCl$_3$) δ 1.40-1.48 (m, 24H, 8CH$_3$), 3.89-4.10 (m, 20H, 4OCH$_3$+4CH$_2$), 5.20 (bp, 2H, 2NH), 5.58-5.59 (2s, 2H, 2CH), 6.80-7.27 (m, 12H, Ar), 8.37-8.38 (bp, 2H, 2NH); $^{13}$C NMR (CDCl$_3$) δ 14.69, 28.28, 55.90, 55.97, 64.51, 92.32, 92.51, 109.64, 109.71, 111.00, 112.74, 114.16, 118.54, 119.61, 121.17, 122.18, 123.05, 125.26, 125.82, 130.00, 131.45, 132.17, 148.16, 149.20, 151.47, 162.54, 167.45.

2 N HCl in Ether (11.4 mL, 22.8 mmol) was added to a stirred solution of (E/Z) ({5-[2-cyano-1-(3-ethoxy-4-methoxy-phenyl)-vinyl]-2-methoxy-phenylcarbamoyl}-methyl)-carbamic acid tert-butyl ester (1.83 g, 3.8 mmol) in CH$_2$Cl$_2$ (40 mL). The reaction mixture was stirred at room temperature for 2 days. Ether (50 mL) was added and the mixture was stirred for 1 h. Filtration and washing with ether (10 mL) gave a mixture of (E/Z) 2-amino-N-{3-[2-cyano-1-(3-ethoxy-4-methoxy-phenyl)-vinyl]-phenyl}-acetamide; hydrochloride as a solid (1.41 g, 89% yield): mp, 161-163° C.; $^1$H NMR (DMSO-d$_6$) δ 1.28-1.34 (t, J=7.0 Hz, 6H, 2CH$_3$), 3.79-4.04 (m, 20H, 4OCH$_3$+4CH$_2$), 6.02-6.16 (2s, 2H, 2CH), 6.74-8.01 (m, 12H, Ar), 8.24 (bp, 6H, 2{NH$_2$.HCl}); $^3$CNMR (DMSO-d$_6$) δ 14.61, 14.63, 40.91, 40.99, 55.51, 55.59, 55.98, 56.07, 63.76, 63.81, 92.83, 92.96, 111.19, 111.35, 111.48, 112.23, 113.74, 118.70, 118.75, 122.23, 122.38, 122.48, 125.27, 126.24, 126.31, 129.11, 129.22, 130.46, 130.52, 147.38, 147.81, 150.16, 150.45, 151.05, 151.43, 161.12, 161.39, 165.33; Anal. Calcd for C$_{21}$H$_{24}$N$_3$O$_4$Cl+0.09H$_2$O: C, 60.12; H, 5.81; N, 10.02; Cl, 8.45. Found: C, 59.93; H, 5.67; N, 10.07; Cl, 8.44.

4.6.2.72 (E/Z) 1-Benzenesulfonyl-3-{5-[2-cyano-1-(3-ethoxy-4-methoxy-phenyl)-vinyl]-2-methoxy-phenyl}-urea

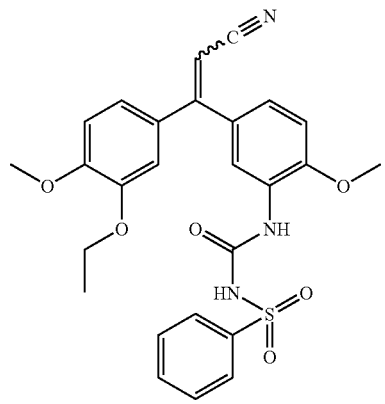

Benzenesulfonyl isocyanate (0.4 mL, 2.6 mmol) was added to a stirred solution of (E/Z) 3-(3-amino-4-methoxy-phenyl)-3-(3-ethoxy-4-methoxy-phenyl)-acrylonitrile (0.70 g, 2.2 mmol) in anhydrous THF (25 mL). The reaction mixture was stirred at room temperature for 2 h. Removal of solvent and chromatography (Silica Gel) gave a mixture of (E/Z) 1-benzenesulfonyl-3-{5-[2-cyano-1-(3-ethoxy-4-methoxy-phenyl)-vinyl]-2-methoxy-phenyl}-urea as a solid (0.66 g, 61% yield): mp, 168-170° C.; $^1$H NMR (CDCl$_3$) δ 1.38-1.46 (m, 6H, 2CH$_3$), 3.87-4.14 (m, 16H, 4OCH$_3$+2CH$_2$), 5.55-5.58 (2s, 2H, 2CH), 6.78-7.98 (m, 22H, Ar), 8.03-9.06 (m, 4H, 4NH); $^{13}$C NMR (CDCl$_3$) δ 14.67, 55.92, 55.97, 56.06, 56.24, 64.53, 92.07, 92.54, 109.82, 109.88, 110.99, 111.07, 112.65, 114.13, 118.58, 118.78, 119.77, 121.04, 122.25, 123.07, 125.52, 125.98, 126.56, 126.80, 127.02, 127.11, 129.35, 129.45, 129.50, 129.87, 131.16, 132.15, 133.96, 134.05, 139.46, 147.88, 148.19, 149.75, 150.25, 150.85, 151.59, 162.14, 162.83; Anal. Calcd for C$_{26}$H$_{25}$N$_3$O$_6$S+0.12H$_2$O: C, 61.27; H, 4.99; N, 8.24; S, 6.29. Found: C, 60.90; H, 5.04; N, 8.05; S, 6.28.

4.6.2.73 (E/Z) 3-{5-[2-Cyano-1-(3-ethoxy-4-methoxy-phenyl)-vinyl]-2-methoxy-phenyl}-1,1-dimethyl-urea

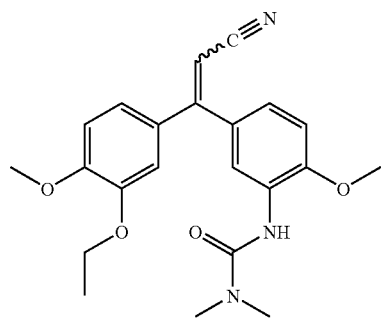

N,N-diisopropylethylamine (1.5 mL, 8.6 mmol) was added to a mixture of (E/Z) 3-(3-amino-4-methoxy-phenyl)-3-(3-ethoxy-4-methoxy-phenyl)-acrylonitrile (0.70 g, 2.2 mmol) and dimethylcarbamyl chloride (1.6 mL, 17.3 mmol). The reaction mixture was heated at 85° C. for 3 h. CH$_2$Cl$_2$ (100 ml) was added and the mixture was extracted with water (2×50 mL), 4 N HCl (2×50 mL), water (2×50 mL), saturated NaHCO$_3$ (2×50 mL), brine (50 mL) and dried (MgSO$_4$). Removal of solvent and chromatography (Silica Gel) gave a mixture of (E/Z) 3-{5-[2-cyano-1-(3-ethoxy-4-methoxy-phenyl)-vinyl]-2-methoxy-phenyl}-1,1-dimethyl-urea as a solid (0.59 g, 69% yield): mp, 143-145° C.; $^1$H NMR (CDCl$_3$) δ 1.40-1.47 (m, 6H, 2CH$_3$), 3.02-3.05 (2s, 12H, 4CH$_3$), 3.88-3.94 (3s, 12H, 4OCH$_3$), 3.99-4.12 (m, 4H, 2CH$_2$), 5.55-5.61 (2s, 2H, 2CH), 6.79-7.18 (m, 12H, Ar), 8.18-8.36 (m, 2H, 2NH); $^{13}$C NMR (CDCl$_3$) δ 14.71, 36.33, 55.93, 56.00, 64.46, 92.06, 92.33, 109.21, 109.30, 110.93, 110.99, 112.74, 114.22, 118.56, 118.69, 118.79, 120.27, 122.25, 123.06, 123.41, 123.74, 128.97, 129.24, 129.73, 130.11, 131.68, 132.25, 147.83, 148.14, 148.81, 149.27, 150.68, 151.37, 155.22, 155.31, 162.66, 163.11; Anal. Calcd for C$_{22}$H$_{25}$N$_3$O$_4$: C, 66.82; H, 6.37; N, 10.63. Found: C, 66.84; H, 6.48; N, 10.43.

4.6.2.74 5-[1-(3,5-Dimethoxy-phenyl)-vinyl]-2-methoxy-phenylamine

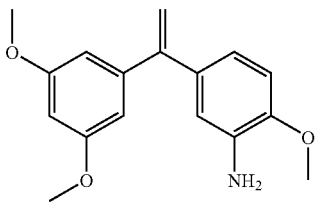

Grignard reagent was prepared in an oven-dried three necked flask outfitted with a reflux condenser, dropping funnel, and magnetic stirrer. Approximately ¼ of a solution of 3,5-bromoveratrole (10 g, 46.1 mmol) in anhydrous THF (60 mL) was added to a mixture of magnesium turnings (1.12 g, 46.1 mmol) in THF (10 mL) with a small piece of iodine. As soon as the solution became colorless (heating sometimes necessary), the remaining 3,5-bromoveratrole solution was added dropwise to the reaction mixture under mild reflux, over 30 min. The resulting mixture was refluxed for 3 h then cooled to room temperature for 30 min. The (3,5-dimethoxy-phenyl) magnesium bromide was then added slowly to a stirred solution of 4-methoxy-3-nitro-benzaldehyde (6.95 g, 38.4 mmol) in THF (60 mL) at 0° C. After complete addition, the reaction mixture was stirred at cold for 10 min and then at room temperature for 2 h. The solution was cooled to 0° C. and quenched with saturated NH$_4$Cl solution (90 mL). The aqueous layer was extracted with ether (3×90 mL). The combined organic layers were washed with water (2×120 mL), brine (120 mL) and dried (MgSO$_4$). Removal of solvent gave the crude (3,5-dimethoxy-phenyl)-(4-methoxy-3-nitro-phenyl)-methanol, which was used in the next step without further purification.

MnO$_2$ (20 g, 231 mmol, 5 equivalent) was added to a stirred solution of the crude (3,5-dimethoxy-phenyl)-(4-methoxy-3-nitro-phenyl)-methanol in CH$_2$Cl$_2$ (100 mL). The reaction mixture was stirred at room temperature for 2 days and MnO$_2$ [6 equivalent (3×2 eq.)] was added during this period of time. The reaction mixture was then filtered through celite and washed with CH$_2$Cl$_2$ (3×60 mL). Removal of solvent from the filtrate and chromatography (Silica Gel) gave (3,5-dimethoxy-phenyl)-(4-methoxy-3-nitro-phenyl)-methanone as a solid (9.61 g, 79% yield): $^1$H NMR (CDCl$_3$) δ 3.83 (s, 6H, 2OCH$_3$), 4.06 (s, 3H, OCH$_3$), 6.68-6.70 (t, J=2.2 Hz, 1H, Ar), 6.85-6.86 (d, J=2.3 Hz, 2H, Ar), 7.16-7.20 (d, J=8.9 Hz, 1H, Ar), 8.06-8.10 (dd, J=2.3 and 8.9 Hz, 1H, Ar), 8.33-8.34 (d, J=2.1 Hz, 1H, Ar); $^{13}$C NMR (CDCl$_3$) δ 55.64, 56.91, 104.96, 107.57, 113.10, 127.86, 129.69, 135.78, 138.66, 139.20, 155.85, 160.79, 193.07.

Lithium bis(trimethylsilyl)amide (5.3 mL, 5.3 mmol) was added dropwise to a stirred suspension of triphenylmethylphosphonium bromide (1.89 g, 5.3 mmol) in anhydrous THF (30 mL) at 0° C. After 10 min at cold, the reaction mixture was stirred at room temperature for 40 min. The Wittig reagent was then added dropwise to a stirred solution of (3,5-dimethoxy-phenyl)-(4-methoxy-3-nitro-phenyl)-methanone (1.40 g, 4.4 mmol) in THF (30 mL) at 0° C. The reaction mixture was stirred at room temperature for 2 h. The solution was poured into ice water (100 mL) and extracted with CH$_2$Cl$_2$ (4×40 mL). The combined organic layers were washed with water (2×40 mL), brine (40 mL) and dried (MgSO$_4$). Removal of solvent and chromatography (Silica Gel) gave 3-(3,5-dimethoxy-phenyl)-3-(4-methoxy-3-nitrophenyl)-acrylonitrile as a solid (1.15 g, 83% yield): $^1$H NMR (CDCl$_3$) δ 3.78 (s, 6H, 2OCH$_3$), 3.98 (s, 3H, OCH$_3$), 5.46-5.47 (d, J=4.3 Hz, 2H, CH$_2$), 6.43-6.47 (m, 3H, Ar), 7.02-7.06 (d, J=8.8 Hz, 1H, Ar), 7.48-7.52 (dd, J=2.4, 8.8 Hz, 1H, Ar), 7.85-7.86 (d, J=2.4 Hz, 1H, Ar); $^3$C NMR (CDCl$_3$) δ 55.39, 56.62, 100.13, 106.53, 113.18, 115.08, 125.10, 133.67, 133.86, 139.49, 142.53, 147.51, 152.41, 160.75.

SnCl$_2$.2H$_2$O (4.41 g, 19.54 mmol) was added to a stirred suspension of 3-(3,5-dimethoxy-phenyl)-3-(4-methoxy-3-nitro-phenyl)-acrylonitrile (1.12 g, 3.55 mmol) in ethanol (200 proof, 20 mL) and ethyl acetate (10 mL). The reaction mixture was heated at 70° C. for 1 h. The solution was cooled down to room temperature, poured into ice water (100 mL), and basified with 10 N NaOH (20 mL) to pH ~12. The aqueous layer was extracted with ethyl acetate (5×35 mL). The combined organic layers were washed with water (60 mL), brine (50 mL) and dried (MgSO$_4$). Removal of solvent and chromatography (Silica Gel) gave 5-[1-(3,5-dimethoxy-phenyl)-vinyl]-2-methoxy-phenylamine as a solid (0.64 g, 63% yield): mp, 93-95° C.; $^1$H NMR (CDCl$_3$) δ 3.77-3.87 (2s+m, 11H, 3OCH$_3$+NH$_2$), 5.31-5.37 (dd, J=1.2, 13.1 Hz, 2H, CH$_2$), 6.43-6.73 (m, 6H, Ar); $^{13}$C NMR (CDCl$_3$) δ 55.36, 55.53, 99.77, 106.69, 109.92, 112.80, 1.14.92, 118.62, 134.13, 135.63, 144.19, 147.21, 149.86, 160.40; Anal. Calcd for C$_{17}$H$_{19}$NO$_3$: C, 71.56; H, 6.71; N, 4.91. Found: C, 71.31; H, 6.76; N, 4.92.

4.6.2.75 (E/Z) 5-[1-(3-Ethoxy-4-methoxy-phenyl)-propenyl]-2-methoxy-phenylamine

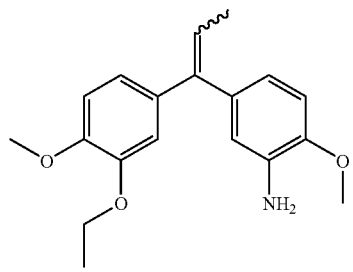

Lithium bis(trimethylsilyl)amide (8.5 mL, 8.5 mmol) was added dropwise to a stirred suspension of (ethyl)triphenylphosphonium bromide (3.14 g, 8.5 mmol) in anhydrous THF (30 mL) at 0° C. After 10 min at cold, the reaction mixture was stirred at room temperature for 40 min. The Wittig reagent was then added dropwise to a stirred suspension of (3-ethoxy-4-methoxy-phenyl)-(4-methoxy-3-nitrophenyl)-methanone (1.40 g, 4.2 mmol) in THF (30 mL) at 0° C. The reaction mixture was stirred at room temperature for 2 h. The solution was poured into ice water (100 mL) and extracted with $CH_2Cl_2$ (4×40 mL). The combined organic layers were washed with water (2×40 mL), brine (40 mL) and dried ($MgSO_4$). Removal of solvent and chromatography (Silica Gel) gave a mixture of (E/Z) 4-[1-(3-ethoxy-4-methoxy-phenyl)-propenyl]-1-methoxy-2-nitro-benzene as a solid (1.12 g, 77% yield): $^1$H NMR ($CDCl_3$) δ 1.41-1.46 (m, 6H, $2CH_3$), 1.75-1.80 (m, 6H, $2CH_3$), 3.86-4.08 (m, 16H, $4OCH_3+2CH_2$), 6.06-6.15 (q, J=7.0 and 14.0 Hz, 2H, 2CH), 6.64-7.74 (m, 12H, Ar).

$SnCl_2.2H_2O$ (3.98 g, 17.6 mmol) was added to a stirred suspension of (E/Z) 4-[1-(3-ethoxy-4-methoxy-phenyl)-propenyl]-1-methoxy-2-nitro-benzene (1.10 g, 3.2 mmol) in ethanol (200 proof, 20 mL) and ethyl acetate (10 mL). The reaction mixture was heated at 70° C. for 1 h. The solution was cooled down to room temperature, poured into ice water (100 mL), and basified with 10 N NaOH (20 mL) to pH ~12. The aqueous layer was extracted with ethyl acetate (5×35 mL). The combined organic layers were washed with water (60 mL), brine (50 mL) and dried ($MgSO_4$). Removal of solvent and chromatography (Silica Gel) gave a mixture of (E/Z) 5-[1-(3-ethoxy-4-methoxy-phenyl) -propenyl]-2-methoxy-phenylamine as a solid (0.73 g, 73% yield): mp, 108-110° C.; $^1$H NMR ($CDCl_3$) δ 1.39-1.46 (m, 6H, $2CH_3$), 1.72-1.77 (m, 6H, $2CH_3$), 3.71-3.75 (bp, 4H, $2NH_2$), 3.83-3.90 (m, 12H, $4OCH_3$), 3.99-4.09 (m, 4H, $2CH_2$), 5.97-6.05 (m, 2H, 2CH), 6.54-6.61 (m, 12H, Ar); $^{13}$C NMR ($CDCl_3$) δ 14.79, 15.67, 15.72, 55.45, 55.52, 55.90, 55.95, 64.21, 64.26, 109.90, 109.95, 110.97, 111.01, 112.13, 114.11, 114.80, 116.83, 117.51, 119.89, 120.35, 121.81, 121.98, 122.44, 132.86, 132.93, 135.52, 135.57, 136.28, 136.49, 141.93, 142.02, 146.25, 146.53, 147.75, 148.02, 148.34; Anal. Calcd for $C_{19}H_{23}NO_3$: C, 73.82; H, 7.40; N, 4.47. Found: C, 72.57; H, 7.47; N, 4.40.

4.6.2.76 5-[1-(3,5-Dimethoxy-phenyl)-propenyl]-2-methoxy-phenylamine

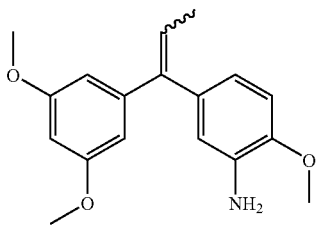

Lithium bis(trimethylsilyl)amide (8.8 mL, 8.8 mmol) was added dropwise to a stirred suspension of (ethyl)triphenylphosphonium bromide (3.28 g, 8.8 mmol) in anhydrous THF (30 mL) at 0° C. After 10 min at cold, the reaction mixture was stirred at room temperature for 40 min. The Wittig reagent was then added dropwise to a stirred solution of (3,5-dimethoxy-phenyl)-(4-methoxy-3-nitro-phenyl)-methanone (1.40 g, 4.4 mmol) in THF (30 mL) at 0° C. The reaction mixture was stirred at room temperature for 1 h. The solution was poured into ice water (100 mL) and extracted with $CH_2Cl_2$ (4×40 mL). The combined organic layers were washed with water (2×40 mL), brine (40 mL) and dried ($MgSO_4$). Removal of solvent and chromatography (Silica Gel) gave a mixture of (E/Z) 4-[1-(3,5-dimethoxy-phenyl)-propenyl]-1-methoxy-2-nitro-benzene as an oil (1.40 g, 97% yield): $^1$H NMR ($CDCl_3$) δ 1.76-1.79 (d, J=6.5 Hz, 6H, $2CH_3$), 3.75-3.78 (2s, 12H, $4OCH_3$), 3.93-3.99 (2s, 6H, $2OCH_3$), 6.12-6.22 (m, 2H, 2CH), 6.29-7.75 (m, 12H, Ar); $^{13}$C NMR ($CDCl_3$) δ 15.68, 15.71, 55.33, 56.57, 99.04, 99.29, 105.82, 107.91, 113.09, 113.27, 123.68, 125.01, 125.92, 127.04, 132.21, 132.48, 135.34, 135.80, 139.92, 140.83, 144.27, 151.63, 151.85, 160.63, 160.85.

$SnCl_2.2H_2O$ (5.20 g, 23.0 mmol) was added to a stirred solution of (E/Z) 4-[1-(3,5-dimethoxy-phenyl)-propenyl]-1-methoxy-2-nitro-benzene (1.10 g, 3.2 mmol) in ethanol (200 proof, 20 mL) and ethyl acetate (10 mL). The reaction mixture was heated at 70° C. for 1 h. The solution was cooled down to room temperature, poured into ice water (100 mL), and basified with 10 N NaOH (20 mL) to pH ~12. The aqueous layer was extracted with ethyl acetate (5×35 mL). The combined organic layers were washed with water (60 mL), brine (50 mL) and dried ($MgSO_4$). Removal of solvent and chromatography (Silica Gel) gave a mixture of (E/Z) 5-[1-(3,5-dimethoxy-phenyl)-propenyl]-2-methoxy-phenylamine as an oil (0.64 g, 51% yield): $^1$H NMR ($CDCl_3$) δ 1.70-1.78 (2d, J=7.0 Hz, 6H, $2CH_3$), 3.74-3.87 (4s+m, 22H, $6OCH_3+2NH_2$), 6.02-6.10 (m, 2H, 2CH), 6.33-6.79 (m, 12H, Ar); $^{13}$C NMR ($CDCl_3$) δ 15.60, 15.73, 55.30, 55.45, 55.52, 98.70, 98.92, 105.72, 107.99, 109.95, 109.99, 113.91, 116.77, 117.30, 120.32, 122.05, 123.83, 132.49, 135.56, 135.61, 142.09, 142.33, 142.50, 145.66, 146.32, 146.56, 160.36, 160.51; Anal. Calcd for $C_{18}H_{21}NO_3$: C, 72.22; H, 7.07; N, 4.68. Found: C, 71.94; H, 7.37; N, 4.54.

4.6.2.77 5-[1-(3-Ethoxy-4-methoxy-phenyl)-vinyl]-2-methoxy-phenylamine

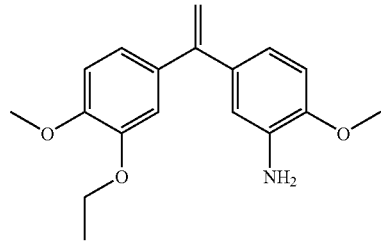

To a stirred suspension of triphenylmethylphosphonium bromide (1.8 g, 5.1 mmol) in THF (30 mL) in an ice bath was added lithium bis(trimethylsilyl)amide (1.0M solution in THF, 5.1 mL, 5.1 mmol) dropwise. The mixture was stirred at room temperature for 40 min. The Wittig reagent was then added slowly to a stirred suspension of (4-methoxy-3-nitrophenyl)-(3-ethoxy-4-methoxy-phenyl)-methanone (1.4 g, 4.2 mmol) in THF (30 mL) in an ice bath. The mixture was stirred at room temperature for 5 hr. The mixture was poured into ice water (100 mL). The aqueous layer was extracted with methyl chloride (4×30 mL). The combined organic layers were washed with water (2×50 mL), brine (50 mL) and dried ($MgSO_4$). Removal of solvent and chromatography (silica gel) gave 1-(3-ethoxy-4-methoxy-phenyl)-1-(3-nitro-4-methoxy-phenyl)-ethene as a solid (0.9 g, 67% yield): $^1$H NMR ($CDCl_3$) δ 1.44 (t, J=7.2 Hz, 3H, $CH_3$), 3.89 (s, 3H, $OCH_3$), 3.98 (s, 3H, $OCH_3$), 4.10 (q, J=7.0 Hz, 2H, $OCH_2$), 5.37 (d, J=9.7 Hz, 2H, $CH_2$), 6.83-6.84 (m, 3H, CH), 7.06(d, J=8.9 Hz, 1H, CH), 7.49-7.54 (dd, J=2.3, 8.9 Hz, 1H, CH), 7.84 (d, J=2.1 Hz, 1H, CH); $^{13}$C NMR (CDCl$_3$) δ 14.70, 55.94, 56.56, 64.35, 111.19, 112.74, 113.10, 113.68, 120.80, 125.11, 133.08, 133.66, 134.27, 139.42, 147.24, 148.03, 149.49, 152.30.

To a stirred solution of 1-(3-ethoxy-4-methoxy-phenyl)-1-(3-nitro-4-methoxy-phenyl)-ethene (0.9 g, 2.8 mmol) in ethyl acetate (10 mL) and ethanol (20 mL) was added tin (II) chloride dihydrate (3.5 g, 15.4 mmol). The mixture was heated at 70° C. for 1 hr. The mixture was poured into ice water (100 mL) and basified with 10 N sodium hydroxide to pH=10. The mixture was extracted with ethyl acetate (5×35 mL). The combined organic layers were washed water (60 mL), brine (60 mL) and dried (MgSO$_4$). Removal of solvent and chromatography (silica gel) gave 5-[1-(3-ethoxy-4-methoxy-phenyl)-vinyl]-2-methoxy-phenylamine as a solid (0.4 g, 48% yield): mp 91-93° C.; $^1$H NMR (CDCl$_3$) δ 1.43 (t, J=7.1 Hz, 3H, CH$_3$), 3.75 (b, 2H, NH$_2$), 3.86 (s, 3H, OCH$_3$), 3.88 (s, 3H, OCH$_3$), 4.06 (q, J=7.1 Hz, 2H, OCH$_2$), 5.28 (d, J=6.5 Hz, 2H, CH$_2$), 6.91-6.72 (m, 6H, CH); $^{13}$C NMR (CDCl$_3$) δ 14.76, 55.50, 55.94, 64.26, 109.85, 110.91, 111.53, 113.12, 115.03, 118.67, 120.92, 134.59, 134.73, 135.58, 147.14, 147.69, 148.97, 149.59; Anal. Calcd for C$_{18}$H$_{21}$NO$_3$: C, 72.22; H, 7.07; N, 4.68. Found: C, 72.16; H, 7.10; N, 4.74.

4.6.2.78 (E/Z) 3-(3-Ethoxy-4-methoxy-phenyl)-3-(3-fluoro-4-methoxy-phenyl)-acrylonitrile

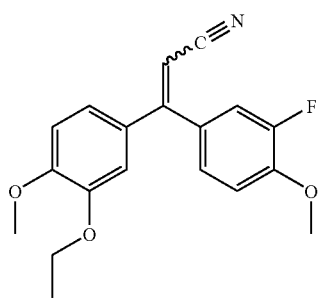

To a solution of 4-bromo-2-ethoxy-1-methoxy-benzene (0.67 g, 2.9 mmol) in THF (10 mL) was added a solution of n-butyllitium in hexane (1.1 mL, 2.5 N, 2.8 mmol) at −78° C. and kept for 20 min. To the mixture was added a solution of 3-fluoro-4,N-dimethoxy-N-methyl-benzamide (0.56 g, 2.6 mmol) in THF (4 mL) at −78° C. After 2 h, isopropanol (1 mL) and water (30 mL) was added to the mixture, and the cold bath was removed. The mixture was stirred at room temperature for 20 min. The mixture was extracted with ethyl acetate (2×50 mL). The combined organic layers was washed with HCl (0.5 N, 50 mL), sodium hydrogen carbonate (50 mL, sat), brine (50 mL) and dried over magnesium sulfate. Removal of solvent and chromatography (Silica Gel) gave (3-ethoxy-4-methoxy-phenyl)-(3-fluoro-4-methoxy-phenyl)-methanone (350 mg, 44% yield): $^1$H NMR (DMSO-d$_6$) δ 1.49 (t, J=7 Hz, 3H, 2CH$_3$), 3.96 (s, 3H, CH$_3$), 3.98 (s, 3H, CH$_3$), 4.16 (q, J=7 Hz, 2H, CH$_2$), 6.90 (d, J=8 Hz, 1H, Ar), 7.02 (t, J=9 Hz, 1H, Ar), 7.35 (dd, J=2, 8 Hz, 1H, Ar), 7.41 (d, J=2 Hz, 1H, Ar), 7.55-7.62 (m, 2H, Ar).

To a stirred solution of cyanomethylphosphonic acid diethyl ester (0.38 mL, 2.4 mmol) in THF (8 mL) in an ice bath was added lithium bis(trimethylsilyl)amide (1.0 M solution in THF, 2.3 mL, 2.3 mmol) dropwise. The mixture was stirred at room temperature for 40 min. (3-Ethoxy-4-methoxy-phenyl)-(3-fluoro-4-methoxy-phenyl)-methanone (0.35 mg, 1.2 mmol) was added to the mixture. The mixture was refluxed overnight. The solution was poured into ice water (30 ml). The aqueous layer was extracted with ethyl acetate (2×50 mL). The combined organic layers was washed with water (50 mL), sodium hydrogen carbonate (50 mL, sat), brine (50 mL) and dried over magnesium sulfate. Removal of solvent and chromatography (Silica Gel) gave a mixture of (E/Z) 3-(3-ethoxy-4-methoxy-phenyl)-3-(3-fluoro-4-methoxy-phenyl)-acrylonitrile as an off-white solid (0.26 g, 69% yield) (isomer ratio is 1:0.8 by HNMR): mp: 122-124° C.; $^1$H NMR (DMSO-d$_6$) δ 1.31 (t, J=7 Hz, 3H, CH$_3$), 3.78 (s, 3H, CH$_3$), [4.83 and 3.87 (2s)], 3.94 (s, 3H, CH$_3$), 4.01 (q, J=7 Hz, 2H, CH$_2$), [6.15 (s)], 6.21 (s, 1H, CH), 6.74 (dd, J=2, 8 Hz, 1H, Ar), 6.92-7.36 (m, 5H, Ar); $^{13}$C NMR (DMSO-d$_6$) δ 14.56, 14.58, 55.49, 56.08, 56.16, 63.84, 93.60, 93.82, 111.39, 111.59, 112.07, 113.53, 113.65, 113.75, 115.34, 115.64, 116.69, 116.99, 118.56, 122.27, 122.33, 125.70, 125.74, 120.22, 126.27, 128.84, 129.59, 129.70, 130.12, 130.86, 130.96, 147.47, 147.89, 148.12, 148.28, 148.88, 149.04, 149.18, 150.27, 151.18, 152.79, 153.06, 159.99, 160.09; Anal. Calcd for C$_{19}$H$_{18}$NO$_3$F: C, 69.71; H, 5.54; N, 4.28. Found: C, 69.55; H, 5.58; N, 4.25.

4.6.2.79 (E/Z) 3-(3,5-Dimethoxy-phenyl)-3-(3-fluoro-4-methoxy-phenyl)-acrylonitrile

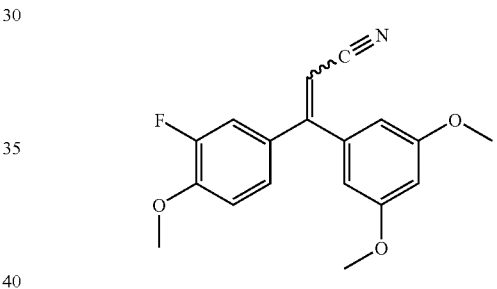

To a solution of 1-bromo-3,5-dimethoxy-benzene (5.0 g, 23.1 mmol) in THF (50 mL) was added a solution of n-butyl-litium in hexane (8.7 mL, 2.5 N, 22 mmol) at −78° C. and kept for 20 min. To the mixture was added 3-fluoro-4-methoxy-benzaldehyde (3.0 g, 19.4 mmol) at −78° C. After 18 h, water (30 mL) was added to the mixture, and the cold bath was removed. The mixture was stirred at room temperature for 20 min. The mixture was extracted with ethyl acetate (2×50 mL). The combined organic layers was washed with HCl (0.5 N, 50 mL), sodium hydrogen carbonate (50 mL, sat), brine (50 mL) and dried over magnesium sulfate. Removal of solvent gave (3,5-dimethoxy-phenyl)-(3-fluoro-4-methoxy-phenyl)-methanol (6 g, 100% crude yield). The sample was used in the next step without further purification.

A mixture of (3,5-dimethoxy-phenyl)-(3-fluoro-4-methoxy-phenyl)-methanol from above and activated MnO$_2$ (10 g, 115 mmol) in methylene chloride (60 mL) was stirred at room temperature for 18 h. More MnO$_2$ (7 g) was added and kept for overnight. The suspension was filtered thru a pad of Celite. Removal of solvent gave (3,5-dimethoxy-phenyl)-(3-fluoro-4-methoxy-phenyl)-methanone as an off-white solid (3.13 g, 56% yield 2 steps). The sample was used in the next step without further purification.

To a stirred solution of cyanomethylphosphonic acid diethyl ester (3.4 mL, 22 mmol) in THF (30 mL) in an ice bath was added lithium bis(trimethylsilyl)amide (1.0 M solution in THF, 21 mL, 21 mmol) dropwise. The mixture was stirred at room temperature for 40 min. (3,5-Dimethoxy-phenyl)-(3-fluoro-4-methoxy-phenyl)-methanone (3.1 g, 11 mmol) was added to the mixture. The mixture was refluxed for 4 h. The solution was poured into ice water (30 mL). The aqueous layer was extracted with ethyl acetate (2×50 mL). The combined organic layers was washed with water (50 mL), sodium hydrogen carbonate (50 mL, sat), brine (50 mL) and dried over magnesium sulfate. Removal of solvent and chromatography (Silica Gel) gave a mixture of (E/Z) 3-(3,5-dimethoxy-phenyl)-3-(3-fluoro-4-methoxy-phenyl)-acrylonitrile as an off-white solid (2.9 g, 86% yield) (isomer ratio is 1:0.7 by HNMR): mp: 91-93° C.; $^1$H NMR (DMSO-d$_6$) δ 3.73 (s, 6H, 2CH$_3$), [3.76 and 3.87 (2s)], 3.92 (s, 3H, CH$_3$), 6.29 (s, 1H, CH), [6.33 (s)], 6.45-6.47 (m, 2H, Ar), 6.62-6.66 (m, 1H, Ar), 7.08-7.41 (m, 3H, Ar); $^{13}$C NMR (DMSO-d$_6$) δ 55.42, 56.11, 56.19, 95.17, 96.31, 101.12, 102.04, 106.69, 107.12, 113.64, 113.72, 113.74, 114.85, 115.16, 116.59, 116.89, 117.98, 118.08, 125.53, 125.58, 126.23, 126.28, 129.18; 129.29, 129.95, 130.05, 138.71, 139.90, 148.26, 148.87, 149.15, 152.77, 153.13, 159.85, 159.99, 160.44; Anal. Calcd for C$_{18}$H$_{16}$NO$_3$F: C, 69.00; H, 5.15; N, 4.47. Found: C, 68.92; H, 4.95; N, 4.42.

4.6.2.80 (E/Z) 3-(3-Ethoxy-4-methoxy-phenyl)-3-(3-pyrrol-1-yl-phenyl)-acrylonitrile

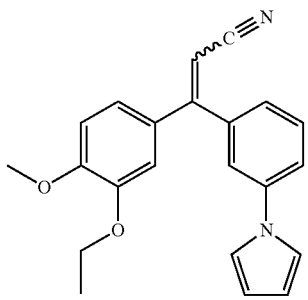

To a solution of 4-bromo-2-ethoxy-1-methoxy-benzene (1.5 g, 6.5 mmol) in THF (30 mL) was added a solution of n-butyllitium in hexane (2.4 mL, 2.5 N, 6.0 mmol) at −78° C. and kept for 20 min. To the mixture was added 3-pyrrol-1-yl-benzaldehyde (1.0 g, 5.8 mmol) at −78° C. After 18 h, water (30 mL) was added to the mixture, and the cold bath was removed. The mixture was stirred at room temperature for 20 min. The mixture was extracted with ethyl acetate (2×50 mL). The combined organic layers was washed with HCl (0.5 N, 50 mL), sodium hydrogen carbonate (50 mL, sat), brine (50 mL) and dried over magnesium sulfate. Removal of solvent gave (3-ethoxy-4-methoxy-phenyl)-(3-pyrrol-1-yl-phenyl)-methanol (1.9 g, 100% crude yield). The sample was used in the next step without further purification.

A mixture of (3-ethoxy-4-methoxy-phenyl)-(3-pyrrol-1-yl-phenyl)-methanol from above and activated MnO$_2$ (2.6 g, 30 mmol) in methylene chloride (30 if L) was stirred at room temperature for 18 h. More MnO$_2$ (2 g) was added and kept for overnight. The suspension was filtered thru a pad of Celite. Removal of solvent gave (3-ethoxy-4-methoxy-phenyl)-(3-pyrrol-1-yl-phenyl)-methanone as a brown oil (1.58 g, 85% crude yield 2 steps). The sample was used in the next step without further purification.

To a stirred solution of cyanomethylphosphonic acid diethyl ester (1.6 mL, 10 mmol) in THF (20 mL) in an ice bath was added lithium bis(trimethylsilyl)amide (1.0 M solution in THF, 10 mL, 10 mmol) dropwise. The mixture was stirred at room temperature for 40 min. A solution of (3-ethoxy-4-methoxy-phenyl)-(3-pyrrol-1-yl-phenyl)-methanone from above in THF (5 mL) was added to the mixture. The mixture was refluxed for 16 h. The solution was poured into ice water (30 mL). The aqueous layer was extracted with ethyl acetate (2×50 mL). The combined organic layers was washed with water (50 mL), sodium hydrogen carbonate (50 mL, sat), brine (50 mL) and dried over magnesium sulfate. Removal of solvent and chromatography (Silica Gel) gave a mixture of (E/Z) 3-(3-ethoxy-4-methoxy-phenyl)-3-(3-pyrrol-1-yl-phenyl)-acrylonitrile as an off-white solid (1.16 g, 58% yield 3 steps) (isomer ratio is 1:0.8 by HNMR): mp: 47-49° C.; $^1$H NMR (DMSO-d$_6$) δ 1.31 (t, J=7 Hz, 3H, CH$_3$), 3.78 (s, 3H, CH$_3$), [3.83 (s)], 4.00 (q, J=7 Hz, 2H, CH$_2$), 6.27-6.29 (m, 2H, Ar), [6.29 (s)], 6.33 (s, 1H, CH), 6.74 (dd, J=2, 8 Hz, 1H, Ar), 6.92-7.20 (m, 1H, Ar), 7.41-7.43 (m, 2H, Ar), 7.44-7.72 (m, 8H, Ar); $^{13}$C NMR (DMSO-d$_6$) δ 14.59, 55.55, 63.87, 94.34, 95.62, 110.73, 110.79, 111.43, 111.64, 111.74, 113.75, 118.46, 118.86, 119.00, 119.16, 120.19, 121.12, 122.36, 122.49, 125.69, 125.86, 128.92, 129.74, 129.87, 129.96, 138.85, 139.87, 140.02, 140.15, 147.45, 147.96, 150.38, 151.27, 160.73, 160.94; Anal. Calcd for C$_{22}$H$_{20}$N$_2$O$_2$+0.2 EtOAc: C, 75.64; H, 6.01; N, 7.74. Found: C, 75.66; H, 5.84; N, 7.75.

4.6.2.81 (E/Z) 3-(3-Ethoxy-4-methoxy-phenyl)-3-(4-methoxy-3-methyl-phenyl)-acrylonitrile

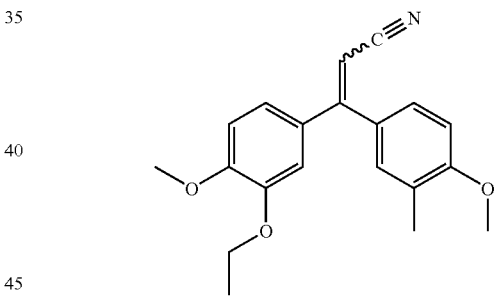

To a solution of 4-bromo-2-ethoxy-1-methoxy-benzene (1.7 g, 7.4 mmol) in THF (20 mL) was added a solution of n-butyllitium in hexane (2.8 mL, 2.5 N, 7.0 mmol) at −78° C. and kept for 20 min. To the mixture was added 4-methoxy-3-methyl-benzaldehyde (1.0 g, 90% pure, 6.0 mmol) at −78° C. After 18 h, water (30 mL) was added to the mixture, and the cold bath was removed. The mixture was stirred at room temperature for 20 min. The mixture was extracted with ethyl acetate (2×50 mL). The combined organic layers was washed with HCl (0.5 N, 50 mL), sodium hydrogen carbonate (50 mL, sat), brine (50 mL) and dried over magnesium sulfate. Removal of solvent gave (3-ethoxy-4-methoxy-phenyl)-(4-methoxy-3-methyl-phenyl)-methanol as a solid (2.0 g, 100% crude yield). The sample was used in the next step without further purification.

A mixture of (3-ethoxy-4-methoxy-phenyl)-(4-methoxy-3-methyl-phenyl)-methanol from above and activated MnO$_2$ (3 g, 35 mmol) in methylene chloride (30 mL) was stirred at room temperature for 18 h. More MnO$_2$ (1.3 g×2) was added and kept for overnight. The suspension was filtered thru a pad of Celite. Removal of solvent gave (3-ethoxy-4-methoxy-phenyl)-(4-methoxy-3-methyl-phenyl)-methanone as a white solid (1.23 g, 68% crude yield 2 steps). The sample was used in the next step without further purification.

To a stirred solution of cyanomethylphosphonic acid diethyl ester (1.3 mL, 8.3 mmol) in THF (20 mL) in an ice bath was added lithium bis(trimethylsilyl)amide (1.0 M solution in THF, 8.3 mL, 8.3 mmol) dropwise. The mixture was stirred at room temperature for 40 min. A solution of (3-ethoxy-4-methoxy-phenyl)-(4-methoxy-3-methyl-phenyl)-methanone from above in THF (10 mL) was added to the mixture. The mixture was refluxed for 4 h. The solution was poured into ice water (30 mL). The aqueous layer was extracted with ethyl acetate (2×50 mL). The combined organic layers was washed with water (50 mL), sodium hydrogen carbonate (50 mL, sat), brine (50 mL) and dried over magnesium sulfate. Removal of solvent and chromatography (Silica Gel) gave a mixture of (E/Z) 3-(3-ethoxy-4-methoxy-phenyl)-3-(4-methoxy-3-methyl-phenyl)-acrylonitrile as a white solid (0.97 g, 75% yield) (isomer ratio is 1:0.8 by HNMR): mp: 86-88° C.; $^1$H NMR (DMSO-$d_6$) δ 1.30 (t, J=7 Hz, 3H, CH$_3$), 2.13 (s, 3H, CH$_3$), [2.17 (s)], 3.78 (s, 3H, CH$_3$), 3.82 (s, 3H, CH$_3$), [3.83 (s), 3.86 (s)], 3.93-4.04 (m, 2H, CH$_2$), 6.01 (s, 1H, CH), [6.08 (s)], 6.72-7.26 (m, 6H, Ar); $^{13}$C NMR (DMSO-$d_6$) 14.56, 14.59, 15.98, 63.77, 92.10, 92.42, 110.04, 110.18, 111.35, 111.51, 112.27, 113.83, 118.92, 122.27, 122.35, 125.61, 125.86, 128.05, 128.60, 128.92, 129.44, 130.14, 130.35, 130.82, 131.29, 147.36, 147.78, 150.15, 151.02, 158.44, 159.28, 161.47, 161.53; Anal. Calcd for C$_{20}$H$_{21}$NO$_3$: C, 74.28; H, 6.55; N, 4.33. Found: C, 74.16; H, 6.48; N, 4.30.

4.6.2.82 (E/Z) Sulfamic Acid 3-[2-cyano-1-(3,5-dimethoxy-phenyl)-vinyl]-phenyl Ester

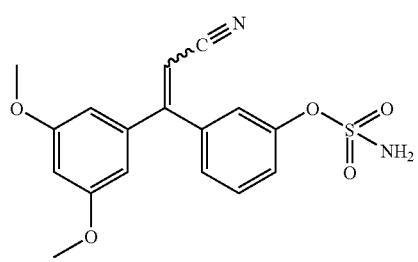

To a solution of 3-(3,5-dimethoxy-phenyl)-3-(3-hydroxy-phenyl) -acrylonitrile (280 mg, 1 mmol) in dimethylacetamide (4 mL) was added a solution of sulfamic chloride in methylene chloride (1 mL, 2.3 mmol/mL, 2.3 mmol) at room temperature. After 15 h, water (30 mL) was added to the mixture. The aqueous layer was extracted with ethyl acetate (2×50 mL). The combined organic layers was washed with water (50 mL), brine (50 mL) and dried over magnesium sulfate. Removal of solvent and chromatography gave (E/Z) sulfamic acid 3-[2-cyano-1-(3,5-dimethoxy-phenyl)-vinyl]-phenyl ester (320 mg, 89% yield): mp: 301-303° C.; $^1$H NMR (DMSO-$d_6$) δ 3.73 (s, 6H, 2CH$_3$), [3.76 (s)], [6.41 (s)], 6.44 (s, 1H, CH), 6.49-6.51 (m, 2H, Ar), 6.63-6.67 (m, 1H, Ar), 7.22 (brs, 1H, Ar), 7.38-7.65 (m, 3H, Ar), 8.07 (brs, 2H, NH$_2$); Anal. Calcd for C$_{17}$H$_{16}$N$_2$O$_5$S+0.1H$_2$O: C, 56.38; H, 4.51; N, 7.73. Found: C, 56.23; H, 4.36; N, 7.55.

4.6.2.83 (E/Z) 3-(3,4-Dihydro-2H-benzo[b][1,4]dioxepin-7-yl)-3-(3,5-dimethoxy-phenyl)-acrylonitrile

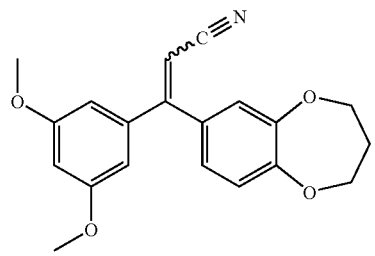

To a solution of 7-bromo-3,4-dihydro-2H-benzo[b][1,4]dioxepine (1.7 g, 7.4 mmol) in THF (10 mL) was added a solution of n-butyllitium in hexane (2.6 mL, 2.5 N, 6.5 mmol) at −78° C. and kept for 20 min. To the mixture was added a solution of 3,5-dimethoxy-benzaldehyde (1.0 g, 6.0 mmol) in THF (10 mL) at −78° C. After 2 h, isopropanol (2 mL) and water (10 mL) was added to the mixture, and the cold bath was removed. The mixture was stirred at room temperature for 20 min. The mixture was extracted with ethyl acetate (50 mL) and water (50 mL). The aqueous layer was extracted with ethyl acetate (50 mL). The combined organic layers was washed with HCl (1N, 50 mL), water (50 mL), brine (50 mL) and dried over MgSO$_4$. Removal of solvent and chromatography (Silica Gel) gave (3,4-dihydro-2H-benzo[b][1,4]dioxepin-7-yl)-(3,5-dimethoxy-phenyl) -methanol as an oil (1.8 g, 95% yield): $^1$H NMR (CDCl$_3$) δ 2.16-2.22 (m, 2H, CH$_2$), 3.77 (s, 6H, 2CH$_3$), 4.16-4.21 (m, 4H, 2CH$_2$), 5.67 (d, J=3 Hz, 1H, CH), 6.35 (t, J=2 Hz, 1H, Ar), 6.54 (d, J=2 Hz, 1H, Ar), 6.92 (d, J=1 Hz, 2H, Ar), 6.98 (s, 1H, Ar).

A mixture of (3,4-dihydro-2H-benzo[b][1,4]dioxepin-7-yl)-(3,5-dimethoxy-phenyl)-methanol (1.8 g, 5.7 mmol) and MnO$_2$ (2.6 g, 30 mmol) in methylene chloride (40 mL) was stirred at room temperature for 4 h. More MnO$_2$ (1.3 g) was added and kept for overnight. The suspension was filtered thru a pad of Celite. Removal of solvent gave (3,4-dihydro-2H-benzo[b][1,4]dioxepin-7-yl)-(3,5-dimethoxy-phenyl) -methanone as an oil (1.3 g, 72% yield): $^1$H NMR (CDCl$_3$) δ 2.22-2.28 (m, 2H, CH$_2$), 3.82 (s, 6H, 2CH$_3$), 4.28-4.31 (m, 4H, 2CH$_2$), 6.64 (t, J=2 Hz, 1H, Ar), 6.88 (d, J=2 Hz, 2H, Ar), 6.99 (d, J=8 Hz, 1H, Ar), 7.42 (dd, J=1, 9 Hz, 1H, Ar), 7.48 (d, J=2 Hz, 1H, Ar).

To a stirred solution of cyanomethylphosphonic acid diethyl ester (1.3 mL, 8.3 mmol) in THF (10 mL) in an ice bath was added lithium bis(trimethylsilyl)amide (1.0 M solution in THF, 8.2 mL, 8.2 mmol) dropwise. The mixture was stirred at room temperature for 40 min. A solution of (3,4-dihydro-2H-benzo[b][1,4]dioxepin-7-yl)-(3,5-dimethoxy-phenyl)-methanone (1.3 g, 4.1 mmol) in anhydrous THF (10 mL) was added to the mixture. The mixture was refluxed overnight. The solution was poured into ice water (20 mL). The aqueous layer was extracted with ethyl acetate (2×50 mL). The combined organic layers was washed with water (50 mL), sodium hydrogen carbonate (50 mL, sat), brine (50 mL) and dried over magnesium sulfate. Removal of solvent and chromatography (Silica Gel) gave a mixture of (E/Z) 3-(3,4-dihydro-2H-benzo[b][1,4]dioxepin-7-yl)-3-(3,5-dimethoxy-phenyl)-acrylonitrile as an oil (1.23 g, 89% yield): $^1$H NMR (DMSO-$d_6$) δ 2.09-2.16 (m, 4H, 2CH$_2$), 3.73 (s, 6H, 2CH$_3$), 4.12-4.25 (m, 8H, 4CH$_2$), 6.24 (s, 1H, CH), 6.30 (s, 1H, CH), 6.44-6.45 (m, 4H, Ar), 6.62-6.65 (m, 2H, Ar), 6.93-7.09 (m, 6H, Ar); $^{13}$C NMR (DMSO-d$_6$) δ 30.97, 31.13, 55.40, 70.37, 70.52, 95.05, 95.87, 100.90, 101.82, 106.72, 107.06, 118.06, 118.12, 121.09, 121.61, 121.64, 122.39, 123.41, 124.47, 131.71, 132.26, 138.98, 140.12, 150.42, 150.55, 152.09, 152.89, 160.31, 160.39, 160.43.

4.6.2.84
3,3-Bis-(4-dimethylamino-phenyl)-acrylonitrile

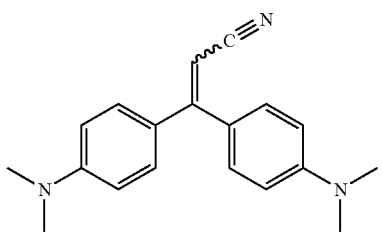

To a solution of cyanomethylphosphonic acid diethyl ester (1.4 mL, 8.9 mmol) in anhydrous THF (15 mL) was added lithium bis(trimethylsilyl)amide (1.0 M solution in THF, 8.9 mL, 8.9 mmol) at 0° C. and stirred for 30 min at room temperature followed by addition of bis-(4-dimethylamino-phenyl)-methanone (1.19 g, 4.4 mmol) in THF (20 mL) and refluxed overnight. The reaction mixture was poured into water (20 mL), extracted with CH$_2$Cl$_2$ (2×50 mL). The combined organic phases were washed with brine (50 mL), dried over MgSO$_4$, and purified via flash column chromatography (EtOAc/Hexane) to give 3,3-bis-(4-dimethylamino-phenyl)-acrylonitrile as a light yellow needle-like solid (0.75 g, 58% yield): mp, 181-183° C.; $^1$H NMR (DMSO-d$_6$) δ 2.96 and 2.98 (2s, 6H, 2N(CH$_3$)$_2$), 5.70 (s, 1H, CH), 6.67-6.80 (m, 4H, Ar), 7.15-7.23 (m, 4H, Ar); $^{13}$C NMR (DMSO-d$_6$) δ 39.7, 39.8, 87.0, 111.3, 111.4, 120.0, 124.2, 125.6, 129.8, 130.7, 151.0, 151.5, 162.2. Anal. Calcd for C$_{19}$H$_{21}$N$_3$: C, 78.32; H, 7.26; N, 14.42. Found: C, 78.33; H, 7.29; N, 14.38.

4.6.2.85 (E/Z)-Amino-acetic acid 5-[2-cyano-1-(3-ethoxy-4-methoxy-phenyl)-vinyl]-2-methoxy-phenyl Ester Hydrochloric Acid

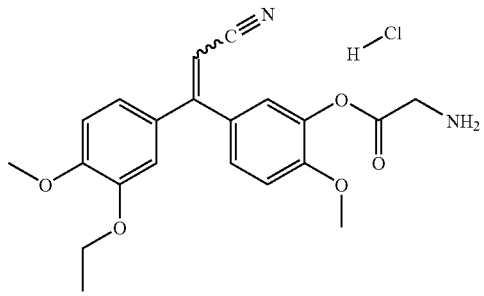

A stirred mixture of 4-bromo-2-ethoxy-1-methoxy-benzene (5.25 g, 22.7 mmol) and dry THF (50 mL) was cooled to −78° C., evacuated and refilled with nitrogen for 10 cycles. To this clear solution was slowly added n-butyllithium (9.1 mL, 22.7 mmol) and stirred for 20 min. Then a mixture of 3-benzyloxy-4-methoxy-benzaldehyde (5.0 g, 20.6 mmol) in dry THF (20 mL) was added and stirred for 1 hour at −78° C. The mixture was quenched with isopropanol (9.4 mL, 248 mmol) and added water (50 mL). The mixture was extracted with EtOAc (3×80 mL). The combined organic phases were washed with water (2×80 mL), dried over MgSO$_4$ and concentrated to oil, which was purified by flash column chromatography (EtOAc/Hexane) to give (3-benzyloxy-4-methoxy-phenyl)-(3-ethoxy-4-methoxy-phenyl)-methanol as an off-white solid (7.26 g, 89% yield): $^1$H NMR (CDCl$_3$) 1.43 (t, J=7 Hz, 3H, CH$_2$CH$_3$), 2.09 (d, J=3 Hz, 1H, OH), 3.86 (s, 3H, OCH$_3$), 3.87 (s, 3H, OCH$_3$), 4.00 (q, J=7 Hz, 2H, CH$_2$CH$_3$), 5.10 (s, 2H, CH$_2$), 5.68 (d, J=3 Hz, 1H, CH), 6.80-6.92 (m, 6H, Ar), 7.26-7.41 (m, 5H, Ar). The product was used in the next step without further purification.

To a stirred solution of (3-benzyloxy-4-methoxy-phenyl)-(3-ethoxy-4-methoxy-phenyl)-methanol (7.22 g, 18.3 mmol) in CH$_2$Cl$_2$ (40 mL) at room temperature was added activated MnO$_2$ powder (4.6 g, 53 mmol) and kept adding 2~3 equivalents of MnO$_2$ every 3~5 h until HPLC showed disappearance of the starting material. The black suspension was filtered through a Celite pad, concentrated in vacuo to give (3-benzyloxy-4-methoxy-phenyl)-(3-ethoxy-4-methoxy-phenyl)-methanone as a brown solid (7.24 g, 100% yield): $^1$H NMR (CDCl$_3$) δ 1.49 (t, J=7 Hz, 3H, CH$_2$CH$_3$), 3.95 (s, 3H, OCH$_3$), 3.97 (s, 3H, OCH$_3$), 4.14 (q, J=7 Hz, 2H, CH$_2$CH$_3$), 5.20 (s, 2H, CH$_2$), 6.83 (d, J=8 Hz, 1H, Ar), 6.94 (d, J=8 Hz, 1H, Ar), 7.23-7.47 (m, 9H, Ar). The product was used in the next step without further purification.

A mixture of (3-benzyloxy-4-methoxy-phenyl)-(3-ethoxy-4-methoxy-phenyl)-methanone (7.24 g), 20% palladium on charcol (0.22 g, 3% weight), and cyclohexene (24 mL) in ethanol (48 mL) was refluxed overnight. The black suspension was filtered through a Celite pad, and the filtrate was evaporated to give (3-ethoxy-4-methoxy-phenyl)-(3-hydroxy-4-methoxy-phenyl)-methanone as an off-white solid (5.25 g, 94% yield): $^1$H NMR (DMSO-d$_6$) δ 1.49 (t, J=7 Hz, 3H, CH$_2$CH$_3$), 3.95 (s, 3H, OCH$_3$), 3.98 (s, 3H, OCH$_3$), 4.16 (q, J=7 Hz, 2H, CH$_2$CH$_3$), 5.69 (s, 1H, OH), 6.87-6.93 (m, 2H, Ar), 7.35-7.43 (m, 4H, Ar). The product was used in the next step without further purification.

To a solution of cyanomethylphosphonic acid diethyl ester (8.1 mL, 51.6 mmol) in anhydrous THF (50 mL) was added lithium bis(trimethylsilyl)amide (1.0 M solution in THF, 51.6 mL, 51.6 mmol) at 0° C. and stirred for 30 min at room temperature followed by addition of (3-ethoxy-4-methoxy-phenyl)-(3-hydroxy-4-methoxy-phenyl)-methanone (5.20 g, 17.2 mmol) in THF (40 mL) and refluxed overnight. The reaction mixture was poured into water (50 mL), extracted with CH$_2$Cl$_2$ (2×60 mL). The combined organic phases were washed with brine (60 mL), dried over MgSO$_4$, and purified via flash column chromatography (EtOAc/Hexane) to give E/Z-3-(3-ethoxy-4-methoxy-phenyl)-3-(3-hydroxy-4-methoxy-phenyl)-acrylonitrile as an off-white solid (5.26 g, 94% yield). The product was used in the next step without further purification.

To a stirred solution of E/Z-3-(3-ethoxy-4-methoxy-phenyl)-3-(3-hydroxy-4-methoxy-phenyl)-acrylonitrile (0.40 g, 1.2 mmol) in CH$_2$Cl$_2$ (10 mL) at room temperature was added tert-butoxycarbonylamino-acetic acid (0.21 g, 1.2 mmol), DCC (0.25 g, 1.2 mmol) and 4-pyrrolidin-1-yl-pyridine (0.02 g, 0.12 mmol). The mixture was stirred for 5 hours and filtered. The filtrate was washed with water (30 mL), dried over MgSO$_4$, and concentrated to an oil, which was purified by flash column chromatography (EtOAc/Hexane) to give E/Z-tert-butoxycarbonylamino-acetic acid 5-[2-cyano-1-(3-ethoxy-4-methoxy-phenyl)-vinyl]-2-methoxy-phenyl ester as a clear oil (0.38 g, 64% yield): $^1$H NMR (CDCl$_3$) δ 1.26 (t, J=7 Hz, 3H, CH$_2$CH$_3$), 1.46 (s, 9H, 3CH$_3$), 3.87-3.98 (ms, 6H, 2OCH$_3$), 4.01-4.14 (m, 2H, CH$_2$CH$_3$), 4.17-4.21 (m, 2H, CH₂NH), 5.04 (brs, 1H, NH), 5.55 and 5.57 (s, 1H, CH), 6.77-7.53 (m, 6H, Ar). The product was used in the next step without further purification.

To a stirred solution of E/Z-tert-butoxycarbonylaminoacetic acid 5-[2-cyano-1-(3-ethoxy-4-methoxy-phenyl)-vinyl]-2-methoxy-phenyl ester (0.36 g, 0.76 mmol) in CH₂Cl₂ (5 mL) was added 2 M HCl in ether (1.9 mL, 3.7 mmol) and kept adding 1~2 equivalents of 2 M HCl in ether until HPLC showed disappearance of the starting material. The suspension was filtered and the resulting white solid was slurried in ether overnight and filtered again to give (E/Z)-Amino-acetic acid 5-[2-cyano-1-(3-ethoxy-4-methoxy-phenyl)-vinyl]-2-methoxy-phenyl ester hydrochloric acid as a white solid (0.18 g, 58% yield): mp, 190-192° C.; $^1$H NMR (DMSO-d₆) δ 1.32 (t, J=7 Hz, 3H, CH₂CH₃), 3.79-3.88 (ms, 6H, 2OCH₃), 3.94-4.04 (m, 2H, CH₂CH₃), 4.10-4.13 (2s, 2H, CH₂NH₂), 6.14 and 6.22 (2s, 1H, CH), 6.73-7.48 (m, 6H, Ar), 8.54 (brs, 3H, NH₃Cl); $^{13}$C NMR (DMSO-d₆) δ 14.6, 14.6, 55.5, 55.6, 56.1, 63.8, 93.5, 93.7, 111.4, 111.6, 112.2, 113.0, 113.2, 113.7, 118.5, 122.1, 122.3, 122.7, 123.6, 127.9, 128.9, 128.9, 129.5, 130.3, 130.8, 137.9, 138.0, 147.5, 147.9, 150.3, 151.1, 151.7, 152.3, 159.9, 160.1, 166.0. Anal. Calcd for C₂₀H₂₃N₂O₅Cl+ 0.5H₂O: C, 58.95; H, 5.65; N, 6.55. Found: C, 58.57; H, 5.52; N, 6.35.

4.6.2.86 (E/Z)-2-Amino-3-methyl-butyric acid 5-[2-cyano-1-(3-ethoxy-4-methoxy-phenyl)-vinyl]-2-methoxy-phenyl Ester Hydrochloric Acid

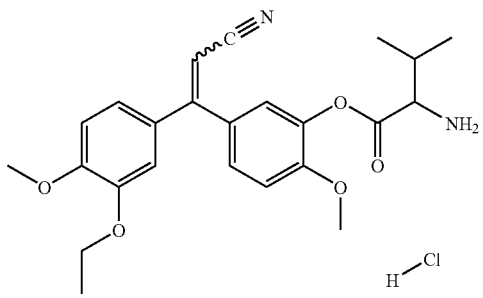

A stirred mixture of 4-bromo-2-ethoxy-1-methoxy-benzene (5.25 g, 22.7 mmol) and dry THF (50 mL) was cooled to −78° C., evacuated and refilled with nitrogen for 10 cycles. To this clear solution was slowly added n-butyllithium (9.1 mL, 22.7 mmol) and stirred for 20 min. Then a mixture of 3-benzyloxy-4-methoxy-benzaldehyde (5.0 g, 20.6 mmol) in dry THF (20 mL) was added and stirred for 1 hour at −78° C. The mixture was quenched with isopropanol (9.4 mL, 248 mmol) and added water (50 mL). The mixture was extracted with EtOAc (3×80 mL). The combined organic phases were washed with water (2×80 mL), dried over MgSO₄ and concentrated to oil, which was purified by flash column chromatography (EtOAc/Hexane) to give (3-benzyloxy-4-methoxy-phenyl)-(3-ethoxy-4-methoxy-phenyl)-methanol as an off-white solid (7.26 g, 89% yield): $^1$H NMR (CDCl₃) δ 1.43 (t, J=7 Hz, 3H, CH₂CH₃), 2.09 (d, J=3 Hz, 1H, OH), 3.86 (s, 3H, OCH₃), 3.87 (s, 3H, OCH₃), 4.00 (q, J=7 Hz, 2H, CH₂CH₃), 5.10 (s, 2H, CH₂), 5.68 (d, J=3 Hz, 1H, CH), 6.80-6.92 (m, 6H, Ar), 7.26-7.41 (m, 5H, Ar). The product was used in the next step without further purification.

To a stirred solution of (3-benzyloxy-4-methoxy-phenyl)-(3-ethoxy-4-methoxy-phenyl)-methanol (7.22 g, 18.3 mmol) in CH₂Cl₂ (40 mL) at room temperature was added activated MnO₂ powder (4.6 g, 53 mmol) and kept adding 2~3 equivalents of MnO₂ every 3~5 h until HPLC showed disappearance of the starting material. The black suspension was filtered through a Celite pad, concentrated in vacuo to give (3-benzyloxy-4-methoxy-phenyl)-(3-ethoxy-4-methoxy-phenyl)-methanone as a brown solid (7.24 g, 100% yield): $^1$H NMR (CDCl₃) δ 1.49 (t, J=7 Hz, 3H, CH₂CH₃), 3.95 (s, 3H, OCH₃), 3.97 (s, 3H, OCH₃), 4.14 (q, J=7 Hz, 2H, CH₂CH₃), 5.20 (s, 2H, CH₂), 6.83 (d, J=8 Hz, 1H, Ar), 6.94 (d, J=8 Hz, 1H, Ar), 7.23-7.47 (m, 9H, Ar). The product was used in the next step without further purification.

A mixture of (3-benzyloxy-4-methoxy-phenyl)-(3-ethoxy-4-methoxy-phenyl)-methanone (7.24 g), 20% palladium on charcol (0.22 g, 3% weight), and cyclohexene (24 mL) in ethanol (48 mL) was refluxed overnight. The black suspension was filtered through a Celite pad, and the filtrate was evaporated to give (3-ethoxy-4-methoxy-phenyl)-(3-hydroxy-4-methoxy-phenyl)-methanone as an off-white solid (5.25 g, 94% yield): $^1$H NMR (DMSO-d₆) δ 1.49 (t, J=7 Hz, 3H, CH₂CH₃), 3.95 (s, 3H, OCH₃), 3.98 (s, 3H, OCH₃), 4.16 (q, J=7 Hz, 2H, CH₂CH₃), 5.69 (s, 1H, OH), 6.87-6.93 (m, 2H, Ar), 7.35-7.43 (m, 4H, Ar). The product was used in the next step without further purification.

To a solution of cyanomethylphosphonic acid diethyl ester (8.1 mL, 51.6 mmol) in anhydrous THF (50 mL) was added lithium bis(trimethylsilyl)amide (1.0 M solution in THF, 51.6 mL, 51.6 mmol) at 0° C. and stirred for 30 min at room temperature followed by addition of (3-ethoxy-4-methoxy-phenyl)-(3-hydroxy-4-methoxy-phenyl)-methanone (5.20 g, 17.2 mmol) in THF (40 mL) and refluxed overnight. The reaction mixture was poured into water (50 mL), extracted with CH₂Cl₂ (2×60 mL). The combined organic phases were washed with brine (60 mL), dried over MgSO₄, and purified via flash column chromatography (EtOAc/Hexane) to give E/Z-3-(3-ethoxy-4-methoxy-phenyl) -3-(3-hydroxy-4-methoxy-phenyl)-acrylonitrile as an off-white solid (5.26 g, 94% yield). The product was used in the next step without further purification.

To a stirred solution of E/Z-3-(3-ethoxy-4-methoxy-phenyl)-3-(3-hydroxy-4-methoxy-phenyl)-acrylonitrile (0.63 g, 1.9 mmol) in CH₂Cl₂ (15 mL) at room temperature was added L-2-tert-butoxycarbonylamino-3-methyl-butyric acid (0.42 g, 1.9 mmol), DCC (0.40 g, 1.9 mmol) and 4-pyrrolidin-1-yl-pyridine (0.03 g, 0.19 mmol). The mixture was stirred for 2 hours and filtered. The filtrate was washed with water (30 mL), dried over MgSO₄, and concentrated to an oil, which was purified by flash column chromatography (EtOAc/Hexane) to give E/Z-2-tert-butoxycarbonylamino-3-methyl-butyricacid-5-[2-cyano-1-(3-ethoxy-4-methoxy-phenyl)-vinyl]-2-methoxy-phenyl ester as an oil (0.82 g, 80% yield): $^1$H NMR (CDCl₃) δ 1.00-1.09 (m, 6H, CH(CH₃)₂), 1.26 (t, J=7 Hz, 3H, CH₂CH₃), 1.45 (2s, 9H, 3CH₃), 2.36 (brs, 1H, CH(CH₃)₂), 3.85-3.93 (ms, 6H, 2OCH₃), 3.98-4.17 (m, 2H, CH₂CH₃), 4.47-4.52 (m, 1H, CHNH), 5.03-5.09 (m, 1H, NH), 5.54 and 5.57 (s, 1H, CH), 6.78-7.53 (m, 6H, Ar). The product was used in the next step without further purification.

To a stirred solution of E/Z-2-tert-butoxycarbonylamino-3-methyl-butyricacid-5-[2-cyano-1-(3-ethoxy-4-methoxy-phenyl)-vinyl]-2-methoxy-phenyl ester (0.82 g, 1.6 mmol) in CH₂Cl₂ (10 mL) was added 2 M HCl in ether (3.9 mL, 7.8 mmol) and kept adding 12 equivalents of 2 M HCl in ether until HPLC showed disappearance of the starting material. The suspension was filtered and the resulting white solid was slurried in ether overnight and filtered again to give (E/Z)-2-amino-3-methyl-butyric acid 5-[2-cyano-1-(3-ethoxy-4-methoxy-phenyl)-vinyl]-2-methoxy-phenyl ester hydrochloric acid as a white solid (0.51 g, 70% yield): mp, 192-194° C.;

$^1$H NMR (DMSO-d$_6$) δ 1.07-1.14 (ms, 6H, CH(CH$_3$)$_2$), 1.32 (t, J=7 Hz, 3H, CH$_2$CH$_3$), 2.30-2.37 (m, 1H, CH(CH$_3$)$_2$), 3.79-3.88 (ms, 6H, 2OCH$_3$), 3.94-4.02 (m, 2H, CH$_2$CH$_3$), 4.13-4.19 (m, 1H, CHNH$_2$), 6.14 and 6.22 (2s, 1H, CH), 6.74-7.45 (m, 6H, Ar), 8.61 (brs, 3H, NH$_3$Cl); $^{13}$C NMR (DMSO-d$_6$) δ 14.6, 17.4, 18.0, 29.5, 55.5, 55.6, 56.0, 56.1, 57.3, 63.8, 93.6, 93.8, 111.4, 111.6, 112.2, 113.0, 113.1, 113.7, 118.5, 122.1, 122.3, 122.6, 123.5, 128.0, 128.8, 129.0, 129.5, 130.9, 137.9, 138.0, 147.5, 147.9, 150.3, 151.2, 151.5, 152.2, 159.9, 160.0, 167.0. Anal. Calcd for C$_{24}$H$_{29}$N$_2$O$_5$Cl+ 0.1H$_2$O: C, 62.29; H, 6.39; N, 6.05; Cl, 7.66%. Found: C, 62.07; H, 6.30; N, 6.06; Cl, 7.63%.

4.6.2.87 (E/Z)-2-Amino-propionic acid 5-[2-cyano-1-(3-ethoxy-4-methoxy-phenyl)-vinyl]-2-methoxy-phenyl ester hydrochloric acid

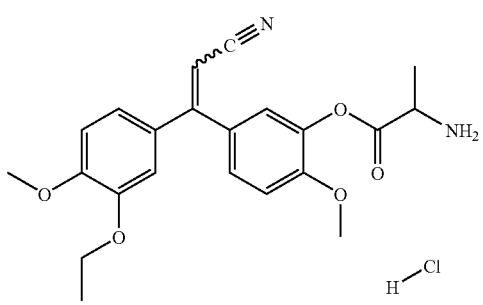

A stirred mixture of 4-bromo-2-ethoxy-1-methoxy-benzene (5.25 g, 22.7 mmol) and dry THF (50 mL) was cooled to −78° C., evacuated and refilled with nitrogen for 10 cycles. To this clear solution was slowly added n-butyllithium (9.1 mL, 22.7 mmol) and stirred for 20 min. Then a mixture of 3-benzyloxy-4-methoxy-benzaldehyde (5.0 g, 20.6 mmol) in dry THF (20 mL) was added and stirred for 1 hour at −78° C. The mixture was quenched with isopropanol (9.4 mL, 248 mmol) and added water (50 mL). The mixture was extracted with EtOAc (3×80 mL). The combined organic phases were washed with water (2×80 mL), dried over MgSO$_4$ and concentrated to oil, which was purified by flash column chromatography (EtOAc/Hexane) to give (3-benzyloxy-4-methoxy-phenyl)-(3-ethoxy-4-methoxy-phenyl)-methanol as an off-white solid (7.26 g, 89% yield): $^1$H NMR (CDCl$_3$) δ 1.43 (t, J=7 Hz, 3H, CH$_2$CH$_3$), 2.09 (d, J=3 Hz, 1H, OH), 3.86 (s, 3H, OCH$_3$), 3.87 (s, 3H, OCH$_3$), 4.00 (q, J=7 Hz, 2H, CH$_2$CH$_3$), 5.10 (s, 2H, CH$_2$), 5.68 (d, J=3 Hz, 1H, CH), 6.80-6.92 (m, 6H, Ar), 7.26-7.41 (m, 5H, Ar). The product was used in the next step without further purification.

To a stirred solution of (3-benzyloxy-4-methoxy-phenyl)-(3-ethoxy-4-methoxy-phenyl)-methanol (7.22 g, 18.3 mmol) in CH$_2$Cl$_2$ (40 mL) at room temperature was added activated MnO$_2$ powder (4.6 g, 53 mmol) and kept adding 2~3 equivalents of MnO$_2$ every 35 h until HPLC showed disappearance of the starting material. The black suspension was filtered through a Celite pad, concentrated in vacuo to give (3-benzyloxy-4-methoxy-phenyl)-(3-ethoxy-4-methoxy-phenyl)-methanone as a brown solid (7.24 g, 100% yield): $^1$H NMR (CDCl$_3$) δ 1.49 (t, J=7 Hz, 3H, CH$_2$CH$_3$), 3.95 (s, 3H, OCH$_3$), 3.97 (s, 3H, OCH$_3$), 4.14 (q, J=7 Hz, 2H, CH$_2$CH$_3$), 5.20 (s, 2H, CH$_2$), 6.83 (d, J=8 Hz, 1H, Ar), 6.94 (d, J=8 Hz, 1H, Ar), 7.23-7.47 (m, 9H, Ar). The product was used in the next step without further purification.

A mixture of (3-benzyloxy-4-methoxy-phenyl)-(3-ethoxy-4-methoxy-phenyl)-methanone (7.24 g), 20% palladium on charcol (0.22 g, 3% weight), and cyclohexene (24 mL) in ethanol (48 mL) was refluxed overnight. The black suspension was filtered through a Celite pad, and the filtrate was evaporated to give (3-ethoxy-4-methoxy-phenyl)-(3-hydroxy-4-methoxy-phenyl)-methanone as an off-white solid (5.25 g, 94% yield): $^1$H NMR (DMSO-d$_6$) δ 1.49 (t, J=7 Hz, 3H, CH$_2$CH$_3$), 3.95 (s, 3H, OCH$_3$), 3.98 (s, 3H, OCH$_3$), 4.16 (q, J=7 Hz, 2H, CH$_2$CH$_3$), 5.69 (s, 1H, OH), 6.87-6.93 (m, 2H, Ar), 7.35-7.43 (m, 4H, Ar). The product was used in the next step without further purification.

To a solution of cyanomethylphosphonic acid diethyl ester (8.1 mL, 51.6 mmol) in anhydrous THF (50 mL) was added lithium bis(trimethylsilyl)amide (1.0 M solution in THF, 51.6 mL, 51.6 mmol) at 0° C. and stirred for 30 min at room temperature followed by addition of (3-ethoxy-4-methoxy-phenyl)-(3-hydroxy-4-methoxy-phenyl)-methanone (5.20 g, 17.2 mmol) in THF (40 mL) and refluxed overnight. The reaction mixture was poured into water (50 mL), extracted with CH$_2$Cl$_2$ (2×60 mL). The combined organic phases were washed with brine (60 mL), dried over MgSO$_4$, and purified via flash column chromatography (EtOAc/Hexane) to give E/Z-3-(3-ethoxy-4-methoxy-phenyl)-3-(3-hydroxy-4-methoxy-phenyl)-acrylonitrile as an off-white solid (5.26 g, 94% yield). The product was used in the next step without further purification.

To a stirred solution of E/Z-3-(3-ethoxy-4-methoxy-phenyl)-3-(3-hydroxy-4-methoxy-phenyl)-acrylonitrile (0.63 g, 1.9 mmol) in CH$_2$Cl$_2$ (15 mL) at room temperature was added L-2-tert-butoxycarbonylamino-propionic acid (0.37 g, 2.0 mmol), DCC (0.40 g, 2.0 mmol) and 4-pyrrolidin-1-yl-pyridine (0.03 g, 0.2 mmol). The mixture was stirred for 2 hours and filtered. The filtrate was washed with water (30 mL), dried over MgSO$_4$, and concentrated to an oil, which was purified by flash column chromatography (EtOAc/Hexane) to give E/Z-2-tert-butoxycarbonylamino-propionic acid 5-[2-cyano-1-(3-ethoxy-4-methoxy-phenyl)-vinyl]-2-methoxy-phenyl ester as an oil (0.89 g, 91% yield). The product was used in the next step without further purification.

To a stirred solution of E/Z-2-tert-butoxycarbonylamino-propionic acid 5-[2-cyano-1-(3-ethoxy-4-methoxy-phenyl)-vinyl]-2-methoxy-phenyl ester (0.89 g, 1.8 mmol in CH$_2$Cl$_2$ (10 mL) was added 2 M HCl in ether (4.5 mL, 9.0 mmol) and kept adding 12 equivalents of 2 M HCl in ether until HPLC showed disappearance of the starting material. The suspension was filtered and the resulting white solid was slurried in ether overnight and filtered again to give (E/Z)-2-amino-propionic acid 5-[2-cyano-1-(3-ethoxy-4-methoxy-phenyl)-vinyl]-2-methoxy-phenyl ester hydrochloric acid as a white solid (0.52 g, 67% yield): mp, 173-175° C.; $^1$H NMR (DMSO-d$_6$) δ 1.32 (t, J=7 Hz, 3H, CH$_2$CH$_3$), 1.55-1.59 (m, 3H, CHCH$_3$), 3.74-3.88 (ms, 6H, 2OCH$_3$), 3.94-4.05 (m, 2H, CH$_2$CH$_3$), 4.30-4.39 (m, 1H, CHCH$_3$), 6.14 and 6.22 (2s, 1H, CH), 6.73-7.42 (m, 6H, Ar), 8.64 (brs, 3H, NH$_3$Cl); $^{13}$C NMR (DMSO-d$_6$) δ 14.6, 14.6, 15.8, 24.4, 25.3, 33.3, 47.5, 47.8, 55.5, 55.6, 56.2, 56.3, 63.8, 93.6, 93.8, 111.4, 111.6, 112.2, 113.0, 113.1, 113.7, 118.5, 122.2, 122.3, 122.5, 123.4, 128.0, 128.9, 129.0, 129.5, 130.2, 130.9, 138.0, 138.2, 147.5, 147.9, 150.3, 151.2, 151.5, 152.3, 159.9, 160.1, 168.3, 168.3. Anal. Calcd for C$_{20}$H$_{25}$N$_2$O$_5$Cl+0.6H$_2$O: C, 59.55; H, 5.95; N, 6.31; Cl, 7.99%. Found: C, 59.20; H, 5.83; N, 6.67; Cl, 7.89%.

4.6.2.88 (E/Z)-3-Benzo[1,3]dioxol-5-yl-3-(3-ethoxy-4-methoxy-phenyl)-acrylonitrile

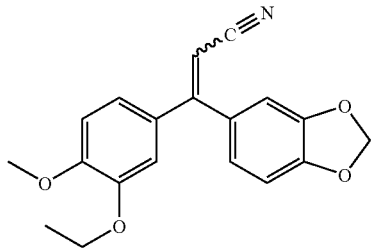

A stirred mixture of 4-bromo-2-ethoxy-1-methoxy-benzene (1.65 g, 7.1 mmol) and dry THF (15 mL) was cooled to −78° C., evacuated and refilled with nitrogen for 10 cycles. To this clear solution was slowly added n-butyllithium (2.9 mL, 7.1 mmol) and stirred for 20 min. Then a mixture of benzo[1,3]dioxole-5-carbaldehyde (0.98 g, 6.5 mmol) in dry THF (20 mL) was added and stirred for 1 hour at −78° C. The mixture was quenched with isopropanol (3.0 mL, 39 mmol) and added water (10 mL). The mixture was extracted with EtOAc (3×50 mL). The combined organic phases were washed with water (2×50 mL), dried over $MgSO_4$ and concentrated to oil, which was purified by flash column chromatography (EtOAc/Hexane) to give benzo[1,3]dioxol-5-yl-(3-ethoxy-4-methoxy-phenyl)-methanol as an off-white solid (1.1 g, 56% yield): $^1$H NMR (CDCl$_3$) δ 1.44 (t, J=7 Hz, 3H, CH$_2$CH$_3$), 2.11 (d, J=3 Hz, 1H, OH), 3.86 (s, 3H, OCH$_3$), 4.07 (q, J=7 Hz, 2H, CH$_2$CH$_3$), 5.71 (d, J=3 Hz, 1H, CH), 5.93 (s, 2H, CH$_2$), 6.74-6.91 (m, 6H, Ar). The product was used in the next step without further purification.

To a stirred solution of benzo[1,3]dioxol-5-yl-(3-ethoxy-4-methoxy-phenyl)-methanol (1.09 g, 3.6 mmol) in CH$_2$Cl$_2$ (20 mL) at room temperature was added activated MnO$_2$ powder (1.6 g, 18.1 mmol) and kept adding 23 equivalents of MnO$_2$ every 35 h until HPLC showed disappearance of the starting material. The black suspension was filtered through a Celite pad, concentrated in vacuo to give benzo[1,3]dioxol-5-yl-(3-ethoxy-4-methoxy-phenyl)-methanone as an off-white solid (1.06 g, 98% yield): $^1$H NMR (CDCl$_3$) δ 1.49 (t, J=7 Hz, 3H, CH$_2$CH$_3$), 3.95 (s, 3H, OCH$_3$), 4.16 (q, J=7 Hz, 2H, CH$_2$CH$_3$), 6.07 (s, 2H, CH$_2$), 6.85-6.91 (m, 2H, Ar), 7.32-7.42 (m, 4H, Ar). The product was used in the next step without further purification.

To a solution of cyanomethylphosphonic acid diethyl ester (1.1 mL, 6.9 mmol) in anhydrous THF (10 mL) was added lithium bis(trimethylsilyl)amide (1.0 M solution in THF, 6.9 mL, 6.9 mmol) at 0° C. and stirred for 30 min at room temperature followed by addition of benzo[1,3]dioxol-5-yl-(3-ethoxy-4-methoxy-phenyl)-methanone (1.03 g, 3.4 mmol) in THF (20 mL) and refluxed for 4 hours. The reaction mixture was poured into water (90 mL), extracted with CH$_2$Cl$_2$ (2×60 mL). The combined organic phases were washed with brine (60 mL), dried over MgSO$_4$, and purified via flash column chromatography (EtOAc/Hexane) to give (E/Z)-3-Benzo[1,3]dioxol-5-yl-3-(3-ethoxy-4-methoxy-phenyl)-acrylonitrile as a white solid (1.02 g, 92% yield): mp, 122-124° C.; $^1$H NMR (DMSO-d$_6$) δ 1.31 (t, J=7 Hz, 3H, CH$_2$CH$_3$), 3.78 and 3.83 (2s, 3H, OCH$_3$), 3.94-4.05 (2q, 2H, CH$_2$CH$_3$), 6.09-6.16 (m, 3H, CH and CH$_2$), 6.74-7.09 (m, 6H, Ar); $^{13}$C NMR (DMSO-d$_6$) δ 14.5, 14.6, 53.7, 55.5, 55.6, 63.8, 63.9, 93.2, 101.6, 101.8, 107.9, 108.1, 108.3, 109.4, 111.3, 111.5, 112.1, 113.8, 118.6, 118.7, 122.3, 122.4, 123.7, 123.9, 129.3, 130.4, 130.9, 132.3, 147.2, 147.4, 147.8, 147.9, 148.4, 149.3, 150.1, 151.1, 161.0, 161.1. Anal. Calcd for C$_{19}$H$_{17}$NO$_4$: C, 70.58; H, 5.30; N, 4.33. Found: C, 70.53; H, 5.16; N, 4.24.

4.6.2.89 (E/Z)-3-(2,3-Dihydro-benzo[1,4]dioxin-6-yl)-3-(3-methoxy-phenyl)-acrylonitrile

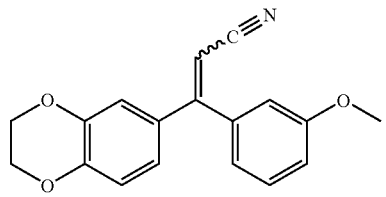

A stirred mixture of 6-bromo-2,3-dihydro-benzo[1,4]dioxine (1.59 g, 7.4 mmol) and dry TRF (10 mL) was cooled to −78° C., evacuated and refilled with nitrogen for 10 cycles. To this clear solution was slowly added n-butyllithium (3.0 mL, 7.4 mmol) and stirred for 20 min. Then a mixture of 3-methoxy-benzaldehyde (0.92 g, 6.7 mmol) in dry THF (10 mL) was added and stirred for 1 hour at −78° C. The mixture was quenched with isopropanol (3.1 mL, 40 mmol) and added water (10 mL). The mixture was extracted with EtOAc (3×30 mL). The combined organic phases were washed with water (2×30 mL), dried over MgSO$_4$ and concentrated to give (2,3-dihydro-benzo[1,4]dioxin-6-yl)-(3-methoxy-phenyl)-methanol as an oil (2.09 g, 114% crude yield). The product was used in the next step without further purification.

To a stirred solution of (2,3-dihydro-benzo[1,4]dioxin-6-yl)-(3-methoxy-phenyl)-methanol (2.08 g crude, 6.7 mmol) in CH$_2$Cl$_2$ (15 mL) at room temperature was added activated MnO$_2$ powder (3.6 g, 41.4 mmol) and kept adding 23 equivalents of MnO$_2$ every 35 h until HPLC showed disappearance of the starting material. The black suspension was filtered through a Celite pad, concentrated in vacuo to give (2,3-dihydro-benzo[1,4]dioxin-6-yl)-(3-methoxy-phenyl)-methanone as an oil (2.0 g, 109% crude yield): $^1$H NMR (CDCl$_3$) δ 3.86 (s, 3H, OCH$_3$), 4.26-4.36 (m, 4H, CH$_2$CH$_2$), 6.84-7.42 (m, 7H, Ar). The product was used in the next step without further purification.

To a solution of cyanomethylphosphonic acid diethyl ester (2.1 mL, 13.5 mmol) in anhydrous THF (15 mL) was added lithium bis(trimethylsilyl)amide (1.0 M solution in THF, 13.5 mL, 13.5 mmol) at 0° C. and stirred for 30 min at room temperature followed by addition of (2,3-dihydro-benzo[1,4]dioxin-6-yl)-(3-methoxy-phenyl)-methanone (2.0 g crude, 6.7 mmol) in THF (15 mL) and refluxed for 30 min. The reaction mixture was poured into water (50 mL), extracted with CH$_2$Cl$_2$ (2×50 mL). The combined organic phases were washed with brine (50 mL), dried over MgSO$_4$, and purified via flash column chromatography (EtOAc, Hexane) to give 3-(2,3-dihydro-benzo[1,4]dioxin-6-yl)-3-(3-methoxy-phenyl)-acrylonitrile as an off-white solid (1.53 g, 77% yield): mp, 64-66° C.; $^1$H NMR (DMSO-d$_6$) δ 3.77 and 3.78 (2s, 3H, OCH$_3$), 4.24-4.36 (m, 4H, CH$_2$CH$_2$), 6.19 and 6.24 (2s, 1H, CH), 6.77-7.09 (m, 6H, Ar), 7.33-7.36 (m, 1H, Ar); $^{13}$C NMR (DMSO-d$_6$) δ 55.2, 55.2, 64.0, 64.0, 64.2, 64.3, 94.3, 95.2, 113.7, 114.6, 114.9, 115.8, 116.7, 117.1, 117.2, 117.9, 118.3, 120.9, 121.2, 121.7, 122.5, 129.7, 129.8, 129.8, 130.6, 138.5, 139.7, 143.1, 143.3, 144.8, 145.6, 159.1, 159.2, 160.8, 160.9. Anal. Calcd for C$_{18}$H$_{15}$NO$_3$: C, 73.71; H, 5.15; N, 4.78. Found: C, 73.48; H, 4.84; N, 4.64.

4.6.2.90 (E/Z)-3-(2,3-Dihydro-benzo[1,4]dioxin-6-yl)-3-(4-methoxy-phenyl)-acrylonitrile

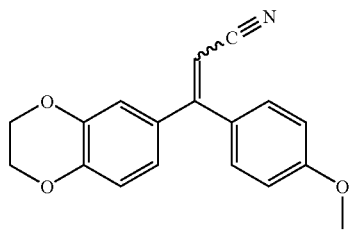

A stirred mixture of 6-bromo-2,3-dihydro-benzo[1,4]dioxine (1.66 g, 7.7 mmol) and dry THF (20 mL) was cooled to −78° C., evacuated and refilled with nitrogen for 10 cycles. To this clear solution was slowly added n-butyllithium (2.9 mL, 7.4 mmol) and stirred for 20 min. Then a mixture of 4-methoxy-benzaldehyde (0.90 g, 6.6 mmol) in dry THF (10 mL) was added and stirred for 1 hour at −78° C. The mixture was quenched with isopropanol (3.4 mL, 44 mmol) and added water (10 mL). The mixture was extracted with EtOAc (3×30 mL). The combined organic phases were washed with water (2×30 mL), dried over MgSO$_4$ and concentrated to give (2,3-dihydro-benzo[1,4]dioxin-6-yl)-(4-methoxy-phenyl)-methanol as an oil (2.04 g, 102% crude yield). The product was used in the next step without further purification.

To a stirred solution of (2,3-dihydro-benzo[1,4]dioxin-6-yl)-(4-methoxy-phenyl)-methanol (2.03 g crude, 7.5 mmol) in CH$_2$Cl$_2$ (20 mL) at room temperature was added activated MnO$_2$ powder (3.4 g, 39 mmol) and kept adding 2~3 equivalents of MnO$_2$ every 3~5 h until HPLC showed disappearance of the starting material. The black suspension was filtered through a Celite pad, concentrated in vacuo to give (2,3-dihydro-benzo[1,4]dioxin-6-yl)-(4-methoxy-phenyl)-methanone as an brown oil (2.09 g, 103% crude yield): $^1$H NMR (CDCl$_3$) δ 3.88 (s, 3H, OCH$_3$), 4.30-4.34 (m, 4H, CH$_2$CH$_2$), 6.91-6.97 (m, 3H, Ar), 7.26-7.36 (m, 2H, Ar), 7.78-7.81 (m, 2H, Ar). The product was used in the next step without further purification.

To a solution of cyanomethylphosphonic acid diethyl ester (2.4 mL, 15.0 mmol) in anhydrous THF (20 mL) was added lithium bis(trimethylsilyl)amide (1.0 M solution in THF, 15.0 mL, 15.0 mmol) at 0° C. and stirred for 30 min at room temperature followed by addition of (2,3-dihydro-benzo[1,4]dioxin-6-yl)-(4-methoxy-phenyl)-methanone (2.02 g crude, 7.5 mmol) in THF (15 mL) and refluxed for 30 min. The reaction mixture was poured into water (50 if L), extracted with CH$_2$Cl$_2$ (2×50 mL). The combined organic phases were washed with brine (50 mL), dried over MgSO$_4$, and purified via flash column chromatography (EtOAc, Hexane) to give 3-(2,3-dihydro-benzo[1,4]dioxin-6-yl)-3-(4-methoxy-phenyl)-acrylonitrile as a yellow solid (1.44 g, 66% yield): mp, 112-114° C.; $^1$H NMR (DMSO-d$_6$) δ 3.79 and 3.83 (2s, 3H, OCH$_3$), 4.25-4.33 (m, 4H, CH$_2$CH$_2$), 6.07 and 6.08 (2s, 1H, CH), 6.77-7.32 (m, 7H, Ar); $^{13}$C NMR (DMSO-d$_6$) δ 55.2, 55.3, 64.0, 64.0, 64.2, 64.3, 92.7, 93.0, 113.9, 114.1, 117.0, 117.2, 118.0, 118.6, 118.7, 121.9, 122.5, 129.1, 130.0, 130.1, 130.4, 130.8, 131.4, 143.1, 143.2, 144.7, 145.5, 160.3, 160.7, 160.8, 161.1. Anal. Calcd for C$_{18}$H$_{15}$NO$_3$+0.1H$_2$O: C, 73.26; H, 5.19; N, 4.75. Found: C, 72.96; H, 5.22; N, 4.67.

4.6.2.91 (E/Z)-3-Benzo[1,3]dioxol-5-yl-3-(3-methoxy-phenyl)-acrylonitrile

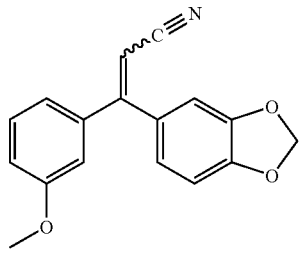

A stirred mixture of 1-bromo-3-methoxy-benzene (1.49 g, 8.0 mmol) and dry THF (20 mL) was cooled to −78° C., evacuated and refilled with nitrogen for 10 cycles. To this clear solution was slowly added n-butyllithium (3.0 mL, 7.6 mmol) and stirred for 20 min. Then a mixture of benzo[1,3]dioxole-5-carbaldehyde (1.03 g, 6.8 mmol) in dry THF (15 mL) was added and stirred for 1 hour at −78° C. The mixture was quenched with isopropanol (3.5 mL, 46 mmol) and added water (10 mL). The mixture was extracted with EtOAc (3×40 mL). The combined organic phases were washed with water (2×40 mL), dried over MgSO$_4$ and concentrated to give benzo[1,3]dioxol-5-yl-(3-methoxy-phenyl)-methanol as an oil (2.23 g, 113% crude yield). The product was used in the next step without further purification.

To a stirred solution of benzo[1,3]dioxol-5-yl-(3-methoxyphenyl) -methanol (2.23 g crude, 7.6 mmol) in CH$_2$Cl$_2$ (20 mL) at room temperature was added activated MnO$_2$ powder (3.5 g, 40 mmol) and kept adding 23 equivalents of MnO$_2$ every 35 h until HPLC showed disappearance of the starting material. The black suspension was filtered through a Celite pad, concentrated in vacuo to give benzo[1,3]dioxol-5-yl-(3-methoxy-phenyl)-methanone as an oil (1.78 g, 89% crude yield). The product was used in the next step without further purification.

To a solution of cyanomethylphosphonic acid diethyl ester (2.1 mL, 13.6 mmol) in anhydrous THF (15 mL) was added lithium bis(trimethylsilyl)amide (1.0 M solution in THF, 13.6 mL, 13.6 mmol) at 0° C. and stirred for 30 min at room temperature followed by addition of benzo[1,3]dioxol-5-yl-(3-methoxy-phenyl)-methanone (1.74 g crude, 6.8 mmol) in THF (15 mL) and refluxed for one hour. The reaction mixture was poured into water (50 mL), extracted with CH$_2$Cl$_2$ (2×50 mL). The combined organic phases were washed with brine (50 mL), dried over MgSO$_4$, and purified via flash column chromatography (EtOAc, Hexane) to give 3-benzo[1,3]dioxol-5-yl-3-(3-methoxy-phenyl)-acrylonitrile as an oil (0.87 g, 46% yield): $^1$H NMR (DMSO-d$_6$) δ 3.77 and 3.78 (2s, 3H, OCH$_3$), 6.10 and 6.13 (2s, 2H, CH$_2$), 6.23 and 6.27 (2s, 1H, CH), 6.69-7.46 (m, 7H, Ar); $^{13}$C NMR (DMSO-d$_6$) δ 55.2, 55.2, 94.4, 95.6, 101.6, 101.8, 107.4, 108.2, 108.3, 109.3, 113.7, 114.6, 115.0, 118.2, 120.9, 121.2, 123.7, 123.8, 129.7, 129.8, 130.6, 131.6, 138.6, 139.6, 147.3, 147.9, 148.5, 149.4, 159.1, 159.2, 160.9, 161.1. LC/MS showed desired peak at 280 for (M+1)$^{+1}$ positive ion mass.

4.6.2.92 (E/Z)-3-Benzo[1,3]dioxol-5-yl-3-(4-methoxy-phenyl)-acrylonitrile

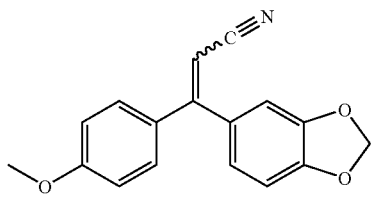

A stirred mixture of 1-bromo-4-methoxy-benzene (1.79 g, 9.6 mmol) and dry THF (25 mL) was cooled to −78° C., evacuated and refilled with nitrogen for 10 cycles. To this clear solution was slowly added n-butyllithium (3.6 mL, 9.1 mmol) and stirred for 20 min. Then a mixture of benzo[1,3]dioxole-5-carbaldehyde (1.23 g, 8.2 mmol) in dry THF (20 mL) was added and stirred for 1 hour at −78° C. The mixture was quenched with isopropanol (4.2 mL, 55 mmol) and added water (10 mL). The mixture was extracted with EtOAc (3×50 mL). The combined organic phases were washed with water (2×50 mL), dried over $MgSO_4$ and concentrated to give benzo[1,3]dioxol-5-yl-(4-methoxy-phenyl)-methanol as an oil (2.54 g, 108% crude yield, HPLC purity 88%): $^1H$ NMR ($CDCl_3$) δ 2.13 (d, J=3 Hz, 1H, OH), 3.79 (s, 3H, —$OCH_3$), 5.72 (d, J=3 Hz, 1H, CH), 5.93 (s, 2H, $CH_2$), 6.74-7.39 (m, 7H, Ar). The product was used in the next step without further purification.

To a stirred solution of benzo[1,3]dioxol-5-yl-(4-methoxy-phenyl)-methanol (2.54 g crude, 9.1 mmol) in $CH_2Cl_2$ (20 mL) at room temperature was added activated $MnO_2$ powder (4.0 g, 45.5 mmol) and kept adding 2~3 equivalents of $MnO_2$ every 3~5 h until HPLC showed disappearance of the starting material. The black suspension was filtered through a Celite pad, concentrated in vacuo to give benzo[1,3]dioxol-5-yl-(4-methoxy-phenyl)-methanone as a yellow solid (2.47 g, 106% crude yield, HPLC purity 93%): $^1H$ NMR ($CDCl_3$) δ 3.89 (s, 3H, —$OCH_3$), 6.06 (s, 2H, $CH_2$), 6.76-6.98 (m, 3H, Ar), 7.26-7.39 (m, 2H, Ar), 7.75-7.80 (m, 2H, Ar). The product was used in the next step without further purification.

To a solution of cyanomethylphosphonic acid diethyl ester (3.0 mL, 18.7 mmol) in anhydrous THF (20 mL) was added lithium bis(trimethylsilyl)amide (1.0 M solution in THF, 18.7 mL, 18.7 mmol) at 0° C. and stirred for 30 min at room temperature followed by addition of benzo[1,3]dioxol-5-yl-(4-methoxy-phenyl)-methanone (2.40 g crude, HPLC purity 93%, 9.4 mmol) in THF (15 mL) and refluxed for 3 hours. The reaction mixture was poured into water (80 mL), extracted with $CH_2Cl_2$ (2×60 mL). The combined organic phases were washed with brine (60 mL), dried over $MgSO_4$, and purified via flash column chromatography (EtOAc, Hexane) to give 3-benzo[1,3]dioxol-5-yl-3-(4-methoxy-phenyl)-acrylonitrile as an oil (1.98 g, 76% yield): $^1H$ NMR (DMSO-$d_6$) δ 3.79 (s, 3H, $OCH_3$), 3.83 (s, 3H, $OCH_3$), 6.10-6.13 (ms, 6H, $2CH_2$ and 2CH), 6.70-7.33 (m, 14H, Ar); $^{13}C$ NMR (DMSO-$d_6$) δ 55.3, 55.4, 93.0, 93.2, 101.6, 101.8, 107.8, 108.2, 108.3, 109.3, 113.9, 114.1, 118.6, 118.7, 123.6, 123.8, 129.3, 129.9, 130.4, 130.8, 130.9, 132.4, 147.3, 147.8, 148.4, 149.3, 160.3, 160.9, 161.0, 161.1. LC/MS showed desired peak at 280 for $(M+1)^{+1}$ positive ion mass.

4.6.2.93 3,3-Bis-(3-ethoxy-4-methoxy-phenyl)-acrylonitrile

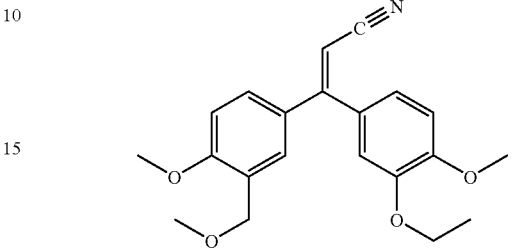

A stirred mixture of 4-bromo-2-ethoxy-1-methoxy-benzene (6.52 g, 28.2 mmol) and dry THF (40 mL) was cooled to −78° C., evacuated and refilled with nitrogen for 10 cycles. To this clear solution was slowly added n-butyllithium (11.3 mL, 28.2 mmol) and stirred for 30 min. Then a mixture of 3-ethoxy-4-methoxy-benzaldehyde (4.62 g, 25.7 mmol) in dry THF (60 mL) was added and stirred for 1 h at −78° C. The mixture was quenched with isopropanol (11.7 mL, 154 mmol) and added water (30 mL). It was extracted with ether (3×50 mL). The combined organic phases were washed with water (2×50 mL), dried over $MgSO_4$ and concentrated to an oil, which was purified by flash column chromatography (EtOAc/Hexane) to give bis-(3-ethoxy-4-methoxy-phenyl)-methanol as an oil (8.85 g, 100% yield): $^1H$ NMR ($CDCl_3$) δ 1.44 (t, J=7 Hz, 6H, $2CH_2CH_3$), 2.12 (d, J=4 Hz, 1H, OH), 3-0.86 (s 6H, $2OCH_3$), 4.06 (q, J=7 Hz, 4H, $2CH_2CH_3$), 5.74 (d, J=4 Hz, 1H, CH), 6.81-6.91 (m, 6H, Ar). The product was used in the next step without further purification.

To a stirred solution of bis-(3-ethoxy-4-methoxy-phenyl)-methanol (8.80 g, 26.5 mmol) in $CH_2Cl_2$ (30 mL) at room temperature was added activated $MnO_2$ powder (11.51 g, 132 mmol) and kept adding 2~3 equivalents of $MnO_2$ every 3~5 h until HPLC showed at least 98% conversion occurred. The black suspension was filtered through a Celite pad, concentrated in vacuo to give bis-(3-ethoxy-4-methoxy-phenyl)-methanone as an off-white solid (7.42 g, 85% yield): $^1H$ NMR ($CDCl_3$) δ 1.49 (t, J=7 Hz, 6H, $2CH_2CH_3$), 3.96 (s, 6H, $2OCH_3$), 6.89-6.92 (m, 2H, Ar), 7.16 (q, J=7 Hz, 4H, $2CH_2CH_3$), 7.35-7.42 (m, 4H, Ar). The product was used in the next step without further purification.

To a solution of cyanomethylphosphonic acid diethyl ester (7.0 mL, 44.4 mmol) in anhydrous THF (20 mL) was added lithium bis(trimethylsilyl)amide (1.0 M solution in THF, 44.4 mL, 44.4 mmol) at 0° C. and stirred for 30 min followed by addition of bis-(3-ethoxy-4-methoxy-phenyl)-methanone (7.34 g, 22.2 mmol) and refluxed for 3 h. The reaction mixture was poured into water (100 mL), extracted with $CH_2Cl_2$ (2×100 mL). The combined organic phases were washed with brine (100 mL), dried over $MgSO_4$, and purified via flash column chromatography (EtOAc/Hexane) to give 3,3-bis-(3-ethoxy-4-methoxy-phenyl)-acrylonitrile as a white solid (3.92 g, 50% yield): $^1H$ NMR (DMSO-$d_6$) δ 1.31 (t, J=7 Hz, 6H, $2CH_2CH_3$), 3.79 (s, 3H, $OCH_3$), 3.83 (s, 3H, $OCH_3$), 3.94-4.04 (two q, J=7 Hz, 4H, $2CH_2CH_3$), 6.11 (s, 1H, CH), 6.77-7.09 (m, 6H, Ar); $^{13}C$ NMR (DMSO-$d_6$) δ 14.6, 14.6, 55.5, 55.5, 63.8, 92.6, 111.3, 111.5, 112.3, 113.8, 118.9, 122.3, 122.4, 129.3, 130.6, 147.3, 147.8, 150.1, 151.0, 161.4;

4.6.2.94 (E/Z)-3-(3-Ethoxy-4-methoxy-phenyl)-3-(3-methoxy-phenyl)-acrylonitrile

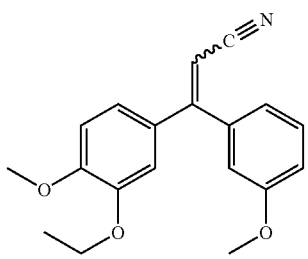

A stirred mixture of 4-bromo-2-ethoxy-1-methoxy-benzene (1.88 g, 8.1 mmol) and dry THF (15 mL) was cooled to −78° C., evacuated and refilled with nitrogen for 10 cycles. To this clear solution was slowly added n-butyllithium (3.3 mL, 8.1 mmol) and stirred for 20 min. Then a mixture of 3-methoxy-benzaldehyde (1.01 g, 7.4 mmol) in dry THF (10 mL) was added and stirred for 1 hour at −78° C. The mixture was quenched with isopropanol (3.4 mL, 44 mmol) and added water (10 mL). The mixture was extracted with EtOAc (3×50 mL). The combined organic phases were washed with water (2×50 mL), dried over $MgSO_4$ and concentrated to oil, which was purified by flash column chromatography (EtOAc/Hexane) to give (3-ethoxy-4-methoxy-phenyl)-(3-methoxy-phenyl)-methanol as an oil (1.92 g, 90% yield): $^1H$ NMR ($CDCl_3$) δ 1.44 (t, J=7 Hz, 3H, $CH_2CH_3$), 2.17 (d, J=4 Hz, 1H, OH), 3.79 (s, 3H, $OCH_3$), 3.85 (s, 3H, $OCH_3$), 4.07 (q, J=7 Hz, 2H, $CH_2CH_3$), 5.76 (d, J=4 Hz, 1H, CH), 6.78-7.28 (m, 7H, Ar). The product was used in the next step without further purification.

To a stirred solution of (3-ethoxy-4-methoxy-phenyl)-(3-methoxy-phenyl)-methanol (1.75 g, 6.1 mmol) in $CH_2Cl_2$ (20 mL) at room temperature was added activated $MnO_2$ powder (3.5 g, 40 mmol) and kept adding 23 equivalents of $MnO_2$ every 35 h until HPLC showed disappearance of the starting material. The black suspension was filtered through a Celite pad, concentrated in vacuo to give (3-ethoxy-4-methoxy-phenyl)-(3-methoxy-phenyl)-methanone as an off-white solid (1.60 g, 92% yield): $^1H$ NMR ($CDCl_3$) δ 1.53 (t, J=7 Hz, 3H, $CH_2CH_3$), 3.86 (s, 3H, $OCH_3$), 3.96 (s, 3H, $OCH_3$), 4.17 (q, J=7 Hz, 2H, $CH_2CH_3$), 6.90 (d, J=8 Hz, 1H, Ar), 7.09-7.14 (m, 1H, Ar), 7.29-7.49 (m, 5H, Ar). The product was used in the next step without further purification.

To a solution of cyanomethylphosphonic acid diethyl ester (1.7 mL, 11.0 mmol) in anhydrous THF (10 mL) was added lithium bis(trimethylsilyl)amide (1.0 M solution in THF, 11.0 mL, 11.0 mmol) at 0° C. and stirred for 30 min at room temperature followed by addition of (3-ethoxy-4-methoxy-phenyl)-(3-methoxy-phenyl)-methanone (1.58 g, 5.5 mmol) in THF (20 mL) and refluxed for 4 hours. The reaction mixture was poured into water (90 mL), extracted with $CH_2Cl_2$ (2×60 mL). The combined organic phases were washed with brine (60 mL), dried over $MgSO_4$, and purified via flash column chromatography (EtOAc/Hexane) to give (E/Z)-3-(3-Ethoxy-4-methoxy-phenyl)-3-(3-methoxy-phenyl)-acrylonitrile as a white solid (1.59 g, 93% yield): mp, 96-98° C.; $^1H$ NMR (DMSO-$d_6$) δ 1.31 (t, J=7 Hz, 3H, $CH_2CH_3$), 3.77-3.83 (ms, 6H, 2$OCH_3$), 3.94-4.05 (2q, 2H, $CH_2CH_3$), 6.18 and 6.29 (2s, 1H, CH), 6.72-7.43 (m, 7H, Ar); $^{13}C$ NMR (DMSO-$d_6$) δ 14.5, 14.6, 55.2, 55.3, 55.5, 55.6, 63.8, 63.9, 93.9, 94.9, 111.3, 111.5, 111.8, 113.7, 114.6, 115.0, 115.9, 118.4, 118.5, 121.0, 121.3, 122.2, 122.4, 129.1, 129.7, 129.8, 129.9, 138.6, 139.8, 147.4, 147.8, 150.3, 151.1, 159.0, 161.2, 161.4. Anal. Calcd for $C_{19}H_{19}NO_3$: C, 73.77; H, 6.19; N, 4.53. Found: C, 73.43; H, 6.13; N, 4.54.

4.6.2.95 (E/Z)-3-(3,5-Dimethoxy-phenyl)-3-(3-ethoxy-phenyl)-acrylonitrile

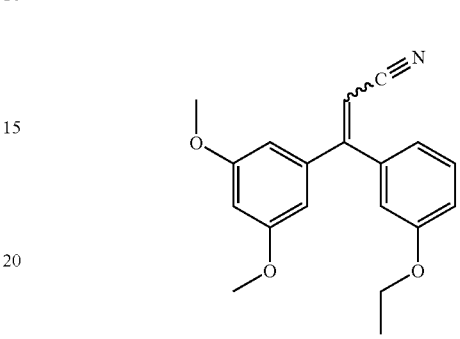

To a stirred solution of benzyl bromide (24.39 g, 142.6 mmol) and 3-bromo phenol (24.92 g, 144 mmol) in 20 mL of fresh acetone was added potassium carbonate (59.72 g, 432 mmol). The suspension was refluxed overnight. The mixture was evaporated and added water (100 mL), extracted with EtOAc (3×80 mL). The combined EtOAc extracts were back washed with water (100 mL), dried over $MgSO_4$, filtered and evaporated to give 1-benzyloxy-3-bromo-benzene as an off-white solid (10.0 g, 67% yield): $^1H$ NMR (DMSO-$d_6$) δ 5.12 (s, 2H, $CH_2$), 7.00-7.46 (m, 9H, Ar). The product was used in the next step without further purification.

A stirred mixture of 1-benzyloxy-3-bromo-benzene (10.56 g, 40.1 mmol) and dry THF (35 mL) was cooled to −78° C., evacuated and refilled with nitrogen for 10 cycles. To this clear solution was slowly added n-butyllithium (17.7 mL, 44.1 mmol) and stirred for 20 min. Then a mixture of 3,5-dimethoxy-benzaldehyde (7.34 g, 44.1 mmol) in dry THF (30 mL) was added and stirred for 1 hour at −78° C. The mixture was quenched with isopropanol (18.5 mL, 241 mmol) and added water (30 mL). The mixture was extracted with EtOAc (3×80 mL). The combined organic phases were washed with water (2×80 mL), dried over $MgSO_4$ and concentrated to oil, which was purified by flash column chromatography (EtOAc/Hexane) to give (3-benzyloxy-phenyl)-(3,5-dimethoxy-phenyl)-methanol as an oil (11.54 g, 82% yield): $^1H$ NMR ($CDCl_3$) δ 2.21 (d, J=4 Hz, 1H, OH), 3.76 (s, 6H, 2$OCH_3$), 5.04 (s, 2H, $CH_2$), 5.72 (d, J=4 Hz, 1H, CH), 6.36 (t, J=2 Hz, 1H, Ar), 6.54 (d, J=2 Hz, 2H, Ar), 6.85-7.04 (m, 3H, Ar), 7.21-7.43 (m, 6H, Ar). The product was used in the next step without further purification.

To a stirred solution of (3-benzyloxy-phenyl)-(3,5-dimethoxy-phenyl)-methanol (11.51 g, 32.9 mmol) in $CH_2Cl_2$ (30 mL) at room temperature was added activated $MnO_2$ powder (13.28 g, 153 mmol) and kept adding 2~3 equivalents of $MnO_2$ every 3~5 h until HPLC showed disappearance of the starting material. The black suspension was filtered through a Celite pad, concentrated in vacuo to give (3-benzyloxy-phenyl)-(3,5-dimethoxy-phenyl)-methanone as a clear oil (10.67 g, 93% yield): $^1H$ NMR ($CDCl_3$) δ 3.82 (s, 6H, $OCH_3$), 5.11 (s, 2H, $CH_2$), 6.67 (t, J=2 Hz, 1H, Ar), 6.92 (d, J=2 Hz, 2H, Ar), 7.17-7.22 (m, 1H, Ar), 7.33-7.45 (m, 8H, Ar). The product was used in the next step without further purification.

To a solution of cyanomethylphosphonic acid diethyl ester (9.6 mL, 61.2 mmol) in anhydrous THF (30 mL) was added lithium bis(trimethylsilyl)amide (1.0 M solution in THF, 61.2 mL, 61.2 mmol) at 0° C. and stirred for 30 min at room temperature followed by addition of (3-benzyloxy-phenyl)-(3,5-dimethoxy-phenyl)-methanone (10.66 g, 30.6 mmol) in THF (40 mL) and refluxed for 5 hours. The reaction mixture was poured into water (100 mL), extracted with CH$_2$Cl$_2$ (2×80 mL). The combined organic phases were washed with brine (80 mL), dried over MgSO$_4$, and purified via flash column chromatography (EtOAc/Hexane) to give (E/Z)-3-(3-benzyloxy-phenyl)-3-(3,5-dimethoxy-phenyl)-acrylonitrile as a white solid (9.82 g, 86% yield): mp, 100-102° C.; $^1$H NMR (DMSO-d$_6$) δ 3.73 and 3.76 (2s, 3H, OCH$_3$), 5.11 and 5.12 (2s, 2H, CH$_2$), 6.38 and 6.40 (2s, 1H, CH), 6.46 (d, J=2 Hz, 2H, Ar), 6.62-6.66 (2t, 1H, Ar), 6.88-7.20 (m, 3H, Ar), 7.31-7.47 (m, 6H, Ar). The product was used in the next step without further purification.

A mixture of (E/Z)-3-(3-benzyloxy-phenyl)-3-(3,5-dimethoxy-phenyl)-acrylonitrile (3.37 g), 20% palladium on charcol (0.1 g, 3% weight), and cyclohexene (11 mL) in ethanol (22 mL) was refluxed overnight. The black suspension was filtered through a Celite pad, and the filtrate was evaporated to give E/Z-3-(3,5-dimethoxy-phenyl)-3-(3-hydroxy-phenyl)-acrylonitrile as an off-white solid (1.79 g, 70% yield): $^1$H NMR (DMSO-d$_6$) δ 3.74 and 3.77 (2s, 6H, 2OCH$_3$), 6.27 and 6.32 (2s, 1H, CH), 6.46 (d, J=2 Hz, 2H, Ar), 6.62-6.92 (m, 4H, Ar), 7.20-7.33 (m, 1H, Ar), 9.65 and 9.73 (2brs, 1H, OH). The product was used in the next step without further purification.

A mixture of E/Z-3-(3,5-dimethoxy-phenyl)-3-(3-hydroxy-phenyl) -acrylonitrile (0.27 g, 1.0 mmol), potassium carbonate (0.20 g, 1.4 mmol), and potassium iodide (4 mg, 0.03 mmol) in dry DMF (6 mL) was heated to 60-65° C. under nitrogen. To this bright yellow cloud was added iodoethane (0.1 mL, 1.2 mmol) slowly via a syringe. The mixture was heated at 60-65° C. overnight. Water (20 mL) and EtOAc (30 mL) were poured into the mixture and extracted with EtOAc (2×30 mL). The combined EtOAc phases were dried over MgSO$_4$, concentrated to an oil, which was purified by flash column chromatography (EtOAc/Hexane) to give (E/Z)-3-(3,5-Dimethoxy-phenyl)-3-(3-ethoxy-phenyl)-acrylonitrile as a white solid (0.25 g, 86% yield): mp, 100-102° C.; $^1$H NMR (DMSO-d$_6$) δ 1.28-1.36 (2t, 3H, CH$_2$CH$_3$), 3.73 and 3.76 (2s, 6H, 2OCH$_3$), 3.98-4.09 (2q, 2H, CH$_2$CH$_3$), 6.37 and 6.38 (2s, 1H, CH), 6.47 (d, J=2 Hz, 2H, Ar), 6.62-6.66 (m, 1H, Ar), 6.84-7.44 (m, 4H, Ar). Anal. Calcd for C$_{19}$H$_{19}$NO$_3$: C, 73.77; H, 6.19; N, 4.53. Found: C, 73.76; H, 6.26; N, 4.50.

4.6.2.96 Z-3-(3,5-Dimethoxy-phenyl)-3-(3-hydroxy-phenyl) -acrylonitrile

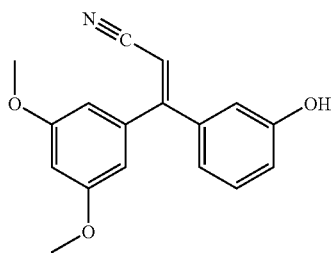

To a stirred solution of benzyl bromide (24.39 g, 142.6 mmol) and 3-bromo phenol (24.92 g, 144 mmol) in 20 mL of fresh acetone was added potassium carbonate (59.72 g, 432 mmol). The suspension was refluxed overnight. The mixture was evaporated and added water (100 mL), extracted with EtOAc (3×80 mL). The combined EtOAc extracts were back washed with water (100 mL), dried over MgSO$_4$, filtered and evaporated to give 1-benzyloxy-3-bromo-benzene as an off-white solid (10.0 g, 67% yield): $^1$H NMR (DMSO-d$_6$) δ 5.12 (s, 2H, CH$_2$), 7.00-7.46 (m, 9H, Ar). The product was used in the next step without further purification.

A stirred mixture of 1-benzyloxy-3-bromo-benzene (10.56 g, 40.1 mmol) and dry THF (35 mL) was cooled to −78° C., evacuated and refilled with nitrogen for 10 cycles. To this clear solution was slowly added n-butyllithium (17.7 mL, 44.1 mmol) and stirred for 20 min. Then a mixture of 3,5-dimethoxy-benzaldehyde (7.34 g, 44.1 mmol) in dry THF (30 mL) was added and stirred for 1 hour at −78° C. The mixture was quenched with isopropanol (18.5 mL, 241 mmol) and added water (30 mL). The mixture was extracted with EtOAc (3×80 mL). The combined organic phases were washed with water (2×80 mL), dried over MgSO$_4$ and concentrated to oil, which was purified by flash column chromatography (EtOAc/Hexane) to give (3-benzyloxy-phenyl)-(3,5-dimethoxy-phenyl)-methanol as an oil (11.54 g, 82% yield): $^1$H NMR (CDCl$_3$) δ 2.21 (d, J=4 Hz, 1H, OH), 3.76 (s, 6H, 2OCH$_3$), 5.04 (s, 2H, CH$_2$), 5.72 (d, J=4 Hz, 1H, CH), 6.36 (t, J=2 Hz, 1H, Ar), 6.54 (d, J=2 Hz, 2H, Ar), 6.85-7.04 (m, 3H, Ar), 7.21-7.43 (m, 6H, Ar). The product was used in the next step without further purification.

To a stirred solution of (3-benzyloxy-phenyl)-(3,5-dimethoxy-phenyl)-methanol (11.51 g, 32.9 mmol) in CH$_2$Cl$_2$ (30 mL) at room temperature was added activated MnO$_2$ powder (13.28 g, 153 mmol) and kept adding 2~3 equivalents of MnO$_2$ every 3~5 h until HPLC showed disappearance of the starting material. The black suspension was filtered through a Celite pad, concentrated in vacuo to give (3-benzyloxy-phenyl)-(3,5-dimethoxy-phenyl)-methanone as a clear oil (10.67 g, 93% yield): $^1$H NMR (CDCl$_3$) δ 3.82 (s, 6H, OCH$_3$), 5.11 (s, 2H, CH$_2$), 6.67 (t, J=2 Hz, 1H, Ar), 6.92 (d, J=2 Hz, 2H, Ar), 7.17-7.22 (m, 1H, Ar), 7.33-7.45 (m, 8H, Ar). The product was used in the next step without further purification.

To a solution of cyanomethylphosphonic acid diethyl ester (9.6 mL, 61.2 mmol) in anhydrous THF (30 mL) was added lithium bis(trimethylsilyl)amide (1.0 M solution in THF, 61.2 mL, 61.2 mmol) at 0° C. and stirred for 30 min at room temperature followed by addition of (3-benzyloxy-phenyl)-(3,5-dimethoxy-phenyl)-methanone (10.66 g, 30.6 mmol) in THF (40 mL) and refluxed for 5 hours. The reaction mixture was poured into water (100 mL), extracted with CH$_2$Cl$_2$ (2×80 mL). The combined organic phases were washed with brine (80 mL), dried over MgSO$_4$, and purified via flash column chromatography (EtOAc/Hexane) to give (E/Z)-3-(3-benzyloxy-phenyl)-3-(3,5-dimethoxy-phenyl)-acrylonitrile as a white solid (9.82 g, 86% yield): mp, 100-102° C.; $^1$H NMR (DMSO-d$_6$) δ 3.73 and 3.76 (2s, 3H, OCH$_3$), 5.11 and 5.12 (2s, 2H, CH$_2$), 6.38 and 6.40 (2s, 1H, CH), 6.46 (d, J=2 Hz, 2H, Ar), 6.62-6.66 (2t, 1H, Ar), 6.88-7.20 (m, 3H, Ar), 7.31-7.47 (m, 6H, Ar). The product was used in the next step without further purification.

A mixture of (E/Z)-3-(3-benzyloxy-phenyl)-3-(3,5-dimethoxy-phenyl) -acrylonitrile (3.37 g), 20% palladium on charcol (0.1 g, 3% weight), and cyclohexene (11 mL) in ethanol (22 mL) was refluxed overnight. The black suspension was filtered through a Celite pad, and the filtrate was evaporated to give E/Z-3-(3,5-dimethoxy-phenyl)-3-(3-hydroxy-phenyl)-acrylonitrile as an off-white solid (1.79 g, 70% yield): $^1$H NMR (DMSO-d$_6$) δ 3.74 and 3.77 (2s, 6H, 2OCH$_3$), 6.27 and 6.32 (2s, 1H, CH), 6.46 (d, J=2 Hz, 2H, Ar), 6.62-6.92 (m, 4H, Ar), 7.20-7.33 (m, 1H, Ar), 9.65 and 9.73 (2brs, 1H, OH). The product was used in the next step without further purification.

E/Z-3-(3,5-dimethoxy-phenyl)-3-(3-hydroxy-phenyl)-acrylonitrile (1.6 g) was purified via preparative HPLC using a mobile phase of 35% acetonitrile and 65% water to give Z-3-(3,5-Dimethoxy-phenyl)-3-(3-hydroxy-phenyl)-acrylonitrile as a white solid (0.52 g, 33% yield): mp, 142-144° C.; $^1$H NMR (DMSO-d$_6$) δ 3.76 (s, 6H, 2OCH$_3$), 6.27 (s, 1H, CH), 6.47 (d, J=2 Hz, 2H, Ar), 6.65 (t, 1H, J=2 Hz, Ar), 6.70 (t, 1H, J=2 Hz, Ar), 6.84-6.89 (mt, 2H, Ar), 7.23 (t, 1H, J=8 Hz, Ar), 9.65 (brs, 1H, OH). The stereo structure was confirmed by NOE. Anal. Calcd for C$_{17}$H$_{15}$NO$_3$: C, 72.58; H, 5.37; N, 4.98. Found: C, 72.36; H, 5.39; N, 4.75.

4.6.2.97 (E/Z)-3-(4-Dimethylamino-phenyl)-3-(3-ethoxy-4-methoxy-phenyl)-acrylonitrile

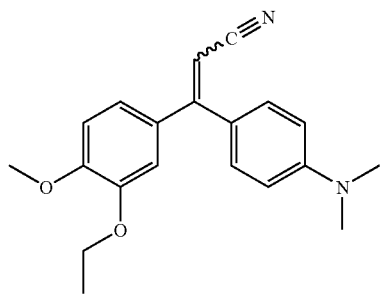

A stirred mixture of 4-bromo-2-ethoxy-1-methoxy-benzene (1.71 g, 7.4 mmol) and dry THF (18 mL) was cooled to −78° C., evacuated and refilled with nitrogen for 10 cycles. To this clear solution was slowly added n-butyllithium (3.0 mL, 7.4 mmol) and stirred for 20 min. Then a mixture of 4-dimethylamino-benzaldehyde (1.00 g, 6.7 mmol) in dry THF (10 mL) was added and stirred for 2 hour at −78° C. The mixture was quenched with isopropanol (3.1 mL, 40 mmol) and added water (10 mL). The mixture was extracted with EtOAc (3×50 mL). The combined organic phases were washed with water (2×50 mL), dried over MgSO$_4$ and concentrated to oil, which was purified by flash column chromatography (EtOAc/Hexane) to give (4-dimethylamino-phenyl)-(3-ethoxy-4-methoxy-phenyl)-methanol as an off-white solid (1.29 g, 64% yield): $^1$H NMR (CDCl$_3$) δ 1.44 (t, J=7 Hz, 3H, CH$_2$CH$_3$), 2.04 (d, J=3 Hz, 1H, OH), 2.93 (s, 6H, N(CH$_3$)$_2$), 3.85 (s, 3H, OCH$_3$), 4.07 (q, J=7 Hz, 2H, CH$_2$CH$_3$), 5.72 (d, J=3 Hz, 1H, CH), 6.68-7.23 (m, 7H, Ar). The product was used in the next step without further purification.

To a stirred solution of (4-dimethylamino-phenyl)-(3-ethoxy-4-methoxy-phenyl)-methanol (1.29 g, 4.3 mmol) in CH$_2$Cl$_2$ (30 mL) at room temperature was added activated MnO$_2$ powder (2.1 g, 24 mmol) and kept adding 2~3 equivalents of MnO$_2$ every 3~5 h until HPLC showed disappearance of the starting material. The black suspension was filtered through a Celite pad, concentrated in vacuo to give (4-dimethylamino-phenyl)-(3-ethoxy-4-methoxy-phenyl)-methanone as an brown oil (0.22 g, 17% yield): $^1$H NMR (CDCl$_3$) δ 1.48 (t, J=7 Hz, 3H, CH$_2$CH$_3$), 3.08 (s, 6H, N(CH$_3$)$_2$), 3.95 (s, 3H, OCH$_3$), 4.16 (q, J=7 Hz, 2H, CH$_2$CH$_3$), 6.67-6.71 (m, 2H, Ar), 6.88-6.92 (m, 1H, Ar), 7.34-7.39 (m, 2H, Ar), 7.77-7.80 (m, 2H, Ar). The product was used in the next step without further purification.

To a solution of cyanomethylphosphonic acid diethyl ester (0.23 mL, 1.5 mmol) in anhydrous THF (6 mL) was added lithium bis(trimethylsilyl)amide (1.0 M solution in THF, 1.5 mL, 1.5 mmol) at 0° C. and stirred for 30 min at room temperature followed by addition of (4-dimethylamino-phenyl)-(3-ethoxy-4-methoxy-phenyl)-methanon (0.22 g, 0.74 mmol) in THF (6 mL) and refluxed overnight. The reaction mixture was poured into water (10 mL), extracted with CH$_2$Cl$_2$ (2×30 mL). The combined organic phases were washed with brine (30 mL), dried over MgSO$_4$, and purified via flash column chromatography (EtOAc/Hexane) to give (E/Z)-3-(4-dimethylamino-phenyl)-3-(3-ethoxy-4-methoxy-phenyl)-acrylonitrile as an off-white solid (0.21 g, 87% yield): mp, 81-83° C.; $^1$H NMR (DMSO-d$_6$) δ 1.28-1.34 (m, 3H, CH$_2$CH$_3$), 2.96 and 2.99 (2s, 6H, N(CH$_3$)$_2$), 3.79 and 3.83 (2s, 3H, OCH$_3$), 3.94-4.03 (2q, 2H, CH$_2$CH$_3$), 5.84 and 5.93 (2s, 1H, CH), 6.68-7.26 (m, 7H, Ar); $^{13}$C NMR (DMSO-d$_6$) δ 14.6, 14.6, 39.6, 39.7, 55.5, 55.5, 63.8, 89.0, 90.0, 111.2, 111.3, 111.4, 111.5, 112.8, 113.9, 119.5, 122.2, 123.7, 124.7, 129.6, 129.8, 130.7, 131.5, 147.3, 147.7, 149.9, 150.8, 151.2, 151.6, 161.7, 161.9. Anal. Calcd for C$_{20}$H$_{22}$N$_2$O$_2$: C, 74.51; H, 6.88; N, 8.69. Found: C, 74.42; H, 7.11; N, 8.61.

4.6.2.98 (E/Z)-3-(3-Ethoxy-4-methoxy-phenyl)-3-(4-methylamino-phenyl)-acrylonitrile

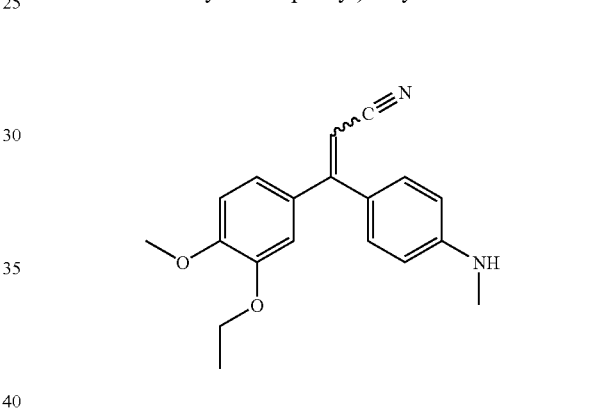

A stirred mixture of 4-bromo-2-ethoxy-1-methoxy-benzene (1.71 g, 7.4 mmol) and dry THF (18 mL) was cooled to −78° C., evacuated and refilled with nitrogen for 10 cycles. To this clear solution was slowly added n-butyllithium (3.0 mL, 7.4 mmol) and stirred for 20 min. Then a mixture of 4-dimethylamino-benzaldehyde (1.00 g, 6.7 mmol) in dry THF (10 mL) was added and stirred for 2 hour at −78° C. The mixture was quenched with isopropanol (3.1 mL, 40 mmol) and added water (10 mL). The mixture was extracted with EtOAc (3×50 mL). The combined organic phases were washed with water (2×50 mL), dried over MgSO$_4$ and concentrated to oil, which was purified by flash column chromatography (EtOAc/Hexane) to give (4-dimethylamino-phenyl)-(3-ethoxy-4-methoxy-phenyl)-methanol as an off-white solid (1.29 g, 64% yield): $^1$H NMR (CDCl$_3$) δ 1.44 (t, J=7 Hz, 3H, CH$_2$CH$_3$), 2.04 (d, J=3 Hz, 1H, OH), 2.93 (s, 6H, N(CH$_3$)$_2$), 3.85 (s, 3H, OCH$_3$), 4.07 (q, J=7 Hz, 2H, CH$_2$CH$_3$), 5.72 (d, J=3 Hz, 1H, CH), 6.68-7.23 (m, 7H, Ar). The product was used in the next step without further purification.

To a stirred solution of (4-dimethylamino-phenyl)-(3-ethoxy-4-methoxy-phenyl)-methanol (1.29 g, 4.3 mmol) in CH$_2$Cl$_2$ (30 mL) at room temperature was added activated MnO$_2$ powder (2.1 g, 24 mmol) and kept adding 23 equivalents of MnO$_2$ every 3~5 h until HPLC showed disappearance of the starting material. The black suspension was filtered through a Celite pad, concentrated in vacuo to give (3-ethoxy-4-methoxy-phenyl)-(4-methylamino-phenyl)-methanone as an brown solid (0.30 g, 23% yield): $^1$H NMR (CDCl$_3$) δ 1.48 (t, J=7 Hz, 3H, CH$_2$CH$_3$), 2.92 (d, J=3 Hz, 3H, NCH$_3$), 3.95 (s, 3H, OCH$_3$), 4.16 (q, J=7 Hz, 2H, CH$_2$CH$_3$), 4.27 (brs, 1H, NH), 6.57-6.62 (m, 2H, Ar), 6.88-6.91 (m, 1H, Ar), 7.33-7.39 (m, 2H, Ar), 7.72-7.76 (m, 2H, Ar). The product was used in the next step without further purification.

To a solution of cyanomethylphosphonic acid diethyl ester (0.40 mL, 2.5 mmol) in anhydrous THF (8 mL) was added lithium bis(trimethylsilyl)amide (1.0 M solution in THF, 2.5 mL, 2.5 mmol) at 0° C. and stirred for 30 min at room temperature followed by addition of (3-ethoxy-4-methoxy-phenyl)-(4-methylamino-phenyl)-methanone (0.29 g, 1.0 mmol) in THF (8 mL) and refluxed overnight. The reaction mixture was poured into water (10 mL), extracted with CH$_2$Cl$_2$ (2×30 mL). The combined organic phases were washed with brine (30 mL), dried over MgSO$_4$, and purified via flash column chromatography (EtOAc/Hexane) to give (E/Z)-3-(3-ethoxy-4-methoxy-phenyl)-3-(4-methylamino-phenyl)-acrylonitrile as an off-white solid (0.26 g, 81% yield): mp, 81-83° C., $^1$H NMR (DMSO-d$_6$) δ 1.28-1.34 (m, 3H, CH$_2$CH$_3$), 2.69 and 2.74 (m, 3H, NCH$_3$), 3.79 and 3.83 (2s, 3H, OCH$_3$), 3.94-4.02 (2q, 2H, CH$_2$CH$_3$), 5.77 and 5.87 (2s, 1H, CH), 6.25-6.36 (m, 1H, NH), 6.50-7.19 (m, 7H, Ar); $^{13}$C NMR (DMSO-d$_6$) δ 14.6, 14.6, 29.2, 29.3, 55.5, 55.5, 63.7, 88.3, 89.4, 110.8, 111.1, 111.3, 111.4, 112.8, 113.9, 119.6, 122.2, 123.4, 124.5, 129.8, 129.9, 130.9, 131.6, 147.3, 147.6, 149.8, 150.7, 151.3, 151.9, 161.9, 162.1. Anal. Calcd for C$_{19}$H$_{20}$N$_2$O$_2$: C, 74.00; H, 6.54; N, 9.08. Found: C, 73.67; H, 6.70; N, 8.81.

4.6.2.99 (Z) {4-[2-cyano-1-(3-ethoxy-4-methoxy-phenyl)-vinyl]-2-methoxy-phenyl}-carbamic Acid Methyl Ester

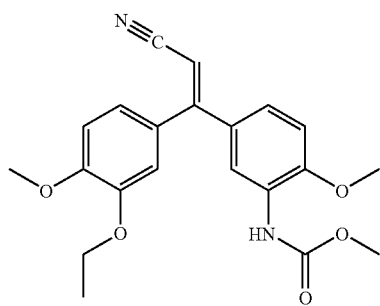

4-amino-2-nitrophenol (0.015 mol, 2.31 g) was suspended in conc. HCl (8 mL) and the mixture was cooled to 0° C. NaNO$_2$ (1.14 g, 1.1 equiv) in H$_2$O (6 mL) was added slowly. The mixture was stirred for 20 minutes. KI (25 g, 10 equiv) in H$_2$O (35 mL) was added dropwise to the stirred suspension. The mixture was then allowed to warm to room temperature and stir for another 12 h. The mixture was then diluted with H$_2$O (50 mL) and extracted with CHCl$_3$ (3×40 mL). The organic extracts were dried (Na$_2$SO$_4$), filtered, and concentrated to afford 4-hydroxy-3-nitroiodobenzene as a yellow powder (3.2 g, 12.0 mmol, 80%). $^1$H NMR (300 M Hz, CDCl$_3$) δ 10.5 (brs, 1H), 8.42 (d, 1H, J=2.1 Hz), 7.83 (dd, 1H, J=9.3, 2.1 Hz), 6.95 (d, 1H, J=9.3 Hz).

4-Hydroxy-3-nitroiodobenzene (3.2 g, 12.0 mmol) was dissolved in acetone (30 mL). K$_2$CO$_3$ (1.8 g, 1.1 equiv) and Me$_2$SO$_4$ (1.23 mL, 1.1 equiv) were added to the solution. The mixture was stirred at 65° C. for 12 h. The reaction was then cooled, concentrated, and diluted with H$_2$O (100 mL) and CHCl$_3$ (100 mL). The mixture was shaken in a separatory funnel. The organic layer was dried (Na$_2$SO$_4$), filtered, and concentrated to afford 4-methoxy-3-nitroiodobenzene as a beige solid (3.3 g, 12.0 mmol, quant.): mp: 92-93° C. $^1$H NMR (300 M Hz, CDCl$_3$) δ 8.13 (d, 1H, J=2.4 Hz), 7.81 (dd, 1H, J=8.7, 2.4 Hz), 6.86 (d, 1H, J=8.7 Hz), 3.95 (s, 3H).

4-Methoxy-3-nitroiodobenzene (1.1 g, 3.95 mmol), activated charcoal (0.13 g), and FeCl$_3$.6H$_2$O (13 mg, 2 mol %) were combined in MeOH (8 mL). The mixture was refluxed for 10 minutes. H$_4$N$_2$.H$_2$O (8 mL) was added dropwise to the solution. The mixture was stirred 12 h at 65° C. The reaction was then filtered through celite. The methanolic solution was concentrated and then cooled in an ice bath. 4-Methoxy-3-aminoiodobenzene crystallizes from the solution as a white solid (0.98 g, quant.): $^1$H NMR (400 M Hz, CDCl$_3$) δ 7.00 (dd, 1H, J=8.8, 2.4 Hz), 7.00 (s, 1H), 6.51 (d, 1H, J=8.8 Hz), 3.82 (s, 3H), 3.80 (br s, 2H).

3-Ethoxy-4-methoxybenzaldehyde (4.5 g, 25 mmol), K$_2$CO$_3$ (5.2 g, 37.5 mmol), and diethylcyanomethyl phosphonate (4.2 mL, 26.3 mmol) were combined in ethanol (75 mL). The mixture was stirred at reflux for 1.5 h. After all benzaldehyde had been consumed, the reaction mixture was concentrated to about 15 mL, and diluted with CH$_2$Cl$_2$ (150 mL) and H$_2$O (150 mL). The mixture was shaken in a separatory funnel and the layers separated. The organic layer was dried with Na$_2$SO$_4$, filtered and concentrated. The crude product was then titurated from ether to afford >99% of the (E)-3-(3-ethoxy-4-methoxyphenyl)-acrylonitrile 3.03 g as a light tan powder, 60%: $^1$H NMR (400 M Hz, CDCl$_3$) δ 7.32 (d, 1H, J=16.4 Hz), 7.03 (dd, 1H, J=8.4, 2.0 Hz), 6.94 (d, 1H, J=2.0 Hz), 6.87 (d, 1H, J=8.4 Hz), 6.51 (d, 1H, J=16.8 Hz), 4.11 (q, 2H, J=6.8 Hz), 3.91 (s, 3H), 1.49 (t, 3H, J=6.8 Hz).

In a 20-mL capacity microwave vessel was combined (E)-3-(3-ethoxy-4-methoxyphenyl)-acrylonitrile (0.41 g, 2.0 mmol), 5-iodo-2-methoxy-phenylamine (0.75 g, 1.5 equiv, 3.0 mmol), Pd(OAc)$_2$ (45 mg, 10 mol %, 0.2 mmol), nBu$_4$NBr (0.71 g, 1.1 equiv, 2.2 mmol), and KOAc (0.49 g, 2.5 equiv, 5.0 mmol) in DMF (8 mL). The mixture was purged with nitrogen gas for 30 seconds and the vessel was sealed. The reaction mixture was stirred in a microwave at 165° C. for 50 min, after which the starting material was consumed (TLC). The mixture was diluted with EtOAc (100 mL), washed with water (2×75 mL), and then brine (50 mL). The organic layer was dried (Na$_2$SO$_4$), filtered, and concentrated. The crude material was purified by column chromatography (SiO$_2$, 7:3 hexanes/EtOAc). Concentration of the desired fractions afforded the title compound (Z)-(3-(4-amino-3-methoxy-phenyl)-3-(3-ethoxy-4-methoxy-phenyl)-acrylonitrile in 90% yield, as the major isomer of a 92:8 mixture: $^1$H NMR δ (400 M Hz, CDCl$_3$) 7.02 (dd, 1H, J=8.4, 2.4 Hz), 6.98 (d, 1H, J=2.4 Hz), 6.90 (d, 1H, J=8.4 Hz), 6.75 (d, 1H, J=8.4 Hz), 6.70 (dd, 1H, J=8.4, 2.4 Hz), 6.65 (d, 1H, J=2.0 Hz), 5.51 (s, 1H), 4.08 (q, 2H, J=6.8 Hz), 3.92 (s, 3H), 3.89 (s, 3H), 1.45 (t, 3H, J=6.8 Hz).

To a stirred solution of 3-(3-amino-4-methoxy-phenyl)-3-(3-ethoxy-4-methoxy-phenyl)-acrylonitrile (0.20 g, 0.62 mmol) under a nitrogen atmosphere in anhydrous DMF (5 mL) was added Cs$_2$CO$_3$ (0.61 g, 1.86 mmol) and tetrabutylammonium iodide (0.69 g, 1.86 mmol). The mixture was stirred at ambient temperature for 30 minutes. Methyl chloroformate (0.14 mL, 1.86 mmol) was added dropwise into the suspension. The reaction mixture was stirred overnight under a nitrogen atmosphere. After this time, the reaction was diluted with ethyl acetate (50 mL). The solution was washed with water (2×50 mL), sodium carbonate (aq, 50 mL), and then brine (50 mL). The organic layer was dried over sodium sulfate, filtered, and then concentrated. The crude product was purified by silica gel chromatography (1:4:5, EtOAc:CH$_2$Cl$_2$: hexanes) followed by tituration with diethyl ether to afford (Z)-{4-[2-cyano-1-(3-ethoxy-4-methoxy-phenyl)-vinyl]-2-methoxy-phenyl}-carbamic acid methyl ester as a white solid (0.13 g, 55% yield): mp: 148-149° C. $^1$H NMR (400M Hz, CDCl$_3$) δ 8.20 (s, 1H), 7.23 (s, 1H), 7.00 (m, 2H), 6.90 (d, 1H, J=8.4 Hz), 6.87 (d, 1H, J=2.0 Hz), 6.81 (d, 1H, J=8.4 Hz), 5.59 (s, 1H), 4.10 (q, 2H, J=6.8 Hz), 3.92(s, 3H), 3.91 (s, 3H), 3.78 (s, 3H), 1.45 (t, 3H, J=6.8 Hz). Anal. Calcd for C$_{21}$H$_{22}$N$_2$O$_5$: C, 65.96; H, 5.80; N, 7.33. Found: C, 65.99; H, 6.05; N, 7.10.

4.6.2.100 (E) 3-Benzo[1,3]dioxol-5-yl-3-(3,5-dimethoxy-phenyl)-acrylonitrile

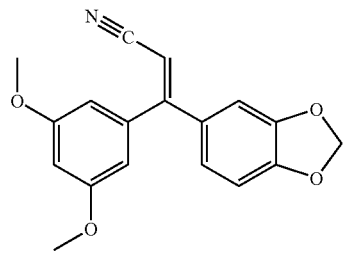

To a solution of 4-bromo-1,2-(methylenedioxy)benzene (5.0 g, 25.0 mmol) in THF (40 mL) cooled to −78° C. was added n-butyllithium (24 mL, 1.6 M, 37.3 mmol) and the mixture kept at −78° C. for 45 min. A solution of I$_2$ (12.6 g, 50 mmol) in THF (40 mL) was then added. After 45 min, the reaction was allowed to warm to room temperature and quenched with water. The THF was removed and the residue treated with EtOAc (400 mL) and saturated Na$_2$S$_2$O$_3$ solution (100 mL). The organic layer was dried over MgSO$_4$ and purified by CC (silica gel, hexanes:EtOAc 1:1) to yield 4-iodo-1,2-(methylenedioxy)benzene (4.6 g, 18.5 mmol) in 74% yield: $^1$H NMR (CDCl$_3$) δ 7.14-7.11 (m, 2H, Ar) 6.58(d, 1H, Ar), 5.94(s, 2H, CH$_2$).

(E)-3-(3,5-dimethoxy-phenyl)-acrylonitrile (0.4 g, 2.1 mmol), 4-iodo-1,2-(methylenedioxy)benzene (0.75 g, 3 mmol), Pd(OAc)$_2$ (0.047 g, 0.21 mmol), KOAc (0.62 g, 6.3 mmol) and tetrabutylammonium bromide (0.75 g, 2.3 mmol) were placed in a microwave vial, DMF (3 mL) added and the reaction mixture degassed. The vial was placed in the microwave oven (Emrys Optimizer) at 150° C. for 1 hour. The contents were poured into a water-EtOAc mixture (40 mL, 1:1) and filtered through Celite® washing the filtrate with EtOAc. The organic layer was separated and the crude product isolated by CC (silica gel, hexanes:EtOAc, 3:1 to 1:1). Sonication of the purified solid with an ether:hexane mixture yields (E) 3-benzo[1,3]dioxol-5-yl-3-(3,5-dimethoxy-phenyl)-acrylonitrile (0.2 g, 0.65 mmol) in 31% yield: m.p 95-96° C.; $^1$H NMR (CDCl$_3$) δ 6.85-6.82 (m, 1H, Ar), 6.79-6.78 (m, 2H, Ar), 6.55-6.52 (m, 3H, Ar), 6.01(s, 2H, CH$_2$), 5.63(s, 1H, CH), 3.8 (s, 6H, 2CH$_3$). Anal. Calcd. for C$_{18}$H$_{15}$NO$_4$: C, 69.89; H, 4.89; N, 4.53. Found: C, 69.69; H, 5.12; N, 4.46.

4.6.2.101 (Z) 3-Benzo[1,3]dioxol-5-yl-3-(4-methoxy-phenyl)-acrylonitrile

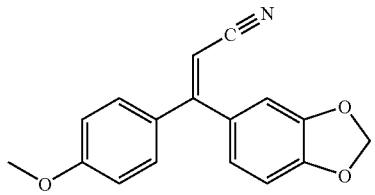

Piperonal (7.5 g, 50 mmol), diethyl(cyanomethyl)phosphonate (10.6 g, 60 mmol), K$_2$CO$_3$ (27.6 g, 200 mmol) and EtOH (300 mL) were combined and heated at reflux for 3 hours. The reaction was cooled to room temperature the solvent removed and the residue treated with EtOAc (400 mL) and water (200 mL). The organic layer was dried over MgSO$_4$ and purified by CC (silica gel, hexanes:EtOAc 2:1) to yield a mixture of (E) and (Z)-3-benzo[1,3]dioxol-5-yl-acrylonitrile as a crude oil. Trituration with hexanes: ether yields a white solid (3.5 g, 20 mmol) in 40% yield as a 9:1 mixture (E):(Z) of 3-benzo[1,3]dioxol-5-yl-acrylonitrile. $^1$H-NMR (CDCl$_3$) δ 7.39 (d, 1H, CH), 7.04-6.94 (m, 3H, Ar), 6.13(s, 2H,), 5.77(d, 1H, CH) (data for the (E)-isomer).

3-Benzo[1,3]dioxol-5-yl-acrylonitrile (9:1 (E):(Z) mixture) (0.3 g, 1.73 mmol), 4-iodo-anisole (0.57 g, 2.43 mmol), Pd(OAc)$_2$ (0.039 g, 0.17 mmol), KOAc (0.5 g, 5.2 mmol) and tetrabutylammonium bromide (0.6 g, 1.9 mmol) were combined in a microwave vial and DMF (3 mL) added, the reaction mixture was then degassed. The reaction vessel was placed in the microwave oven (Emrys Optimizer) at 150° C. for 1 hour. The contents were poured into water, EtOAc mixture (40 mL, 1:1) and filtered through Celite washing with more EtOAc. The organic layer was separated and the crude product isolated by CC (silica gel, hexanes:EtOAc, 3:1 to 1:1). Sonication of the purified compound with an ether: hexane mixture yielded (Z) 3-benzo[1,3]dioxol-5-yl-3-(4-methoxy-phenyl)-acrylonitrile (0.16 g, 0.56 mmol) in 32% yield: m.p 80-81° C.; $^1$H NMR (CDCl$_3$) δ 7.25(d, 2H, Ar), 6.98(dd, 1H, Ar), 6.89-6.86(m, 4H, Ar), 6.03(s, 2H, CH$_2$), 5.56(s, 1H, CH), 3.84 (s, 3H, OCH$_3$); Anal. Calcd for C$_{17}$H$_{13}$NO$_3$: C, 73.11; H, 4.69; N, 5.02 Found: C, 73.02; H, 4.90; N, 4.82.

Equivalents:

The present invention is not to be limited in scope by the specific embodiments described herein. Indeed, various modifications of the invention in addition to those described will become apparent to those skilled in the art from the foregoing description. Such modifications are intended to fall within the scope of the appended claims.

Various publications are cited herein, the disclosures of which are incorporated by reference in their entireties.

What is claimed is:

1. A compound of the formula:

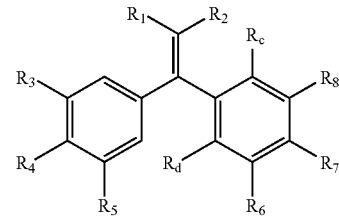

or a pharmaceutically acceptable salt thereof,
wherein:
one of R$_1$ and R$_2$ is —CN, and the other is —H, substituted or unsubstituted lower alkyl, substituted or unsubstituted alkenyl, or substituted or unsubstituted alkynyl;
each occurrence of R$_c$ and R$_d$ is independently —H, substituted or unsubstituted lower alkyl, or substituted or unsubstituted alkoxy;
R$_3$ is substituted or unsubstituted C$_{2-8}$alkyl, or substituted or unsubstituted alkoxy;
R$_4$ is substituted or unsubstituted C$_{2-8}$alkyl, or substituted or unsubstituted alkoxy;
R$_5$ is substituted or unsubstituted C$_{2-8}$alkyl, or substituted or unsubstituted alkoxy;
R$_6$ is —H, substituted or unsubstituted lower alkyl, or substituted or unsubstituted alkoxy;
each occurrence of R$_{16}$ and R$_{17}$ is independently —H or halogen, and wherein $R_8$ with $R_7$, together form —O—C($R_{16}R_{17}$)—O—.

2. The compound of claim 1 wherein:
one of $R_1$ and $R_2$ is —CN, and the other is —H or lower alkyl;
each occurrence of $R_c$ and $R_d$ is —H;
$R_3$ is $C_{2-8}$alkyl or alkoxy;
$R_4$ is $C_{2-8}$alkyl or alkoxy;
$R_5$ is $C_{2-8}$alkyl or alkoxy;
$R_6$ is —H, lower alkyl or alkoxy; and
$R_7$ with $R_8$ together form —O—CH$_2$—O—.

3. A compound or a pharmaceutically acceptable salt thereof of the structure:

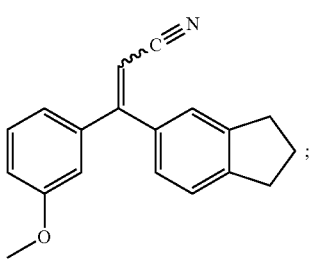;

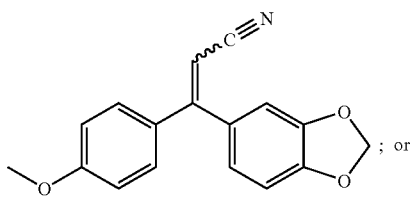; or

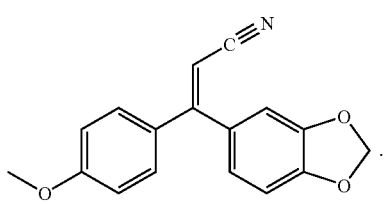.

* * * * *

UNITED STATES PATENT AND TRADEMARK OFFICE
CERTIFICATE OF CORRECTION

PATENT NO. : 7,470,723 B2
APPLICATION NO. : 10/934974
DATED : December 30, 2008
INVENTOR(S) : Muller et al.

Page 1 of 1

It is certified that error appears in the above-identified patent and that said Letters Patent is hereby corrected as shown below:

At claim 3, column 221, line 20, please replace the structure " 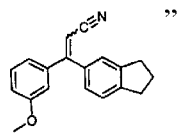 "

with the structure -- 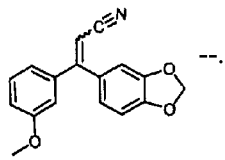 --.

Signed and Sealed this

Third Day of March, 2009

JOHN DOLL
*Acting Director of the United States Patent and Trademark Office*